US011111287B2

(12) United States Patent
Qi et al.

(10) Patent No.: US 11,111,287 B2
(45) Date of Patent: Sep. 7, 2021

(54) CHIMERIC PROTEINS AND METHODS OF IMMUNOTHERAPY

(71) Applicant: The Board of Trustees of the Leland Stanford Junior University, Stanford, CA (US)

(72) Inventors: Lei S. Qi, Stanford, CA (US); Bing C. Wang, Menlo Park, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 337 days.

(21) Appl. No.: 16/414,721

(22) Filed: May 16, 2019

(65) Prior Publication Data

US 2019/0345220 A1    Nov. 14, 2019

Related U.S. Application Data

(60) Division of application No. 16/029,299, filed on Jul. 6, 2018, now Pat. No. 10,336,807, which is a continuation-in-part of application No. PCT/US2017/012881, filed on Jan. 10, 2017.

(60) Provisional application No. 62/277,322, filed on Jan. 11, 2016, provisional application No. 62/351,522, filed on Jun. 17, 2016, provisional application No. 62/399,939, filed on Sep. 26, 2016, provisional application No. 62/399,923, filed on Sep. 26, 2016, provisional application No. 62/399,902, filed on Sep. 26, 2016.

(51) Int. Cl.
| | |
|---|---|
| *C07K 14/725* | (2006.01) |
| *C07K 14/705* | (2006.01) |
| *C07K 16/00* | (2006.01) |
| *C12N 9/22* | (2006.01) |
| *A61P 35/00* | (2006.01) |
| *A61K 35/17* | (2015.01) |
| *C12N 15/10* | (2006.01) |
| *C12N 15/63* | (2006.01) |
| *C12N 15/90* | (2006.01) |
| *A61K 38/00* | (2006.01) |

(52) U.S. Cl.
CPC ........ *C07K 14/70521* (2013.01); *A61K 35/17* (2013.01); *A61P 35/00* (2018.01); *C07K 14/7051* (2013.01); *C07K 16/00* (2013.01); *C12N 9/22* (2013.01); *C12N 15/1086* (2013.01); *C12N 15/63* (2013.01); *C12N 15/90* (2013.01); *A61K 38/00* (2013.01); *C07K 2317/622* (2013.01); *C07K 2319/01* (2013.01); *C07K 2319/03* (2013.01); *C07K 2319/09* (2013.01); *C07K 2319/33* (2013.01); *C07K 2319/74* (2013.01); *Y02A 50/30* (2018.01)

(58) Field of Classification Search
CPC combination set(s) only.
See application file for complete search history.

(56) References Cited

U.S. PATENT DOCUMENTS

| | | | |
|---|---|---|---|
| 5,888,813 | A | 3/1999 | Endl et al. |
| 7,049,076 | B2 | 5/2006 | Lee et al. |
| 8,017,398 | B2 | 9/2011 | Lee et al. |
| 8,349,619 | B2 | 1/2013 | Rossner et al. |
| 8,546,553 | B2 | 10/2013 | Terns et al. |
| 8,697,359 | B1 | 4/2014 | Zhang |
| 8,771,945 | B1 | 7/2014 | Zhang |
| 8,795,965 | B2 | 8/2014 | Zhang |
| 8,865,406 | B2 | 10/2014 | Zhang et al. |
| 8,871,445 | B2 | 10/2014 | Cong et al. |
| 8,889,356 | B2 | 11/2014 | Zhang |
| 8,895,308 | B1 | 11/2014 | Zhang et al. |
| 8,906,616 | B2 | 12/2014 | Zhang et al. |
| 8,932,814 | B2 | 1/2015 | Cong et al. |
| 8,945,839 | B2 | 2/2015 | Zhang |
| 8,993,233 | B2 | 3/2015 | Zhang et al. |
| 8,999,641 | B2 | 4/2015 | Zhang et al. |
| 9,023,649 | B2 | 5/2015 | Mali et al. |
| 9,234,213 | B2 | 1/2016 | Wu |
| 9,260,752 | B1 | 2/2016 | May et al. |
| 9,580,480 | B2 | 2/2017 | Lu et al. |
| 9,587,020 | B2 | 3/2017 | Wu et al. |
| 9,593,338 | B2 | 3/2017 | Liu et al. |
| 9,624,554 | B2 | 4/2017 | Collins et al. |
| 9,772,328 | B2 | 9/2017 | Stein et al. |
| 9,856,497 | B2 | 1/2018 | Qi et al. |
| 10,336,807 | B2 | 7/2019 | Qi et al. |
| 10,457,961 | B2 | 10/2019 | Qi et al. |

(Continued)

FOREIGN PATENT DOCUMENTS

| | | |
|---|---|---|
| CA | 2619833 | 3/2007 |
| EP | 1916903 | 7/2010 |
| EP | 2336362 | 6/2011 |
| EP | 2002021 | 10/2011 |
| EP | 1644734 | 11/2011 |

(Continued)

OTHER PUBLICATIONS

Tanaka et al., "Establishment of an Indicator Cell System for Hepatitis C Virus," Microbiol. Immunol., vol. 54, 2010, pp. 206-220.
"Extended European Search Report," dated Jun. 14, 2019 in European Patent Application No. 17738809.7, 7 pages.

(Continued)

*Primary Examiner* — Laura B Goddard
(74) *Attorney, Agent, or Firm* — Kilpatrick Townsend & Stockton LLP

(57) ABSTRACT

The present disclosure provides systems for immune cell regulation and methods of immunotherapy. Systems of the present disclosure for immune cell regulation comprise a chimeric receptor polypeptide, a chimeric adaptor polypeptide, a gene modulating polypeptide (GMP), and a cleavage moiety.

13 Claims, 49 Drawing Sheets

Specification includes a Sequence Listing.

(56) References Cited

U.S. PATENT DOCUMENTS

| | | |
|---|---|---|
| 2004/0197346 A1 | 10/2004 | O'Hare et al. |
| 2006/0182741 A1 | 8/2006 | Bourel et al. |
| 2007/0224615 A1 | 9/2007 | Lee et al. |
| 2007/0231319 A1 | 10/2007 | Yednock et al. |
| 2008/0274913 A1 | 11/2008 | Lee et al. |
| 2010/0076057 A1 | 3/2010 | Sontheimer et al. |
| 2010/0093617 A1 | 4/2010 | Barrangou et al. |
| 2011/0217739 A1 | 9/2011 | Terns et al. |
| 2012/0077706 A1 | 3/2012 | Lee et al. |
| 2013/0011828 A1 | 1/2013 | Barrangou et al. |
| 2014/0068797 A1 | 3/2014 | Doudna et al. |
| 2014/0113376 A1 | 4/2014 | Sorek et al. |
| 2014/0179770 A1 | 6/2014 | Zhang et al. |
| 2014/0199767 A1 | 7/2014 | Barrangou et al. |
| 2014/0234851 A1 | 8/2014 | Leonard et al. |
| 2014/0271635 A1 | 9/2014 | Brogdon et al. |
| 2014/0273226 A1 | 9/2014 | Wu et al. |
| 2014/0294773 A1 | 10/2014 | Brouns et al. |
| 2014/0295556 A1 | 10/2014 | Joung et al. |
| 2014/0295557 A1 | 10/2014 | Joung et al. |
| 2014/0315985 A1 | 10/2014 | May et al. |
| 2014/0342456 A1 | 11/2014 | Mali et al. |
| 2014/0342457 A1 | 11/2014 | Mali et al. |
| 2014/0342458 A1 | 11/2014 | Mali et al. |
| 2014/0377868 A1 | 12/2014 | Joung et al. |
| 2015/0024499 A1 | 1/2015 | Van et al. |
| 2015/0044772 A1 | 2/2015 | Zhao |
| 2015/0045546 A1 | 2/2015 | Siksnys et al. |
| 2015/0056705 A1 | 2/2015 | Conway et al. |
| 2015/0059010 A1 | 2/2015 | Patten et al. |
| 2015/0211023 A1 | 7/2015 | Weinthal et al. |
| 2015/0232881 A1 | 8/2015 | Glucksmann et al. |
| 2015/0259684 A1 | 9/2015 | Mali et al. |
| 2015/0283265 A1 | 10/2015 | Peyman et al. |
| 2015/0284727 A1 | 10/2015 | Kim et al. |
| 2015/0291966 A1 | 10/2015 | Zhang et al. |
| 2015/0315576 A1 | 11/2015 | Caliando et al. |
| 2015/0322457 A1 | 11/2015 | Cho et al. |
| 2015/0344912 A1 | 12/2015 | Cho et al. |
| 2016/0010076 A1 | 1/2016 | Joung et al. |
| 2016/0017366 A1 | 1/2016 | Davis et al. |
| 2016/0024523 A1 | 1/2016 | Joung et al. |
| 2016/0024524 A1 | 1/2016 | Sander et al. |
| 2016/0046949 A1 | 2/2016 | Berger et al. |
| 2016/0046961 A1 | 2/2016 | Doudna et al. |
| 2016/0046962 A1 | 2/2016 | Berger et al. |
| 2016/0046963 A1 | 2/2016 | Berger et al. |
| 2016/0046978 A1 | 2/2016 | Berger et al. |
| 2016/0060653 A1 | 3/2016 | Doudna et al. |
| 2016/0060654 A1 | 3/2016 | Doudna et al. |
| 2016/0068864 A1 | 3/2016 | Doudna et al. |
| 2016/0068887 A1 | 3/2016 | Berger et al. |
| 2016/0076020 A1 | 3/2016 | Berger et al. |
| 2016/0185862 A1 | 6/2016 | Lim et al. |
| 2016/0186152 A1 | 6/2016 | Van et al. |
| 2016/0186214 A1 | 6/2016 | Brouns et al. |
| 2016/0201089 A1 | 7/2016 | Kabadi et al. |
| 2017/0051310 A1 | 2/2017 | Doudna et al. |
| 2017/0051312 A1 | 2/2017 | Jinek et al. |
| 2017/0058282 A1 | 3/2017 | Mimee et al. |
| 2017/0096680 A1 | 4/2017 | Lu et al. |
| 2017/0198308 A1 | 7/2017 | Qi et al. |
| 2018/0208636 A1* | 7/2018 | Lim ........................ C07K 14/71 |

FOREIGN PATENT DOCUMENTS

| | | |
|---|---|---|
| EP | 2325332 | 10/2012 |
| EP | 2771468 | 2/2015 |
| EP | 2341149 | 11/2016 |
| GB | 2518764 | 3/2016 |
| GB | 2512246 | 7/2016 |
| JP | 2015523856 A | 8/2015 |
| WO | 2005007822 | 1/2005 |
| WO | 2007025097 | 3/2007 |
| WO | 2007032793 | 3/2007 |
| WO | 2007127538 | 11/2007 |
| WO | 2007136815 | 11/2007 |
| WO | 2007149807 | 12/2007 |
| WO | 2012164565 | 12/2012 |
| WO | 2013088446 | 6/2013 |
| WO | 2013098244 | 7/2013 |
| WO | 2013141680 | 9/2013 |
| WO | 2013176772 | 11/2013 |
| WO | 2014018423 | 1/2014 |
| WO | 2014065596 | 5/2014 |
| WO | 2014093479 | 6/2014 |
| WO | 2014099744 | 6/2014 |
| WO | 2014099750 | 6/2014 |
| WO | 2014/145252 A2 | 9/2014 |
| WO | 2014150624 | 9/2014 |
| WO | 2014153118 | 9/2014 |
| WO | 2014196932 | 12/2014 |
| WO | 2014204728 | 12/2014 |
| WO | 2014204729 | 12/2014 |
| WO | 2015026887 | 2/2015 |
| WO | 2015048577 | 4/2015 |
| WO | 2015048690 | 4/2015 |
| WO | 2015071474 | 5/2015 |
| WO | 2015077789 | 5/2015 |
| WO | 2015092024 | 6/2015 |
| WO | WO 2015/092024 | * 6/2015 |
| WO | 2015139139 | 9/2015 |
| WO | 2015142661 | 9/2015 |
| WO | 2015148670 | 10/2015 |
| WO | 2015148863 | 10/2015 |
| WO | 2015150771 | 10/2015 |
| WO | 2015155686 | 10/2015 |
| WO | 2016011210 | 1/2016 |
| WO | 2016070037 | 5/2016 |
| WO | 2016115033 | 7/2016 |
| WO | 2016138034 | 9/2016 |
| WO | 2016149274 | 9/2016 |
| WO | 2016193696 A1 | 12/2016 |
| WO | 2017040694 | 3/2017 |
| WO | 2017044476 | 3/2017 |
| WO | 2017059187 | 4/2017 |
| WO | 2017/123556 | 7/2017 |
| WO | 2017123559 | 7/2017 |

OTHER PUBLICATIONS

"Extended European Search Report," dated Jun. 5, 2019 in European Patent Application No. 17738812.1, 7 pages.

"International Preliminary Report on Patentability," dated Jul. 17, 2018 in International Patent Application No. PCT/US2017/012885, 11 pages.

"Invitation to Pay Additional Fees and, Where Applicable, Protest Fee," dated May 8, 2017 in International Patent Application No. PCT/US2017/012885, 4 pages.

"Non-Final Office Action," dated Dec. 10, 2018 in U.S. Appl. No. 16/029,299, 10 pages.

"Non-Final Office Action," dated Jul. 11, 2017 in U.S. Appl. No. 15/403,058, 19 pages.

"Notice of Allowance," dated Apr. 4, 2019, in U.S. Appl. No. 16/029,299, 9 pages.

"Notice of Allowance," dated Oct. 20, 2017 in U.S. Appl. No. 15/403,058, 5 pages.

"Restriction Requirement," dated May 15, 2017 in U.S. Appl. No. 15/403,058, 11 pages.

"Final Office Action," dated Jun. 19, 2019 in U.S. Appl. No. 15/806,756, 8 pages.

"International Preliminary Report on Patentability," dated Jul. 26, 2018 in International Application No. PCT/US2017/012881, 38 pages.

"Non-Final Office Action," dated Jan. 30, 2019 in U.S. Appl. No. 15/806,756, 11 pages.

"Restriction Requirement," dated Oct. 9, 2018 in U.S. Appl. No. 16/029,299, 13 pages.

UniProtKB 001705, <URL• http://www.uniprot.orgfuniprotfQ01705#seguences>, Jun. 8, 2017, pp. 1-29.

(56) References Cited

OTHER PUBLICATIONS

Barnea et al., "The genetic design of signaling cascades to record receptor activation," PNAS, 105(1), Jan. 2008, pp. 64-69.
Chavez et al., "Highly-efficient Cas9-mediated transcriptional programming", Nat Methods 12(4), 2015, pp. 326-328.
Cheng et al., "Multiplexed Activation of Endogenous Genes by CRISPR-on, An RNA-Guided Transcriptional Activator System", Cell Research, vol. 23, No. 10, Oct. 1, 2013, pp. 1163-1171.
Daringer et al., "Modular extracellular sensor architecture for engineering mammalian cell-based devices", ACS Synthetic Biology, 3, Feb. 2014, pp. 892-902.
Daringer et al., "Modular Extracellular Sensor Architecture for Engineering Mammalian Cell-based Devices", ACS Synthetic Biology, 2014 Available Online at:—http://pubs.acs.org/doi/abs/10.1021/sb400128g, pp. 892-902.
Dominguez et al., "Beyond editing: repurposing CRISPR-Cas9 for precision genome regulation and interrogation", Nature Review Molecular Cell Biology, 17, Jan. 2016, pp. 5-15.
Du et al., "CRISPR technology for genome activation and repression in mammalian cells", Cold Spring Harbor Protocols, Jan. 2016, pp. 40-49.
Gilbert et al., "CRISPR-Mediated Modular RNA-Guided Regulation of Transcription in Eukaryotes", Cell, vol. 154, No. 2, Jul. 1, 2013, pp. 442-451.
Gilbert et al., "Genome-Scale Crispr-Mediated Control of Gene Repression and Activation", Cell, vol. 159, No. 3, Oct. 1, 2014, pp. 647-661.
Hawkins et al., "Targeted transcriptional repression in bacteria using CRISPR interference (CRISPRi)", Methods Mol Bioi., 1311, 2015, pp. 349-362.
Invitrogen, "Tango™ GPR21-bla U2OS Cell-based Assay", Available Online at:—https://www.thermofisher.com/order/catalog/product/K1840, Nov. 8, 2010, 12 pages.
Kobilka, "G Protein Coupled Receptor Structure and Activation", Biochimica et Biophysica Acta 1768(4), 2007, pp. 794-807.
Kopan et al., "The Canonical Notch Signaling Pathway: Unfolding the Activation Mechanism", Cell, vol. 137, No. 2, Apr. 17, 2009, pp. 216-233.
Larson et al., "CRISPR Interference (CRISPRi) for Sequence-Specific Control of Gene Expression", Nature Protocols, vol. 8, No. 11, Nov. 2013, pp. 2180-2196.
Lim et al., "Designing Customized Cell Signaling Circuits", Nat Rev Mol Cell Biol. 11(6), Jun. 2010, pp. 393-403.
Liu et al., "CRISPR-ERA: a comprehensive design tool for CRISPR-mediated gene editing, repression and activation", Bioinformatics, 31 (22), 2015, pp. 3676-3678.
Lucks et al., "Versatile RNA-sensing transcriptional regulators for engineering genetic networks", PNAS, 1 08(21), May 2011, pp. 8617-8622.
Mandegar et al., "CRISPR interference efficiently induces specific and reversible gene silencing in human iPSCs", Cell Stem Cell, 18(4), Apr. 2016, pp. 541-553.
Morsut et al., "Engineering Customized Cell Sensing and Response Behaviors Using Synthetic Notch Receptors", Cell, 164, Feb. 2016, pp. 780-791.
Nunez et al., "Chemical and Biophysical Modulation of Cas9 for Tunable Genome Engineering", ACS Chem. Biol., 11 (3), Feb. 9, 2016, pp. 681-688.
International Search Report for corresponding PCT Appln. No. PCT/US2017/012881, dated May 15, 2017, 5 pages.
International Search Report for PCT Appln. No. PCT/US2017/012885, dated Jun. 29, 2017, 5 pages.
Qi et al., "Repurposing CRISPR as an RNA-Guided Platform for Sequence-Specific Control of Gene Expression", Cell, 152(5), Feb. 2013, pp. 1173-1183.
Roybal et al., "Precision Tumor Recognition by T Cells with Combinatorial Antigen-Sensing Circuits", Cell, 164, Feb. 2016, pp. 770-779.
Wang et al., "CRISPR/Cas9 in genome editing and beyond", Annual Review of Biochemistry, 85, Jun. 2016, pp. 227-264.
Wehr et al., "Chapter 8; G protein-Coupled Receptor Screening Assays", Methods in Molecular Biology; vol. 1272, Jan. 2015, pp. 107-118.
Xiong et al., "CRISPR/Cas9 for human genome engineering and disease research,", Annual Review of Genomics and Human Genetics, 17, Aug. 2016, pp. 131-154.
Zalatan, "Engineering complex synthetic transcriptional programs with CRISPR RNA scaffolds", Cell ePub, vol. 160 No. 1-2, Dec. 18, 2014, pp. 339-350.
U.S. Appl. No. 15/806,756, "Notice of Allowance," dated Aug. 21, 2019, 6 pages.
UNIPROT Knowledgebase (UNIPROTKB), Accession Q01705 (NOTC1_Mouse), Neurogenic locus notch homolog protein 1, Dec. 9, 2015, 21 pages.
Lloyd et al., "Beyond the Antigen Receptor: Editing the Genome of T-cells for Cancer Adoptive Cellular Therapies," Frontiers in Immunology, vol. 4, Article 221, Aug. 5, 2013, pp. 1-7.

* cited by examiner

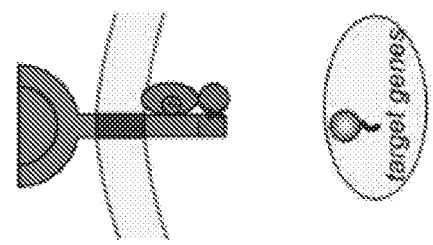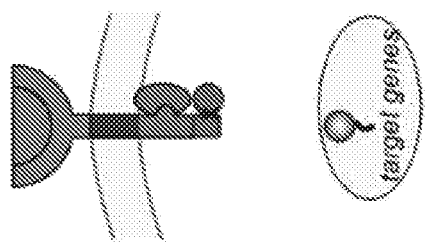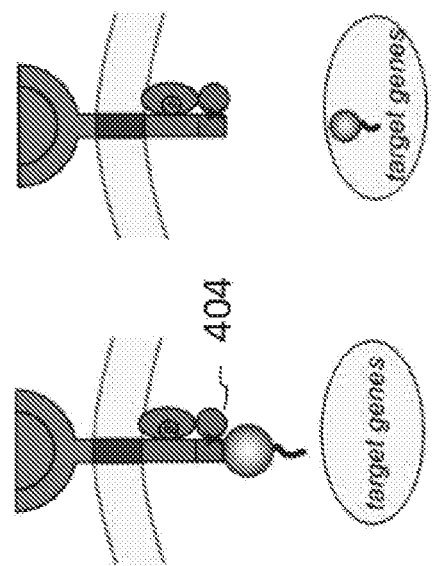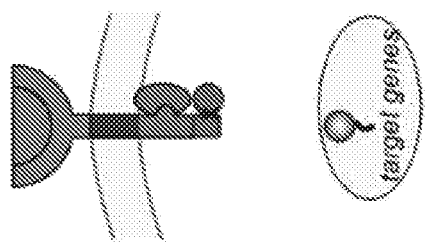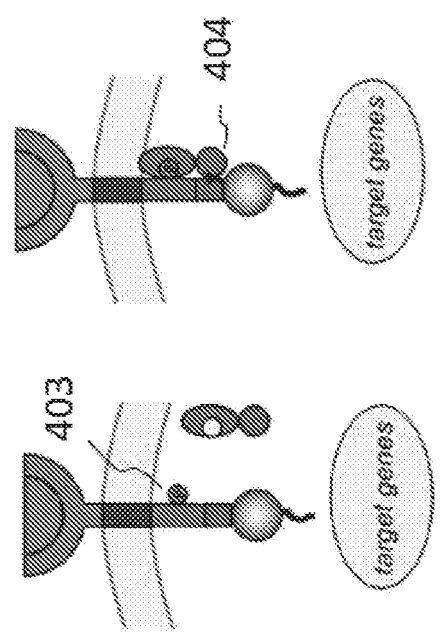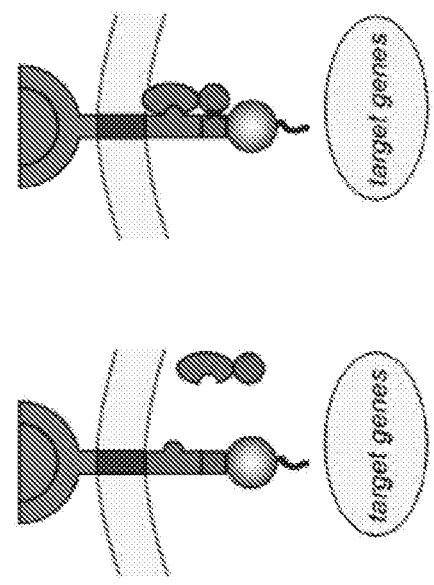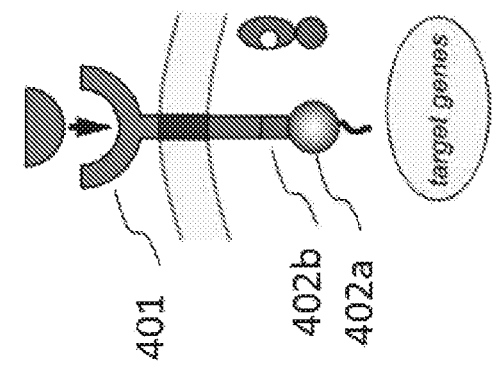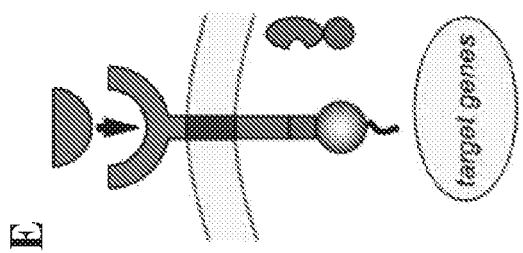

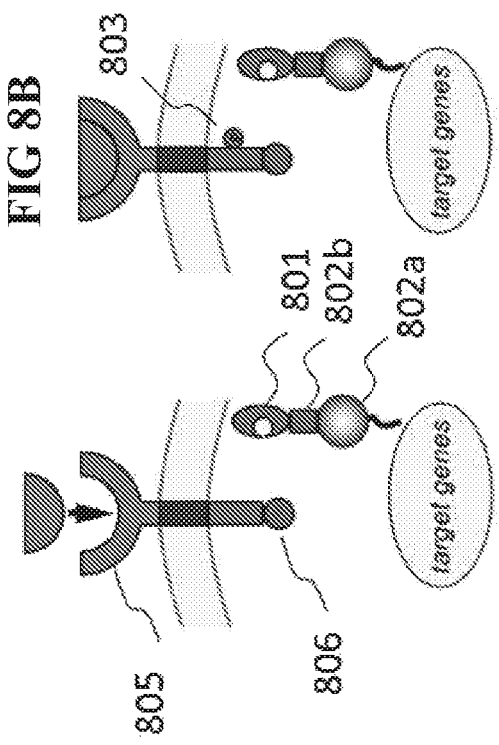
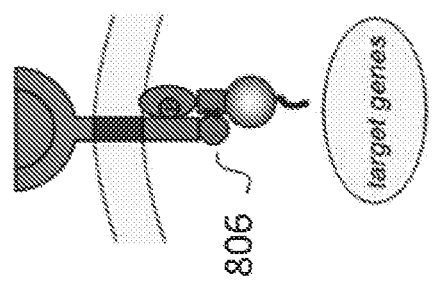
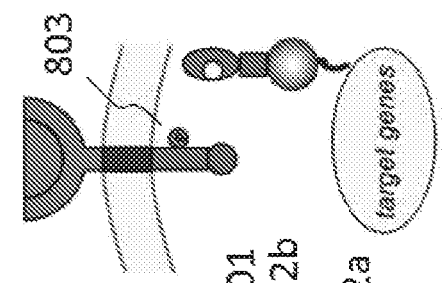
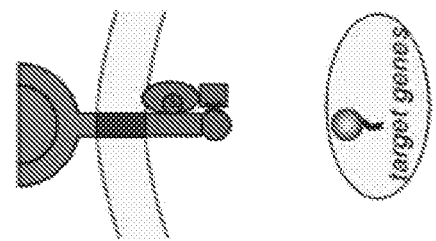
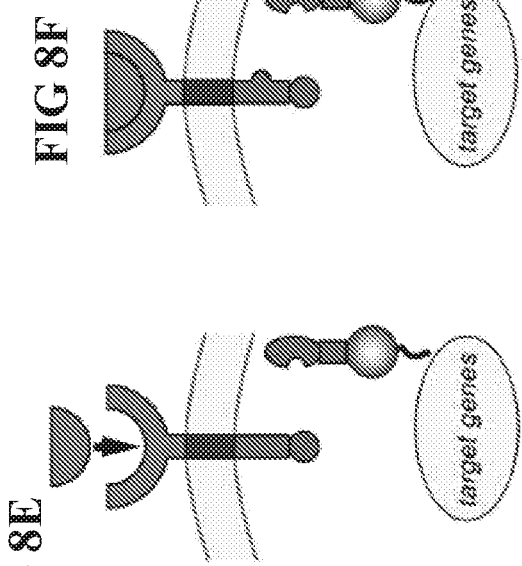
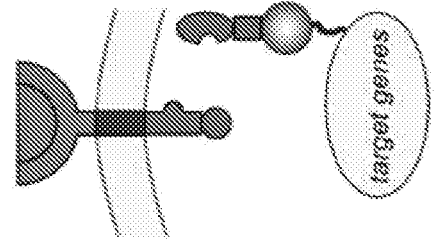
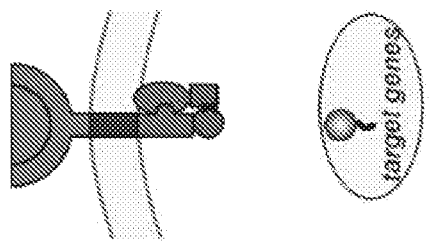

Negative Control

PD1 Positive Cells

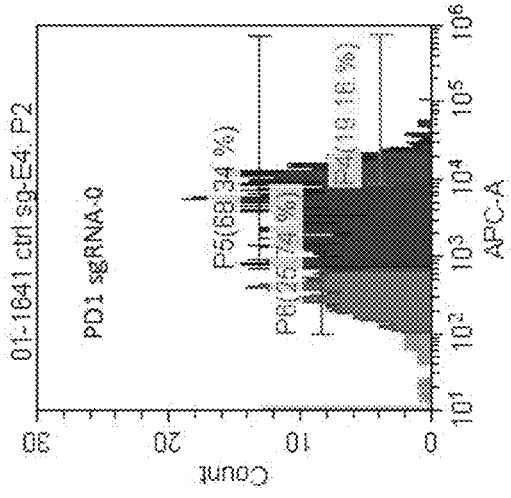
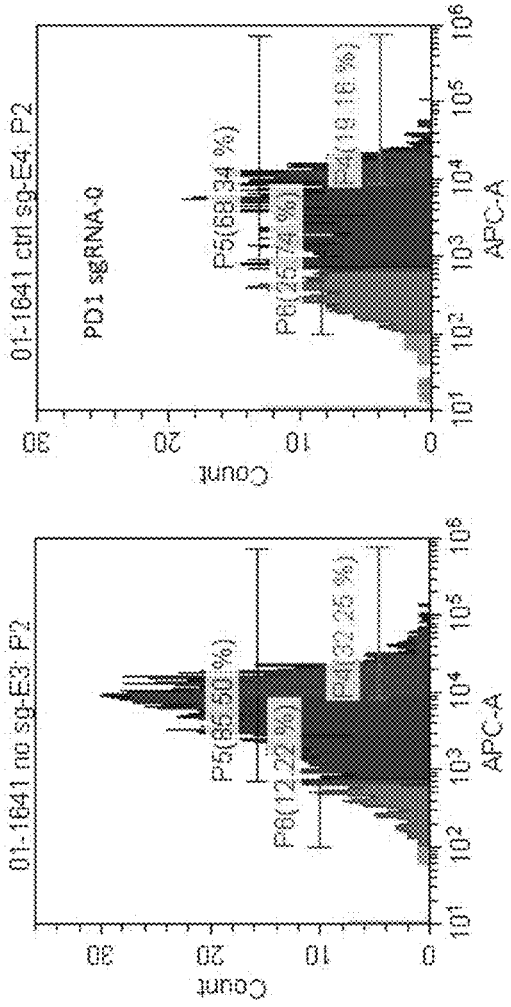
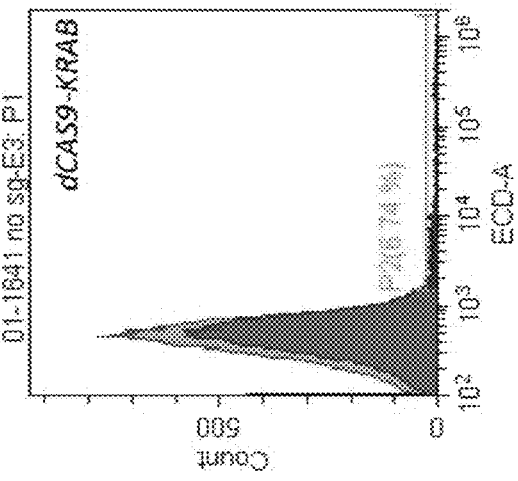
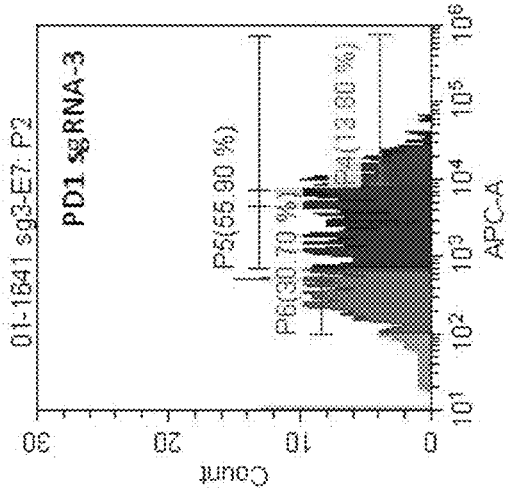
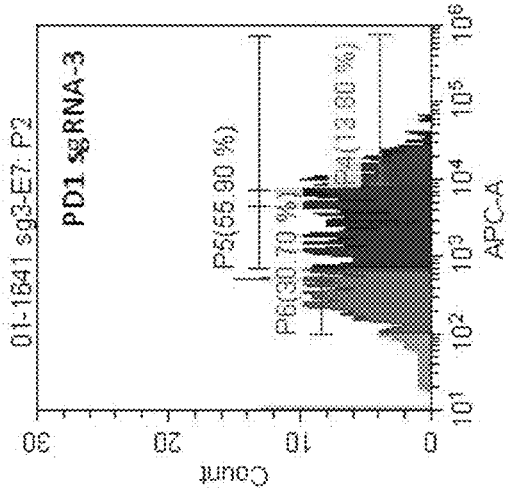
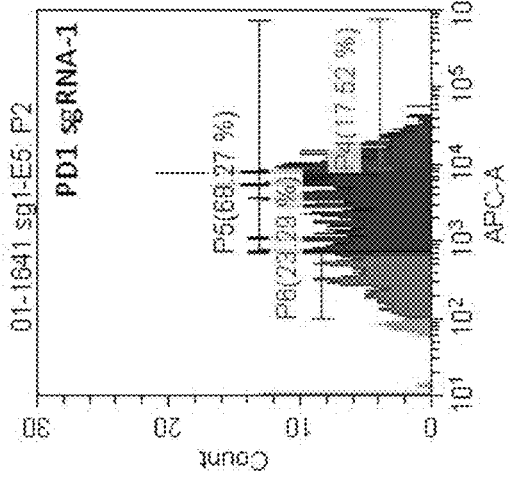

Negative Control

PD1 Positive Cells

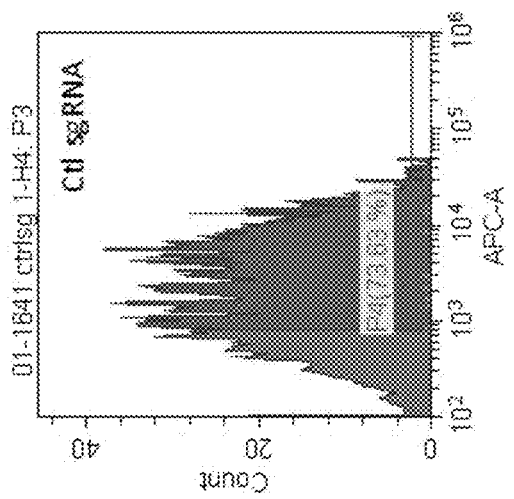
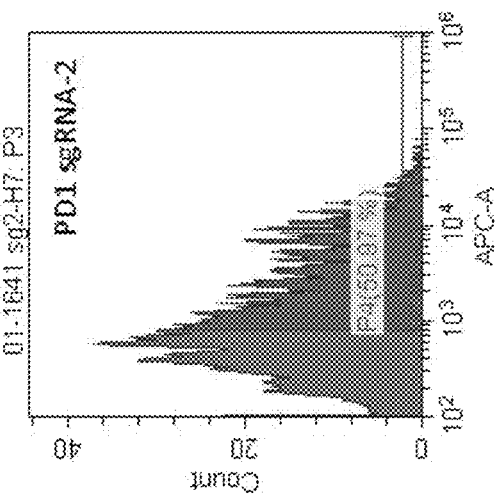
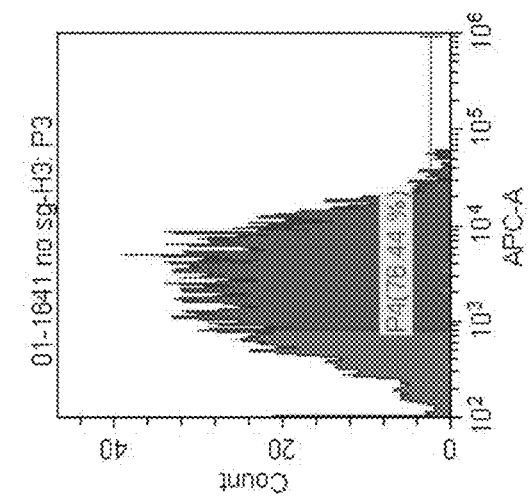
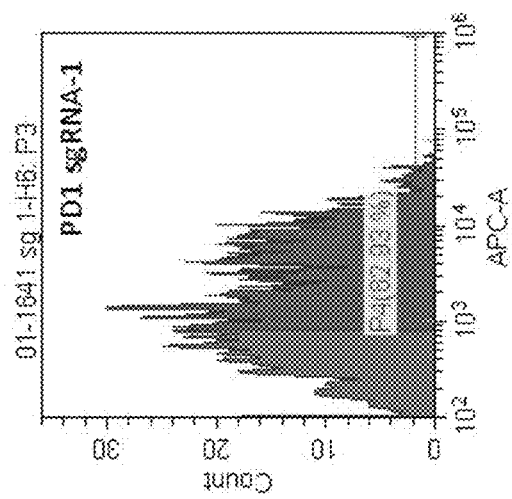
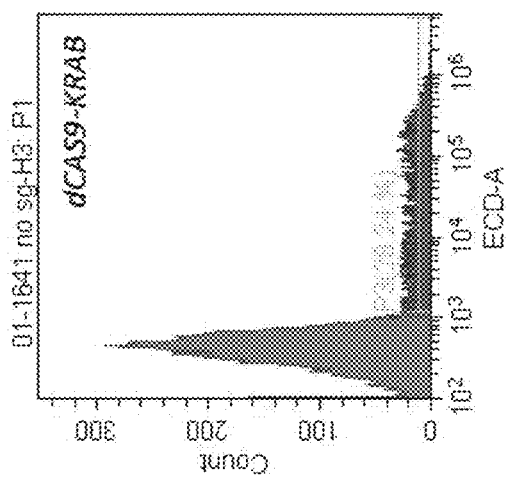

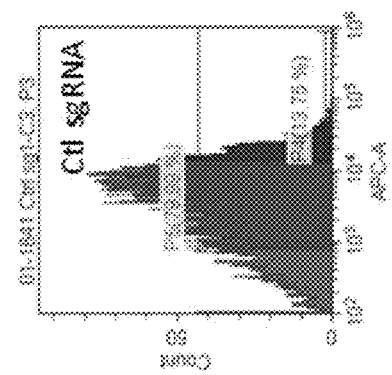
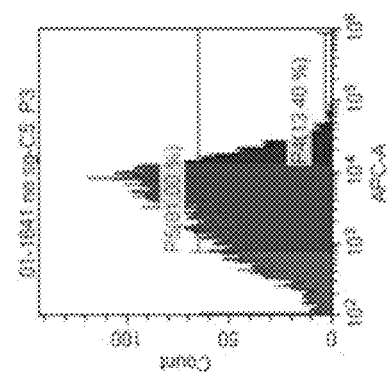
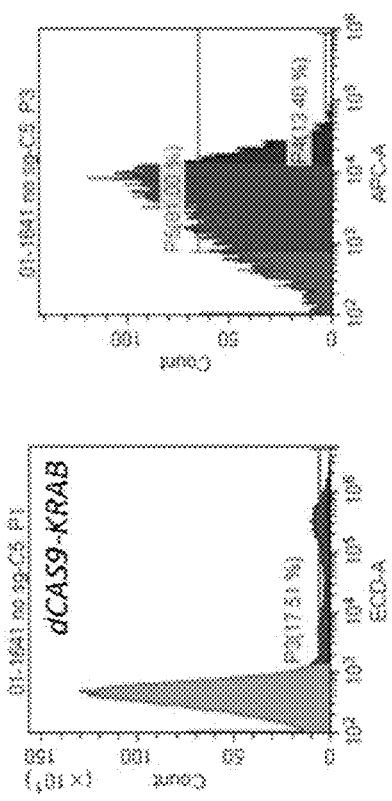
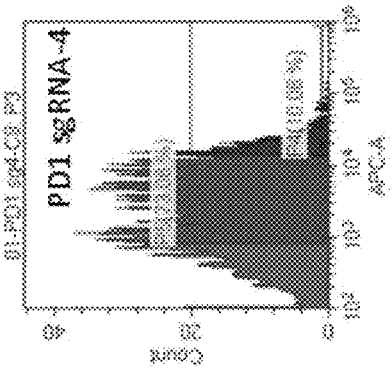
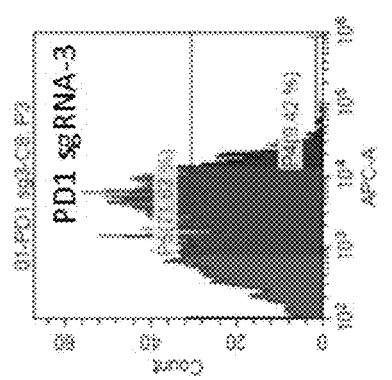
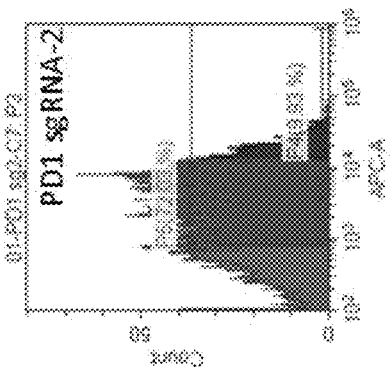

CD19-CAR-T cells with ctrl
sgRNAs + Raji cells

CD19-CAR-T cells with PD-1
sgRNAs + Raji cells

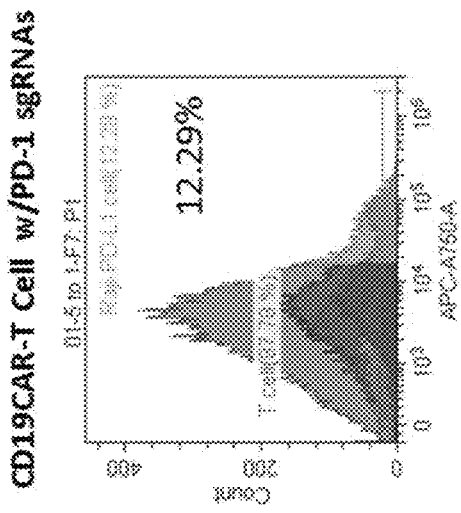
FIG. 34A Control T Cell — 13.79%
FIG. 34B CD19CAR-T Cell w/ctrl sgRNAs — 15.74%
FIG. 34C CD19CAR-T Cell w/PD-1 sgRNAs — 12.29%
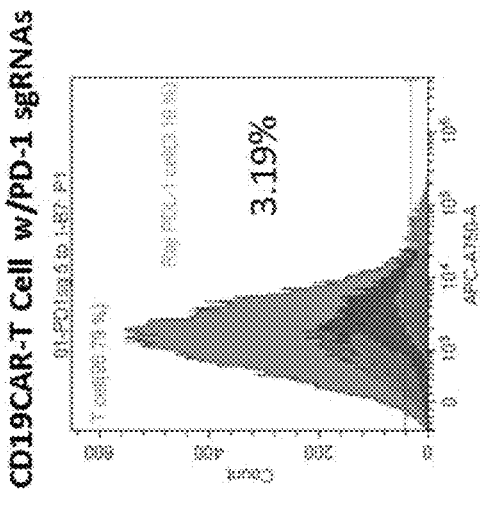
FIG. 35A Control T Cell — 13.10%
FIG. 35B CD19CAR-T Cell w/ctrl sgRNAs — 9.06%
FIG. 35C CD19CAR-T Cell w/PD-1 sgRNAs — 3.19%

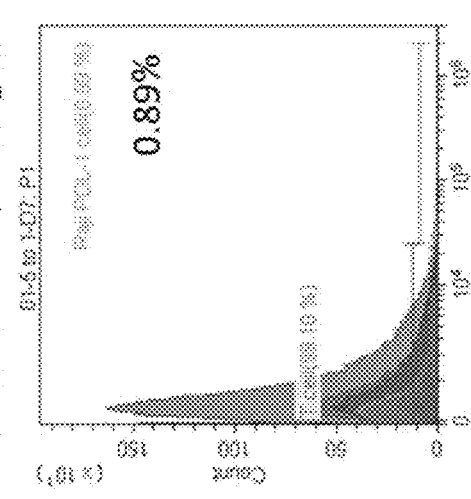
FIG. 36A Control T Cell
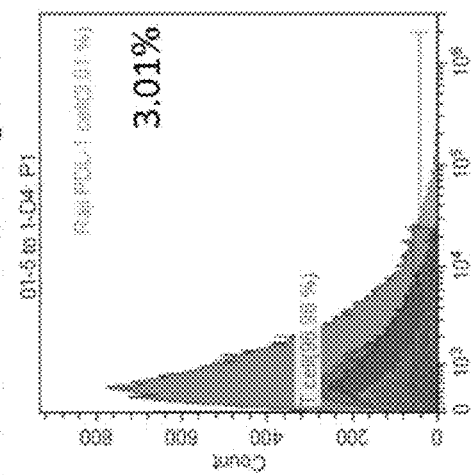
FIG. 36B CD19CAR-T Cell w/ctrl sgRNAs
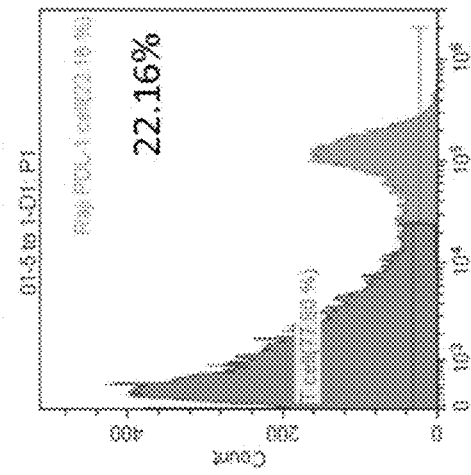
FIG. 36C CD19CAR-T Cell w/PD-1 sgRNAs
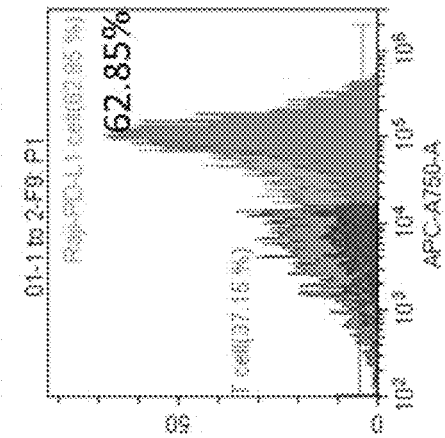
FIG. 37A Control T Cell
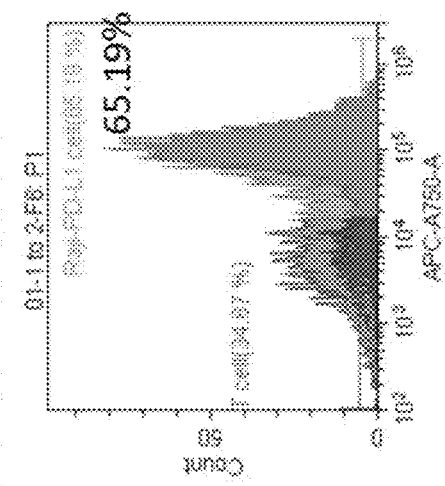
FIG. 37B CD19CAR-T Cell w/ctrl sgRNAs
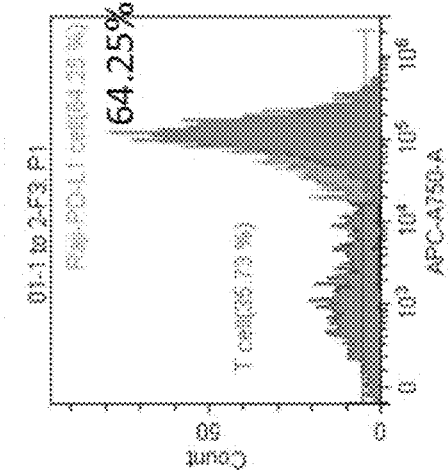
FIG. 37C CD19CAR-T Cell w/PD-1 sgRNAs

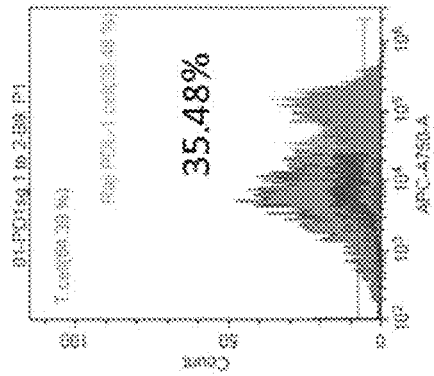
FIG. 38A Control T Cell
FIG. 38B CD19CAR-T Cell w/ctrl sgRNAs
FIG. 38C CD19CAR-T Cell w/PD-1 sgRNAs
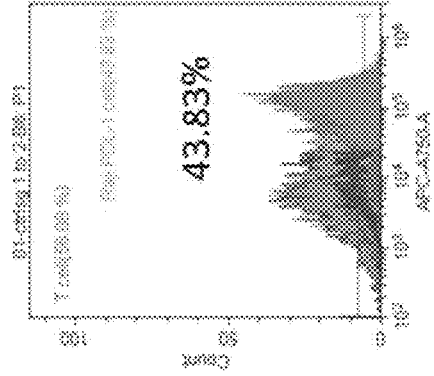
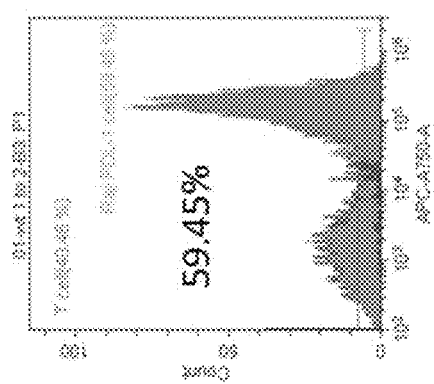
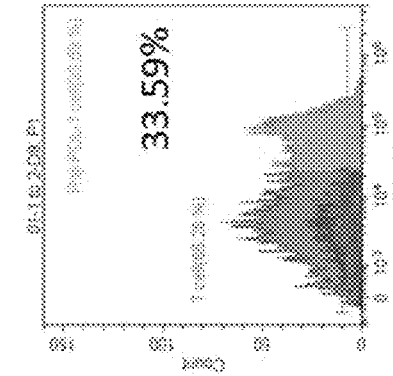
FIG. 39A Control T Cell
FIG. 39B CD19CAR-T Cell w/ctrl sgRNAs
FIG. 39C CD19CAR-T Cell w/PD-1 sgRNAs
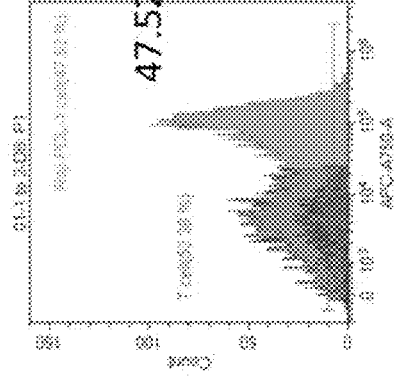
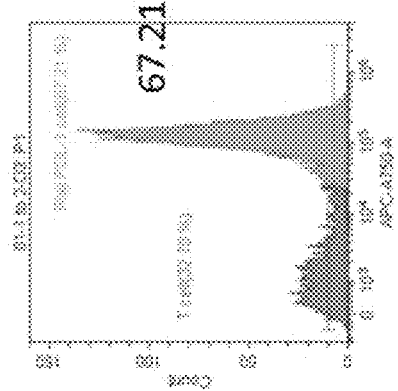

Negative Control

Positive Control

CD19-CAR-dCas-
KRAB/GAD5-TEV with ctrl
sgRNA + Raji cells

CD19-CAR-dCas-
KRAB/GAD5-TEV with
CXCR4 sgRNA + Raji cells

Negative Control

Positive Control

CD19-CAR-dCas-
KRAB/GADS-TEV with ctrl
sgRNA, no Raji cells

CD19-CAR-dCas-
KRAB/GADS-TEV with
CXCR4 sgRNA, no Raji cells

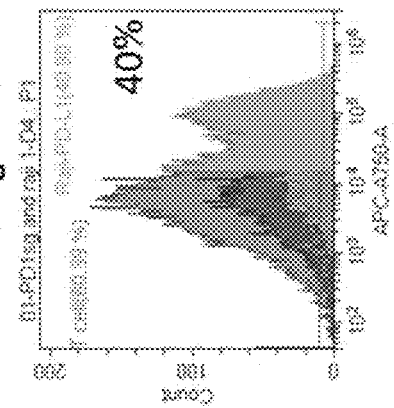
FIG. 44E
CD19CAR-T Cell with PD-1 sgRNAs
FIG. 44F
CD19CAR-T Cell with PD-1 sgRNAs
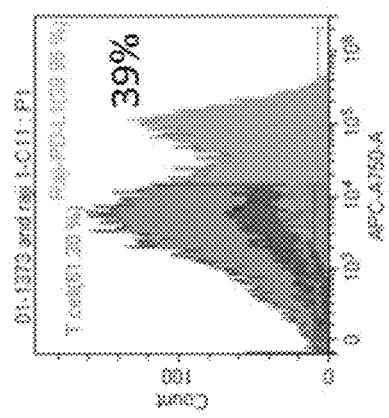
FIG. 44C
CD19CAR-T Cell with control sgRNAs
FIG. 44D
CD19CAR-T Cell with control sgRNAs
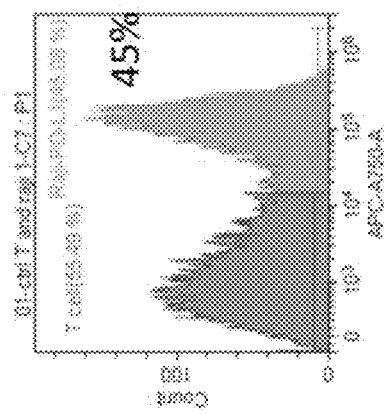
FIG. 44A
Control T Cell
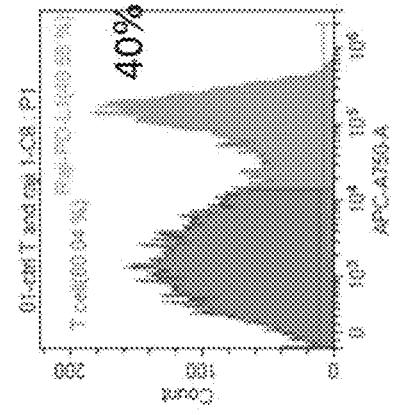
FIG. 44B
Control T Cell

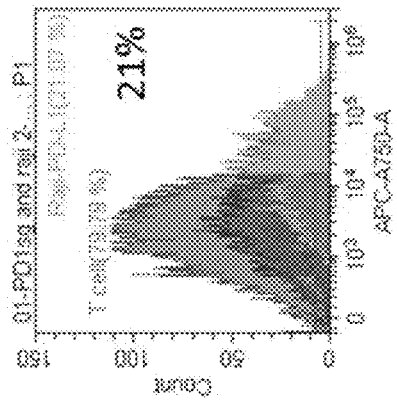
FIG. 44G Control T Cell
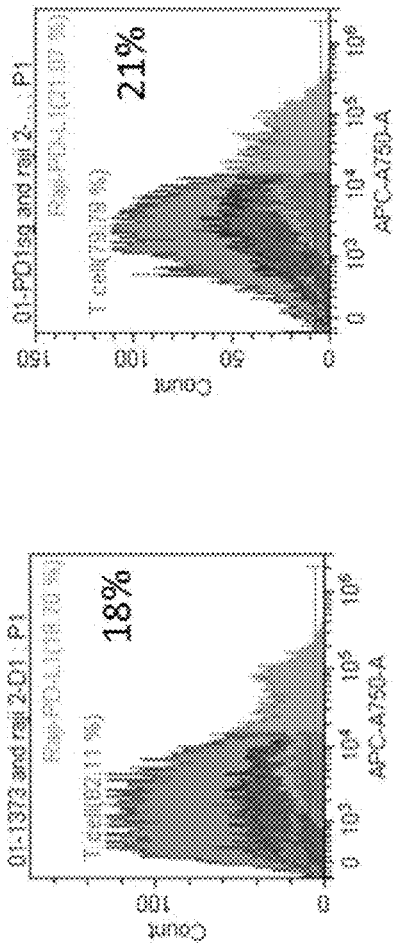
FIG. 44I CD19CAR-T Cell with control sgRNAs
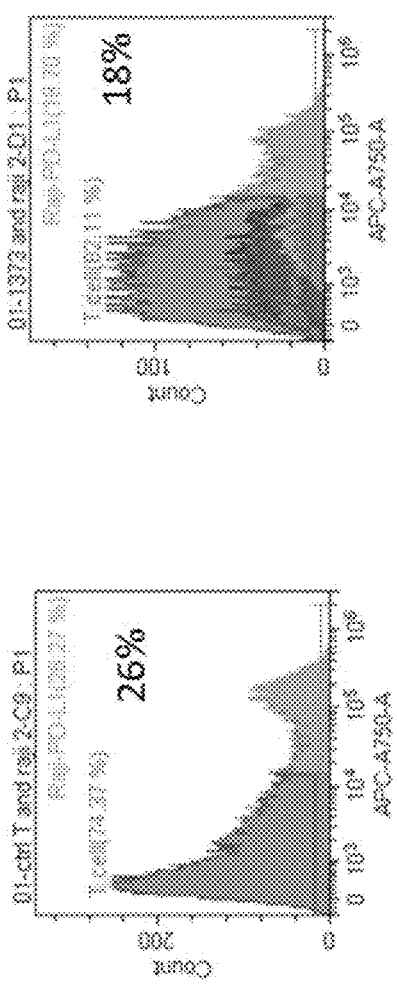
FIG. 44K CD19CAR-T Cell with PD-1 sgRNAs
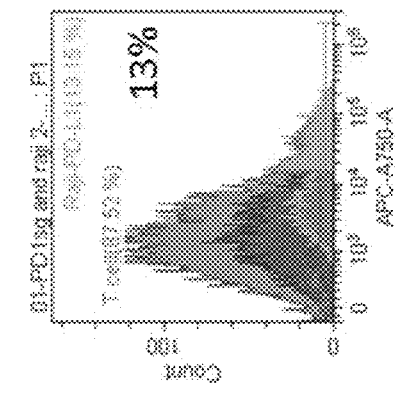
FIG. 44H Control T Cell
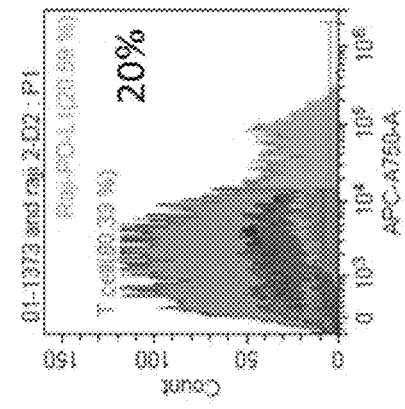
FIG. 44J CD19CAR-T Cell with control sgRNAs
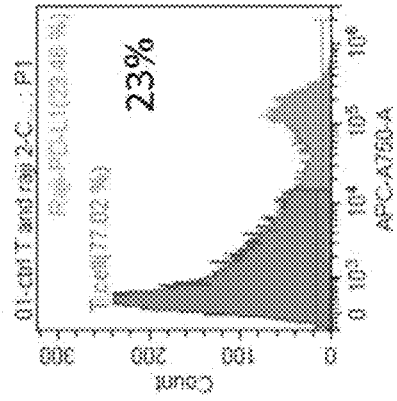
FIG. 44L CD19CAR-T Cell with PD-1 sgRNAs ctrl sgRNA PD1 sgRNA ctrl sgRNA PD1 sgRNA ctrl sgRNA PD1 sgRNA ctrl sgRNA PD1 sgRNA CD19CAR-T Cell with
PD-1 sgRNAs CD19CAR-T Cell with
control sgRNAs Control T Cell CD19CAR-T Cell with
PD-1 sgRNAs CD19CAR-T Cell with
control sgRNAs Control T Cell Control T Cell CD19CAR-T Cell with control sgRNAs CD19CAR-T Cell with PD-1 sgRNAs Control T Cell CD19CAR-T Cell with control sgRNAs CD19CAR-T Cell with PD-1 sgRNAs ctrl sgRNA PD1 sgRNA ctrl sgRNA PD1 sgRNA ctrl sgRNA PD1 sgRNA ctrl sgRNA PD1 sgRNA

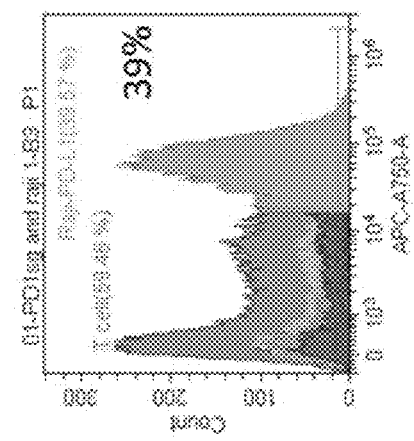
FIG. 48A Control T Cell
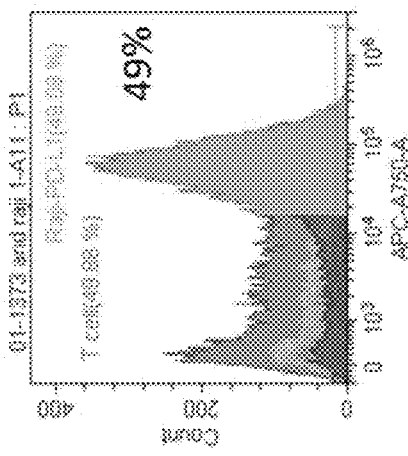
FIG. 48C CD19CAR-T Cell with control sgRNAs
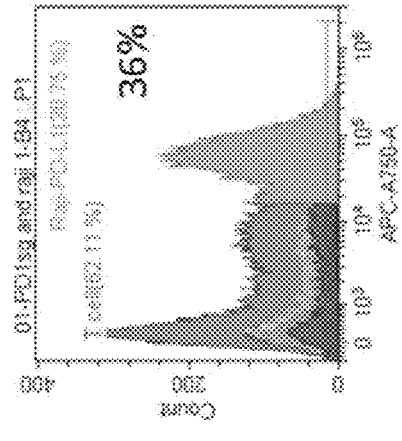
FIG. 48E CD19CAR-T Cell with PD-1 sgRNAs
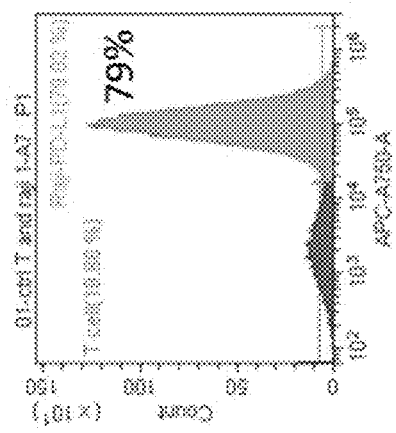
FIG. 48B Control T Cell
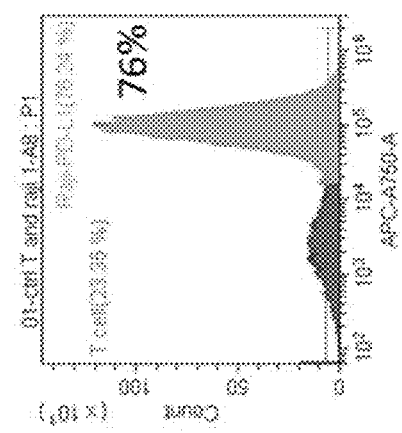
FIG. 48D CD19CAR-T Cell with control sgRNAs
FIG. 48F CD19CAR-T Cell with PD-1 sgRNAs Control T Cell CD19CAR-T Cell with control sgRNAs CD19CAR-T Cell with PD-1 sgRNAs Control T Cell CD19CAR-T Cell with control sgRNAs CD19CAR-T Cell with PD-1 sgRNAs

CHIMERIC PROTEINS AND METHODS OF IMMUNOTHERAPY

CROSS-REFERENCE

This application is a Divisional Application of U.S. patent application Ser. No. 16/029,299 filed Jul. 6, 2018, which is a continuation-in-part of International Application No. PCT/US17/12881 filed on Jan. 10, 2017, which claims the benefit of U.S. Provisional Application Nos. 62/277,322 filed on Jan. 11, 2016, 62/351,522 filed on Jun. 17, 2016, 62/399,902 filed on Sep. 26, 2016, 62/399,923 filed on Sep. 26, 2016, and 62/399,939 filed on Sep. 26, 2016, each of which is incorporated in its entirety herein by reference.

BACKGROUND

Regulation of cell activities can involve the binding of a ligand to a membrane-bound receptor comprising an extracellular ligand binding domain and an intracellular (e.g., cytoplasmic) signaling domain. The formation of a complex between a ligand and the ligand binding domain can result in a conformational and/or chemical modification in the receptor which can result in a signal transduced within the cell. In some situations, the cytoplasmic portion of the receptor is phosphorylated (e.g., trans- and/or auto-phosphorylated), resulting in a change in its activity. These events can be coupled with secondary messengers and/or the recruitment of co-factor proteins. In some instances, the change in the cytoplasmic portion results in binding to other proteins (e.g., co-factor proteins and/or other receptors). These other proteins can be activated and then carry out various functions within a cell.

Attachment of an extracellular domain (e.g., a ligand binding domain) of one protein to an intracellular domain of another protein involved in signal transduction (e.g., a signaling domain) creates a molecule (e.g., a chimeric receptor) that combines the antigen recognition of the former to the signal transduction of the latter. Such chimeric molecules (e.g., chimeric receptors or chimeric antigen receptors) can be useful for various purposes, for example for regulating immune cells in immunotherapy. Immunotherapy can involve modifying a patient's own immune cells to express a chimeric receptor in which arbitrary ligand specificity is grafted onto an immune cell signaling domain. The immune cell signaling domain can be involved in activating and/or de-activating an immune cell to respond to a disease such as cancer.

Conventional methods of immunotherapy suffer from various deficiencies. Such deficiencies include insufficient signaling from co-stimulatory receptors for persistent and/or adequate immune responses for therapeutic effects, inadequate specificity of modified immune cells for diseased cells such as cancer cells (e.g., on-target off-tumor effects and toxicities), and side-effects such as cytokine-release syndrome (CRS). Signaling in immune cells can involve various receptors, including co-stimulatory receptors. Insufficient signals from co-stimulatory receptors may result in decreased immune cell responses and reduced effectiveness of immunotherapy. Off-target effects and side-effects such as cytokine-release syndrome can result in further medical complications including inflammatory responses, organ failure, and, in extreme cases, death.

SUMMARY

In view of the foregoing, there exists a considerable need for alternative compositions and methods to carry out immunotherapy. The compositions and methods of the present disclosure address this need, and provide additional advantages as well. In particular, the various aspects of the disclosure provide systems for immune cell regulation.

In an aspect, the present disclosure provides a system for conditional regulation of an immune cell. The system comprises (a) a chimeric transmembrane receptor polypeptide comprising (i) an extracellular region comprising an antigen interacting domain that binds an antigen and (ii) an intracellular region comprising an immune cell signaling domain; (b) a chimeric adaptor polypeptide comprising a receptor binding moiety that binds the receptor polypeptide when the receptor polypeptide has undergone a receptor modification upon binding to an antigen; (c) an gene modulating polypeptide (GMP) comprising an actuator moiety linked to a cleavage recognition site; and (d) cleavage moiety that cleaves the cleavage recognition site when in proximity to the cleavage recognition site to release the actuator moiety from the GMP; wherein: (i) the cleavage moiety forms a portion of the intracellular region of the receptor polypeptide, and the GMP forms a portion of the chimeric adaptor polypeptide; (ii) the cleavage moiety is complexed with a second adaptor polypeptide that binds the receptor polypeptide that has undergone the receptor modification upon binding to an antigen, and the GMP forms a portion of the chimeric adaptor polypeptide; or (iii) the cleavage moiety forms a portion of the chimeric adaptor polypeptide, and the GMP forms a portion of the intracellular region of the receptor polypeptide. In some embodiments, the cleavage moiety forms a portion of the intracellular region of the receptor polypeptide, and the GMP forms a portion of the chimeric adaptor polypeptide. In some embodiments, the cleavage moiety is complexed with a second adaptor polypeptide that binds the receptor polypeptide that has undergone the receptor modification upon binding to an antigen, and the GMP forms a portion of the chimeric adaptor polypeptide. In some embodiments, the cleavage moiety forms a portion of the chimeric adaptor polypeptide, and the GMP forms a portion of the intracellular region of the receptor polypeptide.

In some embodiments, the immune cell is a lymphocyte. In some embodiments, the lymphocyte is a T cell. In some embodiments, the lymphocyte is a natural killer (NK) cell.

In some embodiments, the antigen interacting domain binds an antibody. In some embodiments, the antigen interacting domain binds at least one of an Fc domain, an Fv domain, a heavy chain, and a light chain of an antibody. In some embodiments, the antigen interacting domain binds an Fc domain of an antibody.

In some embodiments, the antigen interacting domain comprises at least one of a Fab, a single-chain Fv (scFv), an extracellular receptor domain, and an Fc binding domain. In some embodiments, the antigen interacting domain comprises an Fc binding domain comprising an Fc receptor or fragment thereof. In some embodiments, the antigen interacting domain comprises an Fc binding domain comprising FcγRI (CD64), FcγRIa, FcγRIb, FcγRIc, FcγRIIA (CD32), FcγRIIA (CD32, H131), FcγRIIA (CD32, R131), FcγRIIB (CD32), FcγRIIB-1, FcγRIIB-2, FcγRIIIA (CD16a, V158), FcγRIIIA (CD16a, F158), FcγRIIIB (CD16b, FcγRIIIb-NA1), FcγRIIIB (CD16b, FcγRIIIb-NA2), FcεRI, FcεRII (CD23), FcαRI (CD89), Fcα/μR, FcRn, any derivative thereof, any variant thereof, or any fragment thereof.

In some embodiments, the antigen interacting domain binds an antigen comprising an antibody, which in turn binds an antigen selected from the group consisting of: 1-40-β-amyloid, 4-1BB, 5AC, 5T4, activin receptor-like kinase 1, ACVR2B, adenocarcinoma antigen, AGS-22M6, alpha-fetoprotein, angiopoietin 2, angiopoietin 3, anthrax toxin, AOC3 (VAP-1), B7-H3, *Bacillus anthracis* anthrax, BAFF, beta-amyloid, B-lymphoma cell, C242 antigen, C5, CA-125, *Canis lupus familiaris* IL31, carbonic anhydrase 9 (CA-IX), cardiac myosin, CCL11 (eotaxin-1), CCR4, CCR5, CD11, CD18, CD125, CD140a, CD147 (basigin), CD15, CD152, CD154 (CD40L), CD19, CD2, CD20, CD200, CD22, CD221, CD23 (IgE receptor), CD25 (α chain of IL-2receptor), CD27, CD274, CD28, CD3, CD3 epsilon, CD30, CD33, CD37, CD38, CD4, CD40, CD40 ligand, CD41, CD44 v6, CD5, CD51, CD52, CD56, CD6, CD70, CD74, CD79B, CD80, CEA, CEA-related antigen, CFD, ch4D5, CLDN18.2, *Clostridium difficile*, clumping factor A, CSF1R, CSF2, CTLA-4, C—X—C chemokine receptor type 4, cytomegalovirus, cytomegalovirus glycoprotein B, dabigatran, DLL4, DPP4, DR5, *E. coli* shiga toxin type-1, *E. coli* shiga toxin type-2, EGFL7, EGFR, endotoxin, EpCAM, episialin, ERBB3, *Escherichia coli*, F protein of respiratory syncytial virus, FAP, fibrin II beta chain, fibronectin extra domain-B, folate hydrolase, folate receptor 1, folate receptor alpha, Frizzled receptor, ganglioside GD2, GD2, GD3 ganglioside, glypican 3, GMCSF receptor α-chain, GPNMB, growth differentiation factor 8, GUCY2C, hemagglutinin, hepatitis B surface antigen, hepatitis B virus, HER1, HER2/neu, HER3, HGF, HHGFR, histone complex, HIV-1, HLA-DR, HNGF, Hsp90, human scatter factor receptor kinase, human TNF, human beta-amyloid, ICAM-1 (CD54), IFN-α, IFN-γ, IgE, IgE Fc region, IGF-1 receptor, IGF-1, IGHE, IL 17A, IL 17F, IL 20, IL-12, IL-13, IL-17, IL-1β, IL-22, IL-23, IL-31RA, IL-4, IL-5, IL-6, IL-6 receptor, IL-9, ILGF2, influenza A hemagglutinin, influenza A virus hemagglutinin, insulin-like growth factor I receptor, integrin α4β7, integrin α4, integrin α5β1, integrin α7β7, integrin αIIbβ3, integrin αvβ3, interferon α/β receptor, interferon gamma-induced protein, ITGA2, ITGB2 (CD18), KIR2D, Lewis-Y antigen, LFA-1 (CD11a), LINGO-1, lipoteichoic acid, LOXL2, L-selectin (CD62L), LTA, MCP-1, mesothelin, MIF, MS4A1, MSLN, MUC1, mucin CanAg, myelin-associated glycoprotein, myostatin, NCA-90 (granulocyte antigen), neural apoptosis-regulated proteinase 1, NGF, N-glycolylneuraminic acid, NOGO-A, Notch receptor, NRP1, *Oryctolagus cuniculus*, OX-40, oxLDL, PCSK9, PD-1, PDCD1, PDGF-R α, phosphate-sodium co-transporter, phosphatidylserine, platelet-derived growth factor receptor beta, prostatic carcinoma cells, *Pseudomonas aeruginosa*, rabies virus glycoprotein, RANKL, respiratory syncytial virus, RHD, Rhesus factor, RON, RTN4, sclerostin, SDC1, selectin P, SLAMF7, SOST, sphingosine-1-phosphate, *Staphylococcus aureus*, STEAP1, TAG-72, T-cell receptor, TEM1, tenascin C, TFPI, TGF-β1, TGF-β2, TGF-β, TNF-α, TRAIL-R1, TRAIL-R2, tumor antigen CTAA16.88, tumor specific glycosylation of MUC1, tumor-associated calcium signal transducer 2, TWEAK receptor, TYRP1(glycoprotein 75), VEGFA, VEGFR1, VEGFR2, vimentin, and VWF.

In some embodiments, the antigen interacting domain binds an Fc domain of an antibody selected from the group consisting of: 20-(74)-(74) (milatuzumab; veltuzumab), 20-2b-2b, 3F8, 74-(20)-(20) (milatuzumab; veltuzumab), 8H9, A33, AB-16B5, abagovomab, abciximab, abituzumab, ABP 494 (cetuximab biosimilar), abrilumab, ABT-700, ABT-806, Actimab-A (actinium Ac-225 lintuzumab), actoxumab, adalimumab, ADC-1013, ADCT-301, ADCT-402, adecatumumab, aducanumab, afelimomab, AFM13, afutuzumab, AGEN1884, AGS15E, AGS-16C3F, AGS67E, alacizumab pegol, ALD518, alemtuzumab, alirocumab, altumomab pentetate, amatuximab, AMG 228, AMG 820, anatumomab mafenatox, anetumab ravtansine, anifrolumab, anrukinzumab, APN301, APN311, apolizumab, APX003/SIM-BD0801 (sevacizumab), APX005M, arcitumomab, ARX788, ascrinvacumab, aselizumab, ASG-15ME, atezolizumab, atinumab, ATL101, atlizumab (also referred to as tocilizumab), atorolimumab, Avelumab, B-701, bapineuzumab, basiliximab, bavituximab, BAY1129980, BAY1187982, bectumomab, begelomab, belimumab, benralizumab, bertilimumab, besilesomab, Betalutin (177Lu-tetraxetan-tetulomab), bevacizumab, BEVZ92 (bevacizumab biosimilar), bezlotoxumab, BGB-A317, BHQ880, BI 836880, BI-505, biciromab, bimagrumab, bimekizumab, bivatuzumab mertansine, BIW-8962, blinatumomab, blosozumab, BMS-936559, BMS-986012, BMS-986016, BMS-986148, BMS-986178, BNC101, bococizumab, brentuximab vedotin, BrevaRex, briakinumab, brodalumab, brolucizumab, brontictuzumab, C2-2b-2b, canakinumab, cantuzumab mertansine, cantuzumab ravtansine, caplacizumab, capromab pendetide, carlumab, catumaxomab, CBR96-doxorubicin immunoconjugate, CBT124 (bevacizumab), CC-90002, CDX-014, CDX-1401, cedelizumab, certolizumab pegol, cetuximab, CGEN-15001T, CGEN-15022, CGEN-15029, CGEN-15049, CGEN-15052, CGEN-15092, Ch.14.18, citatuzumab bogatox, cixutumumab, clazakizumab, clenoliximab, clivatuzumab tetraxetan, CM-24, codrituzumab, coltuximab ravtansine, conatumumab, concizumab, Cotara (iodine I-131 derlotuximab biotin), cR6261, crenezumab, DA-3111 (trastuzumab biosimilar), dacetuzumab, daclizumab, dalotuzumab, dapirolizumab pegol, daratumumab, Daratumumab Enhanze (daratumumab), Darleukin, dectrekumab, demcizumab, denintuzumab mafodotin, denosumab, Depatuxizumab, Depatuxizumab mafodotin, derlotuximab biotin, detumomab, DI-B4, dinutuximab, diridavumab, DKN-01, DMOT4039A, dorlimomab aritox, drozitumab, DS-1123, DS-8895, duligotumab, dupilumab, durvalumab, dusigitumab, ecromeximab, eculizumab, edobacomab, edrecolomab, efalizumab, efungumab, eldelumab, elgemtumab, elotuzumab, elsilimomab, emactuzumab, emibetuzumab, enavatuzumab, enfortumab vedotin, enlimomab pegol, enoblituzumab, enokizumab, enoticumab, ensituximab, epitumomab cituxetan, epratuzumab, erlizumab, ertumaxomab, etaracizumab, etrolizumab, evinacumab, evolocumab, exbivirumab, fanolesomab, faralimomab, farletuzumab, fasinumab, FBTA05, felvizumab, fezakinumab, FF-21101, FGFR2 Antibody-Drug Conjugate, Fibromun, ficlatuzumab, figitumumab, firivumab, flanvotumab, fletikumab, fontolizumab, foralumab, foravirumab, FPA144, fresolimumab, FS102, fulranumab, futuximab, galiximab, ganitumab, gantenerumab, gavilimomab, gemtuzumab ozogamicin, Gerilimzumab, gevokizumab, girentuximab, glembatumumab vedotin, GNR-006, GNR-011, golimumab, gomiliximab, GSK2849330, GSK2857916, GSK3174998, GSK3359609, guselkumab, Hu14.18K322A MAb, hu3S193, Hu8F4, HuL2G7, HuMab-5B1, ibalizumab, ibritumomab tiuxetan, icrucumab, idarucizumab, IGN002, IGN523, igovomab, IMAB362, IMAB362 (claudiximab), imalumab, IMC-CS4, IMC-D11, imciromab, imgatuzumab, IMGN529, IMMU-102 (yttrium Y-90 epratuzumab tetraxetan), IMMU-114, ImmuTune IMP701 Antagonist Antibody, INCAGN1876, inclacumab, INCSHR1210, indatuximab ravtansine, indusatumab vedotin, infliximab, inolimomab, inotuzumab ozogamicin, intetumumab, Ipafricept, IPH4102, ipilimumab, iratumumab, isatuximab, Istiratumab, itolizumab, ixekizumab, JNJ-56022473, JNJ-61610588, keliximab, KTN3379, L19IL2/L19TNF, Labetuzumab, Labetuzumab Govitecan, LAG525, lambrolizumab, lampalizumab, L-DOS47, lebrikizumab, lemalesomab, lenzilumab, lerdelimumab, Leukotuximab, lexatumumab, libivirumab, lifastuzumab vedotin, ligelizumab, lilotomab satetraxetan, lintuzumab, lirilumab, LKZ145, lodelcizumab, lokivetmab, lorvotuzumab mertansine, lucatumumab, lulizumab pegol, lumiliximab, lumretuzumab, LY3164530, mapatumumab, margetuximab, maslimomab, matuzumab, mavrilimumab, MB311, MCS-110, MEDI0562, MEDI-0639, MEDI0680, MEDI-3617, MEDI-551 (inebilizumab), MEDI-565, MEDI6469, mepolizumab, metelimumab, MGB453, MGD006/580880, MGD007, MGD009, MGD011, milatuzumab, Milatuzumab-SN-38, minretumomab, mirvetuximab soravtansine, mitumomab, MK-4166, MM-111, MM-151, MM-302, mogamulizumab, MOR202, MOR208, MORAb-066, morolimumab, motavizumab, moxetumomab pasudotox, muromonab-CD3, nacolomab tafenatox, namilumab, naptumomab estafenatox, narnatumab, natalizumab, nebacumab, necitumumab, nemolizumab, nerelimomab, nesvacumab, nimotuzumab, nivolumab, nofetumomab merpentan, NOV-10, obiltoxaximab, obinutuzumab, ocaratuzumab, ocrelizumab, odulimomab, ofatumumab, olaratumab, olokizumab, omalizumab, OMP-131R10, OMP-305B83, onartuzumab, ontuxizumab, opicinumab, oportuzumab monatox, oregovomab, orticumab, otelixizumab, otlertuzumab, OX002/MEN1309, oxelumab, ozanezumab, ozoralizumab, pagibaximab, palivizumab, panitumumab, pankomab, PankoMab-GEX, panobacumab, parsatuzumab, pascolizumab, pasotuxizumab, pateclizumab, patritumab, PAT-SC1, PAT-SM6, pembrolizumab, pemtumomab, perakizumab, pertuzumab, pexelizumab, PF-05082566 (utomilumab), PF-06647263, PF-06671008, PF-06801591, pidilizumab, pinatuzumab vedotin, pintumomab, placulumab, polatuzumab vedotin, ponezumab, priliximab, pritoxaximab, pritumumab, PRO 140, Proxinium, PSMA ADC, quilizumab, racotumomab, radretumab, rafivirumab, ralpancizumab, ramucirumab, ranibizumab, raxibacumab, refanezumab, regavirumab, REGN1400, REGN2810/SAR439684, reslizumab, RFM-203, RG7356, RG7386, RG7802, RG7813, RG7841, RG7876, RG7888, RG7986, rilotumumab, rinucumab, rituximab, RM-1929, R07009789, robatumumab, roledumab, romosozumab, rontalizumab, rovelizumab, ruplizumab, sacituzumab govitecan, samalizumab, SAR408701, SAR566658, sarilumab, SAT 012, satumomab pendetide, SCT200, SCT400, SEA-CD40, secukinumab, seribantumab, setoxaximab, sevirumab, SGN-CD19A, SGN-CD19B, SGN-CD33A, SGN-CD70A, SGN-LIV1A, sibrotuzumab, sifalimumab, siltuximab, simtuzumab, siplizumab, sirukumab, sofituzumab vedotin, solanezumab, solitomab, sonepcizumab, sontuzumab, stamulumab, sulesomab, suvizumab, SYD985, SYM004 (futuximab and modotuximab), Sym015, TAB08, tabalumab, tacatuzumab tetraxetan, tadocizumab, talizumab, tanezumab, Tanibirumab, taplitumomab paptox, tarextumab, TB-403, tefibazumab, Teleukin, telimomab aritox, tenatumomab, teneliximab, teplizumab, teprotumumab, tesidolumab, tetulomab, TG-1303, TGN1412, Thorium-227-Epratuzumab Conjugate, ticilimumab, tigatuzumab, tildrakizumab, Tisotumab vedotin, TNX-650, tocilizumab, toralizumab, tosatoxumab, tositumomab, tovetumab, tralokinumab, trastuzumab, trastuzumab emtansine, TRBS07, TRC105, tregalizumab, tremelimumab, trevogrumab, TRPH 011, TRX518, TSR-042, TTI-200.7, tucotuzumab celmoleukin, tuvirumab, U3-1565, U3-1784, ublituximab, ulocuplumab, urelumab, urtoxazumab, ustekinumab, Vadastuximab Talirine, vandortuzumab vedotin, vantictumab, vanucizumab, vapaliximab, varlilumab, vatelizumab, VB6-845, vedolizumab, veltuzumab, vepalimomab, vesencumab, visilizumab, volociximab, vorsetuzumab mafodotin, votumumab, YYB-101, zalutumumab, zanolimumab, zatuximab, ziralimumab, and zolimomab aritox.

In some embodiments, the extracellular region comprises multiple antigen interacting domains, each of which exhibits binding to the same or different antigen. In some embodiments, the antigen interacting domain binds an antigen selected from the group consisting of: 707-AP, a biotinylated molecule, a-Actinin-4, abl-bcr alb-b3 (b2a2), abl-bcr alb-b4 (b3a2), adipophilin, AFP, AIM-2, Annexin II, ART-4, BAGE, b-Catenin, bcr-abl, bcr-abl p190 (e1a2), bcr-abl p210 (b2a2), bcr-abl p210 (b3a2), BING-4, CAG-3, CAIX, CAMEL, Caspase-8, CD171, CD19, CD20, CD22, CD23, CD24, CD30, CD33, CD38, CD44v7/8, CDC27, CDK-4, CEA, CLCA2, Cyp-B, DAM-10, DAM-6, DEK-CAN, EGFRvIII, EGP-2, EGP-40, ELF2, Ep-CAM, EphA2, EphA3, erb-B2, erb-B3, erb-B4, ES-ESO-1a, ETV6/AML, FBP, fetal acetylcholine receptor, FGF-5, FN, G250, GAGE-1, GAGE-2, GAGE-3, GAGE-4, GAGE-5, GAGE-6, GAGE-7B, GAGE-8, GD2, GD3, GnT-V, Gp100, gp75, Her-2, HLA-A*0201-R170I, HMW-MAA, HSP70-2 M, HST-2 (FGF6), HST-2/neu, hTERT, iCE, IL-11Rα, IL-13Rα2, KDR, KIAA0205, K-RAS, L1-cell adhesion molecule, LAGE-1, LDLR/FUT, Lewis Y, MAGE-1, MAGE-10, MAGE-12, MAGE-2, MAGE-3, MAGE-4, MAGE-6, MAGE-A1, MAGE-A2, MAGE-A3, MAGE-A6, MAGE-B1, MAGE-B2, Malic enzyme, Mammaglobin-A, MART-1/Melan-A, MART-2, MC1R, M-CSF, mesothelin, MUC1, MUC16, MUC2, MUM-1, MUM-2, MUM-3, Myosin, NA88-A, Neo-PAP, NKG2D, NPM/ALK, N-RAS, NY-ESO-1, OA1, OGT, oncofetal antigen (h5T4), OS-9, P polypeptide, P15, P53, PRAME, PSA, PSCA, PSMA, PTPRK, RAGE, ROR1, RU1, RU2, SART-1, SART-2, SART-3, SOX10, SSX-2, Survivin, Survivin-2B, SYT/SSX, TAG-72, TEL/AML1, TGFaRII, TGFbRII, TP1, TRAG-3, TRG, TRP-1, TRP-2, TRP-2/INT2, TRP-2-6b, Tyrosinase, VEGF-R2, WT1, α-folate receptor, and κ-light chain.

In some embodiments, the immune cell signaling domain of the receptor polypeptide comprises a primary signaling domain comprising an immunoreceptor tyrosine-based activation motif (ITAM). In some embodiments, the immune cell signaling domain of the receptor polypeptide comprises a primary signaling domain comprising an immunoreceptor tyrosine-based inhibition motif (ITIM). In some embodiments, the immune cell signaling domain comprises a primary signaling domain of a protein selected from the group consisting of: an Fcγ receptor (FcγR), an FCC receptor (FcεR), an Fcα receptor (FcαR), neonatal Fc receptor (FcRn), CD3, CD3 ζ, CD3 γ, CD3 δ, CD3 ε, CD4, CD5, CD8, CD21, CD22, CD28, CD32, CD40L (CD154), CD45, CD66d, CD79a, CD79b, CD80, CD86, CD278 (also known as ICOS), CD247 ζ, CD247 η, DAP10, DAP12, FYN, LAT, Lck, MAPK, MEW complex, NFAT, NF-κB, PLC-γ, iC3b, C3dg, C3d, and Zap70. In some embodiments, the primary signaling domain comprises a CD3 ζ signaling domain. In some embodiments, the primary signaling domain comprises an immunoreceptor tyrosine-based activation motif (ITAM) of CD3 ζ. In some embodiments, the primary signaling domain comprises a signaling domain of an FcγR. In some embodiments, the primary signaling domain comprises a signaling domain of an FcγR selected from FcγRI (CD64), FcγRIIA (CD32), FcγRIIB (CD32), FcγRIIIA (CD16a), and FcγRIIIB (CD16b). In some embodiments, the primary signaling domain comprises a signaling domain of an FcεR. In some embodiments, the primary signaling domain comprises a signaling domain of an FcεR selected from FcɛRI and FcɛRII (CD23). In some embodiments, the primary signaling domain comprises a signaling domain of an FcαR. In some embodiments, the primary signaling domain comprises a signaling domain of an FcαR selected from FcαRI (CD89) and Fcα/μR.

In some embodiments, the immune cell signaling domain comprises a co-stimulatory domain. In some embodiments, the immune cell signaling domain comprises multiple co-stimulatory domains. In some embodiments, the co-stimulatory domain comprises a signaling domain of a MEW class I molecule, a TNF receptor protein, an immunoglobulin-like protein, a cytokine receptor, an integrin, a signaling lymphocytic activation molecule (SLAM protein), an activating NK cell receptor, or a Toll ligand receptor. In some embodiments, the co-stimulatory domain comprises a signaling domain of a molecule selected from the group consisting of: 2B4/CD244/SLAMF4, 4-1BB/TNFSF9/CD137, B7-1/CD80, B7-2/CD86, B7-H1/PD-L1, B7-H2, B7-H3, B7-H4, B7-H6, B7-H7, BAFF R/TNFRSF13C, BAFF/BLyS/TNFSF13B, BLAME/SLAMF8, BTLA/CD272, CD100 (SEMA4D), CD103, CD11a, CD11b, CD11c, CD11d, CD150, CD160 (BY55), CD18, CD19, CD2, CD200, CD229/SLAMF3, CD27 Ligand/TNFSF7, CD27/TNFRSF7, CD28, CD29, CD2F-10/SLAMF9, CD30 Ligand/TNFSF8, CD30/TNFRSF8, CD300a/LMIR1, CD4, CD40 Ligand/TNFSF5, CD40/TNFRSF5, CD48/SLAMF2, CD49a, CD49D, CD49f, CD53, CD58/LFA-3, CD69, CD7, CD8a, CD8 (3, CD82/Kai-1, CD84/SLAMF5, CD90/Thy1, CD96, CDS, CEACAM1, CRACC/SLAMF7, CRTAM, CTLA-4, DAP12, Dectin-1/CLEC7A, DNAM1 (CD226), DPPIV/CD26, DR3/TNFRSF25, EphB6, GADS, Gi24/VISTA/B7-H5, GITR Ligand/TNFSF18, GITR/TNFRSF18, HLA Class I, HLA-DR, HVEM/TNFRSF14, IA4, ICAM-1, ICOS/CD278, Ikaros, IL2R β, IL2R γ, IL7R α, Integrin α4/CD49d, Integrin α4β1, Integrin α4β7/LPAM-1, IPO-3, ITGA4, ITGA6, ITGAD, ITGAE, ITGAL, ITGAM, ITGAX, ITGB1, ITGB2, ITGB7, KIRDS2, LAG-3, LAT, LIGHT/TNFSF14, LTBR, Ly108, Ly9 (CD229), lymphocyte function associated antigen-1 (LFA-1), Lymphotoxin-α/TNF-β, NKG2C, NKG2D, NKp30, NKp44, NKp46, NKp80 (KLRF1), NTB-A/SLAMF6, OX40 Ligand/TNFSF4, OX40/TNFRSF4, PAG/Cbp, PD-1, PDCD6, PD-L2/B7-DC, PSGL1, RELT/TNFRSF19L, SELPLG (CD162), SLAM (SLAMF1), SLAM/CD150, SLAMF4 (CD244), SLAMF6 (NTB-A), SLAMF7, SLP-76, TACI/TNFRSF13B, TCL1A, TCL1B, TIM-1/KIM-1/HAVCR, TIM-4, TL1A/TNFSF15, TNF RII/TNFRSF1B, TNF-α, TRANCE/RANKL, TSLP, TSLP R, VLA1, and VLA-6. In some embodiments, the co-stimulatory domain is operable to regulate a proliferative signal and/or survival signal in the immune cell.

In some embodiments, the receptor comprises at least one targeting peptide which directs transport of the receptor polypeptide to a specific region of a cell. In some embodiments, the targeting peptide directs transport of the receptor polypeptide to a nucleus, mitochondria, endoplasmic reticulum (ER), chloroplast, peroxisome or plasma membrane. In some embodiments, the targeting peptide comprises a nuclear export signal (NES). In some embodiments, the targeting peptide comprises a plasma membrane targeting peptide.

In some embodiments, the receptor modification comprises a chemical modification. In some embodiments, the chemical modification comprises phosphorylation.

In some embodiments, the receptor binding moiety of the chimeric adaptor polypeptide comprises a binding domain of a molecule selected from the group consisting of: ABL1, ABL2, APBA1, APBA2, APBA3, BCAR3, BLK, BLNK, BMX, BTK, CHN2, CISH, CRK, CRKL, CSK, DAPP1, DOK1, DOK2, DOK3, DOK4, DOK5, DOK6, DOK7, EAT-2, EPS8, EPS8L1, EPS8L2, EPS8L3, FER, FES, FGR, FRK, FRS2, FRS3, FYN, GADS, GRAP, GRAP2, GRB10, GRB14, GRB2, GRB7, HCK, HSH2D, INPP5D, INPPL1, IRS1, IRS2, IRS3, IRS4, ITK, JAK2, LAT, LCK, LCP2, LYN, MATK, NCK1, NCK2, PIK3P, PIK3R1, PIK3R2, PIK3R3, PLCG1, PLCG2, PTK6, PTPN11, PTPN6, RASA1, SAP, SH2B1, SH2B2, SH2B3, SH2D1A, SH2D1B, SH2D2A, SH2D3A, SH2D3C, SH2D4A, SH2D4B, SH2D5, SH2D6, SH3BP2, SHB, SHC1, SHC2, SHC3, SHC4, SHD, SHE, SHP1, SHP2, SLA, SLA2, SOCS1, SOCS2, SOCS3, SOCS4, SOCS5, SOCS6, SOCS7, SRC, SRMS, STAT1, STAT2, STAT3, STAT4, STAT5A, STAT5B, STATE, SUPT6H, SYK, TEC, TENC1, TLN1, TLN2, TNS, TNS1, TNS3, TNS4, TXK, VAV1, VAV2, VAV3, YES1, ZAP70, X11a, any derivative thereof, any variant thereof, and fragment thereof.

In some embodiments, the actuator moiety comprises a CRISPR-associated polypeptide (Cas), zinc finger nuclease (ZFN), zinc finger associate gene regulation polypeptides, transcription activator-like effector nuclease (TALEN), transcription activator-like effector associated gene regulation polypeptides, meganuclease, natural master transcription factors, epigenetic modifying enzymes, recombinase, flippase, transposase, RNA-binding proteins (RBP), an Argonaute protein, any derivative thereof, any variant thereof, or any fragment thereof. In some embodiments, the actuator moiety comprises a Cas protein, and the system further comprises a guide RNA (gRNA) which complexes with the Cas protein. In some embodiments, the actuator moiety comprises an RBP complexed with a gRNA which is able to form a complex with a Cas protein. In some embodiments, the gRNA comprises a targeting segment which exhibits at least 80% sequence identity to a target polynucleotide. In some embodiments, the Cas protein substantially lacks DNA cleavage activity.

In some embodiments, the actuator moiety comprises at least one targeting peptide which directs the actuator moiety to a specific region of a cell. In some embodiments, the targeting peptide comprises a nuclear localization signal (NLS).

In some embodiments, the receptor modification comprises modification at multiple modification sites, and each modification site is effective to bind a chimeric adaptor polypeptide and/or a second adaptor polypeptide.

In some embodiments, the cleavage recognition site comprises a polypeptide sequence, and the cleavage moiety comprises protease activity.

In some embodiments, the actuator moiety, upon release from the GMP, binds to a target polynucleotide to regulate gene expression from the target polynucleotide by physical obstruction of the target polynucleotide or recruitment of additional factors effective to suppress or enhance gene expression from the target polynucleotide. In some embodiments, the actuator moiety comprises a transcriptional activator effective to increase gene expression from a target polynucleotide. In some embodiments, the actuator moiety comprises a transcriptional repressor effective to decrease gene expression from a target polynucleotide.

In some embodiments, the target polynucleotide comprises genomic DNA. In some embodiments, the target polynucleotide comprises RNA. In some embodiments, the target polynucleotide comprises an endogenous gene or endogenous gene product. In some embodiments, the endogenous gene or endogenous gene product encodes for a cytokine. In some embodiments, the cytokine is selected from the group consisting of: 4-1BBL, activin βA, activin βB, activin βC, activin βE, artemin (ARTN), BAFF/BLyS/TNFSF138, BMP10, BMP15, BMP2, BMP3, BMP4, BMP5, BMP6, BMP7, BMP8a, BMP8b, bone morphogenetic protein 1 (BMP1), CCL1/TCA3, CCL11, CCL12/MCP-5, CCL13/MCP-4, CCL14, CCL15, CCL16, CCL17/TARC, CCL18, CCL19, CCL2/MCP-1, CCL20, CCL21, CCL22/MDC, CCL23, CCL24, CCL25, CCL26, CCL27, CCL28, CCL3, CCL3L3, CCL4, CCL4L1/LAG-1, CCL5, CCL6, CCL7, CCL8, CCL9, CD153/CD30L/TNFSF8, CD40L/CD154/TNFSF5, CD40LG, CD70, CD70/CD27L/TNFSF7, CLCF1, c-MPL/CD110/TPOR, CNTF, CX3CL1, CXCL1, CXCL10, CXCL11, CXCL12, CXCL13, CXCL14, CXCL15, CXCL16, CXCL17, CXCL2/MIP-2, CXCL3, CXCL4, CXCL5, CXCL6, CXCL7/Ppbp, CXCL9, EDA-A1, FAM19A1, FAM19A2, FAM19A3, FAM19A4, FAM19A5, Fas Ligand/FASLG/CD95L/CD178, GDF10, GDF11, GDF15, GDF2, GDF3, GDF4, GDF5, GDF6, GDF7, GDF8, GDF9, glial cell line-derived neurotrophic factor (GDNF), growth differentiation factor 1 (GDF1), IFNA1, IFNA10, IFNA13, IFNA14, IFNA2, IFNA4, IFNA5/IFNaG, IFNA7, IFNA8, IFNB1, IFNE, IFNG, IFNZ, IFNω/IFNW1, IL11, IL18, IL18BP, IL1A, IL1B, IL1F10, IL1F3/IL1RA, IL1F5, IL1F6, IL1F7, IL1F8, IL1F9, IL1RL2, IL31, IL33, IL6, IL8/CXCL8, inhibin-A, inhibin-B, Leptin, LIF, LTA/TNFB/TNFSF1, LTB/TNFC, neurturin (NRTN), OSM, OX-40L/TNFSF4/CD252, persephin (PSPN), RANKL/OPGL/TNFSF11(CD254), TL1A/TNFSF15, TNFA, TNF-alpha/TNFA, TNFSF10/TRAIL/APO-2L(CD253), TNFSF12, TNFSF13, TNFSF14/LIGHT/CD258, XCL1, and XCL2. In some embodiments, the endogenous gene or endogenous gene product encodes for an immune regulatory protein. In some embodiments, the immune regulatory protein is selected from the group consisting of: A2AR, B7.1, B7-H3/CD276, B7-H4/B7S1/B7x/Vtcn1, B7-H6, BTLA/CD272, CCR4, CD122, 4-1BB/CD137, CD27, CD28, CD40, CD47, CD70, CISH, CTLA-4/CD152, DR3, GITR, ICOS/CD278, IDO, KIR, LAG-3, OX40/CD134, PD-1/CD279, PD2, PD-L1, PD-L2, TIM-3, and VISTA/Dies1/Gi24/PD-1H (C10orf54). In some embodiments, the target polynucleotide comprises a heterologous gene or heterologous gene product. In some embodiments, the heterologous gene or heterologous gene product encodes for an additional chimeric transmembrane receptor polypeptide. In some embodiments, the additional chimeric transmembrane receptor polypeptide comprises: (a) an extracellular region comprising an additional antigen interacting domain that binds an additional antigen; and (b) a co-stimulatory domain. In some embodiments, the additional antigen interacting domain binds an antigen selected from the group consisting of: 707-AP, a biotinylated molecule, a-Actinin-4, abl-bcr alb-b3 (b2a2), abl-bcr alb-b4 (b3a2), adipophilin, AFP, AIM-2, Annexin II, ART-4, BAGE, b-Catenin, bcr-abl, bcr-abl p190 (e1a2), bcr-abl p210 (b2a2), bcr-abl p210 (b3a2), BING-4, CAG-3, CAIX, CAMEL, Caspase-8, CD171, CD19, CD20, CD22, CD23, CD24, CD30, CD33, CD38, CD44v7/8, CDC27, CDK-4, CEA, CLCA2, Cyp-B, DAM-10, DAM-6, DEK-CAN, EGFRvIII, EGP-2, EGP-40, ELF2, Ep-CAM, EphA2, EphA3, erb-B2, erb-B3, erb-B4, ES-ESO-1a, ETV6/AML, FBP, fetal acetylcholine receptor, FGF-5, FN, G250, GAGE-1, GAGE-2, GAGE-3, GAGE-4, GAGE-5, GAGE-6, GAGE-7B, GAGE-8, GD2, GD3, GnT-V, Gp100, gp75, Her-2, HLA-A*0201-R170I, HMW-MAA, HSP70-2 M, HST-2 (FGF6), HST-2/neu, hTERT, iCE, IL-11Rα, IL-13Rα2, KDR, KIAA0205, K-RAS, L1-cell adhesion molecule, LAGE-1, LDLR/FUT, Lewis Y, MAGE-1, MAGE-10, MAGE-12, MAGE-2, MAGE-3, MAGE-4, MAGE-6, MAGE-A1, MAGE-A2, MAGE-A3, MAGE-A6, MAGE-B1, MAGE-B2, Malic enzyme, Mammaglobin-A, MART-1/Melan-A, MART-2, MC1R, M-CSF, mesothelin, MUC1, MUC16, MUC2, MUM-1, MUM-2, MUM-3, Myosin, NA88-A, Neo-PAP, NKG2D, NPM/ALK, N-RAS, NY-ESO-1, OA1, OGT, oncofetal antigen (h5T4), OS-9, P polypeptide, P15, P53, PRAME, PSA, PSCA, PSMA, PTPRK, RAGE, ROR1, RU1, RU2, SART-1, SART-2, SART-3, SOX10, SSX-2, Survivin, Survivin-2B, SYT/SSX, TAG-72, TEL/AML1, TGFaRII, TGFbRII, TP1, TRAG-3, TRG, TRP-1, TRP-2, TRP-2/INT2, TRP-2-6b, Tyrosinase, VEGF-R2, WT1, α-folate receptor, and κ-light chain. In some embodiments, the co-stimulatory domain comprises a signaling domain of a molecule selected from the group consisting of: 2B4/CD244/SLAMF4, 4-1BB/TNFSF9/CD137, B7-1/CD80, B7-2/CD86, B7-H1/PD-L1, B7-H2, B7-H3, B7-H4, B7-H6, B7-H7, BAFF R/TNFRSF13C, BAFF/BLyS/TNFSF13B, BLAME/SLAMF8, BTLA/CD272, CD100 (SEMA4D), CD103, CD11a, CD11b, CD11c, CD11d, CD150, CD160 (BY55), CD18, CD19, CD2, CD200, CD229/SLAMF3, CD27 Ligand/TNFSF7, CD27/TNFRSF7, CD28, CD29, CD2F-10/SLAMF9, CD30 Ligand/TNFSF8, CD30/TNFRSF8, CD300a/LMIR1, CD4, CD40 Ligand/TNFSF5, CD40/TNFRSF5, CD48/SLAMF2, CD49a, CD49D, CD49f, CD53, CD58/LFA-3, CD69, CD7, CD8 α, CD8 β, CD82/Kai-1, CD84/SLAMF5, CD90/Thy1, CD96, CDS, CEACAM1, CRACC/SLAMF7, CRTAM, CTLA-4, DAP12, Dectin-1/CLEC7A, DNAM1 (CD226), DPPIV/CD26, DR3/TNFRSF25, EphB6, GADS, Gi24/VISTA/B7-H5, GITR Ligand/TNFSF18, GITR/TNFRSF18, HLA Class I, HLA-DR, HVEM/TNFRSF14, IA4, ICAM-1, ICOS/CD278, Ikaros, IL2R β, IL2R γ, IL7R α, Integrin α4/CD49d, Integrin α4β1, Integrin α4β7/LPAM-1, IPO-3, ITGA4, ITGA6, ITGAD, ITGAE, ITGAL, ITGAM, ITGAX, ITGB1, ITGB2, ITGB7, KIRDS2, LAG-3, LAT, LIGHT/TNFSF14, LTBR, Ly108, Ly9 (CD229), lymphocyte function associated antigen-1 (LFA-1), Lymphotoxin-α/TNF-β, NKG2C, NKG2D, NKp30, NKp44, NKp46, NKp80 (KLRF1), NTB-A/SLAMF6, OX40 Ligand/TNFSF4, OX40/TNFRSF4, PAG/Cbp, PD-1, PDCD6, PD-L2/B7-DC, PSGL1, RELT/TNFRSF19L, SELPLG (CD162), SLAM (SLAMF1), SLAM/CD150, SLAMF4 (CD244), SLAMF6 (NTB-A), SLAMF7, SLP-76, TACI/TNFRSF13B, TCL1A, TCL1B, TIM-1/KIM-1/HAVCR, TIM-4, TL1A/TNFSF15, TNF RII/TNFRSF1B, TNF-α, TRANCE/RANKL, TSLP, TSLP R, VLA1, and VLA-6.

In an aspect, the present disclosure provides a lymphocyte expressing any system disclosed herein. In some embodiments, the lymphocyte is characterized in that the actuator moiety is released from the GMP by cleavage at the cleavage recognition site when the receptor polypeptide is bound to the antigen. In some embodiments, the released actuator moiety complexes with a target polynucleotide in the lymphocyte.

In some embodiments, complexing of the actuator moiety with the target polynucleotide results in up-regulated expression of a gene in the lymphocyte. In some embodiments, the gene is a heterologous gene. In some embodiments, the heterologous gene encodes for an additional chimeric transmembrane receptor polypeptide. In some embodiments, the additional chimeric transmembrane receptor polypeptide comprises: (a) an extracellular region comprising an additional antigen interacting domain that binds an additional antigen; and (b) a co-stimulatory domain. In some embodiments, the gene is an endogenous gene. In some embodiments, the endogenous gene encodes for a cytokine. In some embodiments, the cytokine is selected from the group consisting of: 4-1BBL, activin activin βB, activin βB, activin βC, artemin (ARTN), BAFF/BLyS/TNFSF138, BMP10, BMP15, BMP2, BMP3, BMP4, BMP5, BMP6, BMP7, BMP8a, BMP8b, bone morphogenetic protein 1 (BMP1), CCL1/TCA3, CCL11, CCL12/MCP-5, CCL13/MCP-4, CCL14, CCL15, CCL16, CCL17/TARC, CCL18, CCL19, CCL2/MCP-1, CCL20, CCL21, CCL22/MDC, CCL23, CCL24, CCL25, CCL26, CCL27, CCL28, CCL3, CCL3L3, CCL4, CCL4L1/LAG-1, CCL5, CCL6, CCL7, CCL8, CCL9, CD153/CD30L/TNFSF8, CD40L/CD154/TNFSF5, CD40LG, CD70, CD70/CD27L/TNFSF7, CLCF1, c-MPL/ CD110/TPOR, CNTF, CX3CL1, CXCL1, CXCL10, CXCL11, CXCL12, CXCL13, CXCL14, CXCL15, CXCL16, CXCL17, CXCL2/MIP-2, CXCL3, CXCL4, CXCL5, CXCL6, CXCL7/Ppbp, CXCL9, EDA-A1, FAM19A1, FAM19A2, FAM19A3, FAM19A4, FAM19A5, Fas Ligand/FASLG/CD95L/CD178, GDF10, GDF11, GDF15, GDF2, GDF3, GDF4, GDF5, GDF6, GDF7, GDF8, GDF9, glial cell line-derived neurotrophic factor (GDNF), growth differentiation factor 1 (GDF1), IFNA1, IFNA10, IFNA13, IFNA14, IFNA2, IFNA4, IFNA5/IFNaG, IFNA7, IFNA8, IFNB1, IFNE, IFNG, IFNZ, IFNω/IFNW1, IL11, IL18, IL18BP, IL1A, IL1B, IL1F10, IL1F3/IL1RA, IL1F5, IL1F6, IL1F7, IL1F8, IL1F9, IL1RL2, IL31, IL33, IL6, IL8/CXCL8, inhibin-A, inhibin-B, Leptin, LIF, LTA/TNFB/ TNFSF1, LTB/TNFC, neurturin (NRTN), OSM, OX-40L/ TNFSF4/CD252, persephin (PSPN), RANKL/OPGL/ TNFSF11(CD254), TL1A/TNFSF15, TNFA, TNF-alpha/ TNFA, TNFSF10/TRAIL/APO-2L(CD253), TNFSF12, TNFSF13, TNFSF14/LIGHT/CD258, XCL1, and XCL2

In some embodiments, complexing of the actuator moiety with a target polynucleotide down-regulates expression of a gene in the lymphocyte. In some embodiments, the gene is an endogenous gene. In some embodiments, the endogenous gene encodes for an immune regulatory protein. In some embodiments, the immune regulatory protein is selected from the group consisting of: A2AR, B7.1, B7-H3/CD276, B7-H4/B7S1/B7x/Vtcn1, B7-H6, BTLA/CD272, CCR4, CD122, 4-1BB/CD137, CD27, CD28, CD40, CD47, CD70, CISH, CTLA-4/CD152, DR3, GITR, ICOS/CD278, IDO, KIR, LAG-3, OX40/CD134, PD-1/CD279, PD2, PD-L1, PD-L2, TIM-3, and VISTA/Dies1/Gi24/PD-1H (C10orf54).

In an aspect, the present disclosure provides a population of lymphocytes expressing any system disclosed herein. In some embodiments, the population of lymphocytes is characterized in that the actuator moiety is released from the GMP by cleavage at the cleavage recognition site when the receptor polypeptide is bound to the antigen.

In an aspect, the present disclosure provides a method of inducing death of a target cell. The method comprises exposing a target cell to a lymphocyte expressing any system disclosed herein. In some embodiments, upon exposing the target cell to the lymphocyte, the receptor polypeptide expressed by the lymphocyte binds an antigen comprising a cell-surface antigen of the target cell or an antigen secreted by the target cell, wherein binding of the receptor polypeptide to the antigen activates cytotoxicity of the lymphocyte, thereby inducing death of the target cell. In some embodiments, the target cell is a cancer cell. In some embodiments, binding of the receptor polypeptide to the antigen activates cytotoxicity of the lymphocyte when the actuator moiety is released from the GMP.

In some embodiments, the actuator moiety regulates gene expression from a target polynucleotide by physical obstruction of the target polynucleotide or recruitment of additional factors effective to suppress or enhance gene expression from the target polynucleotide. In some embodiments, the actuator moiety comprises a transcriptional activator effective to increase gene expression from the target polynucleotide. In some embodiments, the actuator moiety comprises a transcriptional repressor effective to decrease gene expression from the target polynucleotide. In some embodiments, the target polynucleotide comprises genomic DNA. In some embodiments, the target polynucleotide comprises RNA.

In some embodiments, the receptor modification comprises phosphorylation. In some embodiments, the receptor modification comprises modification at multiple modification sites, and each modification is effective to bind a chimeric adaptor polypeptide.

In some embodiments, the actuator moiety comprises a CRISPR-associated polypeptide (Cas), zinc finger nuclease (ZFN), zinc finger associate gene regulation polypeptides, transcription activator-like effector nuclease (TALEN), transcription activator-like effector associated gene regulation polypeptides, meganuclease, natural master transcription factors, epigenetic modifying enzymes, recombinase, flippase, transposase, RNA-binding proteins (RBP), an Argonaute protein, any derivative, any variant thereof, or any fragment thereof. In some embodiments, the actuator moiety comprises a Cas protein that forms a complex with a guide RNA (gRNA). In some embodiments, the actuator moiety comprises a RBP complexed with a guide RNA (gRNA) which is able to form a complex with a Cas protein. In some embodiments, the Cas protein substantially lacks DNA cleavage activity.

In some embodiments, the cleavage recognition site comprises a polypeptide sequence and the cleavage moiety comprises protease activity.

In an aspect, the present disclosure provides a chimeric transmembrane receptor polypeptide. The chimeric transmembrane receptor polypeptide comprises (a) an extracellular region comprising an antigen interacting domain that binds an antigen; and (b) an intracellular region comprising: an immune cell signaling domain; and an gene modulating polypeptide (GMP) linked to the immune cell signaling domain, wherein the GMP comprises an actuator moiety linked to a peptide cleavage domain; wherein upon binding of the antigen to the extracellular region, the actuator moiety is released from the GMP by cleavage at the peptide cleavage domain.

In an aspect, the present disclosure provides a chimeric transmembrane receptor polypeptide. The chimeric transmembrane receptor polypeptide comprises (a) an extracellular region comprising an antigen interacting domain that binds an antigen; and (b) an intracellular region comprising: an immune cell signaling domain; and an actuator moiety linked to the immune cell signaling domain via a peptide cleavage domain; wherein upon binding of the antigen to the extracellular region, the actuator moiety is released from the receptor by cleavage at the peptide cleavage domain.

In an aspect, the present disclosure provides a method for conditional regulation of a lymphocyte. The method comprises contacting a lymphocyte expressing any system disclosed herein with an antigen that binds to the antigen interacting domain of the chimeric transmembrane receptor polypeptide, the contacting effects an activation or deactivation of an immune cell activity, thereby conditionally regulating the lymphocyte. In some embodiments, the immune cell activity is selected from the group consisting of: clonal expansion of the lymphocyte; cytokine release by the lymphocyte; cytotoxicity of the lymphocyte; proliferation of the lymphocyte; differentiation, dedifferentiation or transdifferentiation of the lymphocyte; movement and/or trafficking of the lymphocyte; exhaustion and/or reactivation of the lymphocyte; and release of other intercellular molecules, metabolites, chemical compounds, or combinations thereof by the lymphocyte. In some embodiments, upon binding of the antigen to the antigen interacting domain of the receptor polypeptide, the actuator moiety is released from the GMP to effect the activation or the deactivation.

In an aspect, the present disclosure provides a chimeric adaptor polypeptide. The chimeric adaptor polypeptide comprises (a) a receptor binding moiety that binds a receptor that has undergone a modification upon binding to an antigen, said receptor comprising an intracellular region comprising an immune cell signaling domain; and (b) a gene modulating polypeptide (GMP) linked to the receptor binding moiety, wherein the GMP comprises an actuator moiety linked to a cleavage recognition site; wherein upon binding of the receptor binding moiety to the receptor that has undergone a modification, the actuator moiety is released from the GMP by cleavage at the cleavage recognition site. In some embodiments, the receptor binding moiety comprises a binding domain of a molecule selected from the group consisting of: ABL1, ABL2, APBA1, APBA2, APBA3, BCAR3, BLK, BLNK, BMX, BTK, CHN2, CISH, CRK, CRKL, CSK, DAPP1, DOK1, DOK2, DOK3, DOK4, DOK5, DOK6, DOK7, EAT-2, EPS8, EPS8L1, EPS8L2, EPS8L3, FER, FES, FGR, FRK, FRS2, FRS3, FYN, GADS, GRAP, GRAP2, GRB10, GRB14, GRB2, GRB7, HCK, HSH2D, INPP5D, INPPL1, IRS1, IRS2, IRS3, IRS4, ITK, JAK2, LAT, LCK, LCP2, LYN, MATK, NCK1, NCK2, PIK3P, PIK3R1, PIK3R2, PIK3R3, PLCG1, PLCG2, PTK6, PTPN11, PTPN6, RASA1, SAP, SH2B1, SH2B2, SH2B3, SH2D1A, SH2D1B, SH2D2A, SH2D3A, SH2D3C, SH2D4A, SH2D4B, SH2D5, SH2D6, SH3BP2, SHB, SHC1, SHC2, SHC3, SHC4, SHD, SHE, SHP1, SHP2, SLA, SLA2, SOCS1, SOCS2, SOCS3, SOCS4, SOCS5, SOCS6, SOCS7, SRC, SRMS, STAT1, STAT2, STAT3, STAT4, STAT5A, STAT5B, STAT6, SUPT6H, SYK, TEC, TENC1, TLN1, TLN2, TNS, TNS1, TNS3, TNS4, TXK, VAV1, VAV2, VAV3, YES1, ZAP70, X11a, any derivative thereof, any variant thereof, and any fragment thereof.

In some embodiments, the chimeric adaptor polypeptide comprises at least one targeting peptide which directs transport of the chimeric adaptor polypeptide to a specific region of a cell. In some embodiments, the targeting peptide directs transport of the chimeric adaptor polypeptide to a nucleus, cytoplasm, mitochondria, endoplasmic reticulum (ER), chloroplast, apoplast, peroxisome or plasma membrane.

In some embodiments, the targeting peptide comprises a nuclear export signal (NES). In some embodiments, the NES is linked to the N-terminus of the chimeric adaptor polypeptide. In some embodiments, the targeting peptide comprises a plasma membrane targeting peptide.

In some embodiments, the targeting peptide is linked to the actuator moiety. In some embodiments, the targeting peptide comprises a nuclear localization signal (NLS). In some embodiments, the targeting peptide comprising an NLS is linked to the N-terminus or C-terminus of the actuator moiety. In some embodiments, the targeting peptide comprising an NLS linked to the actuator moiety directs transport of the actuator moiety to a nucleus of a cell following release of the actuator moiety from the GMP by cleavage at the cleavage recognition site.

In some embodiments, the actuator moiety comprises a CRISPR-associated polypeptide (Cas), zinc finger nuclease (ZFN), zinc finger associate gene regulation polypeptides, transcription activator-like effector nuclease (TALEN), transcription activator-like effector associated gene regulation polypeptides, meganuclease, natural master transcription factors, epigenetic modifying enzymes, recombinase, flippase, transposase, RNA-binding proteins (RBP), an Argonaute protein, any derivative thereof, any variant thereof, or any fragment thereof. In some embodiments, the actuator moiety comprises a Cas protein that forms a complex with a guide RNA (gRNA). In some embodiments, the actuator moiety comprises a RBP optionally complexed with a guide RNA which is able to form a complex with a Cas protein. In some embodiments, the Cas protein substantially lacks DNA cleavage activity.

In some embodiments, the actuator moiety regulates expression of a gene by physical obstruction of a target polynucleotide or recruitment of additional factors effective to suppress or enhance gene expression from the target polynucleotide. In some embodiments, the actuator moiety comprises a transcriptional activator effective to increase gene expression from a target polynucleotide. In some embodiments, the actuator moiety comprises a transcriptional repressor effective to decrease gene expression from a target polynucleotide.

In some embodiments, the cleavage recognition site is flanked by the receptor binding moiety and the actuator moiety. In some embodiments, the cleavage recognition site comprises a cleavage recognition sequence recognized by a protease. In some embodiments, the cleavage recognition site comprises multiple cleavage recognition sequences, each cleavage recognition sequence recognized by the same or different protease. In some embodiments, the cleavage recognition sequence is recognized by a protease selected from the group consisting of: achromopeptidase, aminopeptidase, ancrod, angiotensin converting enzyme, bromelain, calpain, calpain I, calpain II, carboxypeptidase A, carboxypeptidase B, carboxypeptidase G, carboxypeptidase P, carboxypeptidase W, carboxypeptidase Y, caspase 1, caspase 2, caspase 3, caspase 4, caspase 5, caspase 6, caspase 7, caspase 8, caspase 9, caspase 10, caspase 11, caspase 12, caspase 13, cathepsin B, cathepsin C, cathepsin D, cathepsin E, cathepsin G, cathepsin H, cathepsin L, chymopapain, chymase, chymotrypsin, clostripain, collagenase, complement C1r, complement C1s, complement Factor D, complement factor I, cucumisin, dipeptidyl peptidase IV, elastase (leukocyte), elastase (pancreatic), endoproteinase Arg-C, endoproteinase Asp-N, endoproteinase Glu-C, endoproteinase Lys-C, enterokinase, factor Xa, ficin, furin, granzyme A, granzyme B, HIV Protease, IGase, kallikrein tissue, leucine aminopeptidase (general), leucine aminopeptidase (cytosol), leucine aminopeptidase (microsomal), matrix metalloprotease, methionine aminopeptidase, neutrase, papain, pepsin, plasmin, prolidase, pronase E, prostate specific antigen, protease alkalophilic from *Streptomyces griseus*, protease from *Aspergillus*, protease from *Aspergillus saitoi*, protease from *Aspergillus sojae*, protease (*B. licheniformis*) (alkaline or alcalase), protease from *Bacillus polymyxa*, protease from *Bacillus* sp, protease from *Rhizopus* sp., protease S, proteasomes, proteinase from *Aspergillus oryzae*, proteinase 3, proteinase A, proteinase K, protein C, pyroglutamate aminopeptidase, rennin, rennin, streptokinase, subtilisin, thermolysin, thrombin, tissue plasminogen activator, trypsin, tryptase and urokinase.

In an aspect, the present disclosure provides a chimeric transmembrane receptor polypeptide. The chimeric transmembrane receptor polypeptide comprises (a) an extracellular region comprising an antigen interacting domain that binds an antigen; and (b) an intracellular region comprising: an immune cell signaling domain; and a gene modulating polypeptide (GMP) linked to the immune cell signaling domain, wherein the GMP comprises an actuator moiety linked to a cleavage recognition site; wherein upon binding of the antigen to the extracellular region, the actuator moiety is released from the GMP by cleavage at the cleavage recognition site.

In some embodiments, the antigen interacting domain binds a membrane-bound antigen. In some embodiments, the antigen interacting domain binds an antigen that is not membrane-bound. In some embodiments, the antigen interacting domain binds an antibody. In some embodiments, the antigen interacting domain binds at least one of an Fc domain, an Fv domain, a heavy chain, and a light chain of an antibody. In some embodiments, the antigen interacting domain binds an Fc domain of an antibody.

In some embodiments, the antigen interacting domain comprises at least one of a Fab, a single-chain Fv (scFv), an extracellular receptor domain, and an Fc binding domain. In some embodiments, the antigen interacting domain comprises an Fc binding domain comprising an Fc receptor or any fragment thereof. In some embodiments, the antigen interacting domain comprises an Fc binding domain comprising FcγRI (CD64), FcγRIa, FcγRIb, FcγRIc, FcγRIIA (CD32), FcγRIIA (CD32, H131), FcγRIIA (CD32, R131), FcγRIIB (CD32), FcγRIIB-2, FcγRIIIA (CD16a, V158), FcγRIIIA (CD16a, F158), FcγRIIIB (CD16b, FcγRIIIb-NA1), FcγRIIIB (CD16b, FcγRIIIb-NA2), FcεRI, FcεRII (CD23), FcαRI (CD89), Fcα/μR, FcRn, any derivative thereof, any variant thereof, or any fragment thereof. In some embodiments, the antigen interacting domain binds an antigen comprising an antibody, which in turn binds an antigen selected from the group consisting of: 1-40-β-amyloid, 4-1BB, SAC, 5T4, activin receptor-like kinase 1, ACVR2B, adenocarcinoma antigen, AGS-22M6, alpha-fetoprotein, angiopoietin 2, angiopoietin 3, anthrax toxin, AOC3 (VAP-1), B7-H3, *Bacillus anthracis* anthrax, BAFF, beta-amyloid, B-lymphoma cell, C242 antigen, C5, CA-125, *Canis lupus familiaris* IL31, carbonic anhydrase 9 (CA-IX), cardiac myosin, CCL11 (eotaxin-1), CCR4, CCR5, CD11, CD18, CD125, CD140a, CD147 (basigin), CD15, CD152, CD154 (CD40L), CD19, CD2, CD20, CD200, CD22, CD221, CD23 (IgE receptor), CD25 (a chain of IL-2receptor), CD27, CD274, CD28, CD3, CD3 epsilon, CD30, CD33, CD37, CD38, CD4, CD40, CD40 ligand, CD41, CD44 v6, CD5, CD51, CD52, CD56, CD6, CD70, CD74, CD79B, CD80, CEA, CEA-related antigen, CFD, ch4D5, CLDN18.2, *Clostridium difficile*, clumping factor A, CSF1R, CSF2, CTLA-4, C—X—C chemokine receptor type 4, cytomegalovirus, cytomegalovirus glycoprotein B, dabigatran, DLL4, DPP4, DR5, *E. coli* shiga toxin type-1, *E. coli* shiga toxin type-2, EGFL7, EGFR, endotoxin, EpCAM, episialin, ERBB3, *Escherichia coli*, F protein of respiratory syncytial virus, FAP, fibrin II beta chain, fibronectin extra domain-B, folate hydrolase, folate receptor 1, folate receptor alpha, Frizzled receptor, ganglioside GD2, GD2, GD3 ganglioside, glypican 3, GMCSF receptor α-chain, GPNMB, growth differentiation factor 8, GUCY2C, hemagglutinin, hepatitis B surface antigen, hepatitis B virus, HER1, HER2/neu, HER3, HGF, HHGFR, histone complex, HIV-1, HLA-DR, HNGF, Hsp90, human scatter factor receptor kinase, human TNF, human beta-amyloid, ICAM-1 (CD54), IFN-α, IFN-γ, IgE, IgE Fc region, IGF-1 receptor, IGF-1, IGHE, IL 17A, IL 17F, IL 20, IL-12, IL-13, IL-17, IL-1β, IL-22, IL-23, IL-31RA, IL-4, IL-5, IL-6, IL-6 receptor, IL-9, ILGF2, influenza A hemagglutinin, influenza A virus hemagglutinin, insulin-like growth factor I receptor, integrin α4β7, integrin α4, integrin α5β1, integrin α7β7, integrin αIIbβ3, integrin αvβ3, interferon α/β receptor, interferon gamma-induced protein, ITGA2, ITGB2 (CD18), KIR2D, Lewis-Y antigen, LFA-1 (CD11a), LINGO-1, lipoteichoic acid, LOXL2, L-selectin (CD62L), LTA, MCP-1, mesothelin, MIF, MS4A1, MSLN, MUC1, mucin CanAg, myelin-associated glycoprotein, myostatin, NCA-90 (granulocyte antigen), neural apoptosis-regulated proteinase 1, NGF, N-glycolylneuraminic acid, NOGO-A, Notch receptor, NRP1, *Oryctolagus cuniculus*, OX-40, oxLDL, PCSK9, PD-1, PDCD1, PDGF-R α, phosphate-sodium co-transporter, phosphatidylserine, platelet-derived growth factor receptor beta, prostatic carcinoma cells, *Pseudomonas aeruginosa*, rabies virus glycoprotein, RANKL, respiratory syncytial virus, RHD, Rhesus factor, RON, RTN4, sclerostin, SDC1, selectin P, SLAMF7, SOST, sphingosine-1-phosphate, *Staphylococcus aureus*, STEAP1, TAG-72, T-cell receptor, TEM1, tenascin C, TFPI, TGF-β1, TGF-β2, TGF-β, TNF-α, TRAIL-R1, TRAIL-R2, tumor antigen CTAA16.88, tumor specific glycosylation of MUC1, tumor-associated calcium signal transducer 2, TWEAK receptor, TYRP1(glycoprotein 75), VEGFA, VEGFR1, VEGFR2, vimentin, and VWF.

In some embodiments, the antigen interacting domain binds an Fc domain of an antibody selected from the group consisting of: 20-(74)-(74) (milatuzumab; veltuzumab), 20-2b-2b, 3F8, 74-(20)-(20) (milatuzumab; veltuzumab), 8H9, A33, AB-16B5, abagovomab, abciximab, abituzumab, ABP 494 (cetuximab biosimilar), abrilumab, ABT-700, ABT-806, Actimab-A (actinium Ac-225 lintuzumab), actoxumab, adalimumab, ADC-1013, ADCT-301, ADCT-402, adecatumumab, aducanumab, afelimomab, AFM13, afutuzumab, AGEN1884, AGS15E, AGS-16C3F, AGS67E, alacizumab pegol, ALD518, alemtuzumab, alirocumab, altumomab pentetate, amatuximab, AMG 228, AMG 820, anatumomab mafenatox, anetumab ravtansine, anifrolumab, anrukinzumab, APN301, APN311, apolizumab, APX003/SIM-BD0801 (sevacizumab), APX005M, arcitumomab, ARX788, ascrinvacumab, aselizumab, ASG-15ME, atezolizumab, atinumab, ATL101, atlizumab (also referred to as tocilizumab), atorolimumab, Avelumab, B-701, bapineuzumab, basiliximab, bavituximab, BAY1129980, BAY1187982, bectumomab, begelomab, belimumab, benralizumab, bertilimumab, besilesomab, Betalutin (177Lu-tetraxetan-tetulomab), bevacizumab, BEVZ92 (bevacizumab biosimilar), bezlotoxumab, BGB-A317, BHQ880, BI 836880, BI-505, biciromab, bimagrumab, bimekizumab, bivatuzumab mertansine, BIW-8962, blinatumomab, blosozumab, BMS-936559, BMS-986012, BMS-986016, BMS-986148, BMS-986178, BNC101, bococizumab, brentuximab vedotin, BrevaRex, briakinumab, brodalumab, brolucizumab, brontictuzumab, C2-2b-2b, canakinumab, cantuzumab mertansine, cantuzumab ravtansine, caplacizumab, capromab pendetide, carlumab, catumaxomab, CBR96-doxorubicin immunoconjugate, CBT124 (bevacizumab), CC-90002, CDX-014, CDX-1401, cedelizumab, certolizumab pegol, cetuximab, CGEN-15001T, CGEN-15022, CGEN-15029, CGEN-15049, CGEN-15052, CGEN-15092, Ch.14.18, citatuzumab bogatox, cixutumumab, clazakizumab, clenoliximab, clivatuzumab tetraxetan, CM-24, codrituzumab, coltuximab ravtansine, conatumumab, concizumab, Cotara (iodine I-131 derlotuximab biotin), cR6261, crenezumab, DA-3111 (trastuzumab biosimilar), dacetuzumab, daclizumab, dalotuzumab, dapirolizumab pegol, daratumumab, Daratumumab Enhanze (daratumumab), Darleukin, dectrekumab, demcizumab, denintuzumab mafodotin, denosumab, Depatuxizumab, Depatuxizumab mafodotin, derlotuximab biotin, detumomab, DI-B4, dinutuximab, diridavumab, DKN-01, DMOT4039A, dorlimomab aritox, drozitumab, DS-1123, DS-8895, duligotumab, dupilumab, durvalumab, dusigitumab, ecromeximab, eculizumab, edobacomab, edrecolomab, efalizumab, efungumab, eldelumab, elgemtumab, elotuzumab, elsilimomab, emactuzumab, emibetuzumab, enavatuzumab, enfortumab vedotin, enlimomab pegol, enoblituzumab, enokizumab, enoticumab, ensituximab, epitumomab cituxetan, epratuzumab, erlizumab, ertumaxomab, etaracizumab, etrolizumab, evinacumab, evolocumab, exbivirumab, fanolesomab, faralimomab, farletuzumab, fasinumab, FBTA05, felvizumab, fezakinumab, FF-21101, FGFR2 Antibody-Drug Conjugate, Fibromun, ficlatuzumab, figitumumab, firivumab, flanvotumab, fletikumab, fontolizumab, foralumab, foravirumab, FPA144, fresolimumab, FS102, fulranumab, futuximab, galiximab, ganitumab, gantenerumab, gavilimomab, gemtuzumab ozogamicin, Gerilimzumab, gevokizumab, girentuximab, glembatumumab vedotin, GNR-006, GNR-011, golimumab, gomiliximab, GSK2849330, GSK2857916, GSK3174998, GSK3359609, guselkumab, Hu14.18K322A MAb, hu3S193, Hu8F4, HuL2G7, HuMab-5B1, ibalizumab, ibritumomab tiuxetan, icrucumab, idarucizumab, IGN002, IGN523, igovomab, IMAB362, IMAB362 (claudiximab), imalumab, IMC-CS4, IMC-D11, imciromab, imgatuzumab, IMGN529, IMMU-102 (yttrium Y-90 epratuzumab tetraxetan), IMMU-114, ImmuTune IMP701 Antagonist Antibody, INCAGN1876, inclacumab, INCSHR1210, indatuximab ravtansine, indusatumab vedotin, infliximab, inolimomab, inotuzumab ozogamicin, intetumumab, Ipafricept, IPH4102, ipilimumab, iratumumab, isatuximab, Istiratumab, itolizumab, ixekizumab, JNJ-56022473, JNJ-61610588, keliximab, KTN3379, L19IL2/L19TNF, Labetuzumab, Labetuzumab Govitecan, LAG525, lambrolizumab, lampalizumab, L-DOS47, lebrikizumab, lemalesomab, lenzilumab, lerdelimumab, Leukotuximab, lexatumumab, libivirumab, lifastuzumab vedotin, ligelizumab, lilotomab satetraxetan, lintuzumab, lirilumab, LKZ145, lodelcizumab, lokivetmab, lorvotuzumab mertansine, lucatumumab, lulizumab pegol, lumiliximab, lumretuzumab, LY3164530, mapatumumab, margetuximab, maslimomab, matuzumab, mavrilimumab, MB311, MCS-110, MEDI0562, MEDI-0639, MEDI0680, MEDI-3617, MEDI-551 (inebilizumab), MEDI-565, MEDI6469, mepolizumab, metelimumab, MGB453, MGD006/S80880, MGD007, MGD009, MGD011, milatuzumab, Milatuzumab-SN-38, minretumomab, mirvetuximab soravtansine, mitumomab, MK-4166, MM-111, MM-151, MM-302, mogamulizumab, MOR202, MOR208, MORAb-066, morolimumab, motavizumab, moxetumomab pasudotox, muromonab-CD3, nacolomab tafenatox, namilumab, naptumomab estafenatox, narnatumab, natalizumab, nebacumab, necitumumab, nemolizumab, nerelimomab, nesvacumab, nimotuzumab, nivolumab, nofetumomab merpentan, NOV-10, obiltoxaximab, obinutuzumab, ocaratuzumab, ocrelizumab, odulimomab, ofatumumab, olaratumab, olokizumab, omalizumab, OMP-131R10, OMP-305B83, onartuzumab, ontuxizumab, opicinumab, oportuzumab monatox, oregovomab, orticumab, otelixizumab, otlertuzumab, OX002/MEN1309, oxelumab, ozanezumab, ozoralizumab, pagibaximab, palivizumab, panitumumab, pankomab, PankoMab-GEX, panobacumab, parsatuzumab, pascolizumab, pasotuxizumab, patecliumab, patritumab, PAT-SC1, PAT-SM6, pembrolizumab, pemtumomab, perakizumab, pertuzumab, pexelizumab, PF-05082566 (utomilumab), PF-06647263, PF-06671008, PF-06801591, pidilizumab, pinatuzumab vedotin, pintumomab, placulumab, polatuzumab vedotin, ponezumab, priliximab, pritoxaximab, pritumumab, PRO 140, Proxinium, PSMA ADC, quilizumab, racotumomab, radretumab, rafivirumab, ralpancizumab, ramucirumab, ranibizumab, raxibacumab, refanezumab, regavirumab, REGN1400, REGN2810/SAR439684, reslizumab, RFM-203, RG7356, RG7386, RG7802, RG7813, RG7841, RG7876, RG7888, RG7986, rilotumumab, rinucumab, rituximab, RM-1929, R07009789, robatumumab, roledumab, romosozumab, rontalizumab, rovelizumab, ruplizumab, sacituzumab govitecan, samalizumab, SAR408701, SAR566658, sarilumab, SAT 012, satumomab pendetide, SCT200, SCT400, SEA-CD40, secukinumab, seribantumab, setoxaximab, sevirumab, SGN-CD19A, SGN-CD19B, SGN-CD33A, SGN-CD70A, SGN-LIV1A, sibrotuzumab, sifalimumab, siltuximab, simtuzumab, siplizumab, sirukumab, sofituzumab vedotin, solanezumab, solitomab, sonepcizumab, sontuzumab, stamulumab, sulesomab, suvizumab, SYD985, SYM004 (futuximab and modotuximab), Sym015, TAB08, tabalumab, tacatuzumab tetraxetan, tadocizumab, talizumab, tanezumab, Tanibirumab, taplitumomab paptox, tarextumab, TB-403, tefibazumab, Teleukin, telimomab aritox, tenatumomab, teneliximab, teplizumab, teprotumumab, tesidolumab, tetulomab, TG-1303, TGN1412, Thorium-227-Epratuzumab Conjugate, ticilimumab, tigatuzumab, tildrakizumab, Tisotumab vedotin, TNX-650, tocilizumab, toralizumab, tosatoxumab, tositumomab, tovetumab, tralokinumab, trastuzumab, trastuzumab emtansine, TRBS07, TRC105, tregalizumab, tremelimumab, trevogrumab, TRPH 011, TRX518, TSR-042, TTI-200.7, tucotuzumab celmoleukin, tuvirumab, U3-1565, U3-1784, ublituximab, ulocuplumab, urelumab, urtoxazumab, ustekinumab, Vadastuximab Talirine, vandortuzumab vedotin, vantictumab, vanucizumab, vapaliximab, varlilumab, vatelizumab, VB6-845, vedolizumab, veltuzumab, vepalimomab, vesencumab, visilizumab, volociximab, vorsetuzumab mafodotin, votumumab, YYB-101, zalutumumab, zanolimumab, zatuximab, ziralimumab, and zolimomab aritox.

In some embodiments, the extracellular region comprises multiple antigen interacting domains, each of which exhibits binding to the same or different antigen.

In some embodiments, the antigen interacting domain binds an antigen selected from the group consisting of: 707-AP, a biotinylated molecule, a-Actinin-4, abl-bcr alb-b3 (b2a2), abl-bcr alb-b4 (b3a2), adipophilin, AFP, AIM-2, Annexin II, ART-4, BAGE, b-Catenin, bcr-abl, bcr-abl p190 (e1a2), bcr-abl p210 (b2a2), bcr-abl p210 (b3a2), BING-4, CAG-3, CAIX, CAMEL, Caspase-8, CD171, CD19, CD20, CD22, CD23, CD24, CD30, CD33, CD38, CD44v7/8, CDC27, CDK-4, CEA, CLCA2, Cyp-B, DAM-10, DAM-6, DEK-CAN, EGFRvIII, EGP-2, EGP-40, ELF2, Ep-CAM, EphA2, EphA3, erb-B2, erb-B3, erb-B4, ES-ESO-1a, ETV6/AML, FBP, fetal acetylcholine receptor, FGF-5, FN, G250, GAGE-1, GAGE-2, GAGE-3, GAGE-4, GAGE-5, GAGE-6, GAGE-7B, GAGE-8, GD2, GD3, GnT-V, Gp100, gp75, Her-2, HLA-A*0201-R170I, HMW-MAA, HSP70-2 M, HST-2 (FGF6), HST-2/neu, hTERT, iCE, IL-11Rα, IL-13Rα2, KDR, KIAA0205, K-RAS, L1-cell adhesion molecule, LAGE-1, LDLR/FUT, Lewis Y, MAGE-1, MAGE-10, MAGE-12, MAGE-2, MAGE-3, MAGE-4, MAGE-6, MAGE-A1, MAGE-A2, MAGE-A3, MAGE-A6, MAGE-B1, MAGE-B2, Malic enzyme, Mammaglobin-A, MART-1/Melan-A, MART-2, MC1R, M-CSF, mesothelin, MUC1, MUC16, MUC2, MUM-1, MUM-2, MUM-3, Myosin, NA88-A, Neo-PAP, NKG2D, NPM/ALK, N-RAS, NY-ESO-1, OA1, OGT, oncofetal antigen (h5T4), OS-9, P polypeptide, P15, P53, PRAME, PSA, PSCA, PSMA, PTPRK, RAGE, ROR1, RU1, RU2, SART-1, SART-2, SART-3, SOX10, SSX-2, Survivin, Survivin-2B, SYT/SSX, TAG-72, TEL/AML1, TGFaRII, TGFbRII, TP1, TRAG-3, TRG, TRP-1, TRP-2, TRP-2/INT2, TRP-2-6b, Tyrosinase, VEGF-R2, WT1, α-folate receptor, and κ-light chain.

In some embodiments, the immune cell signaling domain comprises a primary signaling domain comprising an immunoreceptor tyrosine-based activation motif (ITAM). In some embodiments, the immune cell signaling domain comprises a primary signaling domain comprising an immunoreceptor tyrosine-based inhibition motif (ITIM). In some embodiments, the immune cell signaling domain comprises a primary signaling domain of a protein selected from: an Fcγ receptor (FcγR), an FCε receptor (FcεR), an Fcα receptor (FcαR), neonatal Fc receptor (FcRn), CD3, CD3 ζ, CD3 γ, CD3 δ, CD3 ε, CD4, CD5, CD8, CD21, CD22, CD28, CD32, CD40L (CD154), CD45, CD66d, CD79a, CD79b, CD80, CD86, CD278 (also known as ICOS), CD247 ζ, CD247 η, DAP10, DAP12, FYN, LAT, Lck, MAPK, MEW complex, NFAT, NF-κB, PLC-γ, iC3b, C3dg, C3d, and Zap70. In some embodiments, the primary signaling domain comprises a CD3 ζ signaling domain. In some embodiments, the primary signaling domain comprises an immunoreceptor tyrosine-based activation motif (ITAM) of CD3 ζ. In some embodiments, the primary signaling domain comprises an FcγR signaling domain. In some embodiments, the primary signaling domain comprises an FcγR signaling domain selected from FcγRI (CD64), FcγRIIA (CD32), FcγRIIB (CD32), FcγRIIIA (CD16a), and FcγRIIIB (CD16b). In some embodiments, the primary signaling domain comprises an FcεR signaling domain. In some embodiments, the primary signaling domain comprises an FcεR signaling domain selected from FcεRI and FcεRII (CD23). In some embodiments, the primary signaling domain comprises an FcαR signaling domain. In some embodiments, the primary signaling domain comprises an FcαR signaling domain selected from FcαRI (CD89) and Fcα/μR.

In some embodiments, the immune cell signaling domain comprises a co-stimulatory domain. In some embodiments, the immune cell signaling domain comprises multiple co-stimulatory domains. In some embodiments, the co-stimulatory domain comprises a signaling domain of a MEW class I molecule, a TNF receptor protein, an immunoglobulin-like protein, a cytokine receptor, an integrin, a signaling lymphocytic activation molecule (SLAM protein), an activating NK cell receptor, or a Toll ligand receptor. In some embodiments, the co-stimulatory domain comprises a signaling domain of a molecule selected from the group consisting of: 2B4/CD244/SLAMF4, 4-1BB/TNFSF9/CD137, B7-1/CD80, B7-2/CD86, B7-H1/PD-L1, B7-H2, B7-H3, B7-H4, B7-H6, B7-H7, BAFF R/TNFRSF13C, BAFF/BLyS/TNFSF13B, BLAME/SLAMF8, BTLA/CD272, CD100 (SEMA4D), CD103, CD11a, CD11b, CD11c, CD11d, CD150, CD160 (BY55), CD18, CD19, CD2, CD200, CD229/SLAMF3, CD27 Ligand/TNFSF7, CD27/TNFRSF7, CD28, CD29, CD2F-10/SLAMF9, CD30 Ligand/TNFSF8, CD30/TNFRSF8, CD300a/LMIR1, CD4, CD40 Ligand/TNFSF5, CD40/TNFRSF5, CD48/SLAMF2, CD49a, CD49D, CD49f, CD53, CD58/LFA-3, CD69, CD7, CD8 α, CD8 β, CD82/Kai-1, CD84/SLAMF5, CD90/Thy1, CD96, CDS, CEACAM1, CRACC/SLAMF7, CRTAM, CTLA-4, DAP12, Dectin-1/CLEC7A, DNAM1 (CD226), DPPIV/CD26, DR3/TNFRSF25, EphB6, GADS, Gi24/VISTA/B7-H5, GITR Ligand/TNFSF18, GITR/TNFRSF18, HLA Class I, HLA-DR, HVEM/TNFRSF14, IA4, ICAM-1, ICOS/CD278, Ikaros, IL2R β, IL2R γ, IL7R α, Integrin α4/CD49d, Integrin α4β1, Integrin α4β7/LPAM-1, IPO-3, ITGA4, ITGA6, ITGAD, ITGAE, ITGAL, ITGAM, ITGAX, ITGB1, ITGB2, ITGB7, KIRDS2, LAG-3, LAT, LIGHT/TNFSF14, LTBR, Ly108, Ly9 (CD229), lymphocyte function associated antigen-1 (LFA-1), Lymphotoxin-α/TNF-0, NKG2C, NKG2D, NKp30, NKp44, NKp46, NKp80 (KLRF1), NTB-A/SLAMF6, OX40 Ligand/TNFSF4, OX40/TNFRSF4, PAG/Cbp, PD-1, PDCD6, PD-L2/B7-DC, PSGL1, RELT/TNFRSF19L, SELPLG (CD162), SLAM (SLAMF1), SLAM/CD150, SLAMF4 (CD244), SLAMF6 (NTB-A), SLAMF7, SLP-76, TACI/TNFRSF13B, TCL1A, TCL1B, TIM-1/KIM-1/HAVCR, TIM-4, TL1A/TNFSF15, TNF RII/TNFRSF1B, TNF-α, TRANCE/RANKL, TSLP, TSLP R, VLA1, and VLA-6. In some embodiments, the co-stimulatory domain regulates an immune cell proliferative signal and/or survival signal.

In some embodiments, the actuator moiety comprises a CRISPR-associated polypeptide (Cas), zinc finger nuclease (ZFN), zinc finger associated gene regulation polypeptide, transcription activator-like effector nuclease (TALEN), transcription activator-like effector associated gene regulation polypeptide, meganuclease, natural master transcription factor, epigenetic modifying enzyme, recombinase, flippase, transposase, RNA-binding proteins (RBP), an Argonaute protein, any derivative thereof, any variant thereof, or any fragment thereof. In some embodiments, the actuator moiety comprises a Cas protein that forms a complex with a guide RNA (gRNA). In some embodiments, the actuator moiety comprises an RBP optionally complexed with a guide RNA (gRNA) which is able to form a complex with a Cas protein. In some embodiments, the Cas protein substantially lacks DNA cleavage activity.

In some embodiments, the actuator moiety regulates expression of a gene by physical obstruction of a target polynucleotide or recruitment of additional factors effective to suppress or enhance gene expression from the target nucleic acid. In some embodiments, the actuator moiety comprises a transcriptional activator effective to increase gene expression from a target polynucleotide. In some embodiments, the actuator moiety comprises a transcriptional repressor effective to decrease gene expression from a target polynucleotide.

In some embodiments, the cleavage recognition site is flanked by the immune cell signaling domain and the actuator moiety. In some embodiments, the cleavage recognition site comprises a cleavage recognition sequence recognized by a protease. In some embodiments, the cleavage recognition site comprises multiple cleavage recognition sequences, each cleavage recognition sequence recognized by the same or different protease. In some embodiments, the cleavage recognition sequence is recognized by a protease selected from the group consisting of: achromopeptidase, aminopeptidase, ancrod, angiotensin converting enzyme, bromelain, calpain, calpain I, calpain II, carboxypeptidase A, carboxypeptidase B, carboxypeptidase G, carboxypeptidase P, carboxypeptidase W, carboxypeptidase Y, caspase 1, caspase 2, caspase 3, caspase 4, caspase 5, caspase 6, caspase 7, caspase 8, caspase 9, caspase 10, caspase 11, caspase 12, caspase 13, cathepsin B, cathepsin C, cathepsin D, cathepsin E, cathepsin G, cathepsin H, cathepsin L, chymopapain, chymase, chymotrypsin, clostripain, collagenase, complement C1r, complement C1s, complement Factor D, complement factor I, cucumisin, dipeptidyl peptidase IV, elastase (leukocyte), elastase (pancreatic), endoproteinase Arg-C, endoproteinase Asp-N, endoproteinase Glu-C, endoproteinase Lys-C, enterokinase, factor Xa, ficin, furin, granzyme A, granzyme B, HIV Protease, IGase, kallikrein tissue, leucine aminopeptidase (general), leucine aminopeptidase (cytosol), leucine aminopeptidase (microsomal), matrix metalloprotease, methionine aminopeptidase, neutrase, papain, pepsin, plasmin, prolidase, pronase E, prostate specific antigen, protease alkalophilic from *Streptomyces griseus*, protease from *Aspergillus*, protease from *Aspergillus saitoi*, protease from *Aspergillus sojae*, protease (*B. licheniformis*) (alkaline or alcalase), protease from *Bacillus polymyxa*, protease from *Bacillus* sp, protease from *Rhizopus* sp., protease S, proteasomes, proteinase from *Aspergillus oryzae*, proteinase 3, proteinase A, proteinase K, protein C, pyroglutamate aminopeptidase, rennin, rennin, streptokinase, subtilisin, thermolysin, thrombin, tissue plasminogen activator, trypsin, tryptase and urokinase. In some embodiments, the chimeric transmembrane receptor polypeptide further comprises at least one targeting peptide which directs transport of the receptor to a specific region of a cell. In some embodiments, the targeting peptide directs transport of the receptor to a nucleus, mitochondria, endoplasmic reticulum (ER), chloroplast, peroxisome or plasma membrane. In some embodiments, the targeting peptide comprises a nuclear export signal (NES). In some embodiments, the targeting peptide comprises a plasma membrane targeting peptide.

In some embodiments, the targeting peptide is linked to the actuator moiety. In some embodiments, the targeting peptide comprises a nuclear localization signal (NLS). In some embodiments, the targeting peptide comprising an NLS is linked to the N-terminus or C-terminus of the actuator moiety. In some embodiments, the targeting peptide comprising an NLS linked to the actuator moiety directs transport of the actuator moiety to a nucleus of a cell following release of the actuator moiety from the GMP by cleavage at the cleavage recognition site.

In an aspect, the present disclosure provides a method of inducing death of a target cell. The method comprises (a) expressing a system in a lymphocyte; and (b) contacting the target cell with the lymphocyte under conditions that induce the death of the target cell, wherein the system expressed in the lymphocyte comprises (i) a chimeric transmembrane receptor polypeptide comprising a ligand binding domain, an immune cell signaling domain, and a gene modulating polypeptide (GMP), wherein the GMP comprises an actuator moiety linked to a cleavage recognition site; and (ii) a chimeric adaptor polypeptide comprising a receptor binding moiety linked to a cleavage moiety, wherein the cleavage moiety is capable of cleaving the cleavage recognition site on the receptor when the receptor binding moiety binds the receptor polypeptide in response to binding of the ligand binding domain to a ligand; wherein, upon contacting the target cell to the lymphocyte, the ligand binding domain binds a ligand present on the target cell to (i) activate cytotoxicity of the lymphocyte, and (ii) release the actuator moiety from the GMP via cleavage by the cleavage moiety at the cleavage site, wherein the actuator moiety in turn modulates expression and/or activity of an immune regulatory protein that enhances lymphocyte cytotoxicity and/or reduces a side effect of lymphocyte activation.

In some embodiments, modulation of expression and/or activity of the immune regulatory protein enhances cytotoxicity of the lymphocyte compared to a system in which the immune regulatory protein expression and/or activity is not modulated. In some embodiments, modulation of expression and/or activity of the immune regulatory protein reduces a side effect of lymphocyte activation compared to a system in which the immune regulatory protein expression and/or activity is not modulated, wherein the side effect is hypercytokinemia.

In some embodiments, the actuator moiety up-regulates expression and/or activity of the immune regulatory protein. In some embodiments, the actuator moiety down-regulates expression and/or activity of the immune regulatory protein. In some embodiments, the immune regulatory is selected from A2AR, B7.1, B7-H3/CD276, B7-H4/B7S1/B7x/Vtcn1, B7-H6, BTLA/CD272, CCR4, CD122, 4-1BB/CD137, CD27, CD28, CD40, CD47, CD70, CISH, CTLA-4/CD152, DR3, GITR, ICOS/CD278, IDO, KIR, LAG-3, OX40/CD134, PD-1/CD279, PD2, PD-L1, PD-L2, TIM-3, and VISTA/Dies1/Gi24/PD-1H (C10orf54). In some embodiments, the immune regulatory protein is PD-1 or CTLA-4. In some embodiments, the immune regulatory protein is an immune checkpoint receptor.

In some embodiments, the target cell is a cancer cell. In some embodiments, the cancer cell is of hematopoietic lineage. In some embodiments, the cancer cell is a B-cell lymphoma cell. In some embodiments, the cancer cell expresses a ligand indicative of a B-cell lymphoma. In some embodiments, the ligand is CD19.

In some embodiments, the lymphocyte exhibits an enhanced ability to induce death of the target cell compared to a control lymphocyte. The control lymphocyte may, in some cases, be a lymphocyte in which expression and/or activity of the immune regulatory protein is not modulated. In some embodiments, the enhanced ability to induce death of the target cell is at least a 1.5-fold increase in induced cell death.

In some embodiments, upon binding of the ligand binding domain to the ligand, the receptor undergoes a receptor modification comprising phosphorylation. In some embodiments, the receptor modification comprises phosphorylation at multiple modification sites, and each modification site is effective to bind a chimeric adaptor polypeptide.

In an aspect, the present disclosure provides a system capable of inducing death of a target cell. The system comprises (a) a chimeric transmembrane receptor polypeptide comprising a ligand binding domain, an immune cell signaling domain, and a gene modulating polypeptide (GMP), the GMP comprising an actuator moiety linked to a cleavage recognition site; and (b) a chimeric adaptor polypeptide comprising a receptor binding moiety linked to a cleavage moiety capable of cleaving the cleavage recognition site when in proximity to the cleavage recognition site, wherein upon ligand binding to the ligand binding domain, the immune cell signaling domain activates cytotoxicity of a lymphocyte and the adaptor polypeptide binds the receptor polypeptide to effect release of the actuator moiety by cleavage of the cleavage recognition site by the cleavage moiety, the released actuator moiety exhibiting the ability to modulate expression and/or activity of an immune regulatory protein within the lymphocyte.

In some embodiments, the ligand binding domain comprises a single-chain variable fragment (scFv). In some embodiments, the ligand binding domain binds CD19 or a fragment thereof.

In some embodiments, the immune cell signaling domain comprises an immunoreceptor tyrosine-based activation motif (ITAM).

In some embodiments, the actuator moiety comprises a CRISPR-associated polypeptide (Cas), a zinc finger nuclease (ZFN), a transcription activator-like effector nuclease (TALEN), a meganuclease, a recombinase, a flippase, a transposase, or an Argonaute protein. In some embodiments, the actuator moiety comprises a Cas protein that forms a complex with a guide RNA (gRNA). In some embodiments, the Cas protein is Cas9, Cpf1, or C2c2. In some embodiments, the Cas protein substantially lacks DNA cleavage activity. In some embodiments, Cas protein is linked to a transcriptional repressor or a transcriptional activator. In some embodiments, the cleavage recognition site comprises a polypeptide sequence and the cleavage moiety comprises a protease. In some embodiments, the cleavage moiety is a TEV protease, and wherein the cleavage recognition site is a TEV protease cleavage site.

In some embodiments, the receptor binding moiety comprises a linker for activation of T cells (LAT) protein or a fragment thereof.

In an aspect, the present disclosure provides a method of inducing death of a target cell. The method comprises (a) expressing a system in a lymphocyte; and (b) contacting the target cell with the lymphocyte under conditions that induce the death of the target cell, wherein the system expressed in the lymphocyte comprises (i) a chimeric transmembrane receptor polypeptide comprising a single-chain variable fragment (scFv) capable of binding CD19 expressed on the target cell, an immune cell signaling domain comprising a CD3 ζ immunoreceptor tyrosine-based activation motif (ITAM), and a gene modulating polypeptide (GMP), wherein the GMP comprises a dCas9-KRAB linked to a tobacco etch virus (TEV) protease cleavage site; and (ii) a chimeric adaptor polypeptide comprising a linker for activation of T cells (LAT) protein linked to a TEV protease, wherein the TEV protease is capable of cleaving the TEV protease cleavage site on the receptor when the LAT protein binds the receptor polypeptide in response to binding of the scFv to CD19, wherein, upon contacting the target cell to the lymphocyte, the scFv binds CD19 present on the target cell to (i) activate cytotoxicity of the lymphocyte, and (ii) release the dCas9-KRAB from the GMP via cleavage by TEV protease at the TEV protease cleavage site, wherein the dCas9-KRAB in turn modulates expression and/or activity of programmed cell death protein 1 (PD-1).

In an aspect, the present disclosure provides a lymphocyte expressing any one of the systems disclosed herein.

In an aspect, the present disclosure provides a population of lymphocyte cells, individual lymphocyte cells expressing any one of the systems disclosed herein, wherein the population of lymphocyte cells is characterized in that: upon exposing the population of lymphocyte cells to a target cell population in an in vitro cell death assay, the population of lymphocyte cells induces death of at least 45% of the target cells within about 2 days when the ratio of the number of lymphocyte cells in the population of lymphocyte cells to the number of target cells in the target cell population is about 1:2 or less.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIGS. 4A-D illustrate schematically the release of an actuator moiety from a GMP in a system comprising a receptor which undergoes phosphorylation; FIGS. 4E-H illustrate schematically the release of an actuator moiety from a GMP in a system comprising a receptor which undergoes a conformational change.

FIGS. 8A-D illustrate schematically the release of an actuator moiety from a GMP in a system comprising a receptor which undergoes phosphorylation; FIGS. 8E-H illustrate schematically the release of an actuator moiety from a GMP in a system comprising a receptor which undergoes a conformational change.

FIGS. 23A-22C depict flow cytometry results of CD19-CAR-dCas9-KRAB expressing and LAT-TEV expressing T cells, with FITC detecting GFP signal from CD19-CAR-dCas9-KRAB expression (FIG. 23A and y-axis of FIG. 23C) and ECD-A detecting m-cherry signal from LAT-TEV expression (FIG. 23B and x-axis of FIG. 23C).

FIGS. 26A, 26B, 26C, 26D, 26E, and 26F depict flow cytometry data using ECD to detect dCas9-KRAB expression and APC to detect PD-1 expression.

FIGS. 29A, 29B, 29C, 29D, 29E, and 29F depict flow cytometry data using ECD to detect dCas9-KRAB expression and APC to detect PD-1 expression.

FIGS. 34A, 34B, and 34C depict flow cytometry data using APC-A750 to detect CD19 expression after the indicated T cells were incubated with Raji cells expressing PD-L1 (Raji-PD-L1 cells) at a 5 to 1 ratio for 4 hours.

FIGS. 35A, 35B, and 35C depict flow cytometry data using APC-A750 to detect CD19 expression after the indicated T cells were incubated with Raji-PD-L1 cells at a 5 to 1 ratio for 1 day.

FIGS. 36A, 36B, and 36C depict flow cytometry data using APC-A750 to detect CD19 expression after the indicated T cells were incubated with Raji-PD-L1 cells at a 5 to 1 ratio for 2 day.

FIGS. 37A, 37B, and 37C depict flow cytometry data using APC-A750 to detect CD19 expression after the indicated T cells were incubated with Raji-PD-L1 cells at a 1 to 2 ratio for 4 hours.

FIGS. 38A, 38B, and 38C depict flow cytometry data using APC-A750 to detect CD19 expression after the indicated T cells were incubated with Raji-PD-L1 cells at a 1 to 2 ratio for 1 day.

FIGS. 39A, 39B, and 39C depict flow cytometry data using APC-A750 to detect CD19 expression after the indicated T cells were incubated with Raji-PD-L1 cells at a 1 to 2 ratio for 2 days.

FIGS. 44A, 44B, 44C, 44D, 44E, 44F, 44G, 44H, 44I, 44J, 44K, and 44L depict flow cytometry data using APC-A750 to detect CD19 expression.

FIGS. 48A, 48B, 48C, 48D, 48E, 48F, 48G, 48H, 48I, 48J, 48K, and 48L depict flow cytometry data using APC-A750 to detect CD19 expression.

DETAILED DESCRIPTION OF THE INVENTION

Figure 1:
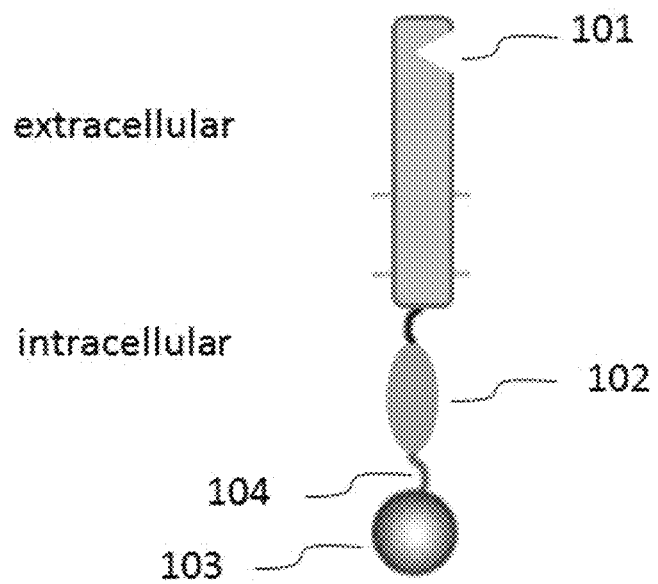
FIG. 1 shows an exemplary chimeric transmembrane receptor polypeptide comprising an antigen interacting domain, an immune cell signaling domain, and gene modulating polypeptide (GMP).

The practice of some methods disclosed herein employ, unless otherwise indicated, conventional techniques of immunology, biochemistry, chemistry, molecular biology, microbiology, cell biology, genomics and recombinant DNA, which are within the skill of the art. See for example Sambrook and Green, Molecular Cloning: A Laboratory Manual, 4th Edition (2012); the series Current Protocols in Molecular Biology (F. M. Ausubel, et al. eds.); the series Methods In Enzymology (Academic Press, Inc.), PCR 2: A Practical Approach (M. J. MacPherson, B. D. Hames and G. R. Taylor eds. (1995)), Harlow and Lane, eds. (1988) Antibodies, A Laboratory Manual, and Culture of Animal Cells: A Manual of Basic Technique and Specialized Applications, 6th Edition (R. I. Freshney, ed. (2010)).

As used in the specification and claims, the singular forms "a," "an," and "the" include plural references unless the context clearly dictates otherwise. For example, the term "a chimeric transmembrane receptor polypeptide" includes a plurality of chimeric transmembrane receptor polypeptides.

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 20%, up to 10%, up to 5%, or up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated, the term "about" meaning within an acceptable error range for the particular value should be assumed.

As used herein, a "cell" can generally refer to a biological cell. A cell can be the basic structural, functional and/or biological unit of a living organism. A cell can originate from any organism having one or more cells. Some non-limiting examples include: a prokaryotic cell, eukaryotic cell, a bacterial cell, an archaeal cell, a cell of a single-cell eukaryotic organism, a protozoa cell, a cell from a plant (e.g. cells from plant crops, fruits, vegetables, grains, soy bean, corn, maize, wheat, seeds, tomatoes, rice, cassava, sugarcane, pumpkin, hay, potatoes, cotton, *cannabis*, tobacco, flowering plants, conifers, gymnosperms, ferns, clubmosses, hornworts, liverworts, mosses), an algal cell, (e.g., *Botryococcus braunii, Chlamydomonas reinhardtii, Nannochloropsis gaditana, Chlorella pyrenoidosa, Sargassum patens C. Agardh*, and the like), seaweeds (e.g. kelp), a fungal cell (e.g., a yeast cell, a cell from a mushroom), an animal cell, a cell from an invertebrate animal (e.g. fruit fly, cnidarian, echinoderm, nematode, etc.), a cell from a vertebrate animal (e.g., fish, amphibian, reptile, bird, mammal), a cell from a mammal (e.g., a pig, a cow, a goat, a sheep, a rodent, a rat, a mouse, a non-human primate, a human, etc.), and etcetera. Sometimes a cell is not originating from a natural organism (e.g. a cell can be a synthetically made, sometimes termed an artificial cell).

The term "antigen," as used herein, refers to a molecule or a fragment thereof capable of being bound by a selective binding agent. As an example, an antigen can be a ligand that can be bound by a selective binding agent such as a receptor. As another example, an antigen can be an antigenic molecule that can be bound by a selective binding agent such as an immunological protein (e.g., an antibody). An antigen can also refer to a molecule or fragment thereof capable of being used in an animal to produce antibodies capable of binding to that antigen.

The term "antibody," as used herein, refers to a proteinaceous binding molecule with immunoglobulin-like functions. The term antibody includes antibodies (e.g., monoclonal and polyclonal antibodies), as well as derivatives, variants, and fragments thereof. Antibodies include, but are not limited to, immunoglobulins (Ig's) of different classes (i.e. IgA, IgG, IgM, IgD and IgE) and subclasses (such as IgG1, IgG2, etc.). A derivative, variant or fragment thereof can refer to a functional derivative or fragment which retains the binding specificity (e.g., complete and/or partial) of the corresponding antibody. Antigen-binding fragments include Fab, Fab', F(ab')$_2$, variable fragment (Fv), single chain variable fragment (scFv), minibodies, diabodies, and single-domain antibodies ("sdAb" or "nanobodies" or "camelids"). The term antibody includes antibodies and antigen-binding fragments of antibodies that have been optimized, engineered or chemically conjugated. Examples of antibodies that have been optimized include affinity-matured antibodies. Examples of antibodies that have been engineered include Fc optimized antibodies (e.g., antibodies optimized in the fragment crystallizable region) and multispecific antibodies (e.g., bispecific antibodies).

The terms "Fc receptor" or "FcR," as used herein, generally refers to a receptor, or any derivative, variant or fragment thereof, that can bind to the Fc region of an antibody. In certain embodiments, the FcR is one which binds an IgG antibody (a gamma receptor, Fcgamma R) and includes receptors of the Fcgamma RI (CD64), Fcgamma RII (CD32), and Fcgamma RIII (CD16) subclasses, including allelic variants and alternatively spliced forms of these receptors. Fcgamma RII receptors include Fcgamma RIIA (an "activating receptor") and Fcgamma RIIB (an "inhibiting receptor"), which have similar amino acid sequences that differ primarily in the cytoplasmic domains thereof. The term "FcR" also includes the neonatal receptor, FcRn, which is responsible for the transfer of maternal IgGs to the fetus.

The term "nucleotide," as used herein, generally refers to a base-sugar-phosphate combination. A nucleotide can comprise a synthetic nucleotide. A nucleotide can comprise a synthetic nucleotide analog. Nucleotides can be monomeric units of a nucleic acid sequence (e.g. deoxyribonucleic acid (DNA) and ribonucleic acid (RNA)). The term nucleotide can include ribonucleoside triphosphates adenosine triphosphate (ATP), uridine triphosphate (UTP), cytosine triphosphate (CTP), guanosine triphosphate (GTP) and deoxyribonucleoside triphosphates such as dATP, dCTP, dITP, dUTP, dGTP, dTTP, or derivatives thereof. Such derivatives can include, for example, [αS]dATP, 7-deaza-dGTP and 7-deaza-dATP, and nucleotide derivatives that confer nuclease resistance on the nucleic acid molecule containing them. The term nucleotide as used herein can refer to dideoxyribonucleoside triphosphates (ddNTPs) and their derivatives. Illustrative examples of dideoxyribonucleoside triphosphates can include, but are not limited to, ddATP, ddCTP, ddGTP, ddITP, and ddTTP. A nucleotide can be unlabeled or detectably labeled by well-known techniques. Labeling can also be carried out with quantum dots. Detectable labels can include, for example, radioactive isotopes, fluorescent labels, chemiluminescent labels, bioluminescent labels and enzyme labels. Fluorescent labels of nucleotides can include but are not limited fluorescein, 5-carboxyfluorescein (FAM), 2'7'-dimethoxy-4'5-dichloro-6-carboxyfluorescein (JOE), rhodamine, 6-carboxyrhodamine (R6G), N,N,N',N'-tetramethyl-6-carboxyrhodamine (TAMRA), 6-carboxy-X-rhodamine (ROX), 4-(4'dimethylaminophenylazo) benzoic acid (DABCYL), Cascade Blue, Oregon Green, Texas Red, Cyanine and 5-(2'-aminoethyl)aminonaphthalene-1-sulfonic acid (EDANS). Specific examples of fluorescently labeled nucleotides can include [R6G]dUTP, [TAMRA]dUTP, [R110]dCTP, [R6G]dCTP, [TAMRA]dCTP, [JOE]ddATP, [R6G]ddATP, [FAM]ddCTP, [R110]ddCTP, [TAMRA] ddGTP, [ROX]ddTTP, [dR6G]ddATP, [dR110]ddCTP,

[dTAMRA]ddGTP, and [dROX]ddTTP available from Perkin Elmer, Foster City, Calif.; FluoroLink DeoxyNucleotides, FluoroLink Cy3-dCTP, FluoroLink Cy5-dCTP, FluoroLink Fluor X-dCTP, FluoroLink Cy3-dUTP, and FluoroLink Cy5-dUTP available from Amersham, Arlington Heights, Ill.; Fluorescein-15-dATP, Fluorescein-12-dUTP, Tetramethyl-rodamine-6-dUTP, IR770-9-dATP, Fluorescein-12-ddUTP, Fluorescein-12-UTP, and Fluorescein-15-2'-dATP available from Boehringer Mannheim, Indianapolis, Ind.; and Chromosome Labeled Nucleotides, BODIPY-FL-14-UTP, BODIPY-FL-4-UTP, BODIPY-TMR-14-UTP, BODIPY-TMR-14-dUTP, BODIPY-TR-14-UTP, BODIPY-TR-14-dUTP, Cascade Blue-7-UTP, Cascade Blue-7-dUTP, fluorescein-12-UTP, fluorescein-12-dUTP, Oregon Green 488-5-dUTP, Rhodamine Green-5-UTP, Rhodamine Green-5-dUTP, tetramethylrhodamine-6-UTP, tetramethylrhodamine-6-dUTP, Texas Red-5-UTP, Texas Red-5-dUTP, and Texas Red-12-dUTP available from Molecular Probes, Eugene, Oreg. Nucleotides can also be labeled or marked by chemical modification. A chemically-modified single nucleotide can be biotin-dNTP. Some non-limiting examples of biotinylated dNTPs can include, biotin-dATP (e.g., bio-N6-ddATP, biotin-14-dATP), biotin-dCTP (e.g., biotin-11-dCTP, biotin-14-dCTP), and biotin-dUTP (e.g. biotin-11-dUTP, biotin-16-dUTP, biotin-20-dUTP).

The terms "polynucleotide," "oligonucleotide," and "nucleic acid" are used interchangeably to refer to a polymeric form of nucleotides of any length, either deoxyribonucleotides or ribonucleotides, or analogs thereof, either in single-, double-, or multi-stranded form. A polynucleotide can be exogenous or endogenous to a cell. A polynucleotide can exist in a cell-free environment. A polynucleotide can be a gene or fragment thereof. A polynucleotide can be DNA. A polynucleotide can be RNA. A polynucleotide can have any three dimensional structure, and can perform any function, known or unknown. A polynucleotide can comprise one or more analogs (e.g. altered backbone, sugar, or nucleobase). If present, modifications to the nucleotide structure can be imparted before or after assembly of the polymer. Some non-limiting examples of analogs include: 5-bromouracil, peptide nucleic acid, xeno nucleic acid, morpholinos, locked nucleic acids, glycol nucleic acids, threose nucleic acids, dideoxynucleotides, cordycepin, 7-deaza-GTP, fluorophores (e.g. rhodamine or fluorescein linked to the sugar), thiol containing nucleotides, biotin linked nucleotides, fluorescent base analogs, CpG islands, methyl-7-guanosine, methylated nucleotides, inosine, thiouridine, pseudouridine, dihydrouridine, queuosine, and wyosine. Non-limiting examples of polynucleotides include coding or non-coding regions of a gene or gene fragment, loci (locus) defined from linkage analysis, exons, introns, messenger RNA (mRNA), transfer RNA (tRNA), ribosomal RNA (rRNA), short interfering RNA (siRNA), short-hairpin RNA (shRNA), micro-RNA (miRNA), ribozymes, cDNA, recombinant polynucleotides, branched polynucleotides, plasmids, vectors, isolated DNA of any sequence, isolated RNA of any sequence, cell-free polynucleotides including cell-free DNA (cfDNA) and cell-free RNA (cfRNA), nucleic acid probes, and primers. The sequence of nucleotides can be interrupted by non-nucleotide components.

The term "gene," as used herein, refers to a nucleic acid (e.g., DNA such as genomic DNA and cDNA) and its corresponding nucleotide sequence that is involved in encoding an RNA transcript. The term as used herein with reference to genomic DNA includes intervening, non-coding regions as well as regulatory regions and can include 5' and 3' ends. In some uses, the term encompasses the transcribed sequences, including 5' and 3' untranslated regions (5'-UTR and 3'-UTR), exons and introns. In some genes, the transcribed region will contain "open reading frames" that encode polypeptides. In some uses of the term, a "gene" comprises only the coding sequences (e.g., an "open reading frame" or "coding region") necessary for encoding a polypeptide. In some cases, genes do not encode a polypeptide, for example, ribosomal RNA genes (rRNA) and transfer RNA (tRNA) genes. In some cases, the term "gene" includes not only the transcribed sequences, but in addition, also includes non-transcribed regions including upstream and downstream regulatory regions, enhancers and promoters. A gene can refer to an "endogenous gene" or a native gene in its natural location in the genome of an organism. A gene can refer to an "exogenous gene" or a non-native gene. A non-native gene can refer to a gene not normally found in the host organism but which is introduced into the host organism by gene transfer. A non-native gene can also refer to a gene not in its natural location in the genome of an organism. A non-native gene can also refer to a naturally occurring nucleic acid or polypeptide sequence that comprises mutations, insertions and/or deletions (e.g., non-native sequence).

The terms "target polynucleotide" and "target nucleic acid," as used herein, refer to a nucleic acid or polynucleotide which is targeted by an actuator moiety of the present disclosure. A target polynucleotide can be DNA (e.g., endogenous or exogenous). DNA can refer to template to generate mRNA transcripts and/or the various regulatory regions which regulate transcription of mRNA from a DNA template. A target polynucleotide can be a portion of a larger polynucleotide, for example a chromosome or a region of a chromosome. A target polynucleotide can refer to an extra-chromosomal sequence (e.g., an episomal sequence, a mini-circle sequence, a mitochondrial sequence, a chloroplast sequence, etc.) or a region of an extrachromosomal sequence. A target polynucleotide can be RNA. RNA can be, for example, mRNA which can serve as template encoding for proteins. A target polynucleotide comprising RNA can include the various regulatory regions which regulate translation of protein from an mRNA template. A target polynucleotide can encode for a gene product (e.g., DNA encoding for an RNA transcript or RNA encoding for a protein product) or comprise a regulatory sequence which regulates expression of a gene product. In general, the term "target sequence" refers to a nucleic acid sequence on a single strand of a target nucleic acid. The target sequence can be a portion of a gene, a regulatory sequence, genomic DNA, cell free nucleic acid including cfDNA and/or cfRNA, cDNA, a fusion gene, and RNA including mRNA, miRNA, rRNA, and others. A target polynucleotide, when targeted by an actuator moiety, can result in altered gene expression and/or activity. A target polynucleotide, when targeted by an actuator moiety, can result in an edited nucleic acid sequence. A target nucleic acid can comprise a nucleic acid sequence that may not be related to any other sequence in a nucleic acid sample by a single nucleotide substitution. A target nucleic acid can comprise a nucleic acid sequence that may not be related to any other sequence in a nucleic acid sample by a 2, 3, 4, 5, 6, 7, 8, 9, or 10 nucleotide substitutions. In some embodiments, the substitution may not occur within 5, 10, 15, 20, 25, 30, or 35 nucleotides of the 5' end of a target nucleic acid. In some embodiments, the substitution may not occur within 5, 10, 15, 20, 25, 30, 35 nucleotides of the 3' end of a target nucleic acid.

The term "expression" refers to one or more processes by which a polynucleotide is transcribed from a DNA template (such as into an mRNA or other RNA transcript) and/or the process by which a transcribed mRNA is subsequently translated into peptides, polypeptides, or proteins. Transcripts and encoded polypeptides can be collectively referred to as "gene product." If the polynucleotide is derived from genomic DNA, expression can include splicing of the mRNA in a eukaryotic cell. "Up-regulated," with reference to expression, generally refers to an increased expression level of a polynucleotide (e.g., RNA such as mRNA) and/or polypeptide sequence relative to its expression level in a wild-type state while "down-regulated" generally refers to a decreased expression level of a polynucleotide (e.g., RNA such as mRNA) and/or polypeptide sequence relative to its expression in a wild-type state.

The terms "complement," "complements," "complementary," and "complementarity," as used herein, generally refer to a sequence that is fully complementary to and hybridizable to the given sequence. In some cases, a sequence hybridized with a given nucleic acid is referred to as the "complement" or "reverse-complement" of the given molecule if its sequence of bases over a given region is capable of complementarily binding those of its binding partner, such that, for example, A-T, A-U, G-C, and G-U base pairs are formed. In general, a first sequence that is hybridizable to a second sequence is specifically or selectively hybridizable to the second sequence, such that hybridization to the second sequence or set of second sequences is preferred (e.g. thermodynamically more stable under a given set of conditions, such as stringent conditions commonly used in the art) to hybridization with non-target sequences during a hybridization reaction. Typically, hybridizable sequences share a degree of sequence complementarity over all or a portion of their respective lengths, such as between 25%-100% complementarity, including at least 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99%, and 100% sequence complementarity. Sequence identity, such as for the purpose of assessing percent complementarity, can be measured by any suitable alignment algorithm, including but not limited to the Needleman-Wunsch algorithm (see e.g. the EMBOSS Needle aligner available at www.ebi.ac.uk/Tools/psa/emboss_needle/nucleotide.html, optionally with default settings), the BLAST algorithm (see e.g. the BLAST alignment tool available at blast.ncbi.nlm.nih.gov/Blast.cgi, optionally with default settings), or the Smith-Waterman algorithm (see e.g. the EMBOSS Water aligner available at www.ebi.ac.uk/Tools/psa/emboss_water/nucleotide.html, optionally with default settings). Optimal alignment can be assessed using any suitable parameters of a chosen algorithm, including default parameters.

Complementarity can be perfect or substantial/sufficient. Perfect complementarity between two nucleic acids can mean that the two nucleic acids can form a duplex in which every base in the duplex is bonded to a complementary base by Watson-Crick pairing. Substantial or sufficient complementary can mean that a sequence in one strand is not completely and/or perfectly complementary to a sequence in an opposing strand, but that sufficient bonding occurs between bases on the two strands to form a stable hybrid complex in set of hybridization conditions (e.g., salt concentration and temperature). Such conditions can be predicted by using the sequences and standard mathematical calculations to predict the Tm of hybridized strands, or by empirical determination of Tm by using routine methods.

The term "regulating" with reference to expression or activity, as used herein, refers to altering the level of expression or activity. Regulation can occur at the transcription level and/or translation level.

The terms "peptide," "polypeptide," and "protein" are used interchangeably herein to refer to a polymer of at least two amino acid residues joined by peptide bond(s). This term does not connote a specific length of polymer, nor is it intended to imply or distinguish whether the peptide is produced using recombinant techniques, chemical or enzymatic synthesis, or is naturally occurring. The terms apply to naturally occurring amino acid polymers as well as amino acid polymers comprising at least one modified amino acid. In some cases, the polymer can be interrupted by non-amino acids. The terms include amino acid chains of any length, including full length proteins, and proteins with or without secondary and/or tertiary structure (e.g., domains). The terms also encompass an amino acid polymer that has been modified, for example, by disulfide bond formation, glycosylation, lipidation, acetylation, phosphorylation, oxidation, and any other manipulation such as conjugation with a labeling component. The terms "amino acid" and "amino acids," as used herein, generally refer to natural and non-natural amino acids, including, but not limited to, modified amino acids and amino acid analogues. Modified amino acids can include natural amino acids and non-natural amino acids, which have been chemically modified to include a group or a chemical moiety not naturally present on the amino acid. Amino acid analogues can refer to amino acid derivatives. The term "amino acid" includes both D-amino acids and L-amino acids.

The terms "derivative," "variant," and "fragment," when used herein with reference to a polypeptide, refers to a polypeptide related to a wild type polypeptide, for example either by amino acid sequence, structure (e.g., secondary and/or tertiary), activity (e.g., enzymatic activity) and/or function. Derivatives, variants and fragments of a polypeptide can comprise one or more amino acid variations (e.g., mutations, insertions, and deletions), truncations, modifications, or combinations thereof compared to a wild type polypeptide.

The term "percent (%) identity," as used herein, refers to the percentage of amino acid (or nucleic acid) residues of a candidate sequence that are identical to the amino acid (or nucleic acid) residues of a reference sequence after aligning the sequences and introducing gaps, if necessary, to achieve the maximum percent identity (i.e., gaps can be introduced in one or both of the candidate and reference sequences for optimal alignment and non-homologous sequences can be disregarded for comparison purposes). Alignment, for purposes of determining percent identity, can be achieved in various ways that are within the skill in the art, for instance, using publicly available computer software such as BLAST, ALIGN, or Megalign (DNASTAR) software. Percent identity of two sequences can be calculated by aligning a test sequence with a comparison sequence using BLAST, determining the number of amino acids or nucleotides in the aligned test sequence that are identical to amino acids or nucleotides in the same position of the comparison sequence, and dividing the number of identical amino acids or nucleotides by the number of amino acids or nucleotides in the comparison sequence.

The term "gene modulating polypeptide" or "GMP," as used herein, refers to a polypeptide comprising at least an actuator moiety capable of regulating expression or activity of a gene and/or editing a nucleic acid sequence. A GMP can comprise additional peptide sequences which are not involved in modulating gene expression, for example cleavage recognition sites, linker sequences, targeting sequences, etc.

The term "actuator moiety," as used herein, refers to a moiety which can regulate expression or activity of a gene and/or edit a nucleic acid sequence, whether exogenous or endogenous. An actuator moiety can regulate expression of a gene at the transcription level and/or the translation level. An actuator moiety can regulate gene expression at the transcription level, for example, by regulating the production of mRNA from DNA, such as chromosomal DNA or cDNA. In some embodiments, an actuator moiety recruits at least one transcription factor that binds to a specific DNA sequence, thereby controlling the rate of transcription of genetic information from DNA to mRNA. An actuator moiety can itself bind to DNA and regulate transcription by physical obstruction, for example preventing proteins such as RNA polymerase and other associated proteins from assembling on a DNA template. An actuator moiety can regulate expression of a gene at the translation level, for example, by regulating the production of protein from mRNA template. In some embodiments, an actuator moiety regulates gene expression by affecting the stability of an mRNA transcript. In some embodiments, an actuator moiety regulates expression of a gene by editing a nucleic acid sequence (e.g., a region of a genome). In some embodiments, an actuator moiety regulates expression of a gene by editing an mRNA template. Editing a nucleic acid sequence can, in some cases, alter the underlying template for gene expression.

A Cas protein referred to herein can be a type of protein or polypeptide. A Cas protein can refer to a nuclease. A Cas protein can refer to an endoribonuclease. A Cas protein can refer to any modified (e.g., shortened, mutated, lengthened) polypeptide sequence or homologue of the Cas protein. A Cas protein can be codon optimized. A Cas protein can be a codon-optimized homologue of a Cas protein. A Cas protein can be enzymatically inactive, partially active, constitutively active, fully active, inducible active and/or more active, (e.g. more than the wild type homologue of the protein or polypeptide.). A Cas protein can be Cas9. A Cas protein can be Cpf1. A Cas protein can be C2c2. A Cas protein (e.g., variant, mutated, enzymatically inactive and/or conditionally enzymatically inactive site-directed polypeptide) can bind to a target nucleic acid. A Cas protein (e.g., variant, mutated, enzymatically inactive and/or conditionally enzymatically inactive endoribonuclease) can bind to a target RNA or DNA.

The term "crRNA," as used herein, can generally refer to a nucleic acid with at least about 5%, 10%, 20%, 30%, 40%, 50%, 60%, 70%, 80%, 90%, or 100% sequence identity and/or sequence similarity to a wild type exemplary crRNA (e.g., a crRNA from S. pyogenes). crRNA can generally refer to a nucleic acid with at most about 5%, 10%, 20%, 30%, 40%, 50%, 60%, 70%, 80%, 90%, or 100% sequence identity and/or sequence similarity to a wild type exemplary crRNA (e.g., a crRNA from S. pyogenes). crRNA can refer to a modified form of a crRNA that can comprise a nucleotide change such as a deletion, insertion, or substitution, variant, mutation, or chimera. A crRNA can be a nucleic acid having at least about 60% sequence identity to a wild type exemplary crRNA (e.g., a crRNA from S. pyogenes) sequence over a stretch of at least 6 contiguous nucleotides. For example, a crRNA sequence can be at least about 60% identical, at least about 65% identical, at least about 70% identical, at least about 75% identical, at least about 80% identical, at least about 85% identical, at least about 90% identical, at least about 95% identical, at least about 98% identical, at least about 99% identical, or 100% identical to a wild type exemplary crRNA sequence (e.g., a crRNA from S. pyogenes) over a stretch of at least 6 contiguous nucleotides.

The term "tracrRNA," as used herein, can generally refer to a nucleic acid with at least about 5%, 10%, 20%, 30%, 40%, 50%, 60%, 70%, 80%, 90%, or 100% sequence identity and/or sequence similarity to a wild type exemplary tracrRNA sequence (e.g., a tracrRNA from S. pyogenes). tracrRNA can refer to a nucleic acid with at most about 5%, 10%, 20%, 30%, 40%, 50%, 60%, 70%, 80%, 90%, or 100% sequence identity and/or sequence similarity to a wild type exemplary tracrRNA sequence (e.g., a tracrRNA from S. pyogenes). tracrRNA can refer to a modified form of a tracrRNA that can comprise a nucleotide change such as a deletion, insertion, or substitution, variant, mutation, or chimera. A tracrRNA can refer to a nucleic acid that can be at least about 60% identical to a wild type exemplary tracrRNA (e.g., a tracrRNA from S. pyogenes) sequence over a stretch of at least 6 contiguous nucleotides. For example, a tracrRNA sequence can be at least about 60% identical, at least about 65% identical, at least about 70% identical, at least about 75% identical, at least about 80% identical, at least about 85% identical, at least about 90% identical, at least about 95% identical, at least about 98% identical, at least about 99% identical, or 100% identical to a wild type exemplary tracrRNA (e.g., a tracrRNA from S. pyogenes) sequence over a stretch of at least 6 contiguous nucleotides.

As used herein, a "guide nucleic acid" can refer to a nucleic acid that can hybridize to another nucleic acid. A guide nucleic acid can be RNA. A guide nucleic acid can be DNA. The guide nucleic acid can be programmed to bind to a sequence of nucleic acid site-specifically. The nucleic acid to be targeted, or the target nucleic acid, can comprise nucleotides. The guide nucleic acid can comprise nucleotides. A portion of the target nucleic acid can be complementary to a portion of the guide nucleic acid. The strand of a double-stranded target polynucleotide that is complementary to and hybridizes with the guide nucleic acid can be called the complementary strand. The strand of the double-stranded target polynucleotide that is complementary to the complementary strand, and therefore may not be complementary to the guide nucleic acid can be called noncomplementary strand. A guide nucleic acid can comprise a polynucleotide chain and can be called a "single guide nucleic acid." A guide nucleic acid can comprise two polynucleotide chains and can be called a "double guide nucleic acid." If not otherwise specified, the term "guide nucleic acid" can be inclusive, referring to both single guide nucleic acids and double guide nucleic acids.

A guide nucleic acid can comprise a segment that can be referred to as a "nucleic acid-targeting segment" or a "nucleic acid-targeting sequence." A nucleic acid-targeting segment can comprise a sub-segment that can be referred to as a "protein binding segment" or "protein binding sequence" or "Cas protein binding segment".

The term "cleavage recognition site," as used herein, with reference to peptides, refers to a site of a peptide at which a chemical bond, such as a peptide bond or disulfide bond, can be cleaved. Cleavage can be achieved by various methods. Cleavage of peptide bonds can be facilitated, for example, by an enzyme such as a protease or by protein splicing (e.g., inteins). Cleavage of a disulfide bond can be facilitated, for example, by an enzyme such as an oxidoreductase.

The term "targeting sequence," as used herein, refers to a nucleotide sequence and the corresponding amino acid sequence which encodes a targeting polypeptide which mediates the localization (or retention) of a protein to a sub-cellular location, e.g., plasma membrane or membrane of a given organelle, nucleus, cytosol, mitochondria, endoplasmic reticulum (ER), Golgi, chloroplast, apoplast, peroxisome or other organelle. For example, a targeting sequence can direct a protein (e.g., a receptor polypeptide or an adaptor polypeptide) to a nucleus utilizing a nuclear localization signal (NLS); outside of a nucleus of a cell, for example to the cytoplasm, utilizing a nuclear export signal (NES); mitochondria utilizing a mitochondrial targeting signal; the endoplasmic reticulum (ER) utilizing an ER-retention signal; a peroxisome utilizing a peroxisomal targeting signal; plasma membrane utilizing a membrane localization signal; or combinations thereof.

As used herein, "fusion" can refer to a protein and/or nucleic acid comprising one or more non-native sequences (e.g., moieties). A fusion can comprise one or more of the same non-native sequences. A fusion can comprise one or more of different non-native sequences. A fusion can be a chimera. A fusion can comprise a nucleic acid affinity tag. A fusion can comprise a barcode. A fusion can comprise a peptide affinity tag. A fusion can provide for subcellular localization of the site-directed polypeptide (e.g., a nuclear localization signal (NLS) for targeting to the nucleus, a mitochondrial localization signal for targeting to the mitochondria, a chloroplast localization signal for targeting to a chloroplast, an endoplasmic reticulum (ER) retention signal, and the like). A fusion can provide a non-native sequence (e.g., affinity tag) that can be used to track or purify. A fusion can be a small molecule such as biotin or a dye such as Alexa fluor dyes, Cyanine3 dye, Cyanine5 dye.

A fusion can refer to any protein with a functional effect. For example, a fusion protein can comprise methyltransferase activity, demethylase activity, dismutase activity, alkylation activity, depurination activity, oxidation activity, pyrimidine dimer forming activity, integrase activity, transposase activity, recombinase activity, polymerase activity, ligase activity, helicase activity, photolyase activity or glycosylase activity, acetyltransferase activity, deacetylase activity, kinase activity, phosphatase activity, ubiquitin ligase activity, deubiquitinating activity, adenylation activity, deadenylation activity, SUMOylating activity, deSUMOylating activity, ribosylation activity, deribosylation activity, myristoylation activity, remodelling activity, protease activity, oxidoreductase activity, transferase activity, hydrolase activity, lyase activity, isomerase activity, synthase activity, synthetase activity, or demyristoylation activity. An effector protein can modify a genomic locus. A fusion protein can be a fusion in a Cas protein. An fusion protein can be a non-native sequence in a Cas protein.

As used herein, "non-native" can refer to a nucleic acid or polypeptide sequence that is not found in a native nucleic acid or protein. Non-native can refer to affinity tags. Non-native can refer to fusions. Non-native can refer to a naturally occurring nucleic acid or polypeptide sequence that comprises mutations, insertions and/or deletions. A non-native sequence may exhibit and/or encode for an activity (e.g., enzymatic activity, methyltransferase activity, acetyltransferase activity, kinase activity, ubiquitinating activity, etc.) that can also be exhibited by the nucleic acid and/or polypeptide sequence to which the non-native sequence is fused. A non-native nucleic acid or polypeptide sequence may be linked to a naturally-occurring nucleic acid or polypeptide sequence (or a variant thereof) by genetic engineering to generate a chimeric nucleic acid and/or polypeptide sequence encoding a chimeric nucleic acid and/or polypeptide.

The terms "subject," "individual," and "patient" are used interchangeably herein to refer to a vertebrate, preferably a mammal such as a human. Mammals include, but are not limited to, murines, simians, humans, farm animals, sport animals, and pets. Tissues, cells and their progeny of a biological entity obtained in vivo or cultured in vitro are also encompassed.

The terms "treatment" and "treating," as used herein, refer to an approach for obtaining beneficial or desired results including but not limited to a therapeutic benefit and/or a prophylactic benefit. For example, a treatment can comprise administering a system or cell population disclosed herein. By therapeutic benefit is meant any therapeutically relevant improvement in or effect on one or more diseases, conditions, or symptoms under treatment. For prophylactic benefit, a composition can be administered to a subject at risk of developing a particular disease, condition, or symptom, or to a subject reporting one or more of the physiological symptoms of a disease, even though the disease, condition, or symptom may not have yet been manifested.

The term "effective amount" or "therapeutically effective amount" refers to the quantity of a composition, for example a composition comprising immune cells such as lymphocytes (e.g., T lymphocytes and/or NK cells) comprising a system of the present disclosure, that is sufficient to result in a desired activity upon administration to a subject in need thereof. Within the context of the present disclosure, the term "therapeutically effective" refers to that quantity of a composition that is sufficient to delay the manifestation, arrest the progression, relieve or alleviate at least one symptom of a disorder treated by the methods of the present disclosure.

In an aspect, the present disclosure provides systems for conditional regulation of an immune cell. An exemplary system comprises (a) a chimeric transmembrane receptor polypeptide comprising (i) an extracellular region comprising an antigen interacting domain that binds an antigen and (ii) an intracellular region comprising an immune cell signaling domain, (b) a chimeric adaptor polypeptide comprising a receptor binding moiety that binds the chimeric transmembrane receptor polypeptide when the receptor polypeptide has undergone modification upon binding to an antigen, (c) a gene modulating polypeptide (GMP) comprising an actuator moiety linked to a cleavage recognition site, and (d) a cleavage moiety that cleaves the cleavage recognition site only when in proximity to the cleavage recognition site to release the actuator moiety from the GMP, wherein (i) the GMP forms a portion of the intracellular region of the receptor, and the cleavage moiety forms a portion of the adaptor polypeptide, (ii) the GMP forms a portion of the adaptor polypeptide, and the cleavage moiety forms a portion of the intracellular region of the receptor, or (iii) the cleavage moiety is complexed with a second adaptor polypeptide that binds the chimeric transmembrane receptor polypeptide in response to the receptor modification, and the GMP forms a portion of the chimeric adaptor polypeptide.

The chimeric transmembrane receptor polypeptide, chimeric adaptor polypeptide, gene modulating polypeptide (GMP), and cleavage moiety of a subject system can be arranged in a variety of configurations. In an exemplary configuration, the GMP forms a portion of the intracellular region of the chimeric transmembrane receptor polypeptide and the cleavage moiety forms a portion of the chimeric adaptor polypeptide. A chimeric transmembrane receptor polypeptide of an exemplary configuration can comprise (a) an extracellular region comprising an antigen interacting domain that binds an antigen; and (b) an intracellular region comprising (i) an immune cell signaling domain; and (ii) a gene modulating polypeptide (GMP) linked to the immune cell signaling domain, wherein the GMP comprises an actuator moiety linked to a cleavage recognition site; wherein only upon binding of the antigen to the extracellular region of the chimeric transmembrane receptor polypeptide comprising an antigen interacting domain, the actuator moiety is released from the GMP by cleavage of the cleavage recognition site.

In an illustrative example shown in FIG. 1, the extracellular region of a receptor can comprise an antigen interacting domain 101 and the intracellular region can comprise (i) an immune cell signaling domain 102 and (ii) a GMP comprising an actuator moiety 103 linked to a cleavage recognition site 104.

An antigen interacting domain of a chimeric transmembrane receptor polypeptide can comprise any protein or molecule that can bind to an antigen. An antigen interacting domain of a chimeric transmembrane receptor polypeptide disclosed herein can be a monoclonal antibody, a polyclonal antibody, a recombinant antibody, a human antibody, a humanized antibody, or a functional derivative, variant or fragment thereof, including, but not limited to, a Fab, a Fab', a F(ab')$_2$, an Fv, a single-chain Fv (scFv), minibody, a diabody, and a single-domain antibody such as a heavy chain variable domain (VH), a light chain variable domain (VL) and a variable domain (VHH) of camelid derived Nanobody. In some embodiments, an antigen interacting domain comprises at least one of a Fab, a Fab', a F(ab')$_2$, an Fv, and a scFv. In some embodiments, an antigen interacting domain comprises an antibody mimetic. Antibody mimetics refer to molecules which can bind a target molecule with an affinity comparable to an antibody, and include single-chain binding molecules, cytochrome b562-based binding molecules, fibronectin or fibronectin-like protein scaffolds (e.g., adnectins), lipocalin scaffolds, calixarene scaffolds, A-domains and other scaffolds. In some embodiments, an antigen interacting domain comprises a transmembrane receptor, or any derivative, variant, or fragment thereof. For example, an antigen interacting domain can comprise at least a ligand binding domain of a transmembrane receptor.

In some embodiments, the antigen interacting domain comprises a humanized antibody. A humanized antibody can be produced using a variety of techniques including, but not limited to, CDR-grafting, veneering or resurfacing, chain shuffling, and other techniques. Human variable domains, including light and heavy chains, can be selected to reduce the immunogenicity of humanized antibodies. In some embodiments, the antigen interacting domain of a chimeric transmembrane receptor polypeptide comprises a fragment of a humanized antibody which binds an antigen with high affinity and possesses other favorable biological properties, such as reduced and/or minimal immunogenicity. A humanized antibody or antibody fragment can retain a similar antigenic specificity as the corresponding non-humanized antibody.

In some embodiments, the antigen interacting domain comprises a single-chain variable fragment (scFv). scFv molecules can be produced by linking the heavy chain (VH) and light chain (VL) regions of immunoglobulins together using flexible linkers, such as polypeptide linkers. scFvs can be prepared according to various methods.

In some embodiments, the antigen interacting domain is engineered to bind a specific target antigen. For example, the antigen interacting domain can be an engineered scFv. An antigen interacting domain comprising a scFv can be engineered using a variety of methods, including but not limited to display libraries such as phage display libraries, yeast display libraries, cell based display libraries (e.g., mammalian cells), protein-nucleic acid fusions, ribosome display libraries, and/or an E. coli periplasmic display libraries. In some embodiments, an antigen interacting domain which is engineered may bind to an antigen with a higher affinity than an analogous antibody or an antibody which has not undergone engineering.

In some embodiments, the antigen interacting domain binds multiple antigens, e.g., at least 2, 3, 4, 5, 6, 7, 8, 9, or 10 antigens. An antigen interacting domain can bind two related antigens, such as two subtypes of botulin toxin (e.g., botulinum neurotoxin subtype A1 and subtype A2). An antigen interacting domain can bind two unrelated proteins, such as receptor tyrosine kinase erbB-2 (also referred to as Neu, ERBB2, and HER2) and vascular endothelial growth factor (VEGF). An antigen interacting domain capable of binding two antigens can comprise an antibody engineered to bind two unrelated protein targets at distinct but overlapping sites of the antibody. In some embodiments, an antigen interacting domain which binds multiple antigens comprises a bispecific antibody molecule. A bispecific antibody molecule can have a first immunoglobulin variable domain sequence which has binding specificity for a first epitope and a second immunoglobulin variable domain sequence that has binding specificity for a second epitope. In some embodiments, the first and second epitopes are on the same antigen, e.g., the same protein (or subunit of a multimeric protein). The first and second epitopes can overlap. In some embodiments, the first and second epitopes do not overlap. In some embodiments, the first and second epitopes are on different antigens, e.g., different proteins (or different subunits of a multimeric protein). In some embodiments a bispecific antibody molecule comprises a heavy chain variable domain sequence and a light chain variable domain sequence which have binding specificity for a first epitope and a heavy chain variable domain sequence and a light chain variable domain sequence which have binding specificity for a second epitope. In some embodiments, a bispecific antibody molecule comprises a half antibody having binding specificity for a first epitope and a half antibody having binding specificity for a second epitope. In some embodiments, a bispecific antibody molecule comprises a half antibody, or fragment thereof, having binding specificity for a first epitope and a half antibody, or fragment thereof, having binding specificity for a second epitope.

In some embodiments, the extracellular region of a chimeric transmembrane receptor polypeptide comprises multiple antigen interacting domains, for example at least 2 antigen interacting domains (e.g., at least 3, 4, 5, 6, 7, 8, 9, or 10 antigen interacting domains). The multiple antigen interacting domains can exhibit binding to the same or different antigen. In some embodiments, the extracellular region comprises at least two antigen interacting domains, for example at least two scFvs linked in tandem. In some embodiments, two scFv fragments are linked by a peptide linker.

The antigen interacting domain of an extracellular region of a chimeric transmembrane receptor polypeptide can bind a membrane bound antigen, for example an antigen at the extracellular surface of a cell (e.g., a target cell). In some embodiments, the antigen interacting domain binds an antigen that is not membrane bound (e.g., non membrane-bound), for example an extracellular antigen that is secreted by a cell (e.g., a target cell) or an antigen located in the cytoplasm of a cell (e.g., a target cell). Antigens (e.g., membrane bound and non-membrane bound) can be associated with a disease such as a viral, bacterial, and/or parasitic infection; inflammatory and/or autoimmune disease; or neoplasm such as a cancer and/or tumor. Non-limiting examples of antigens which can be bound by an antigen interacting domain of a chimeric transmembrane receptor polypeptide of a subject system include, but are not limited to, 1-40-β-amyloid, 4-1BB, SAC, 5T4, 707-AP, A kinase anchor protein 4 (AKAP-4), activin receptor type-2B (ACVR2B), activin receptor-like kinase 1 (ALK1), adenocarcinoma antigen, adipophilin, adrenoceptor β3 (ADRB3), AGS-22M6, α folate receptor, α-fetoprotein (AFP), AIM-2, anaplastic lymphoma kinase (ALK), androgen receptor, angiopoietin 2, angiopoietin 3, angiopoietin-binding cell surface receptor 2 (Tie 2), anthrax toxin, AOC3 (VAP-1), B cell maturation antigen (BCMA), B7-H3 (CD276), *Bacillus anthracis* anthrax, B-cell activating factor (BAFF), B-lymphoma cell, bone marrow stromal cell antigen 2 (BST2), Brother of the Regulator of Imprinted Sites (BORIS), C242 antigen, C5, CA-125, cancer antigen 125 (CA-125 or MUC16), Cancer/testis antigen 1 (NY-ESO-1), Cancer/testis antigen 2 (LAGE-1a), carbonic anhydrase 9 (CA-IX), Carcinoembryonic antigen (CEA), cardiac myosin, CCCTC-Binding Factor (CTCF), CCL11 (eotaxin-1), CCR4, CCR5, CD11, CD123, CD125, CD140a, CD147 (basigin), CD15, CD152, CD154 (CD40L), CD171, CD179a, CD18, CD19, CD2, CD20, CD200, CD22, CD221, CD23 (IgE receptor), CD24, CD25 (a chain of IL-2receptor), CD27, CD274, CD28, CD3, CD3 ε, CD30, CD300 molecule-like family member f (CD300LF), CD319 (SLAMF7), CD33, CD37, CD38, CD4, CD40, CD40 ligand, CD41, CD44 v7, CD44 v8, CD44 v6, CD5, CD51, CD52, CD56, CD6, CD70, CD72, CD74, CD79A, CD79B, CD80, CD97, CEA-related antigen, CFD, ch4D5, chromosome X open reading frame 61 (CXORF61), claudin 18.2 (CLDN18.2), claudin 6 (CLDN6), *Clostridium difficile*, clumping factor A, CLCA2, colony stimulating factor 1 receptor (CSF1R), CSF2, CTLA-4, C-type lectin domain family 12 member A (CLEC12A), C-type lectin-like molecule-1 (CLL-1 or CLECL1), C—X—C chemokine receptor type 4, cyclin B1, cytochrome P4501B1 (CYP1B1), cyp-B, cytomegalovirus, cytomegalovirus glycoprotein B, dabigatran, DLL4, DPP4, DRS, *E. coli* shiga toxin type-1, *E. coli* shiga toxin type-2, ecto-ADP-ribosyltransferase 4 (ART4), EGF-like module-containing mucin-like hormone receptor-like 2 (EMR2), EGF-like-domain multiple 7 (EGFL7), elongation factor 2 mutated (ELF2M), endotoxin, Ephrin A2, Ephrin B2, ephrin type-A receptor 2, epidermal growth factor receptor (EGFR), epidermal growth factor receptor variant III (EGFRvIII), episialin, epithelial cell adhesion molecule (EpCAM), epithelial glycoprotein 2 (EGP-2), epithelial glycoprotein 40 (EGP-40), ERBB2, ERBB3, ERBB4, ERG (transmembrane protease, serine 2 (TMPRSS2) ETS fusion gene), *Escherichia coli*, ETS translocation-variant gene 6, located on chromosome 12p (ETV6-AML), F protein of respiratory syncytial virus, FAP, Fc fragment of IgA receptor (FCAR or CD89), Fc receptor-like 5 (FCRL5), fetal acetylcholine receptor, fibrin II β chain, fibroblast activation protein α (FAP), fibronectin extra domain-B, FGF-5, Fms-Like Tyrosine Kinase 3 (FLT3), folate binding protein (FBP), folate hydrolase, folate receptor 1, folate receptor α, folate receptor β, Fos-related antigen 1, Frizzled receptor, Fucosyl GM1, G250, G protein-coupled receptor 20 (GPR20), G protein-coupled receptor class C group 5, member D (GPRC5D), ganglioside G2 (GD2), GD3 ganglioside, glycoprotein 100 (gp100), glypican-3 (GPC3), GMCSF receptor α-chain, GPNMB, GnT-V, growth differentiation factor 8, GUCY2C, heat shock protein 70-2 mutated (mut hsp70-2), hemagglutinin, Hepatitis A virus cellular receptor 1 (HAVCR1), hepatitis B surface antigen, hepatitis B virus, HER1, HER2/neu, HER3, hexasaccharide portion of globoH glycoceramide (GloboH), HGF, HHGFR, high molecular weight-melanoma-associated antigen (HMW-MAA), histone complex, HIV-1, HLA-DR, HNGF, Hsp90, HST-2 (FGF6), human papilloma virus E6 (HPV E6), human papilloma virus E7 (HPV E7), human scatter factor receptor kinase, human Telomerase reverse transcriptase (hTERT), human TNF, ICAM-1 (CD54), iCE, IFN-α, IFN-β, IFN-γ, IgE, IgE Fc region, IGF-1, IGF-1 receptor, IGHE, IL-12, IL-13, IL-17, IL-17A, IL-17F, IL-1β, IL-20, IL-22, IL-23, IL-31, IL-31RA, IL-4, IL-5, IL-6, IL-6 receptor, IL-9, immunoglobulin lambda-like polypeptide 1 (IGLL1), influenza A hemagglutinin, insulin-like growth factor 1 receptor (IGF-I receptor), insulin-like growth factor 2 (ILGF2), integrin α4β7, integrin β2, integrin α2, integrin α4, integrin α5β1, integrin α7β7, integrin αIIbβ3, integrin αvβ3, interferon α/β receptor, interferon γ-induced protein, Interleukin 11 receptor α (IL-11Rα), Interleukin-13 receptor subunit α-2 (IL-13Ra2 or CD213A2), intestinal carboxyl esterase, kinase domain region (KDR), KIR2D, KIT (CD117), L1-cell adhesion molecule (L1-CAM), legumain, leukocyte immunoglobulin-like receptor subfamily A member 2 (LILRA2), leukocyte-associated immunoglobulin-like receptor 1 (LAIR1), Lewis-Y antigen, LFA-1 (CD11a), LINGO-1, lipoteichoic acid, LOXL2, L-selectin (CD62L), lymphocyte antigen 6 complex, locus K 9 (LY6K), lymphocyte antigen 75 (LY75), lymphocyte-specific protein tyrosine kinase (LCK), lymphotoxin-α (LT-α) or Tumor necrosis factor-β (TNF-β), macrophage migration inhibitory factor (MIF or MMIF), M-CSF, mammary gland differentiation antigen (NY-BR-1), MCP-1, melanoma cancer testis antigen-1 (MAD-CT-1), melanoma cancer testis antigen-2 (MAD-CT-2), melanoma inhibitor of apoptosis (ML-IAP), melanoma-associated antigen 1 (MAGE-A1), mesothelin, mucin 1, cell surface associated (MUC1), MUC-2, mucin CanAg, myelin-associated glycoprotein, myostatin, N-Acetyl glucosaminyl-transferase V (NA17), NCA-90 (granulocyte antigen), nerve growth factor (NGF), neural apoptosis-regulated proteinase 1, neural cell adhesion molecule (NCAM), neurite outgrowth inhibitor (e.g., NOGO-A, NOGO-B, NOGO-C), neuropilin-1 (NRP1), N-glycolyl-neuraminic acid, NKG2D, Notch receptor, o-acetyl-GD2 ganglioside (OAcGD2), olfactory receptor 51E2 (OR51E2), oncofetal antigen (h5T4), oncogene fusion protein consisting of breakpoint cluster region (BCR) and Abelson murine leukemia viral oncogene homolog 1 (Abl) (bcr-abl), *Oryctolagus cuniculus*, OX-40, oxLDL, p53 mutant, paired box protein Pax-3 (PAX3), paired box protein Pax-5 (PAX5), pannexin 3 (PANX3), phosphate-sodium co-transporter, phosphatidylserine, placenta-specific 1 (PLAC1), platelet-derived growth factor receptor α (PDGF-R α), platelet-derived growth factor receptor β (PDGFR-β), polysialic acid, proacrosin binding protein sp32 (OY-TES1), programmed cell death protein 1 (PD-1), proprotein convertase subtilisin/kexin type 9 (PCSK9), prostase, prostate carcinoma tumor antigen-1 (PCTA-1 or Galectin 8), melanoma antigen recognized by T cells 1 (MelanA or MART1), P15, P53, PRAME, prostate stem cell antigen (PSCA), prostate-specific membrane antigen (PSMA), prostatic acid phosphatase (PAP), prostatic carcinoma cells, prostein, Protease Serine 21 (Testisin or PRSS21), Proteasome (Prosome, Macropain) Subunit, β Type, 9 (LMP2), *Pseudomonas* aeruginosa, rabies virus glycoprotein, RAGE, Ras Homolog Family Member C (RhoC), receptor activator of nuclear factor kappa-B ligand (RANKL), Receptor for Advanced Glycation Endproducts (RAGE-1), receptor tyrosine kinase-like orphan receptor 1 (ROR1), renal ubiquitous 1 (RU1), renal ubiquitous 2 (RU2), respiratory syncytial virus, Rh blood group D antigen, Rhesus factor, sarcoma translocation breakpoints, sclerostin (SOST), selectin P, sialyl Lewis adhesion molecule (sLe), sperm protein 17 (SPA17), sphingosine-1-phosphate, squamous cell carcinoma antigen recognized by T Cells 1, 2, and 3 (SART1, SART2, and SART3), stage-specific embryonic antigen-4 (SSEA-4), *Staphylococcus aureus*, STEAP1, surviving, syndecan 1 (SDC1)+A314, SOX10, survivin, surviving-2B, synovial sarcoma, X breakpoint 2 (SSX2), T-cell receptor, TCR Γ Alternate Reading Frame Protein (TARP), telomerase, TEM1, tenascin C, TGF-β (e.g., TGF-β 1, TGF-β 2, TGF-β 3), thyroid stimulating hormone receptor (TSHR), tissue factor pathway inhibitor (TFPI), Tn antigen ((Tn Ag) or (GalNAca-Ser/Thr)), TNF receptor family member B cell maturation (BCMA), TNF-α, TRAIL-R1, TRAIL-R2, TRG, transglutaminase 5 (TGS5), tumor antigen CTAA16.88, tumor endothelial marker 1 (TEM1/CD248), tumor endothelial marker 7-related (TEM7R), tumor protein p53 (p53), tumor specific glycosylation of MUC1, tumor-associated calcium signal transducer 2, tumor-associated glycoprotein 72 (TAG72), tumor-associated glycoprotein 72 (TAG-72)+A327, TWEAK receptor, tyrosinase, tyrosinase-related protein 1 (TYRP1 or glycoprotein 75), tyrosinase-related protein 2 (TYRP2), uroplakin 2 (UPK2), vascular endothelial growth factor (e.g., VEGF-A, VEGF-B, VEGF-C, VEGF-D, PlGF), vascular endothelial growth factor receptor 1 (VEGFR1), vascular endothelial growth factor receptor 2 (VEGFR2), vimentin, v-myc avian myelocytomatosis viral oncogene neuroblastoma derived homolog (MYCN), von Willebrand factor (VWF), Wilms tumor protein (WT1), X Antigen Family, Member 1A (XAGE1), β-amyloid, and κ-light chain.

In some embodiments, the antigen interacting domain binds an antigen selected from the group consisting of: 707-AP, a biotinylated molecule, a-Actinin-4, abl-bcr alb-b3 (b2a2), abl-bcr alb-b4 (b3a2), adipophilin, AFP, AIM-2, Annexin II, ART-4, BAGE, b-Catenin, bcr-abl, bcr-abl p190 (e1a2), bcr-abl p210 (b2a2), bcr-abl p210 (b3a2), BING-4, CAG-3, CAIX, CAMEL, Caspase-8, CD171, CD19, CD20, CD22, CD23, CD24, CD30, CD33, CD38, CD44v7/8, CDC27, CDK-4, CEA, CLCA2, Cyp-B, DAM-10, DAM-6, DEK-CAN, EGFRvIII, EGP-2, EGP-40, ELF2, Ep-CAM, EphA2, EphA3, erb-B2, erb-B3, erb-B4, ES-ESO-1a, ETV6/AML, FBP, fetal acetylcholine receptor, FGF-5, FN, G250, GAGE-1, GAGE-2, GAGE-3, GAGE-4, GAGE-5, GAGE-6, GAGE-7B, GAGE-8, GD2, GD3, GnT-V, Gp100, gp75, Her-2, HLA-A*0201-R170I, HMW-MAA, HSP70-2 M, HST-2 (FGF6), HST-2/neu, hTERT, iCE, IL-11Rα, IL-13Rα2, KDR, KIAA0205, K-RAS, L1-cell adhesion molecule, LAGE-1, LDLR/FUT, Lewis Y, MAGE-1, MAGE-10, MAGE-12, MAGE-2, MAGE-3, MAGE-4, MAGE-6, MAGE-A1, MAGE-A2, MAGE-A3, MAGE-A6, MAGE-B1, MAGE-B2, Malic enzyme, Mammaglobin-A, MART-1/Melan-A, MART-2, MC1R, M-CSF, mesothelin, MUC1, MUC16, MUC2, MUM-1, MUM-2, MUM-3, Myosin, NA88-A, Neo-PAP, NKG2D, NPM/ALK, N-RAS, NY-ESO-1, OA1, OGT, oncofetal antigen (h5T4), OS-9, P polypeptide, P15, P53, PRAME, PSA, PSCA, PSMA, PTPRK, RAGE, ROR1, RU1, RU2, SART-1, SART-2, SART-3, SOX10, SSX-2, Survivin, Survivin-2B, SYT/SSX, TAG-72, TEL/AML1, TGFaRII, TGFbRII, TP1, TRAG-3, TRG, TRP-1, TRP-2, TRP-2/INT2, TRP-2-6b, Tyrosinase, VEGF-R2, WT1, α-folate receptor, and κ-light chain. In some embodiments, the antigen interacting domain binds to a tumor associated antigen.

In some embodiments, the antigen interacting domain binds an antigen comprising an antibody e.g., an antibody bound to a cell surface protein or polypeptide. The protein or polypeptide on the cell surface bound by an antibody can comprise an antigen associated with a disease such as a viral, bacterial, and/or parasitic infection; inflammatory and/or autoimmune disease; or neoplasm such as a cancer and/or tumor. In some embodiments, the antibody binds a tumor associated antigen (e.g., protein or polypeptide). In some embodiments, an antigen interacting domain of a chimeric transmembrane receptor polypeptide disclosed herein can bind a monoclonal antibody, a polyclonal antibody, a recombinant antibody, a human antibody, a humanized antibody, or a functional derivative, variant or fragment thereof, including, but not limited to, a Fab, a Fab', a F(ab')$_2$, an Fc, an Fv, a scFv, minibody, a diabody, and a single-domain antibody such as a heavy chain variable domain (VH), a light chain variable domain (VL) and a variable domain (VHH) of camelid derived Nanobody. In some embodiments, an antigen interacting domain can bind at least one of a Fab, a Fab', a F(ab')$_2$, an Fc, an Fv, and a scFv. In some embodiments, the antigen interacting domain binds an Fc domain of an antibody.

In some embodiments, the antigen interacting domain binds an antibody selected from the group consisting of: 20-(74)-(74) (milatuzumab; veltuzumab), 20-2b-2b, 3F8, 74-(20)-(20) (milatuzumab; veltuzumab), 8H9, A33, AB-16B5, abagovomab, abciximab, abituzumab, ABP 494 (cetuximab biosimilar), abrilumab, ABT-700, ABT-806, Actimab-A (actinium Ac-225 lintuzumab), actoxumab, adalimumab, ADC-1013, ADCT-301, ADCT-402, adecatumumab, aducanumab, afelimomab, AFM13, afutuzumab, AGEN1884, AGS15E, AGS-16C3F, AGS67E, alacizumab pegol, ALD518, alemtuzumab, alirocumab, altumomab pentetate, amatuximab, AMG 228, AMG 820, anatumomab mafenatox, anetumab ravtansine, anifrolumab, anrukinzumab, APN301, APN311, apolizumab, APX003/SIM-BD0801 (sevacizumab), APX005M, arcitumomab, ARX788, ascrinvacumab, aselizumab, ASG-15ME, atezolizumab, atinumab, ATL101, atlizumab (also referred to as tocilizumab), atorolimumab, Avelumab, B-701, bapineuzumab, basiliximab, bavituximab, BAY1129980, BAY1187982, bectumomab, begelomab, belimumab, benralizumab, bertilimumab, besilesomab, Betalutin (177Lu-tetraxetan-tetulomab), bevacizumab, BEVZ92 (bevacizumab biosimilar), bezlotoxumab, BGB-A317, BHQ880, BI 836880, BI-505, biciromab, bimagrumab, bimekizumab, bivatuzumab mertansine, BIW-8962, blinatumomab, blosozumab, BMS-936559, BMS-986012, BMS-986016, BMS-986148, BMS-986178, BNC101, bococizumab, brentuximab vedotin, BrevaRex, briakinumab, brodalumab, brolucizumab, brontictuzumab, C2-2b-2b, canakinumab, cantuzumab mertansine, cantuzumab ravtansine, caplacizumab, capromab pendetide, carlumab, catumaxomab, CBR96-doxorubicin immunoconjugate, CBT124 (bevacizumab), CC-90002, CDX-014, CDX-1401, cedelizumab, certolizumab pegol, cetuximab, CGEN-15001T, CGEN-15022, CGEN-15029, CGEN-15049, CGEN-15052, CGEN-15092, Ch.14.18, citatuzumab bogatox, cixutumumab, clazakizumab, clenoliximab, clivatuzumab tetraxetan, CM-24, codrituzumab, coltuximab ravtansine, conatumumab, concizumab, Cotara (iodine 1-131 derlotuximab biotin), cR6261, crenezumab, DA-3111 (trastuzumab biosimilar), dacetuzumab, daclizumab, dalotuzumab, dapirolizumab pegol, daratumumab, Daratumumab Enhanze (daratumumab), Darleukin, dectrekumab, demciztumab, denintuzumab mafodotin, denosumab, Depatuxizumab, Depatuxizumab mafodotin, derlotuximab biotin, detumomab, DI-B4, dinutuximab, diridavumab, DKN-01, DMOT4039A, dorlimomab aritox, drozitumab, DS-1123, DS-8895, duligotumab, dupilumab, durvalumab, dusigitumab, ecromeximab, eculizumab, edobacomab, edrecolomab, efalizumab, efungumab, eldelumab, elgemtumab, elotuzumab, elsilimomab, emactuzumab, emibetuzumab, enavatuzumab, enfortumab vedotin, enlimomab pegol, enoblituzumab, enokizumab, enoticumab, ensituximab, epitumomab cituxetan, epratuzumab, erlizumab, ertumaxomab, etaracizumab, etrolizumab, evinacumab, evolocumab, exbivirumab, fanolesomab, faralimomab, farletuzumab, fasinumab, FBTA05, felvizumab, fezakinumab, FF-21101, FGFR2 Antibody-Drug Conjugate, Fibromun, ficlatuzumab, figitumumab, firivumab, flanvotumab, fletikumab, fontolizumab, foralumab, foravirumab, FPA144, fresolimumab, F S102, fulranumab, futuximab, galiximab, ganitumab, gantenerumab, gavilimomab, gemtuzumab ozogamicin, Gerilimzumab, gevokizumab, girentuximab, glembatumumab vedotin, GNR-006, GNR-011, golimumab, gomiliximab, GSK2849330, GSK2857916, GSK3174998, GSK3359609, guselkumab, Hu14.18K322A MAb, hu3S193, Hu8F4, HuL2G7, HuMab-5B1, ibalizumab, ibritumomab tiuxetan, icrucumab, idarucizumab, IGN002, IGN523, igovomab, IMAB362, IMAB362 (claudiximab), imalumab, IMC-CS4, IMC-D11, imciromab, imgatuzumab, IMGN529, IMMU-102 (yttrium Y-90 epratuzumab tetraxetan), IMMU-114, ImmuTune IMP701 Antagonist Antibody, INCAGN1876, inclacumab, INCSHR1210, indatuximab ravtansine, indusatumab vedotin, infliximab, inolimomab, inotuzumab ozogamicin, intetumumab, Ipafricept, IPH4102, ipilimumab, iratumumab, isatuximab, Istiratumab, itolizumab, ixekizumab, JNJ-56022473, JNJ-61610588, keliximab, KTN3379, L19IL2/L19TNF, Labetuzumab, Labetuzumab Govitecan, LAG525, lambrolizumab, lampalizumab, L-DOS47, lebrikizumab, lemalesomab, lenzilumab, lerdelimumab, Leukotuximab, lexatumumab, libivirumab, lifastuzumab vedotin, ligelizumab, lilotomab satetraxetan, lintuzumab, lirilumab, LKZ145, lodelcizumab, lokivetmab, lorvotuzumab mertansine, lucatumumab, lulizumab pegol, lumiliximab, lumretuzumab, LY3164530, mapatumumab, margetuximab, maslimomab, matuzumab, mavrilimumab, MB311, MCS-110, MEDI0562, MEDI-0639, MEDI0680, MEDI-3617, MEDI-551 (inebilizumab), MEDI-565, MEDI6469, mepolizumab, metelimumab, MGB453, MGD006/S80880, MGD007, MGD009, MGD011, milatuzumab, Milatuzumab-SN-38, minretumomab, mirvetuximab soravtansine, mitumomab, MK-4166, MM-111, MM-151, MM-302, mogamulizumab, MOR202, MOR208, MORAb-066, morolimumab, motavizumab, moxetumomab pasudotox, muromonab-CD3, nacolomab tafenatox, namilumab, naptumomab estafenatox, narnatumab, natalizumab, nebacumab, necitumumab, nemolizumab, nerelimomab, nesvacumab, nimotuzumab, nivolumab, nofetumomab merpentan, NOV-10, obiltoxaximab, obinutuzumab, ocaratuzumab, ocrelizumab, odulimomab, ofatumumab, olaratumab, olokizumab, omalizumab, OMP-131R10, OMP-305B83, onartuzumab, ontuxizumab, opicinumab, oportuzumab monatox, oregovomab, orticumab, otelixizumab, otlertuzumab, OX002/MEN1309 oxelumab, ozanezumab, ozoralizumab, pagibaximab, palivizumab, panitumumab, pankomab, PankoMab-GEX, panobacumab, parsatuzumab, pascolizumab, pasotuxizumab, pateclizumab, patritumab, PAT-SC1, PAT-SM6, pembrolizumab, pemtumomab, perakizumab, pertuzumab, pexelizumab, PF-05082566 (utomilumab), PF-06647263, PF-06671008, PF-06801591, pidilizumab, pinatuzumab vedotin, pintumomab, placulumab, polatuzumab vedotin, ponezumab, priliximab, pritoxaximab, pritumumab, PRO 140, Proxinium, PSMA ADC, quilizumab, racotumomab, radretumab, rafivirumab, ralpancizumab, ramucirumab, ranibizumab, raxibacumab, refanezumab, regavirumab, REGN1400, REGN2810/SAR439684, reslizumab, RFM-203, RG7356, RG7386, RG7802, RG7813, RG7841, RG7876, RG7888, RG7986, rilotumumab, rinucumab, rituximab, RM-1929, R07009789, robatumumab, roledumab, romosozumab, rontalizumab, rovelizumab, ruplizumab, sacituzumab govitecan, samalizumab, SAR408701, SAR566658, sarilumab, SAT 012, satumomab pendetide, SCT200, SCT400, SEA-CD40, secukinumab, seribantumab, setoxaximab, sevirumab, SGN-CD19A, SGN-CD19B, SGN-CD33A, SGN-CD70A, SGN-LIV1A, sibrotuzumab, sifalimumab, siltuximab, simtuzumab, siplizumab, sirukumab, sofituzumab vedotin, solanezumab, solitomab, sonepcizumab, sontuzumab, stamulumab, sulesomab, suvizumab, SYD985, SYM004 (futuximab and modotuximab), Sym015, TAB08, tabalumab, tacatuzumab tetraxetan, tadocizumab, talizumab, tanezumab, Tanibirumab, taplitumomab paptox, tarextumab, TB-403, tefibazumab, Teleukin, telimomab aritox, tenatumomab, teneliximab, teplizumab, teprotumumab, tesidolumab, tetulomab, TG-1303, TGN1412, Thorium-227-Epratuzumab Conjugate, ticilimumab, tigatuzumab, tildrakizumab, Tisotumab vedotin, TNX-650, tocilizumab, toralizumab, tosatoxumab, tositumomab, tovetumab, tralokinumab, trastuzumab, trastuzumab emtansine, TRBS07, TRC105, tregalizumab, tremelimumab, trevogrumab, TRPH 011, TRX518, TSR-042, TTI-200.7, tucotuzumab celmoleukin, tuvirumab, U3-1565, U3-1784, ublituximab, ulocuplumab, urelumab, urtoxazumab, ustekinumab, Vadastuximab Talirine, vandortuzumab vedotin, vantictumab, vanucizumab, vapaliximab, varlilumab, vatelizumab, VB6-845, vedolizumab, veltuzumab, vepalimomab, vesencumab, visilizumab, volociximab, vorsetuzumab mafodotin, votumumab, YYB-101, zalutumumab, zanolimumab, zatuximab, ziralimumab, and zolimomab aritox. In certain embodiments, the antigen interacting domain binds an Fc domain of an aforementioned antibody.

In some embodiments, the antigen interacting domain binds an antibody which in turn binds an antigen selected from the group consisting of: 1-40-β-amyloid, 4-1BB, SAC, 5T4, activin receptor-like kinase 1, ACVR2B, adenocarcinoma antigen, AGS-22M6, alpha-fetoprotein, angiopoietin 2, angiopoietin 3, anthrax toxin, AOC3 (VAP-1), B7-H3, *Bacillus anthracis* anthrax, BAFF, beta-amyloid, B-lymphoma cell, C242 antigen, C5, CA-125, *Canis lupus familiaris* IL31, carbonic anhydrase 9 (CA-IX), cardiac myosin, CCL11 (eotaxin-1), CCR4, CCR5, CD11, CD18, CD125, CD140a, CD147 (basigin), CD15, CD152, CD154 (CD40L), CD19, CD2, CD20, CD200, CD22, CD221, CD23 (IgE receptor), CD25 (α chain of IL-2receptor), CD27, CD274, CD28, CD3, CD3 epsilon, CD30, CD33, CD37, CD38, CD4, CD40, CD40 ligand, CD41, CD44 v6, CDS, CD51, CD52, CD56, CD6, CD70, CD74, CD79B, CD80, CEA, CEA-related antigen, CFD, ch4D5, CLDN18.2, *Clostridium difficile*, clumping factor A, CSF1R, CSF2, CTLA-4, C—X—C chemokine receptor type 4, cytomegalovirus, cytomegalovirus glycoprotein B, dabigatran, DLL4, DPP4, DRS, *E. coli* shiga toxin type-1, *E. coli* shiga toxin type-2, EGFL7, EGFR, endotoxin, EpCAM, episialin, ERBB3, *Escherichia coli*, F protein of respiratory syncytial virus, FAP, fibrin II beta chain, fibronectin extra domain-B, folate hydrolase, folate receptor 1, folate receptor alpha, Frizzled receptor, ganglioside GD2, GD2, GD3 ganglioside, glypican 3, GMCSF receptor α-chain, GPNMB, growth differentiation factor 8, GUCY2C, hemagglutinin, hepatitis B surface antigen, hepatitis B virus, HER1, HER2/neu, HER3, HGF, HHGFR, histone complex, HIV-1, HLA-DR, HNGF, Hsp90, human scatter factor receptor kinase, human TNF, human beta-amyloid, ICAM-1 (CD54), IFN-α, IFN-γ, IgE, IgE Fc region, IGF-1 receptor, IGF-1, IGHE, IL 17A, IL 17F, IL 20, IL-12, IL-13, IL-17, IL-1β, IL-22, IL-23, IL-31RA, IL-4, IL-5, IL-6, IL-6 receptor, IL-9, ILGF2, influenza A hemagglutinin, influenza A virus hemagglutinin, insulin-like growth factor I receptor, integrin α4β7, integrin α4, integrin α5β1, integrin α7β7, integrin αIIbβ3, integrin αvβ3, interferon α/β receptor, interferon gamma-induced protein, ITGA2, ITGB2 (CD18), KIR2D, Lewis-Y antigen, LFA-1 (CD11a), LINGO-1, lipoteichoic acid, LOXL2, L-selectin (CD62L), LTA, MCP-1, mesothelin, MIF, MS4A1, MSLN, MUC1, mucin CanAg, myelin-associated glycoprotein, myostatin, NCA-90 (granulocyte antigen), neural apoptosis-regulated proteinase 1, NGF, N-glycolylneuraminic acid, NOGO-A, Notch receptor, NRP1, *Oryctolagus cuniculus*, OX-40, oxLDL, PCSK9, PD-1, PDCD1, PDGF-R α, phosphate-sodium co-transporter, phosphatidylserine, platelet-derived growth factor receptor beta, prostatic carcinoma cells, *Pseudomonas aeruginosa*, rabies virus glycoprotein, RANKL, respiratory syncytial virus, RHD, Rhesus factor, RON, RTN4, sclerostin, SDC1, selectin P, SLAMF7, SOST, sphingosine-1-phosphate, *Staphylococcus aureus*, STEAP1, TAG-72, T-cell receptor, TEM1, tenascin C, TFPI, TGF-β 1, TGF-β 2, TGF-β, TNF-α, TRAIL-R1, TRAIL-R2, tumor antigen CTAA16.88, tumor specific glycosylation of MUC1, tumor-associated calcium signal transducer 2, TWEAK receptor, TYRP1(glycoprotein 75), VEGFA, VEGFR1, VEGFR2, vimentin, and VWF.

In some embodiments, an antigen interacting domain can bind an antibody mimetic. Antibody mimetics, as described elsewhere herein, can bind a target molecule with an affinity comparable to an antibody. In some embodiments, the antigen interacting domain can bind a humanized antibody which is described elsewhere herein. In some embodiments, the antigen interacting domain of a chimeric transmembrane receptor polypeptide can bind a fragment of a humanized antibody. In some embodiments, the antigen interacting domain can bind a single-chain variable fragment (scFv).

In some embodiments, the antigen interacting domain binds an Fc portion of an immunoglobulin (e.g., IgG, IgA, IgM, or IgE) of a suitable mammal (e.g., human, mouse, rat, goat, sheep, or monkey). Suitable Fc binding domains may be derived from naturally occurring proteins such as mammalian Fc receptors or certain bacterial proteins (e.g., protein A and protein G). Additionally, Fc binding domains may be synthetic polypeptides engineered specifically to bind the Fc portion of any of the Ig molecules described herein with desired affinity and specificity. For example, such an Fc binding domain can be an antibody or an antigen-binding fragment thereof that specifically binds the Fc portion of an immunoglobulin. Examples include, but are not limited to, a single-chain variable fragment (scFv), a domain antibody, and a nanobody. Alternatively, an Fc binding domain can be a synthetic peptide that specifically binds the Fc portion, such as a Kunitz domain, a small modular immunopharmaceutical (SMIP), an adnectin, an avimer, an affibody, a DARPin, or an anticalin, which may be identified by screening a peptide library for binding activities to Fc.

In some embodiments, the antigen interacting domain comprises an Fc binding domain comprising an extracellular ligand-binding domain of a mammalian Fc receptor. Fc receptors are generally cell surface receptors expressed on the surface of many immune cells (including B cells, dendritic cells, natural killer (NK) cells, macrophages, neutorphils, mast cells, and eosinophils) and exhibit binding specificity to the Fc domain of an antibody. In some cases, binding of an Fc receptor to an Fc portion of the antibody can trigger antibody dependent cell-mediated cytotoxicity (ADCC) effects. The Fc receptor used for constructing a chimeric transmembrane receptor polypeptide described herein may be a naturally-occurring polymorphism variant, such as a variant which may have altered (e.g., increased or decreased) affinity to an Fc domain as compared to a wild-type counterpart. Alternatively, the Fc receptor may be a functional variant of a wild-type counterpart, carrying one or more mutations (e.g., up to 10 amino acid residue substitutions) that alters the binding affinity to the Fc portion of an Ig molecule. In some embodiments, the mutation may alter the glycosylation pattern of the Fc receptor and thus the binding affinity to an Fc domain.

Table 1 lists a number of exemplary polymorphisms in Fc receptor extracellular domains (see, e.g., Kim et al., J. Mol. Evol. 53:1-9, 2001).

TABLE 1

Exemplary Polymorphisms in Fc Receptors

| | Amino Acid Number | | | | | | | | |
|---|---|---|---|---|---|---|---|---|---|
| | 19 | 48 | 65 | 89 | 105 | 130 | 134 | 141 | 142 | 158 |
| FCR10 | R | S | D | I | D | G | F | Y | T | V |
| P08637 | R | S | D | I | D | G | F | Y | I | F |
| S76824 | R | S | D | I | D | G | F | Y | I | V |
| J04162 | R | N | D | V | D | D | F | H | I | V |
| M31936 | S | S | N | I | D | D | F | H | I | V |
| M24854 | S | S | N | I | E | D | S | H | I | V |
| X07934 | R | S | N | I | D | D | F | H | I | V |
| X14356 (FcγRII) | N | N | N | S | E | S | S | S | I | I |
| M31932 (FcγRI) | S | T | N | R | E | A | F | T | I | G |
| X06948 (FcαεI) | R | S | E | S | Q | S | E | S | I | V |

Fc receptors can generally be classified based on the isotype of the antibody to which it is able to bind. For example, Fc-gamma receptors (FcγR) generally bind to IgG antibodies (e.g., IgG1, IgG2, IgG3, and IgG4); Fc-alpha receptors (FcαR) generally bind to IgA antibodies; and Fc-epsilon receptors (FcεR) generally bind to IgE antibodies. In some embodiments, the antigen interacting domain comprises an Fcγ receptor or any derivative, variant or fragment thereof. In some embodiments, the antigen interacting domain comprises an Fc binding domain comprising an FcR selected from FcγRI (CD64), FcγRIa, FcγRIb, FcγRIc, FcγRIIA (CD32) including allotypes H131 and R131, FcγRIIB (CD32) including FcγRIIB-1 and FcγRIIB-2, FcγRIIIA (CD16a) including allotypes V158 and F158, FcγRIIIB (CD16b) including allotypes FcγRIIIb-NA1 and FcγRIIIb-NA2, any derivative thereof, any variant thereof, and any fragment thereof. An FcγR may be from any organism, including but not limited to humans, mice, rats, rabbits, and monkeys. Mouse FcγRs include but are not limited to FcγRI (CD64), FcγRII (CD32), FcγRIII (CD16), and FcγRIII-2 (CD16-2). In some embodiments, the antigen interacting domain comprises an Fcε receptor or any derivative, variant or fragment thereof. In some embodiments, the antigen interacting domain comprises a FcR selected from FcεRI, FcεRII (CD23), any derivative thereof, any variant thereof, and any fragment thereof. In some embodiments, the antigen interacting domain comprises an Fcα receptor or any derivative, variant or fragment thereof. In some embodiments, the antigen interacting domain comprises an FcR selected from FcαRI (CD89), Fcα/μR, any derivative thereof, any variant thereof, and any fragment thereof. In some embodiments, the antigen interacting domain comprises an FcR selected from FcRn, any derivative thereof, any variant thereof, and any fragment thereof. Selection of the ligand binding domain of an Fc receptor for use in the chimeric transmembrane receptor polypeptides may depend on various factors such as the isotype of the antibody to which binding of the Fc binding domain is desired and the desired affinity of the binding interaction.

In some embodiments, the antigen interacting domain comprises the extracellular ligand-binding domain of CD16, which may incorporate a naturally occurring polymorphism that can modulate affinity for an Fc domain. In some embodiments, the antigen interacting domain comprises the extracellular ligand-binding domain of CD16 incorporating a polymorphism at position 158 (e.g., valine or phenylalanine). In some embodiments, the antigen interacting domain is produced under conditions that alter its glycosylation state and its affinity for an Fc domain. In some embodiments, the antigen interacting domain comprises the extracellular ligand-binding domain of CD16 incorporating modifications that render the chimeric transmembrane receptor polypeptide incorporating it specific for a subset of IgG antibodies. For example, mutations that increase or decrease the affinity for an IgG subtype (e.g., IgG1) may be incorporated. In some embodiments, the antigen interacting domain comprises the extracellular ligand-binding domain of CD32, which may incorporate a naturally occurring polymorphism that may modulate affinity for an Fc domain. In some embodiments, the antigen interacting domain comprises the extracellular ligand-binding domain of CD32 incorporating modifications that render the chimeric transmembrane receptor polypeptide incorporating it specific for a subset of IgG antibodies. For example, mutations that increase or decrease the affinity for an IgG subtype (e.g., IgG1) may be incorporated.

In some embodiments, the antigen interacting domain comprises the extracellular ligand-binding domain of CD64, which may incorporate a naturally occurring polymorphism that may modulate affinity for an Fc domain. In some embodiments, the antigen interacting domain is produced under conditions that alter its glycosylation state and its affinity for an Fc domain. In some embodiments, the antigen interacting domain comprises the extracellular ligand-binding domain of CD64 incorporating modifications that render the chimeric transmembrane receptor polypeptide incorporating it specific for a subset of IgG antibodies. For example, mutations that increase or decrease the affinity for an IgG subtype (e.g., IgG1) may be incorporated.

In other embodiments, the antigen interacting domain comprises a naturally occurring bacterial protein that is capable of binding to the Fc portion of an IgG molecule, or any derivative, variant or fragment thereof (e.g., protein A, protein G). In some embodiments, the antigen interacting domain comprises protein A, or any derivative, variant or fragment thereof. Protein A refers to a 42 kDa surface protein originally found in the cell wall of the bacterium *Staphylococcus aureus*. It is composed of five domains that each fold into a three-helix bundle and are able to bind IgG through interactions with the Fc region of most antibodies as well as the Fab region of human VH3 family antibodies. In some embodiments, the antigen interacting domain comprises protein G, or any derivative, variant or fragment thereof. Protein G refers to an approximately 60-kDa protein expressed in group C and G Streptococcal bacteria that binds to both the Fab and Fc region of mammalian IgGs. While native protein G also binds albumin, recombinant variants have been engineered that eliminate albumin binding.

Antigen interacting domains can also be created de novo using combinatorial biology or directed evolution methods. Starting with a protein scaffold (e.g., an scFv derived from IgG, a Kunitz domain derived from a Kunitz-type protease inhibitor, an ankyrin repeat, the Z domain from protein A, a lipocalin, a fibronectin type III domain, an SH3 domain from Fyn, or others), amino acid side chains for a set of residues on the surface may be randomly substituted in order to create a large library of variant scaffolds. From large libraries, it is possible to isolate variants with affinity for a target like the Fc domain by first selecting for binding, followed by amplification by phage, ribosome or cell display. Repeated rounds of selection and amplification can be used to isolate those proteins with the highest affinity for the target. Exemplary Fc-binding peptides may comprise the amino acid sequence of ETQRCTWHMGELVWCEREHN (SEQ ID NO: 19), KEASCSYWLGELVWCVAGVE (SEQ ID NO: 20), or DCAWHLGELVWCT (SEQ ID NO: 21).

Any of the Fc binders described herein may have a suitable binding affinity for the Fc domain of an antibody. Binding affinity refers to the apparent association constant or $K_A$. The $K_A$ is the reciprocal of the dissociation constant, $K_D$. The extracellular ligand-binding domain of an Fc receptor domain of the chimeric transmembrane receptor polypeptides described herein may have a binding affinity $K_D$ of at least $10^{-5}$, $10^{-6}$, $10^{-7}$, $10^{-8}$, $10^{-9}$, $10^{-10}$ M or lower for the Fc portion of an antibody. In some embodiments, the antigen interacting domain which binds an Fc portion of an antibody has a high binding affinity for antibody, isotype of antibodies, or subtype(s) thereof, as compared to the binding affinity of the antigen interacting domain to another antibody, isotype of antibodies or subtypes thereof.

In some embodiments, the extracellular ligand-binding domain of an Fc receptor has specificity for an antibody, isotype of antibodies, or subtype(s) thereof, as compared to binding of the extracellular ligand-binding domain of an Fc receptor to another antibody, isotype of antibodies, or subtypes thereof. Fcγ receptors with relatively high affinity binding include CD64A, CD64B, and CD64C. Fcγ receptors with relatively low affinity binding include CD32A, CD32B, CD16A, and CD16B. An Fcε receptor with relatively high affinity binding includes FcεRI, and an Fcε receptor with relatively low affinity binding includes FcεRII/CD23.

The binding affinity or binding specificity for an Fc receptor, or any derivative, variant, or fragment thereof or for a chimeric transmembrane receptor polypeptide comprising an Fc binding domain can be determined by a variety of methods including equilibrium dialysis, equilibrium binding, gel filtration, ELISA, surface plasmon resonance, and spectroscopy.

In some embodiments, an antigen interacting domain comprising the extracellular ligand-binding domain of an Fc receptor comprises an amino acid sequence that is at least 90% (e.g., 91%, 92%, 93%, 94%, 95%, 96%, 97%, 98%, 99% or greater) identical to the amino acid sequence of the extracellular ligand-binding domain of a naturally-occurring Fcγ receptor, an Fcα receptor, an Fcε receptor, or FcRn. The "percent identity" or "% identity" of two amino acid sequences can be determined using the algorithm of Karlin and Altschul Proc. Natl. Acad. Sci. USA 87:2264-68, 1990, modified as in Karlin and Altschul Proc. Natl. Acad. Sci. USA 90:5873-77, 1993. Such an algorithm is incorporated into the NBLAST and XBLAST programs (version 2.0) of Altschul, et al. J. Mol. Biol. 215:403-10, 1990. BLAST protein searches can be performed with the XBLAST program, score=50, wordlength=3 to obtain amino acid sequences homologous to the protein molecules of the disclosure. Where gaps exist between two sequences, Gapped BLAST can be utilized as described in Altschul et al., Nucleic Acids Res. 25(17):3389-3402, 1997. When utilizing BLAST and Gapped BLAST programs, the default parameters of the respective programs (e.g., XBLAST and NBLAST) can be used.

In some embodiments, the antigen interacting domain comprises an Fc binding domain comprising a variant of an extracellular ligand-binding domain of an Fc receptor. In some embodiments, the variant extracellular ligand-binding domain of an Fc receptor may comprise up to 10 amino acid residue variations (e.g., 1, 2, 3, 4, 5, 6, 7, 8, 9 or 10) relative to the amino acid sequence of the reference extracellular ligand-binding domain. In some embodiments, the variant can be a naturally-occurring variant due to gene polymorphism. In other embodiments, the variant can be a non-naturally occurring modified molecule. For example, mutations can be introduced into the extracellular ligand-binding domain of an Fc receptor to alter its glycosylation pattern and thus its binding affinity to the corresponding Fc domain.

In some examples, the antigen interacting domain comprises a Fc binding comprising an Fc receptor selected from CD16A, CD16B, CD32A, CD32B, CD32C, CD64A, CD64B, CD64C, or a variant, fragment or derivative thereof as described herein. The extracellular ligand-binding domain of an Fc receptor may comprise up to 10 amino acid residue variations (e.g., 1, 2, 3, 4, 5, 6, 7, 8, 9 or 10) relative to the amino acid sequence of the extracellular ligand-binding domain of CD16A, CD16B, CD32A, CD32B, CD32C, CD64A, CD64B, CD64C as described herein. Mutation of amino acid residues of the extracellular ligand-binding domain of an Fc receptor may result in an increase in binding affinity for the Fc receptor domain to bind to an antibody, isotype of antibodies, or subtype(s) thereof relative to Fc receptor domains that do not comprise the mutation. For example, mutation of residue 158 of the Fc-gamma receptor CD16A may result in an increase in binding affinity of the Fc receptor to an Fc portion of an antibody. In some embodiments, the mutation is a substitution of a phenylalanine to a valine at residue 158 of the Fcγ receptor CD16A. Various suitable alternative or additional mutations can be made in the extracellular ligand-binding domain of an Fc receptor that may enhance or reduce the binding affinity to an Fc portion of a molecule such as an antibody.

The extracellular region comprising an antigen interacting domain can be linked to the intracellular region, for example by a membrane spanning segment. In some embodiments, the membrane spanning segment comprises a polypeptide. The membrane spanning polypeptide linking the extracellular region and the intracellular region of the chimeric transmembrane receptor can have any suitable polypeptide sequence. In some cases, the membrane spanning polypeptide comprises a polypeptide sequence of a membrane spanning portion of an endogenous or wild-type membrane spanning protein. In some embodiments, the membrane spanning polypeptide comprises a polypeptide sequence having at least 1 (e.g., at least 2, 3, 4, 5, 6, 7, 8, 9, 10 or greater) of an amino acid substitution, deletion, and insertion compared to a membrane spanning portion of an endogenous or wild-type membrane spanning protein. In some embodiments, the membrane spanning polypeptide comprises a non-natural polypeptide sequence, such as the sequence of a polypeptide linker. The polypeptide linker may be flexible or rigid. The polypeptide linker can be structured or unstructured. In some embodiments, the membrane spanning polypeptide transmits a signal from the extracellular region to the intracellular region of the receptor, for example a signal indicating ligand-binding.

An immune cell signaling domain of an intracellular region of a chimeric transmembrane receptor polypeptide of a subject system can comprise a primary signaling domain. A primary signaling domain can be any signaling domain, or derivative, variant or fragment thereof, involved in immune cell signaling. For example, a signaling domain is involved in regulating primary activation of the TCR complex either in a stimulatory way or in an inhibitory way. An primary signaling domain can comprise a signaling domain of an Fcγ receptor (FcγR), an Fcε receptor (FcεR), an Fcα receptor (FcαR), neonatal Fc receptor (FcRn), CD3, CD3 ζ, CD3 γ, CD3 δ, CD3 ε, CD4, CD5, CD8, CD21, CD22, CD28, CD32, CD40L (CD154), CD45, CD66d, CD79a, CD79b, CD80, CD86, CD278 (also known as ICOS), CD247 ζ, CD247 η, DAP10, DAP12, FYN, LAT, Lck, MAPK, MHC complex, NFAT, NF-κB, PLC-γ, iC3b, C3dg, C3d, and Zap70. In some embodiments, the primary signaling domain comprises an immunoreceptor tyrosine-based activation motif or ITAM. A primary signaling domain comprising an ITAM can comprise two repeats of the amino acid sequence YxxL/I separated by 6-8 amino acids, wherein each x is independently any amino acid, producing the conserved motif YxxL/Ix$_{(6-8)}$YxxL/I. A primary signaling domain comprising an ITAM can be modified, for example, by phosphorylation when the antigen interacting domain is bound to an antigen. A phosphorylated ITAM can function as a docking site for other proteins, for example proteins involved in various signaling pathways. In some embodiments, the primary signaling domain comprises a modified ITAM domain, e.g., a mutated, truncated, and/or optimized ITAM domain, which has altered (e.g., increased or decreased) activity compared to the native ITAM domain.

In some embodiments, the primary signaling domain comprises an FcγR signaling domain (e.g., ITAM). The FcγR signaling domain can be selected from FcγRI (CD64), FcγRIIA (CD32), FcγRIIB (CD32), FcγRIIIA (CD16a), and FcγRIIIB (CD16b). In some embodiments, the primary signaling domain comprises an FcεR signaling domain (e.g., ITAM). The FcεR signaling domain can be selected from FcεRI and FcεRII (CD23). In some embodiments, the primary signaling domain comprises an FcαR signaling domain (e.g., ITAM). The FcαR signaling domain can be selected from FcγRI (CD89) and Fcα/μt. In some embodiments, the primary signaling domain comprises a CD3 ζ signaling domain. In some embodiments, the primary signaling domain comprises an ITAM of CD3 ζ.

In some embodiments, a primary signaling domain comprises an immunoreceptor tyrosine-based inhibition motif or ITIM. A primary signaling domain comprising an ITIM can comprise a conserved sequence of amino acids (S/I/V/LxYxxI/V/L) that is found in the cytoplasmic tails of some inhibitory receptors of the immune system. A primary signaling domain comprising an ITIM can be modified, for example phosphorylated, by enzymes such as a Src kinase family member (e.g., Lck). Following phosphorylation, other proteins, including enzymes, can be recruited to the ITIM. These other proteins include, but are not limited to, enzymes such as the phosphotyrosine phosphatases SHP-1 and SHP-2, the inositol-phosphatase called SHIP, and proteins having one or more SH2 domains (e.g., ZAP70). A primary signaling domain can comprise a signaling domain (e.g., ITIM) of BTLA, CD5, CD31, CD66a, CD72, CMRF35H, DCIR, EPO-R, FcγRIIB (CD32), Fc receptor-like protein 2 (FCRL2), Fc receptor-like protein 3 (FCRL3), Fc receptor-like protein 4 (FCRL4), Fc receptor-like protein 5 (FCRL5), Fc receptor-like protein 6 (FCRL6), protein G6b (G6B), interleukin 4 receptor (IL4R), immunoglobulin superfamily receptor translocation-associated 1(IRTA1), immunoglobulin superfamily receptor translocation-associated 2 (IRTA2), killer cell immunoglobulin-like receptor 2DL1 (KIR2DL1), killer cell immunoglobulin-like receptor 2DL2 (KIR2DL2), killer cell immunoglobulin-like receptor 2DL3 (KIR2DL3), killer cell immunoglobulin-like receptor 2DL4 (KIR2DL4), killer cell immunoglobulin-like receptor 2DL5 (KIR2DL5), killer cell immunoglobulin-like receptor 3DL1 (KIR3DL1), killer cell immunoglobulin-like receptor 3DL2 (KIR3DL2), leukocyte immunoglobulin-like receptor subfamily B member 1 (LIR1), leukocyte immunoglobulin-like receptor subfamily B member 2 (LIR2), leukocyte immunoglobulin-like receptor subfamily B member 3 (LIR3), leukocyte immunoglobulin-like receptor subfamily B member 5 (LIR5), leukocyte immunoglobulin-like receptor subfamily B member 8 (LIR8), leukocyte-associated immunoglobulin-like receptor 1 (LAIR-1), mast cell function-associated antigen (MAFA), NKG2A, natural cytotoxicity triggering receptor 2 (NKp44), NTB-A, programmed cell death protein 1 (PD-1), PILR, SIGLECL1, sialic acid binding Ig like lectin 2 (SIGLEC2 or CD22), sialic acid binding Ig like lectin 3 (SIGLEC3 or CD33), sialic acid binding Ig like lectin 5 (SIGLEC5 or CD170), sialic acid binding Ig like lectin 6 (SIGLEC6), sialic acid binding Ig like lectin 7 (SIGLEC7), sialic acid binding Ig like lectin 10 (SIGLEC10), sialic acid binding Ig like lectin 11 (SIGLEC11), sialic acid binding Ig like lectin 4 (SIGLEC4), sialic acid binding Ig like lectin 8 (SIGLEC8), sialic acid binding Ig like lectin 9 (SIGLEC9), platelet and endothelial cell adhesion molecule 1 (PECAM-1), signal regulatory protein (SIRP 2), and signaling threshold regulating transmembrane adaptor 1 (SIT). In some embodiments, the primary signaling domain comprises a modified ITIM domain, e.g., a mutated, truncated, and/or optimized ITIM domain, which has altered (e.g., increased or decreased) activity compared to the native ITIM domain.

In some embodiments, the immune cell signaling domain comprises multiple primary signaling domains. For example, the immune cell signaling domain can comprise at least 2 primary signaling domains, e.g., at least 2, 3, 4, 5, 7, 8, 9, or 10 primary signaling domains. In some embodiments, the immune cell signaling domain comprises at least 2 ITAM domains (e.g., at least 3, 4, 5, 6, 7, 8, 9, or 10 ITAM domains). In some embodiments, the immune cell signaling domain comprises at least 2 ITIM domains (e.g., at least 3, 4, 5, 6, 7, 8, 9, or 10 ITIM domains) (e.g., at least 2 primary signaling domains). In some embodiments, the immune cell signaling domain comprises both ITAM and ITIM domains.

Figure 2:
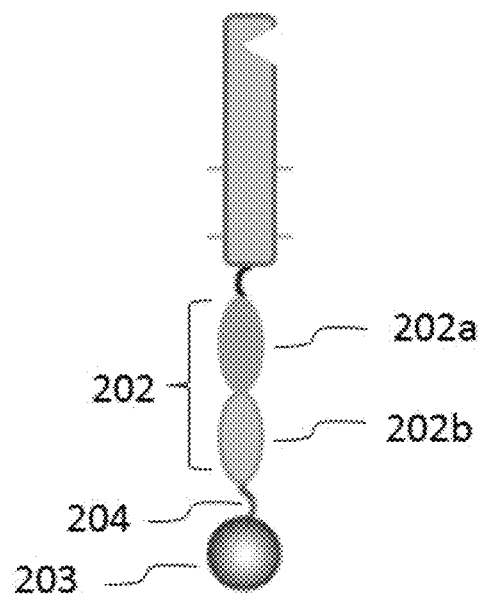
FIG. 2 shows an exemplary chimeric transmembrane receptor polypeptide comprising at least one co-stimulatory domain.

The immune cell signaling domain of an intracellular region of a chimeric transmembrane receptor polypeptide can include a co-stimulatory domain. In some embodiments, a co-stimulatory domain, for example from co-stimulatory molecule, can provide co-stimulatory signals for immune cell signaling, such as signaling from ITAM and/or ITIM domains, e.g., for the activation and/or deactivation of immune cells. In an exemplary configuration of a chimeric transmembrane receptor shown in FIG. 2, an immune cell signaling domain 202 comprises a primary signaling domain 202a and at least one co-stimulatory domain 202b. The intracellular region of the receptor also includes a GMP comprising an actuator moiety 203 linked to a cleavage recognition site 204. In some embodiments, a costimulatory domain is operable to regulate a proliferative and/or survival signal in the immune cell. In some embodiments, a co-stimulatory signaling domain comprises a signaling domain of a MHC class I protein, MEW class II protein, TNF receptor protein, immunoglobulin-like protein, cytokine receptor, integrin, signaling lymphocytic activation molecule (SLAM protein), activating NK cell receptor, BTLA, or a Toll ligand receptor. In some embodiments, the co-stimulatory domain comprises a signaling domain of a molecule selected from the group consisting of: 2B4/CD244/SLAMF4, 4-1BB/TNFSF9/CD137, B7-1/CD80, B7-2/CD86, B7-H1/PD-L1, B7-H2, B7-H3, B7-H4, B7-H6, B7-H7, BAFF R/TNFRSF13C, BAFF/BLyS/TNFSF13B, BLAME/SLAMF8, BTLA/CD272, CD100 (SEMA4D), CD103, CD11a, CD11b, CD11c, CD11d, CD150, CD160 (BY55), CD18, CD19, CD2, CD200, CD229/SLAMF3, CD27 Ligand/TNFSF7, CD27/TNFRSF7, CD28, CD29, CD2F-10/SLAMF9, CD30 Ligand/TNFSF8, CD30/TNFRSF8, CD300a/LMIR1, CD4, CD40 Ligand/TNFSF5, CD40/TNFRSF5, CD48/SLAMF2, CD49a, CD49D, CD49f, CD53, CD58/LFA-3, CD69, CD7, CD8 α, CD8 β, CD82/Kai-1, CD84/SLAMF5, CD90/Thyl, CD96, CDS, CEACAM1, CRACC/SLAMF7, CRTAM, CTLA-4, DAP12, Dectin-1/CLEC7A, DNAM1 (CD226), DPPIV/CD26, DR3/TNFRSF25, EphB6, GADS, Gi24/VISTA/B7-H5, GITR Ligand/TNFSF18, GITR/TNFRSF18, HLA Class I, HLA-DR, HVEM/TNFRSF14, IA4, ICAM-1, ICOS/CD278, Ikaros, IL2R β, IL2R γ, IL7R α, Integrin α4/CD49d, Integrin α4β1, Integrin α4β7/LPAM-1, IPO-3, ITGA4, ITGA6, ITGAD, ITGAE, ITGAL, ITGAM, ITGAX, ITGB1, ITGB2, ITGB7, KIRDS2, LAG-3, LAT, LIGHT/TNFSF14, LTBR, Ly108, Ly9 (CD229), lymphocyte function associated antigen-1 (LFA-1), Lymphotoxin-α/TNF-β, NKG2C, NKG2D, NKp30, NKp44, NKp46, NKp80 (KLRF1), NTB-A/SLAMF6, OX40 Ligand/TNFSF4, OX40/TNFRSF4, PAG/Cbp, PD-1, PDCD6, PD-L2/B7-DC, PSGL1, RELT/TNFRSF19L, SELPLG (CD162), SLAM (SLAMF1), SLAM/CD150, SLAMF4 (CD244), SLAMF6 (NTB-A), SLAMF7, SLP-76, TACI/TNFRSF13B, TCL1A, TCL1B, TIM-1/KIM-1/HAVCR, TIM-4, TL1A/TNFSF15, TNF RII/TNFRSF1B, TNF-α, TRANCE/RANKL, TSLP, TSLP R, VLA1, and VLA-6. In some embodiments, the immune cell signaling domain comprises multiple co-stimulatory domains, for example at least two, e.g., at least 3, 4, or 5 co-stimulatory domains.

The immune cell signaling domain can be linked to a gene modulating polypeptide (GMP). A GMP can comprise an actuator moiety linked to a cleavage recognition site. The actuator moiety can comprise a nuclease (e.g., DNA nuclease and/or RNA nuclease), modified nuclease (e.g., DNA nuclease and/or RNA nuclease) that is nuclease-deficient or has reduced nuclease activity compared to a wild-type nuclease, a derivative thereof, a variant thereof, or a fragment thereof. The actuator moiety can regulate expression and/or activity of a gene or edit the sequence of a nucleic acid (e.g., a gene and/or gene product). In some embodiments, the actuator moiety comprises a DNA nuclease such as an engineered (e.g., programmable or targetable) DNA nuclease to induce genome editing of a target DNA sequence. In some embodiments, the actuator moiety comprises a RNA nuclease such as an engineered (e.g., programmable or targetable) RNA nuclease to induce editing of a target RNA sequence. In some embodiments, the actuator moiety has reduced or minimal nuclease activity. An actuator moiety having reduced or minimal nuclease activity can regulate expression and/or activity of a gene by physical obstruction of a target polynucleotide or recruitment of additional factors effective to suppress or enhance expression of the target polynucleotide. In some embodiments, the actuator moiety comprises a nuclease-null DNA binding protein derived from a DNA nuclease that can induce transcriptional activation or repression of a target DNA sequence. In some embodiments, the actuator moiety comprises a nuclease-null RNA binding protein derived from a RNA nuclease that can induce transcriptional activation or repression of a target RNA sequence. An actuator moiety can regulate expression or activity of a gene and/or edit a nucleic acid sequence, whether exogenous or endogenous.

Any suitable nuclease can be used in an actuator moiety. Suitable nucleases include, but are not limited to, CRISPR-associated (Cas) proteins or Cas nucleases including type I CRISPR-associated (Cas) polypeptides, type II CRISPR-associated (Cas) polypeptides, type III CRISPR-associated (Cas) polypeptides, type IV CRISPR-associated (Cas) polypeptides, type V CRISPR-associated (Cas) polypeptides, and type VI CRISPR-associated (Cas) polypeptides; zinc finger nucleases (ZFN); transcription activator-like effector nucleases (TALEN); meganucleases; RNA-binding proteins (RBP); CRISPR-associated RNA binding proteins; recombinases; flippases; transposases; Argonaute proteins; any derivative thereof; any variant thereof and any fragment thereof.

The regulation of genes can be of any gene of interest. It is contemplated that genetic homologues of a gene described herein are covered. For example, a gene can exhibit a certain identity and/or homology to genes disclosed herein. Therefore, it is contemplated that a gene that exhibits or exhibits about 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, or 100% homology (at the nucleic acid or protein level) can be modified. It is also contemplated that a gene that exhibits or exhibits about 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, or 100% identity (at the nucleic acid or protein level) can be modified.

In some embodiments, the actuator moiety comprises a CRISPR-associated (Cas) protein or a Cas nuclease which functions in a non-naturally occurring CRISPR (Clustered Regularly Interspaced Short Palindromic Repeats)/Cas (CRISPR-associated) system. In bacteria, this system can provide adaptive immunity against foreign DNA (Barrangou, R., et al, "CRISPR provides acquired resistance against viruses in prokaryotes," Science (2007) 315: 1709-1712; Makarova, K. S., et al, "Evolution and classification of the CRISPR-Cas systems," Nat Rev Microbiol (2011) 9:467-477; Garneau, J. E., et al, "The CRISPR/Cas bacterial immune system cleaves bacteriophage and plasmid DNA," Nature (2010) 468:67-71; Sapranauskas, R., et al, "The *Streptococcus thermophilus* CRISPR/Cas system provides immunity in *Escherichia coli*," Nucleic Acids Res (2011) 39: 9275-9282).

In a wide variety of organisms including diverse mammals, animals, plants, and yeast, a CRISPR/Cas system (e.g., modified and/or unmodified) can be utilized as a genome engineering tool. A CRISPR/Cas system can comprise a guide nucleic acid such as a guide RNA (gRNA) complexed with a Cas protein for targeted regulation of gene expression and/or activity or nucleic acid editing. An RNA-guided Cas protein (e.g., a Cas nuclease such as a Cas9 nuclease) can specifically bind a target polynucleotide (e.g., DNA) in a sequence-dependent manner. The Cas protein, if possessing nuclease activity, can cleave the DNA (Gasiunas, G., et al, "Cas9-crRNA ribonucleoprotein complex mediates specific DNA cleavage for adaptive immunity in bacteria," Proc Natl Acad Sci USA (2012) 109: E2579-E2 86; Jinek, M., et al, "A programmable dual-RNA-guided DNA endonuclease in adaptive bacterial immunity," Science (2012) 337:816-821; Sternberg, S. H., et al, "DNA interrogation by the CRISPR RNA-guided endonuclease Cas9," Nature (2014) 507:62; Deltcheva, E., et al, "CRISPR RNA maturation by trans-encoded small RNA and host factor RNase III," Nature (2011) 471:602-607), and has been widely used for programmable genome editing in a variety of organisms and model systems (Cong, L., et al, "Multiplex genome engineering using CRISPR Cas systems," Science (2013) 339: 819-823; Jiang, W., et al, "RNA-guided editing of bacterial genomes using CRISPR-Cas systems," Nat. Biotechnol. (2013) 31: 233-239; Sander, J. D. & Joung, J. K, "CRISPR-Cas systems for editing, regulating and targeting genomes," Nature Biotechnol. (2014) 32:347-355).

In some cases, the Cas protein is mutated and/or modified to yield a nuclease deficient protein or a protein with decreased nuclease activity relative to a wild-type Cas protein. A nuclease deficient protein can retain the ability to bind DNA, but may lack or have reduced nucleic acid cleavage activity. An actuator moiety comprising a Cas nuclease (e.g., retaining wild-type nuclease activity, having reduced nuclease activity, and/or lacking nuclease activity) can function in a CRISPR/Cas system to regulate the level and/or activity of a target gene or protein (e.g., decrease, increase, or elimination). The Cas protein can bind to a target polynucleotide and prevent transcription by physical obstruction or edit a nucleic acid sequence to yield nonfunctional gene products.

In some embodiments, the actuator moiety comprises a Cas protein that forms a complex with a guide nucleic acid, such as a guide RNA (gRNA). In some embodiments, the actuator moiety comprises a Cas protein that forms a complex with a single guide nucleic acid, such as a single guide RNA (sgRNA). In some embodiments, the actuator moiety comprises a RNA-binding protein (RBP) optionally complexed with a guide nucleic acid, such as a guide RNA (e.g., sgRNA), which is able to form a complex with a Cas protein.

Figure 3A:
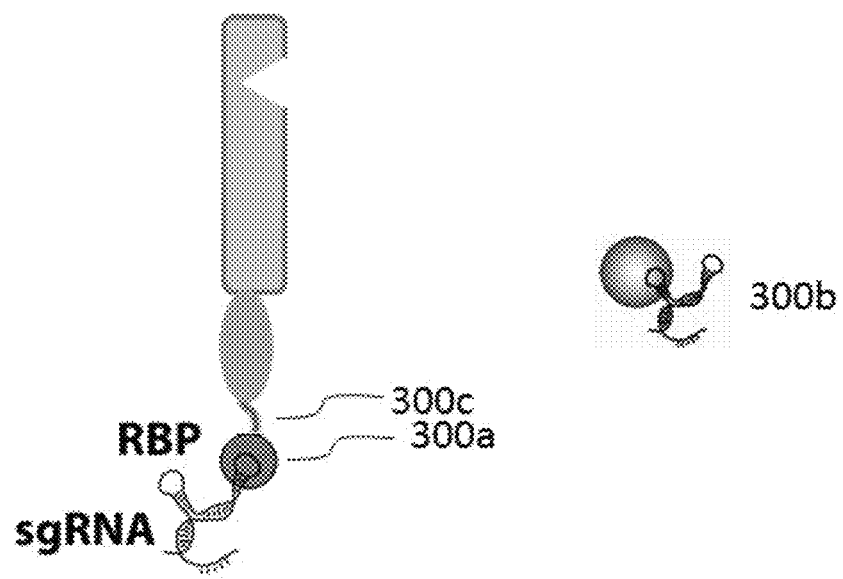
FIG. 3A shows an exemplary chimeric receptor polypeptide including an actuator moiety comprising an RNA-binding protein optionally complexed to a guide nucleic acid (e.g., sgRNA).

FIG. 3A illustrates schematically a system comprising a chimeric receptor polypeptide in which the actuator moiety comprises an RNA-binding protein 300a optionally complexed with a guide nucleic acid (e.g., sgRNA). Upon release from the RNA-binding protein (RBP), for example by dissociation of the guide nucleic acid from the RBP or cleavage of the cleavage recognition site 300c, the guide nucleic acid can form a complex with a Cas protein 300b which is operable to regulate gene expression and/or activity or to edit a nucleic acid sequence. In some embodiments, the actuator moiety comprises a nuclease-null DNA binding protein derived from a DNA nuclease that can induce transcriptional activation or repression of a target DNA sequence. In some embodiments, the actuator moiety comprises a nuclease-null RNA binding protein derived from a RNA nuclease that can induce transcriptional activation or repression of a target RNA sequence. For example, an actuator moiety can comprise a Cas protein which lacks cleavage activity.

Figure 17:
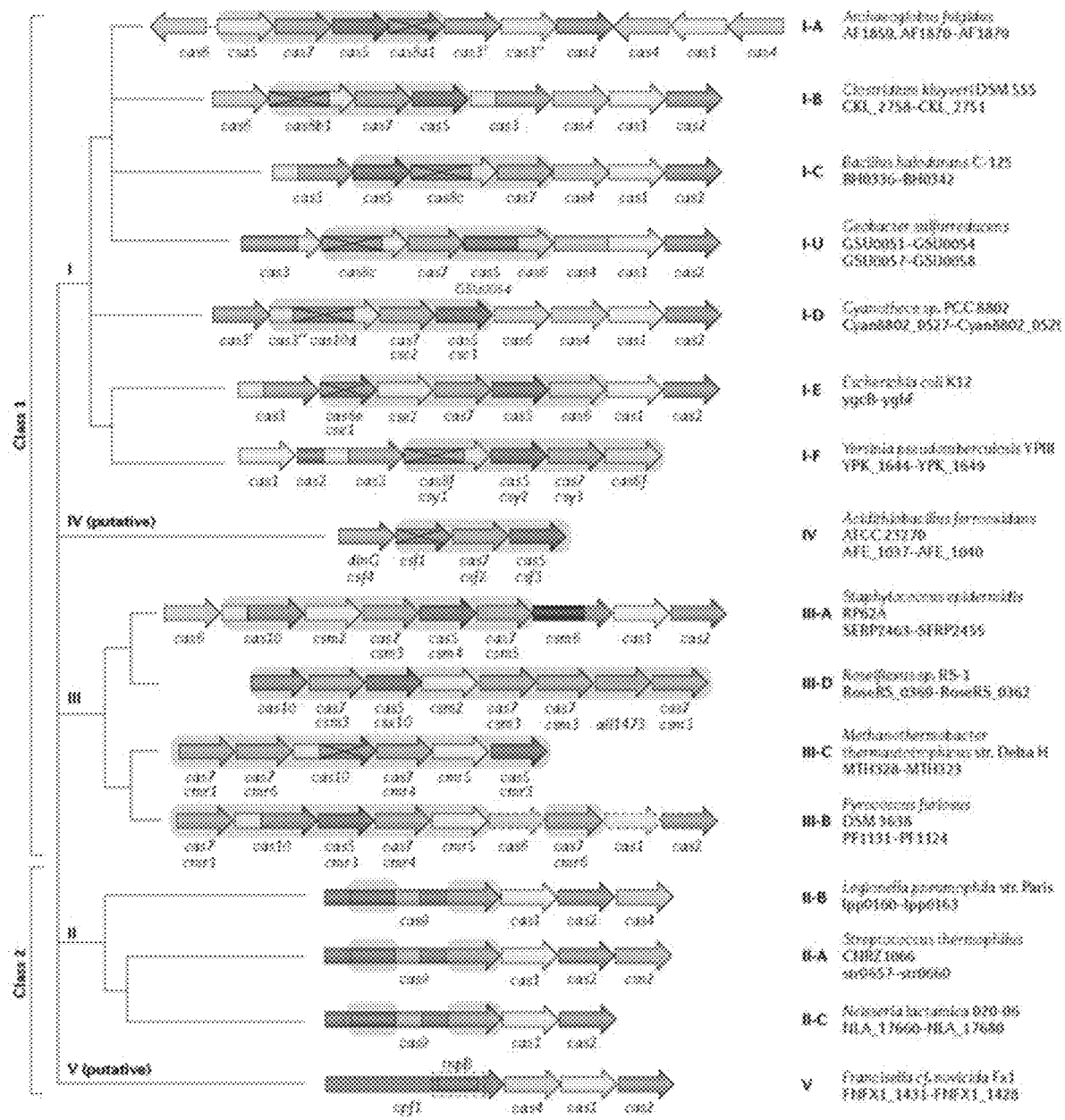
FIG. 17 shows an illustration adapted from FIG. 2 of Makarova, K. S. et al, "An updated evolutionary classification of CRISPR-Cas systems," Nat Rev Microbiol (2015) 13:722-736 providing architectures of the genomic loci for subtypes of CRISPR-Cas systems.

Any suitable CRISPR/Cas system can be used. A CRISPR/Cas system can be referred to using a variety of naming systems. Exemplary naming systems are provided in Makarova, K. S. et al, "An updated evolutionary classification of CRISPR-Cas systems," Nat Rev Microbiol (2015) 13:722-736 and Shmakov, S. et al, "Discovery and Functional Characterization of Diverse Class 2 CRISPR-Cas Systems," Mol Cell (2015) 60:1-13. A CRISPR/Cas system can be a type I, a type II, a type III, a type IV, a type V, a type VI system, or any other suitable CRISPR/Cas system. A CRISPR/Cas system as used herein can be a Class 1, Class 2, or any other suitably classified CRISPR/Cas system. Class 1 or Class 2 determination can be based upon the genes encoding the effector module. Class 1 systems generally have a multi-subunit crRNA-effector complex, whereas Class 2 systems generally have a single protein, such as Cas9, Cpf1, C2c1, C2c2, C2c3, or a crRNA-effector complex. A Class 1 CRISPR/Cas system can use a complex of multiple Cas proteins to effect regulation. A Class 1 CRISPR/Cas system can comprise, for example, type I (e.g., I, IA, IB, IC, ID, IE, IF, IU), type III (e.g., III, IIIA, IIIB, IIIC, IIID), and type IV (e.g., IV, IVA, IVB) CRISPR/Cas type. A Class 2 CRISPR/Cas system can use a single large Cas protein to effect regulation. A Class 2 CRISPR/Cas systems can comprise, for example, type II (e.g., II, IIA, IIB) and type V CRISPR/Cas type. CRISPR systems can be complementary to each other, and/or can lend functional units in trans to facilitate CRISPR locus targeting. FIG. 17 shows an illustration adapted from FIG. 2 of Makarova, K. S. et al, "An updated evolutionary classification of CRISPR-Cas systems," Nat Rev Microbiol (2015) 13:722-736 providing architectures of the genomic loci for subtypes of CRISPR-Cas systems.

An actuator moiety comprising a Cas protein can be a Class 1 or a Class 2 Cas protein. A Cas protein can be a type I, type II, type III, type IV, type V, or type VI Cas protein. A Cas protein can comprise one or more domains. Non-limiting examples of domains include, guide nucleic acid recognition and/or binding domain, nuclease domains (e.g., DNase or RNase domains, RuvC, HNH), DNA binding domain, RNA binding domain, helicase domains, protein-protein interaction domains, and dimerization domains. A guide nucleic acid recognition and/or binding domain can interact with a guide nucleic acid. A nuclease domain can comprise catalytic activity for nucleic acid cleavage. A nuclease domain can lack catalytic activity to prevent nucleic acid cleavage. A Cas protein can be a chimeric Cas protein that is fused to other proteins or polypeptides. A Cas protein can be a chimera of various Cas proteins, for example, comprising domains from different Cas proteins.

Non-limiting examples of Cas proteins include c2c1, C2c2, c2c3, Cas1, Cas1B, Cas2, Cas3, Cas4, Cas5, Cas5e (CasD), Cash, Cas6e, Cas6f, Cas7, Cas8a, Cas8al, Cas8a2, Cas8b, Cas8c, Cas9 (Csn1 or Csx12), Cas10, Cas10d, Cas1O, Cas1Od, CasF, CasG, CasH, Cpf1, Csy1, Csy2, Csy3, Cse1 (CasA), Cse2 (CasB), Cse3 (CasE), Cse4 (CasC), Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx1O, Csx16, CsaX, Csx3, Csx1, Csx15, Csf1, Csf2, Csf3, Csf4, and Cu1966, and homologs or modified versions thereof.

A Cas protein can be from any suitable organism. Non-limiting examples include *Streptococcus pyogenes*, *Streptococcus thermophilus*, *Streptococcus* sp., *Staphylococcus aureus*, *Nocardiopsis dassonvillei*, *Streptomyces pristinae spiralis*, *Streptomyces viridochromo* genes, *Streptomyces viridochromogenes*, *Streptosporangium roseum*, *Streptosporangium roseum*, *AlicyclobacHlus acidocaldarius*, *Bacillus pseudomycoides*, *Bacillus selenitireducens*, *Exiguobacterium sibiricum*, *Lactobacillus delbrueckii*, *Lactobacillus salivarius*, *Microscilla marina*, *Burkholderiales bacterium*, *Polaromonas naphthalenivorans*, *Polaromonas* sp., *Crocosphaera watsonii*, *Cyanothece* sp., *Microcystis aeruginosa*, *Pseudomonas aeruginosa*, *Synechococcus* sp., *Acetohalobium arabaticum*, *Ammonifex degensii*, *Caldicelulosiruptor becscii*, *Candidatus Desulforudis*, *Clostridium botulinum*, *Clostridium difficile*, *Finegoldia magna*, *Natranaerobius thermophilus*, *Pelotomaculum thermopropionicum*, *Acidithiobacillus caldus*, *Acidithiobacillus ferrooxidans*, *Allochromatium vinosum*, *Marinobacter* sp., *Nitrosococcus halophilus*, *Nitrosococcus watsoni*, *Pseudoalteromonas haloplanktis*, *Ktedonobacter racemifer*, *Methanohalobium evestigatum*, *Anabaena variabilis*, *Nodularia spumigena*, *Nostoc* sp., *Arthrospira maxima*, *Arthrospira platensis*, *Arthrospira* sp., *Lyngbya* sp., *Microcoleus chthonoplastes*, *Oscillatoria* sp., *Petrotoga mobilis*, *Thermosipho africanus*, *Acaryochloris marina*, *Leptotrichia shahii*, and *Francisella novicida*. In some aspects, the organism is *Streptococcus pyogenes* (*S. pyogenes*). In some aspects, the organism is *Staphylococcus aureus* (*S. aureus*). In some aspects, the organism is *Streptococcus thermophilus* (*S. thermophilus*).

A Cas protein can be derived from a variety of bacterial species including, but not limited to, *Veillonella atypical*, *Fusobacterium nucleatum*, *Filifactor alocis*, *Solobacterium moorei*, *Coprococcus catus*, *Treponema denticola*, *Peptoniphilus duerdenii*, *Catenibacterium mitsuokai*, *Streptococcus mutans*, *Listeria innocua*, *Staphylococcus pseudintermedius*, *Acidaminococcus intestine*, *Olsenella uli*, *Oenococcus kitaharae*, *Bifidobacterium bifidum*, *Lactobacillus rhamnosus*, *Lactobacillus gasseri*, *Finegoldia magna*, *Mycoplasma mobile*, *Mycoplasma gallisepticum*, *Mycoplasma ovipneumoniae*, *Mycoplasma canis*, *Mycoplasma synoviae*, *Eubacterium rectale*, *Streptococcus thermophilus*, *Eubacterium dolichum*, *Lactobacillus coryniformis* subsp. *Torquens*, *Ilyobacter polytropus*, *Ruminococcus albus*, *Akkermansia muciniphila*, *Acidothermus cellulolyticus*, *Bifidobacterium longum*, *Bifidobacterium dentium*, *Corynebacterium diphtheria*, *Elusimicrobium minutum*, *Nitratifractor salsuginis*, *Sphaerochaeta globus*, *Fibrobacter succinogenes* subsp. *Succinogenes*, *Bacteroides fragilis*, *Capnocytophaga ochracea*, *Rhodopseudomonas palustris*, *Prevotella micans*, *Prevotella ruminicola*, *Flavobacterium columnare*, *Aminomonas paucivorans*, *Rhodospirillum rubrum*, *Candidatus Puniceispirillum marinum*, *Verminephrobacter eiseniae*, *Ralstonia syzygii*, *Dinoroseobacter shibae*, *Azospirillum*, *Nitrobacter hamburgensis*, *Bradyrhizobium*, *Wolinella succinogenes*, *Campylobacter jejuni* subsp. *Jejuni*, *Helicobacter mustelae*, *Bacillus cereus*, *Acidovorax ebreus*, *Clostridium perfringens*, *Parvibaculum lavamentivorans*, *Roseburia intestinalis*, *Neisseria meningitidis*, *Pasteurella multocida* subsp. *Multocida*, *Sutterella wadsworthensis*, *proteobacterium*, *Legionella pneumophila*, *Parasutterella excrementihominis*, *Wolinella succinogenes*, and *Francisella novicida*.

A Cas protein as used herein can be a wildtype or a modified form of a Cas protein. A Cas protein can be an active variant, inactive variant, or fragment of a wild type or modified Cas protein. A Cas protein can comprise an amino acid change such as a deletion, insertion, substitution, variant, mutation, fusion, chimera, or any combination thereof relative to a wild-type version of the Cas protein. A Cas protein can be a polypeptide with at least about 5%, 10%, 20%, 30%, 40%, 50%, 60%, 70%, 80%, 90%, 91%, 92%, 93%, 94%, 95%, 96%, 97%, 98%, 99%, or 100% sequence identity or sequence similarity to a wild type exemplary Cas protein. A Cas protein can be a polypeptide with at most about 5%, 10%, 20%, 30%, 40%, 50%, 60%, 70%, 80%, 90%, 100% sequence identity and/or sequence similarity to a wild type exemplary Cas protein. Variants or fragments can comprise at least about 5%, 10%, 20%, 30%, 40%, 50%, 60%, 70%, 80%, 90%, 91%, 92%, 93%, 94%, 95%, 96%, 97%, 98%, 99%, or 100% sequence identity or sequence similarity to a wild type or modified Cas protein or a portion thereof. Variants or fragments can be targeted to a nucleic acid locus in complex with a guide nucleic acid while lacking nucleic acid cleavage activity.

A Cas protein can comprise one or more nuclease domains, such as DNase domains. For example, a Cas9 protein can comprise a RuvC-like nuclease domain and/or an HNH-like nuclease domain. The RuvC and HNH domains can each cut a different strand of double-stranded DNA to make a double-stranded break in the DNA. A Cas protein can comprise only one nuclease domain (e.g., Cpf1 comprises RuvC domain but lacks HNH domain).

A Cas protein can comprise an amino acid sequence having at least about 5%, 10%, 20%, 30%, 40%, 50%, 60%, 70%, 80%, 90%, 91%, 92%, 93%, 94%, 95%, 96%, 97%, 98%, 99%, or 100% sequence identity or sequence similarity to a nuclease domain (e.g., RuvC domain, HNH domain) of a wild-type Cas protein.

A Cas protein can be modified to optimize regulation of gene expression. A Cas protein can be modified to increase or decrease nucleic acid binding affinity, nucleic acid binding specificity, and/or enzymatic activity. Cas proteins can also be modified to change any other activity or property of the protein, such as stability. For example, one or more nuclease domains of the Cas protein can be modified, deleted, or inactivated, or a Cas protein can be truncated to remove domains that are not essential for the function of the protein or to optimize (e.g., enhance or reduce) the activity of the Cas protein for regulating gene expression.

A Cas protein can be a fusion protein. For example, a Cas protein can be fused to a cleavage domain, an epigenetic modification domain, a transcriptional activation domain, or a transcriptional repressor domain. A Cas protein can also be fused to a heterologous polypeptide providing increased or decreased stability. The fused domain or heterologous polypeptide can be located at the N-terminus, the C-terminus, or internally within the Cas protein.

A Cas protein can be provided in any form. For example, a Cas protein can be provided in the form of a protein, such as a Cas protein alone or complexed with a guide nucleic acid. A Cas protein can be provided in the form of a nucleic acid encoding the Cas protein, such as an RNA (e.g., messenger RNA (mRNA)) or DNA.

The nucleic acid encoding the Cas protein can be codon optimized for efficient translation into protein in a particular cell or organism.

Nucleic acids encoding Cas proteins can be stably integrated in the genome of the cell. Nucleic acids encoding Cas proteins can be operably linked to a promoter active in the cell. Nucleic acids encoding Cas proteins can be operably linked to a promoter in an expression construct. Expression constructs can include any nucleic acid constructs capable of directing expression of a gene or other nucleic acid sequence of interest (e.g., a Cas gene) and which can transfer such a nucleic acid sequence of interest to a target cell.

In some embodiments, a Cas protein is a dead Cas protein. A dead Cas protein can be a protein that lacks nucleic acid cleavage activity.

A Cas protein can comprise a modified form of a wild type Cas protein. The modified form of the wild type Cas protein can comprise an amino acid change (e.g., deletion, insertion, or substitution) that reduces the nucleic acid-cleaving activity of the Cas protein. For example, the modified form of the Cas protein can have less than 90%, less than 80%, less than 70%, less than 60%, less than 50%, less than 40%, less than 30%, less than 20%, less than 10%, less than 5%, or less than 1% of the nucleic acid-cleaving activity of the wild-type Cas protein (e.g., Cas9 from *S. pyogenes*). The modified form of Cas protein can have no substantial nucleic acid-cleaving activity. When a Cas protein is a modified form that has no substantial nucleic acid-cleaving activity, it can be referred to as enzymatically inactive and/or "dead" (abbreviated by "d"). A dead Cas protein (e.g., dCas, dCas9) can bind to a target polynucleotide but may not cleave the target polynucleotide. In some aspects, a dead Cas protein is a dead Cas9 protein.

A dCas9 polypeptide can associate with a single guide RNA (sgRNA) to activate or repress transcription of target DNA. sgRNAs can be introduced into cells expressing the engineered chimeric receptor polypeptide. In some cases, such cells contain one or more different sgRNAs that target the same nucleic acid. In other cases, the sgRNAs target different nucleic acids in the cell. The nucleic acids targeted by the guide RNA can be any that are expressed in a cell such as an immune cell. The nucleic acids targeted can be a gene involved in immune cell regulation. In some embodiments, the nucleic acid is associated with cancer. The nucleic acid associated with cancer can be a cell cycle gene, cell response gene, apoptosis gene, or phagocytosis gene. The recombinant guide RNA can be recognized by a CRISPR protein, a nuclease-null CRISPR protein, variants thereof, derivatives thereof, or fragments thereof.

Enzymatically inactive can refer to a polypeptide that can bind to a nucleic acid sequence in a polynucleotide in a sequence-specific manner, but may not cleave a target polynucleotide. An enzymatically inactive site-directed polypeptide can comprise an enzymatically inactive domain (e.g. nuclease domain). Enzymatically inactive can refer to no activity. Enzymatically inactive can refer to substantially no activity. Enzymatically inactive can refer to essentially no activity. Enzymatically inactive can refer to an activity less than 1%, less than 2%, less than 3%, less than 4%, less than 5%, less than 6%, less than 7%, less than 8%, less than 9%, or less than 10% activity compared to a wild-type exemplary activity (e.g., nucleic acid cleaving activity, wild-type Cas9 activity).

One or a plurality of the nuclease domains (e.g., RuvC, HNH) of a Cas protein can be deleted or mutated so that they are no longer functional or comprise reduced nuclease activity. For example, in a Cas protein comprising at least two nuclease domains (e.g., Cas9), if one of the nuclease domains is deleted or mutated, the resulting Cas protein, known as a nickase, can generate a single-strand break at a CRISPR RNA (crRNA) recognition sequence within a double-stranded DNA but not a double-strand break. Such a nickase can cleave the complementary strand or the non-complementary strand, but may not cleave both. If all of the nuclease domains of a Cas protein (e.g., both RuvC and HNH nuclease domains in a Cas9 protein; RuvC nuclease domain in a Cpf1 protein) are deleted or mutated, the resulting Cas protein can have a reduced or no ability to cleave both strands of a double-stranded DNA. An example of a mutation that can convert a Cas9 protein into a nickase is a D10A (aspartate to alanine at position 10 of Cas9) mutation in the RuvC domain of Cas9 from *S. pyogenes*. H939A (histidine to alanine at amino acid position 839) or H840A (histidine to alanine at amino acid position 840) in the HNH domain of Cas9 from *S. pyogenes* can convert the Cas9 into a nickase. An example of a mutation that can convert a Cas9 protein into a dead Cas9 is a D10A (aspartate to alanine at position 10 of Cas9) mutation in the RuvC domain and H939A (histidine to alanine at amino acid position 839) or H840A (histidine to alanine at amino acid position 840) in the HNH domain of Cas9 from S. pyogenes.

A dead Cas protein can comprise one or more mutations relative to a wild-type version of the protein. The mutation can result in less than 90%, less than 80%, less than 70%, less than 60%, less than 50%, less than 40%, less than 30%, less than 20%, less than 10%, less than 5%, or less than 1% of the nucleic acid-cleaving activity in one or more of the plurality of nucleic acid-cleaving domains of the wild-type Cas protein. The mutation can result in one or more of the plurality of nucleic acid-cleaving domains retaining the ability to cleave the complementary strand of the target nucleic acid but reducing its ability to cleave the non-complementary strand of the target nucleic acid. The mutation can result in one or more of the plurality of nucleic acid-cleaving domains retaining the ability to cleave the non-complementary strand of the target nucleic acid but reducing its ability to cleave the complementary strand of the target nucleic acid. The mutation can result in one or more of the plurality of nucleic acid-cleaving domains lacking the ability to cleave the complementary strand and the non-complementary strand of the target nucleic acid. The residues to be mutated in a nuclease domain can correspond to one or more catalytic residues of the nuclease. For example, residues in the wild type exemplary S. pyogenes Cas9 polypeptide such as Asp10, His840, Asn854 and Asn856 can be mutated to inactivate one or more of the plurality of nucleic acid-cleaving domains (e.g., nuclease domains). The residues to be mutated in a nuclease domain of a Cas protein can correspond to residues Asp10, His840, Asn854 and Asn856 in the wild type S. pyogenes Cas9 polypeptide, for example, as determined by sequence and/or structural alignment.

As non-limiting examples, residues D10, G12, G17, E762, H840, N854, N863, H982, H983, A984, D986, and/or A987 (or the corresponding mutations of any of the Cas proteins) can be mutated. For example, e.g., D10A, G12A, G17A, E762A, H840A, N854A, N863A, H982A, H983A, A984A, and/or D986A. Mutations other than alanine substitutions can be suitable.

A D10A mutation can be combined with one or more of H840A, N854A, or N856A mutations to produce a Cas9 protein substantially lacking DNA cleavage activity (e.g., a dead Cas9 protein). A H840A mutation can be combined with one or more of D10A, N854A, or N856A mutations to produce a site-directed polypeptide substantially lacking DNA cleavage activity. A N854A mutation can be combined with one or more of H840A, D10A, or N856A mutations to produce a site-directed polypeptide substantially lacking DNA cleavage activity. A N856A mutation can be combined with one or more of H840A, N854A, or D10A mutations to produce a site-directed polypeptide substantially lacking DNA cleavage activity.

In some embodiments, a Cas protein is a Class 2 Cas protein. In some embodiments, a Cas protein is a type II Cas protein. In some embodiments, the Cas protein is a Cas9 protein, a modified version of a Cas9 protein, or derived from a Cas9 protein. For example, a Cas9 protein lacking cleavage activity. In some embodiments, the Cas9 protein is a Cas9 protein from S. pyogenes (e.g., SwissProt accession number Q99ZW2). In some embodiments, the Cas9 protein is a Cas9 from S. aureus (e.g., SwissProt accession number J7RUA5). In some embodiments, the Cas9 protein is a modified version of a Cas9 protein from S. pyogenes or S. Aureus. In some embodiments, the Cas9 protein is derived from a Cas9 protein from S. pyogenes or S. Aureus. For example, a S. pyogenes or S. Aureus Cas9 protein lacking cleavage activity.

Cas9 can generally refer to a polypeptide with at least about 5%, 10%, 20%, 30%, 40%, 50%, 60%, 70%, 80%, 90%, 100% sequence identity and/or sequence similarity to a wild type exemplary Cas9 polypeptide (e.g., Cas9 from S. pyogenes). Cas9 can refer to a polypeptide with at most about 5%, 10%, 20%, 30%, 40%, 50%, 60%, 70%, 80%, 90%, 100% sequence identity and/or sequence similarity to a wild type exemplary Cas9 polypeptide (e.g., from S. pyogenes). Cas9 can refer to the wildtype or a modified form of the Cas9 protein that can comprise an amino acid change such as a deletion, insertion, substitution, variant, mutation, fusion, chimera, or any combination thereof.

In some embodiments, the actuator moiety comprises a "zinc finger nuclease" or "ZFN." ZFNs refer to a fusion between a cleavage domain, such as a cleavage domain of FokI, and at least one zinc finger motif (e.g., at least 2, 3, 4, or 5 zinc finger motifs) which can bind polynucleotides such as DNA and RNA. The heterodimerization at a certain position in a polynucleotide of two individual ZFNs in certain orientation and spacing can lead to cleavage of the polynucleotide. For example, a ZFN binding to DNA can induce a double-strand break in the DNA. In order to allow two cleavage domains to dimerize and cleave DNA, two individual ZFNs can bind opposite strands of DNA with their C-termini at a certain distance apart. In some cases, linker sequences between the zinc finger domain and the cleavage domain can require the 5' edge of each binding site to be separated by about 5-7 base pairs. In some cases, a cleavage domain is fused to the C-terminus of each zinc finger domain. Exemplary ZFNs include, but are not limited to, those described in Urnov et al., Nature Reviews Genetics, 2010, 11:636-646; Gaj et al., Nat Methods, 2012, 9(8):805-7; U.S. Pat. Nos. 6,534,261; 6,607,882; 6,746,838; 6,794,136; 6,824,978; 6,866,997; 6,933,113; 6,979,539; 7,013,219; 7,030,215; 7,220,719; 7,241,573; 7,241,574; 7,585,849; 7,595,376; 6,903,185; 6,479,626; and U.S. Application Publication Nos. 2003/0232410 and 2009/0203140.

In some embodiments, an actuator moiety comprising a ZFN can generate a double-strand break in a target polynucleotide, such as DNA. A double-strand break in DNA can result in DNA break repair which allows for the introduction of gene modification(s) (e.g., nucleic acid editing). DNA break repair can occur via non-homologous end joining (NHEJ) or homology-directed repair (HDR). In HDR, a donor DNA repair template that contains homology arms flanking sites of the target DNA can be provided. In some embodiments, a ZFN is a zinc finger nickase which induces site-specific single-strand DNA breaks or nicks, thus resulting in HDR. Descriptions of zinc finger nickases are found, e.g., in Ramirez et al., Nucl Acids Res, 2012, 40(12):5560-8; Kim et al., Genome Res, 2012, 22(7):1327-33. In some embodiments, a ZFN binds a polynucleotide (e.g., DNA and/or RNA) but is unable to cleave the polynucleotide.

In some embodiments, the cleavage domain of an actuator moiety comprising a ZFN comprises a modified form of a wild type cleavage domain. The modified form of the cleavage domain can comprise an amino acid change (e.g., deletion, insertion, or substitution) that reduces the nucleic acid-cleaving activity of the cleavage domain. For example, the modified form of the cleavage domain can have less than 90%, less than 80%, less than 70%, less than 60%, less than 50%, less than 40%, less than 30%, less than 20%, less than 10%, less than 5%, or less than 1% of the nucleic acid-cleaving activity of the wild-type cleavage domain. The modified form of the cleavage domain can have no substantial nucleic acid-cleaving activity. In some embodiments, the cleavage domain is enzymatically inactive.

In some embodiments, an actuator moiety comprises a "TALEN" or "TAL-effector nuclease." TALENs refer to engineered transcription activator-like effector nucleases that generally contain a central domain of DNA-binding tandem repeats and a cleavage domain. TALENs can be produced by fusing a TAL effector DNA binding domain to a DNA cleavage domain. In some cases, a DNA-binding tandem repeat comprises 33-35 amino acids in length and contains two hypervariable amino acid residues at positions 12 and 13 that can recognize at least one specific DNA base pair. A transcription activator-like effector (TALE) protein can be fused to a nuclease such as a wild-type or mutated FokI endonuclease or the catalytic domain of FokI. Several mutations to FokI have been made for its use in TALENs, which, for example, improve cleavage specificity or activity. Such TALENs can be engineered to bind any desired DNA sequence. TALENs can be used to generate gene modifications (e.g., nucleic acid sequence editing) by creating a double-strand break in a target DNA sequence, which in turn, undergoes NHEJ or HDR. In some cases, a single-stranded donor DNA repair template is provided to promote HDR. Detailed descriptions of TALENs and their uses for gene editing are found, e.g., in U.S. Pat. Nos. 8,440,431; 8,440,432; 8,450,471; 8,586,363; and 8,697,853; Scharenberg et al., Curr Gene Ther, 2013, 13(4):291-303; Gaj et al., Nat Methods, 2012, 9(8):805-7; Beurdeley et al., Nat Commun, 2013, 4:1762; and Joung and Sander, Nat Rev Mol Cell Biol, 2013, 14(1):49-55.

In some embodiments, a TALEN is engineered for reduced nuclease activity. In some embodiments, the nuclease domain of a TALEN comprises a modified form of a wild type nuclease domain. The modified form of the nuclease domain can comprise an amino acid change (e.g., deletion, insertion, or substitution) that reduces the nucleic acid-cleaving activity of the nuclease domain. For example, the modified form of the nuclease domain can have less than 90%, less than 80%, less than 70%, less than 60%, less than 50%, less than 40%, less than 30%, less than 20%, less than 10%, less than 5%, or less than 1% of the nucleic acid-cleaving activity of the wild-type nuclease domain. The modified form of the nuclease domain can have no substantial nucleic acid-cleaving activity. In some embodiments, the nuclease domain is enzymatically inactive.

In some embodiments, the transcription activator-like effector (TALE) protein is fused to a domain that can modulate transcription and does not comprise a nuclease. In some embodiments, the transcription activator-like effector (TALE) protein is designed to function as a transcriptional activator. In some embodiments, the transcription activator-like effector (TALE) protein is designed to function as a transcriptional repressor. For example, the DNA-binding domain of the transcription activator-like effector (TALE) protein can be fused (e.g., linked) to one or more transcriptional activation domains, or to one or more transcriptional repression domains. Non-limiting examples of a transcriptional activation domain include a herpes simplex VP16 activation domain and a tetrameric repeat of the VP16 activation domain, e.g., a VP64 activation domain. A non-limiting example of a transcriptional repression domain includes a Krüppel-associated box domain.

In some embodiments, an actuator moiety comprises a meganuclease. Meganucleases generally refer to rare-cutting endonucleases or homing endonucleases that can be highly specific. Meganucleases can recognize DNA target sites ranging from at least 12 base pairs in length, e.g., from 12 to 40 base pairs, 12 to 50 base pairs, or 12 to 60 base pairs in length. Meganucleases can be modular DNA-binding nucleases such as any fusion protein comprising at least one catalytic domain of an endonuclease and at least one DNA binding domain or protein specifying a nucleic acid target sequence. The DNA-binding domain can contain at least one motif that recognizes single- or double-stranded DNA. The meganuclease can be monomeric or dimeric. In some embodiments, the meganuclease is naturally-occurring (found in nature) or wild-type, and in other instances, the meganuclease is non-natural, artificial, engineered, synthetic, rationally designed, or man-made. In some embodiments, the meganuclease of the present disclosure includes an I-CreI meganuclease, I-CeuI meganuclease, I-MsoI meganuclease, I-SceI meganuclease, variants thereof, derivatives thereof, and fragments thereof. Detailed descriptions of useful meganucleases and their application in gene editing are found, e.g., in Silva et al., Curr Gene Ther, 2011, 11(1):11-27; Zaslavoskiy et al., BMC Bioinformatics, 2014, 15:191; Takeuchi et al., Proc Natl Acad Sci USA, 2014, 111(11):4061-4066, and U.S. Pat. Nos. 7,842,489; 7,897,372; 8,021,867; 8,163,514; 8,133,697; 8,021,867; 8,119,361; 8,119,381; 8,124,36; and 8,129,134.

In some embodiments, the nuclease domain of a meganuclease comprises a modified form of a wild type nuclease domain. The modified form of the nuclease domain can comprise an amino acid change (e.g., deletion, insertion, or substitution) that reduces the nucleic acid-cleaving activity of the nuclease domain. For example, the modified form of the nuclease domain can have less than 90%, less than 80%, less than 70%, less than 60%, less than 50%, less than 40%, less than 30%, less than 20%, less than 10%, less than 5%, or less than 1% of the nucleic acid-cleaving activity of the wild-type nuclease domain. The modified form of the nuclease domain can have no substantial nucleic acid-cleaving activity. In some embodiments, the nuclease domain is enzymatically inactive. In some embodiments, a meganuclease can bind DNA but cannot cleave the DNA.

In some embodiments, the actuator moiety is fused to one or more transcription repressor domains, activator domains, epigenetic domains, recombinase domains, transposase domains, flippase domains, nickase domains, or any combination thereof. The activator domain can include one or more tandem activation domains located at the carboxyl terminus of the protein. In some cases, the actuator moiety includes one or more tandem repressor domains located at the carboxyl terminus of the protein. Non-limiting exemplary activation domains include GAL4, herpes simplex activation domain VP16, VP64 (a tetramer of the herpes simplex activation domain VP16), NF-κB p65 subunit, Epstein-Barr virus R transactivator (Rta) and are described in Chavez et al., Nat Methods, 2015, 12(4):326-328 and U.S. Patent App. Publ. No. 20140068797. Non-limiting exemplary repression domains include the KRAB (Kruppel-associated box) domain of Kox1, the Mad mSIN3 interaction domain (SID), ERF repressor domain (ERD), and are described in Chavez et al., Nat Methods, 2015, 12(4):326-328 and U.S. Patent App. Publ. No. 20140068797. In some embodiments, the actuator moiety includes one or more tandem repressor domains located at the amino terminus of the protein.

An actuator moiety can also be fused to a heterologous polypeptide providing increased or decreased stability. The fused domain or heterologous polypeptide can be located at the N-terminus, the C-terminus, or internally within the actuator moiety.

An actuator moiety can comprise a heterologous polypeptide for ease of tracking or purification, such as a fluorescent protein, a purification tag, or an epitope tag. Examples of fluorescent proteins include green fluorescent proteins (e.g., GFP, GFP-2, tagGFP, turboGFP, eGFP, Emerald, Azami Green, Monomeric Azami Green, CopGFP, AceGFP, ZsGreen1), yellow fluorescent proteins (e.g., YFP, eYFP, Citrine, Venus, YPet, PhiYFP, ZsYellow1), blue fluorescent proteins (e.g. eBFP, eBFP2, Azurite, mKalama1, GFPuv, Sapphire, T-sapphire), cyan fluorescent proteins (e.g. eCFP, Cerulean, CyPet, AmCyan1, Midoriishi-Cyan), red fluorescent proteins (mKate, mKate2, mPlum, DsRed monomer, mCherry, mRFP1, DsRed-Express, DsRed2, DsRed-Monomer, HcRed-Tandem, HcRed1, AsRed2, eqFP611, mRaspberry, mStrawberry, Jred), orange fluorescent proteins (mOrange, mKO, Kusabira-Orange, Monomeric Kusabira-Orange, mTangerine, tdTomato), and any other suitable fluorescent protein. Examples of tags include glutathione-S-transferase (GST), chitin binding protein (CBP), maltose binding protein, thioredoxin (TRX), poly (NANP), tandem affinity purification (TAP) tag, myc, AcV5, AU1, AUS, E, ECS, E2, FLAG, hemagglutinin (HA), nus, Softag 1, Softag 3, Strep, SBP, Glu-Glu, HSV, KT3, S, SI, T7, V5, VSV-G, histidine (His), biotin carboxyl carrier protein (BCCP), and calmodulin.

Figure 3B:
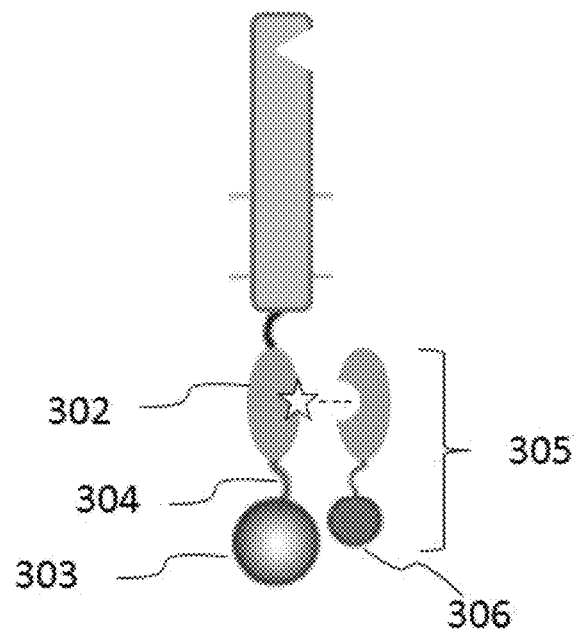
FIG. 3B shows an exemplary system comprising a chimeric transmembrane receptor polypeptide comprising an antigen interacting domain, an immune cell signaling domain, and gene modulating polypeptide (GMP) and a chimeric adaptor polypeptide comprising a cleavage moiety.

The actuator moiety can be released from the GMP by cleavage of the cleavage recognition site. The cleavage recognition site of a GMP can be flanked by the immune cell signaling domain and the actuator moiety in a chimeric transmembrane receptor polypeptide. A cleavage moiety can recognize and/or cleave a cleavage recognition site, for example, when in proximity to the cleavage recognition site. A cleavage moiety can comprise a polypeptide sequence. The cleavage moiety can form a portion of the chimeric adaptor polypeptide. The cleavage moiety can form the N-terminus, C-terminus, or an internal portion of the chimeric adaptor polypeptide. In some embodiments, the cleavage moiety is complexed to the chimeric adaptor polypeptide. The cleavage moiety can be complexed to the N-terminus, C-terminus, or an internal portion of the chimeric adaptor polypeptide. FIG. 3B shows an exemplary arrangement of the various components of a subject system. The cleavage recognition site 304 of a GMP is flanked by the immune cell signaling domain 302 and the actuator moiety 303, and the cleavage moiety 306 forms a portion of a chimeric adaptor polypeptide 305.

FIGS. 4A-D illustrate schematically the release of an actuator moiety from a GMP. FIG. 4A shows the binding of an antigen to a transmembrane chimeric receptor polypeptide. The transmembrane chimeric receptor polypeptide comprises an extracellular region having an antigen interacting domain 401 and an intracellular region comprising a GMP. The intracellular region also comprises an immune cell signaling domain. The GMP includes an actuator moiety 402a linked to a cleavage recognition site 402b. In response to antigen binding, the receptor is modified by phosphorylation 403 in the intracellular region of the receptor (FIG. 4B). Following receptor modification (e.g., phosphorylation), an adaptor protein comprising a receptor binding moiety is recruited to the receptor as shown in FIG. 4C. The receptor comprises a cleavage moiety 404; the cleavage moiety may be complexed with the adaptor or linked, for example by a peptide bond and/or peptide linker, to the receptor binding moiety. When in proximity to the cleavage recognition site, the cleavage moiety can cleave the recognition site to release the actuator moiety from the GMP as shown in FIG. 4D. Upon release, the actuator moiety can enter the nucleus to regulate the expression and/or activity of a target gene or edit a nucleic acid sequence. FIGS. 4E-H show an analogous system wherein receptor modification comprises a conformational change. In some embodiments, the adaptor protein is tethered to the membrane (e.g., as a membrane bound protein).

In some embodiments, the cleavage moiety only cleaves the recognition site when in proximity to the cleavage recognition site. The cleavage recognition site can comprise a polypeptide sequence that is a recognition sequence of a protease. The cleavage moiety can comprise protease activity which recognizes the polypeptide sequence. A cleavage moiety comprising protease activity can be a protease, or any derivative, variant or fragment thereof. A protease refers to any enzyme that performs proteolysis, in which polypeptides are cleaved into smaller polypeptides or amino acids. Various proteases are suitable for use as a cleavage moiety. Some proteases can be highly promiscuous such that a wide range of protein substrates are hydrolysed. Some proteases can be highly specific and only cleave substrates with a certain sequence, e.g., a cleavage recognition sequence or peptide cleavage domain. In some embodiments, the cleavage recognitions site comprises multiple cleavage recognition sequences, and each cleavage recognition sequence can be recognized by the same or different cleavage moiety comprising protease activity (e.g., protease). Sequence-specific proteases that can be used as cleavage moieties include, but are not limited to, superfamily CA proteases, e.g., families C1, C2, C6, C10, C12, C16, C19, C28, C31, C32, C33, C39, C47, C51, C54, C58, C64, C65, C66, C67, C70, C71, C76, C78, C83, C85, C86, C87, C93, C96, C98, and C101, including papain (*Carica papaya*), bromelain (*Ananas comosus*), cathepsin K (liverwort) and calpain (*Homo sapiens*); superfamily CD proteases, e.g., family C11, C13, C14, C25, C50, C80, and C84: such as caspase-1 (*Rattus norvegicus*) and separase (*Saccharomyces cerevisiae*); superfamily CE protease, e.g., family C5, C48, C55, C57, C63, and C79 including adenain (human adenovirus type 2); superfamily CF proteases, e.g., family C15 including pyroglutamyl-peptidase I (*Bacillus amyloliquefaciens*); superfamily CL proteases, e.g., family C60 and C82 including sortase A (*Staphylococcus aureus*); superfamily CM proteases, e.g. family C18 including hepatitis C virus peptidase 2 (hepatitis C virus); superfamily CN proteases, e.g., family C9 including sindbis virus-type nsP2 peptidase (sindbis virus); superfamily CO proteases, e.g., family C40 including dipeptidyl-peptidase VI (*Lysinibacillus sphaericus*); superfamily CP proteases, e.g., family C97 including DeSI-1 peptidase (*Mus musculus*); superfamily PA proteases, e.g., family C3, C4, C24, C30, C37, C62, C74, and C99 including TEV protease (Tobacco etch virus); superfamily PB proteases, e.g., family C44, C45, C59, C69, C89, and C95 including amidophosphoribosyltransferase precursor (*Homo sapiens*); superfamily PC proteases, families C26, and C56 including γ-glutamyl hydrolase (*Rattus norvegicus*); superfamily PD proteases, e.g., family C46 including Hedgehog protein (*Drosophila melanogaster*); superfamily PE proteases, e.g., family P1 including DmpA aminopeptidase (*Ochrobactrum anthropi*); others proteases, e.g., family C7, C8, C21, C23, C27, C36, C42, C53 and C75. Additional proteases include serine proteases, e.g., those of superfamily SB, e.g., families S8 and S53 including subtilisin (*Bacillus licheniformis*); those of superfamily SC, e.g., families S9, S10, S15, S28, S33, and S37 including prolyl oligopeptidase (*Sus scrofa*); those of superfamily SE, e.g., families S11, S12, and S13 including D-Ala-D-Ala peptidase C (*Escherichia coli*); those of superfamily SF, e.g., families S24 and S26 including signal peptidase I (*Escherichia coli*); those of Superfamily SJ, e.g., families S16, S50, and S69 including lon-A peptidase (*Escherichia coli*); those of Superfamily SK, e.g., families S14, S41, and S49 including Clp protease (*Escherichia coli*); those of Superfamily SO, e.g., families S74 including Phage K1F endosialidase CIMCD self-cleaving protein (Enterobacteria phage K1F); those of superfamily SP, e.g., family S59 including nucleoporin 145 (*Homo sapiens*); those of superfamily SR, e.g., family S60 including Lactoferrin (*Homo sapiens*); those of superfamily SS, families S66 including murein tetrapeptidase LD-carboxypeptidase (*Pseudomonas aeruginosa*); those of superfamily ST, e.g., families S54 including rhomboid-1 (*Drosophila melanogaster*); those of superfamily PA, e.g., families S1, S3, S6, S7, S29, S30, S31, S32, S39, S46, S55, S64, S65, and S75 including Chymotrypsin A (*Bos taurus*); those of superfamily PB, e.g., families S45 and S63 including penicillin G acylase precursor (*Escherichia coli*); those of superfamily PC, e.g., families S51 including dipeptidase E (*Escherichia coli*); those of superfamily PE, e.g., families P1 including DmpA aminopeptidase (*Ochrobactrum anthropi*); those unassigned, e.g., families S48, S62, S68, S71, S72, S79, and S81 threonine proteases, e.g., those of superfamily PB clan, e.g., families T1, T2, T3, and T6 including archaean proteasome, β component (*Thermoplasma acidophilum*); and those of superfamily PE clan, e.g., family T5 including ornithine acetyltransferase (*Saccharomyces cerevisiae*); aspartic proteases, e.g., BACE1, BACE2; cathepsin D; cathepsin E; chymosin; napsin-A; nepenthesin; pepsin; plasmepsin; presenilin; renin; and HIV-1 protease, and metalloproteinases, e.g., exopeptidases, metalloexopeptidases; endopeptidases, and metalloendopeptidases. A cleavage recognition sequence (e.g., polypeptide sequence) can be recognized by any of the proteases disclosed herein.

In some embodiments, the cleavage recognition site comprises a cleavage recognition sequence (e.g., polypeptide sequence or peptide cleavage domain) that is recognized by a protease selected from the group consisting of: achromopeptidase, aminopeptidase, ancrod, angiotensin converting enzyme, bromelain, calpain, calpain I, calpain II, carboxypeptidase A, carboxypeptidase B, carboxypeptidase G, carboxypeptidase P, carboxypeptidase W, carboxypeptidase Y, caspase 1, caspase 2, caspase 3, caspase 4, caspase 5, caspase 6, caspase 7, caspase 8, caspase 9, caspase 10, caspase 11, caspase 12, caspase 13, cathepsin B, cathepsin C, cathepsin D, cathepsin E, cathepsin G, cathepsin H, cathepsin L, chymopapain, chymase, chymotrypsin, clostripain, collagenase, complement C1r, complement C1s, complement Factor D, complement factor I, cucumisin, dipeptidyl peptidase IV, elastase (leukocyte), elastase (pancreatic), endoproteinase Arg-C, endoproteinase Asp-N, endoproteinase Glu-C, endoproteinase Lys-C, enterokinase, factor Xa, ficin, furin, granzyme A, granzyme B, HIV Protease, IGase, kallikrein tissue, leucine aminopeptidase (general), leucine aminopeptidase (cytosol), leucine aminopeptidase (microsomal), matrix metalloprotease, methionine aminopeptidase, neutrase, papain, pepsin, plasmin, prolidase, pronase E, prostate specific antigen, protease alkalophilic from *Streptomyces griseus*, protease from *Aspergillus*, protease from *Aspergillus saitoi*, protease from *Aspergillus sojae*, protease (*B. licheniformis*) (alkaline or alcalase), protease from *Bacillus polymyxa*, protease from *Bacillus* sp, protease from *Rhizopus* sp., protease S, proteasomes, proteinase from *Aspergillus oryzae*, proteinase 3, proteinase A, proteinase K, protein C, pyroglutamate aminopeptidase, rennin, rennin, streptokinase, subtilisin, thermolysin, thrombin, tissue plasminogen activator, trypsin, tryptase and urokinase.

Table 2 lists exemplary proteases and associated recognition sequences that can be used in systems of the disclosure.

TABLE 2

Exemplary proteases and associated recognition sequences

| Protease name | Synonyms | Recognition sequence |
|---|---|---|
| Arg-C | Arginyl peptidase, Endoproteinase Arg-C, Tissue kallikrein | R-x |
| Asp-N | Endoproteinase Asp-N, Peptidyl-Asp metalloendopeptidase | x-D |
| Asp-N (N-terminal Glu) | Endoproteinase Asp-N, Peptidyl-Asp metalloendopeptidase | x-[DE] |
| BNPS or NCS/urea | 3-Bromo-3-methyl-2-(2-nitrophenylthio)-3H-indole, BNPS-skatol, N-chlorosuccinimide/urea | W-x |
| Caspase-1 | ICE, Interleukin-1β-Converting Enzyme | [FLWY]-x-[AHT]-D-{DEKPQR} |
| Caspase-10 | Flice2, Mch4 | I-E-A-D-x |
| Caspase-2 | Ich-1, Nedd2 | D-V-A-D-{DEKPQR} or D-E-H-D-{DEKPQR} |
| Caspase-3 | Apopain, CPP32, Yama | D-M-Q-D-{DEKPQR} or D-E-V-D-{DEKPQR} |
| Caspase-4 | ICE(rel)II, Ich-2, TX | L-E-V-D-{DEKPQR} or [LW]-E-H-D-{DEKPQR} |
| Caspase-5 | ICE(rel)III, TY | [LW]-E-H-D-x |
| Caspase-6 | Mch2 | V-E-[HI]-D-{DEKPQR} |
| Caspase-7 | CMH-1, ICE-LAP3, Mch-3 | D-E-V-D-{DEKPQR} |
| Caspase-8 | FLICE, MASH, Mch5 | [IL]-E-T-D-{DEKPQR} |
| Caspase-9 | ICE-Lap6, Mch6 | L-E-H-D-x |
| Chymotrypsin | | [FY]-{P} or W-{MP} |
| Chymotrypsin (low specificity) | | [FLY]-{P} or W-{MP} or M-{PY} or H-{DMPW} |
| Clostripain | Clostridiopeptidase B | R-x |
| CNBr | Cyanogen bromide | M-x |
| CNBr (methyl-Cys) | Cyanogen bromide | M-x or x-C |
| CNBr (with acids) | Cyanogen bromide | [MW]-x |
| Enterokinase | Enteropeptidase | [DE](4)-K-x |
| Factor Xa | Coagulation factor Xa | [AFGILTVM]-[DE]-G-R-x |
| Formic acid | | D-x |
| Glu-C (AmAc buffer) | Endoproteinase Glu-C, V8 protease, Glutamyl endopeptidase | E-x |

TABLE 2-continued

Exemplary proteases and associated recognition sequences

| Protease name | Synonyms | Recognition sequence |
|---|---|---|
| Glu-C (Phos buffer) | Endoproteinase Glu-C, V8 protease, Glutamyl endopeptidase | [DE]-x |
| Granzyme B | Cytotoxic T-lymphocyte proteinase 2, Granzyme-2, GranzymeB, Lymphocyte protease, SECT, T-cell serine protease 1-3E | I-E-P-D-x |
| HRV3C protease | Human rhinovirus 3C protease, Picornain 3C, Protease 3C | L-E-V-L-F-Q-G-P |
| Hydroxylamine | Hydroxylammonium | N-G |
| Iodosobenzoic acid | 2-Iodosobenzoic acid | W-x |
| Lys-C | Endoproteinase Lys-C, Lysyl endopeptidase | K-x |
| Lys-N | Endoproteinase Lys-N, Peptidyl-Lys metalloendopeptidase, Armillaria mellea neutral proteinase | x-K |
| Lys-N (Cys modified) | Endoproteinase Lys-N, Peptidyl-Lys metalloendopeptidase, Armillaria mellea neutral proteinase | x-[CK] |
| Mild acid hydrolysis | | D-P |
| NBS (long exposure) | N-Bromosuccinimide | [HWY]-x |
| NBS (short exposure) | N-Bromosuccinimide | [WY]-x |
| NTCB | 2-Nitro-5-thiocyanatobenzoic acid, 2-Nitro-5-thiocyanobenzoic acid | x-C |
| Pancreatic elastase | Pancreatopeptidase E, Elastase-1 | [AGSV]-x |
| Pepsin A | Pepsin | {HKR}-{P}-{R}-[FLWY]-{P} or {HKR}-{P}-[FLWY]-x-{P} |
| Pepsin A (low specificity) | Pepsin | {HKR}-{P}-{R}-[FL]-{P} or {HKR}-{P}-[FL]-x-{P} |
| Prolyl endopeptidase | Prolyl oligopeptidase, Post-proline cleaving enzyme | [HKR]-P-{P} |
| Proteinase K | Endopeptidase K, Peptidase K | [AEFILTVWY]-x |
| TEV protease | Tobacco etch virus protease, Nuclear-inclusion-a endopeptidase | E-x-x-Y-x-Q-[GS] |
| Thermolysin | Thermophilic-bacterial protease | {DE}-[AFILMV]-{P} |
| Thrombin | Factor IIa | x-x-G-R-G-x or [AFGILTVW]-[AFGILTVW]-P-R-{DE}-{DE} |
| Trypsin | Trypsin-1 | x-[KR]-{P} or W-K-P or M-R-P But not: [CD]-K-D or C-K-[HY] or C-R-K or R-R-[HR] |
| Trypsin (Arg blocked) | | K-{P} |
| Trypsin (Cys modified) | | [RKC]-{P} |
| Trypsin (Lys blocked) | | R-{P} |

Proteases selected for use as cleavage moieties can be selected based on desired characteristics such as peptide bond selectivity, activity at certain pHs, molecular mass, etc. The properties of exemplary proteases are provided in Table 3.

TABLE 3

Exemplary proteases and protease characteristics

| Protease | EC no. | Class | Peptide bond selectivity | pH optimum | Molecular mass (kDa) | Accession no. |
|---|---|---|---|---|---|---|
| Endoproteinase | | | | | | |
| Trypsin (bovine) | 3.4.21.4 | serine | $P_1$-$P_1^1$- ($P_1$ = Lys, Arg) | 8.0-9.0 | 23.5 | P00760[S] |
| Chymotrypsin (bovine) | 3.4.21.1 | serine | $P_1$-$P_1^1$- ($P_1$ = aromatic, $P_1^1$ = nonspecific) | 7.5-8.5 | 25 | P00766[S] |

TABLE 3-continued

Exemplary proteases and protease characteristics

| Protease | EC no. | Class | Peptide bond selectivity | pH optimum | Molecular mass (kDa) | Accession no. |
|---|---|---|---|---|---|---|
| Endoproteinase Asp-N (*Pseudomonas fragi*) | 3.4.24.33 | metallo | $P_1$-Asp- (and -$P_1$-cysteic acid) | 6.0-8.0 | 27 | φ |
| Endoproteinase Arg-C (mouse submaxillary gland) | φ | serine | -Arg-$P_1$- | 8.0-8.5 | 30 | n.a. |
| Endoproteinase Glu-C (V8 protease) (*Staphylococcus aureus*) | 3.4.21.19 | serine | -Glu-$P_1^1$- (and -Asp-$P_1^1$-) (2) | 8.0 | 27 | P04188$^S$ |
| Endoproteinase Lys-C (*Lysobacter enzymogenes*) | 3.4.21.50 | serine | -Lys-$P_1^1$- | 8.0 | $30^{NR}$ $33^R$ | S77957$^P$ |
| Pepsin (porcine) | 3.4.23.1 | aspartic | $P_1$-$P_1^1$- ($P_1$ = hydrophobic preferred) | 2.0-4.0 | 34.5 | P00791$^S$ |
| Thermolysin (*Bacillus thermoproteolyticus*) | 3.4.24.27 | metallo | $P_1$-$P_1^1$- (P1 = Leu, Phe, Ile, Val, Met, Ala) | 7.0-9.0 | 37.5 | P00800$^S$ |
| Elastase (porcine) | 3.4.21.36 | serine | $P_1$-$P_1^1$- ($P_1$ = uncharged, nonaromatic) | 7.8-8.5 | 25.9 | P00772$^S$ |
| Papain (*Carica papaya*) | 3.4.22.2 | cysteine | $P_1$-$P_1^1$- ($P_1$ = Arg, Lys preferred) | 6.0-7.0 | 23 | P00784$^S$ |
| Proteinase K (*Tritirachium album*) | 3.4.21.64 | serine | $P_1$-$P_1^1$- ($P_1$ = aromatic, hydrophobic preferred) | 7.5-12.0 | 18.5 | P06873$^S$ |
| Subtilisin (*Bacillus subtilis*) | 3.4.21.62 | serine | $P_1$-$P_1^1$- ($P_1$ = neutral/ acidic preferred) | 7.0-11.0 | $30^S$ $27.3^L$ | P04189$^S$ |
| Clostripain (endoproteinase-Arg-C) (*Clostridium histolyticum*) | 3.4.22.8 | cysteine | -Arg-$P_1$- ($P_1$ = Pro preferred) | 7.1-7.6 | 59 | P09870$^S$ |
| Exopeptidase | | | | | | |
| Carboxypeptidase A (bovine) | 3.4.17.1 | metallo | $P_1$-$P_1^1$- ($P_1$ cannot be Arg, Lys, Pro) | 7.0-8.0 | 34.5 | P00730$^S$ |
| Carboxypeptidase B (porcine) | 3.4.17.2 | metallo | $P_1$-$P_1^1$- ($P_1$= Lys, Arg) | 7.0-9.0 | 34.6 | P00732$^S$ |
| Carboxypeptidase P (*Penicillium janthinellum*) | φ | serine | $P_1$-$P_1^1$- (nonspecific) | 4.0-5.0 | 51 | n.a. |
| Carboxypeptidase Y (yeast) | 3.4.16.5 | serine | $P_1$-$P_1^1$- (nonspecific) | 5.5-6.5 | 61 | P00729$^S$ |
| Cathepsin C | 3.4.14.1 | cysteine | X-$P_1$-$P_1^1$- (removes amino-terminal dipeptide) | 5.5 | 210 | n.a. |
| Acylamino-acid-releasing enzyme (porcine) | 3.4.19.1 | serine | Ac-$P_1$-$P_1^1$- ($P_1$ = Ser, Ala, Met preferred) | 7.5 | $80^H$ $360^P$ | P19205$^S$+ |
| Pyroglutamate aminopeptidase (bovine) | 3.4.19.3 | cysteine | $P_1$-$P_1^1$- ($P_1$ = 5-oxoproline or pyroglutamate) | 7.0-9.0 | $70-80^B$ | n.a. |

In some embodiments, the cleavage recognition site comprises a first portion of an intein sequence that reacts with the second portion of the intein sequence to release the actuator moiety. A heterologous split intein system can be used to facilitate release of the actuator moiety from the chimeric receptor polypeptide. The actuator moiety can be covalently linked to the first portion of the intein sequence. The actuator moiety can be linked via its N-terminus or C-terminus to the first portion of the intein sequence. The second portion of the intein sequence can be a part of the chimeric adaptor polypeptide. The second portion of the intein sequence can serve as a cleavage moiety. The first portion or second portion of the intein sequence can be the N-terminal intein, the C-terminal intein, or any other suitable portion of an intein that can facilitate release of the actuator moiety. The intein sequences can be from any suitable source. The first and second portion can be from the same or different sources (e.g., organism, protein).

Figure 12:
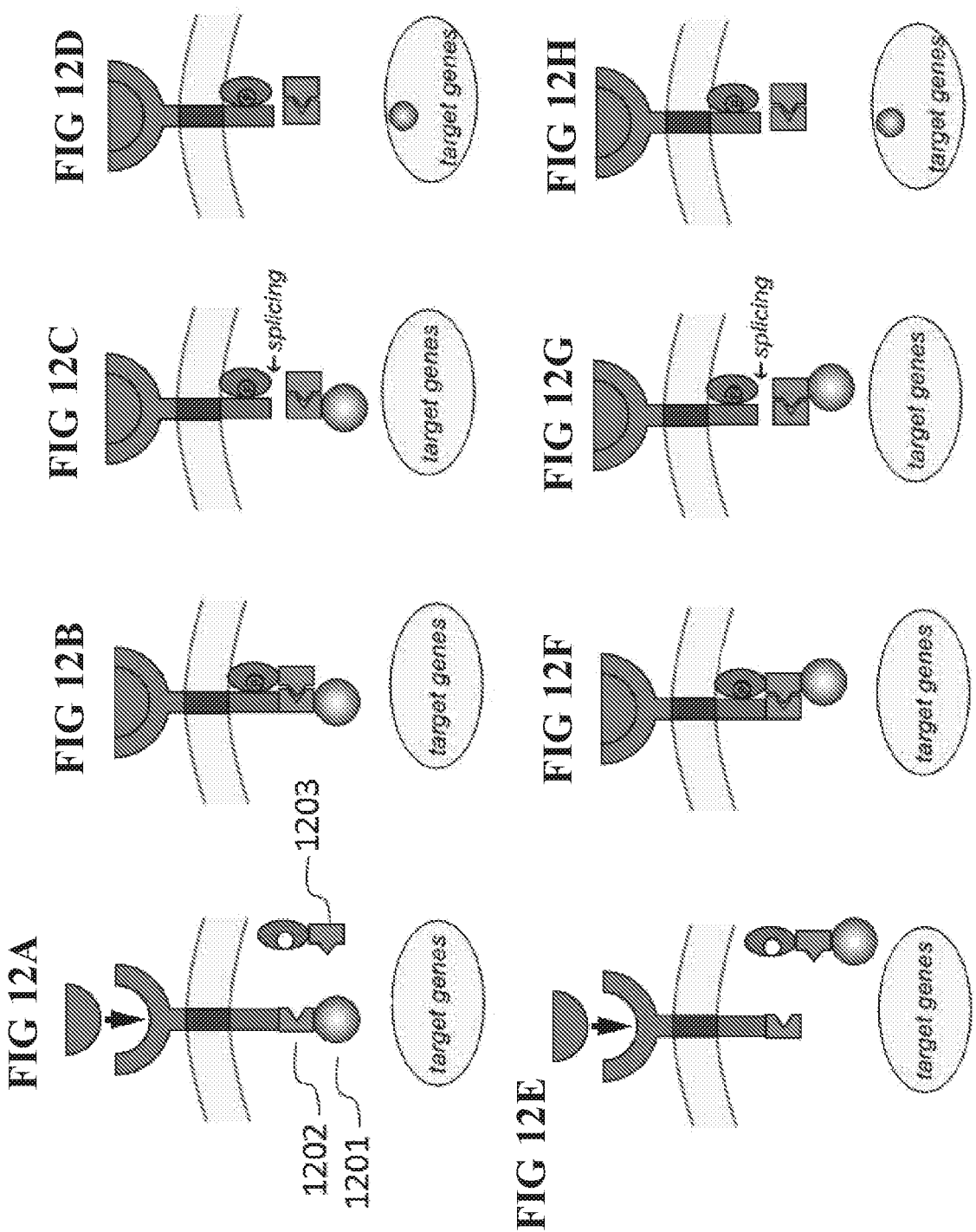
FIGS. 12A-D illustrate schematically a system in which the cleavage recognition site comprises an intein sequence.
FIGS. 12E-H illustrate an alternative arrangement of a system in which the cleavage recognition site comprises an intein sequence.

In an illustrative example shown in FIG. 12A, a chimeric receptor polypeptide comprises an actuator moiety 1201 covalently linked (e.g., at its N-terminus or C-terminus) via a peptide bond to a first portion of the intein sequence 1202, which comprises an N-terminal intein. The actuator moiety-N-terminal intein fusion can be contacted with a second portion of the intein sequence 1203 comprising a C-terminal intein as shown in FIG. 12B, for example a second portion of the intein sequence linked to an adaptor polypeptide. This contacting of the first and second portion of the intein sequences can result in a site specific cleavage (e.g., at a site between the actuator moiety and the N-terminal intein) as shown in FIG. 12C, thereby releasing the actuator moiety as shown in FIG. 12D. In an alternative configuration shown in FIGS. 12E-H, the actuator moiety is linked and/or complexed to the adaptor polypeptide rather than the receptor polypeptide. In another illustrative example, an actuator moiety can be covalently linked (e.g., at its N-terminus or C-terminus) via a peptide bond to a first portion of the intein comprising a C-terminal intein. The actuator moiety-C-terminal intein fusion can be contacted with a second portion of the intein sequence comprising an N-terminal intein. This contacting of the first and second portion of the inteins can result in a site-specific cleavage (e.g., at a suitable site between the actuator moiety and the C-terminal intein), thereby releasing the actuator moiety.

Figure 13:
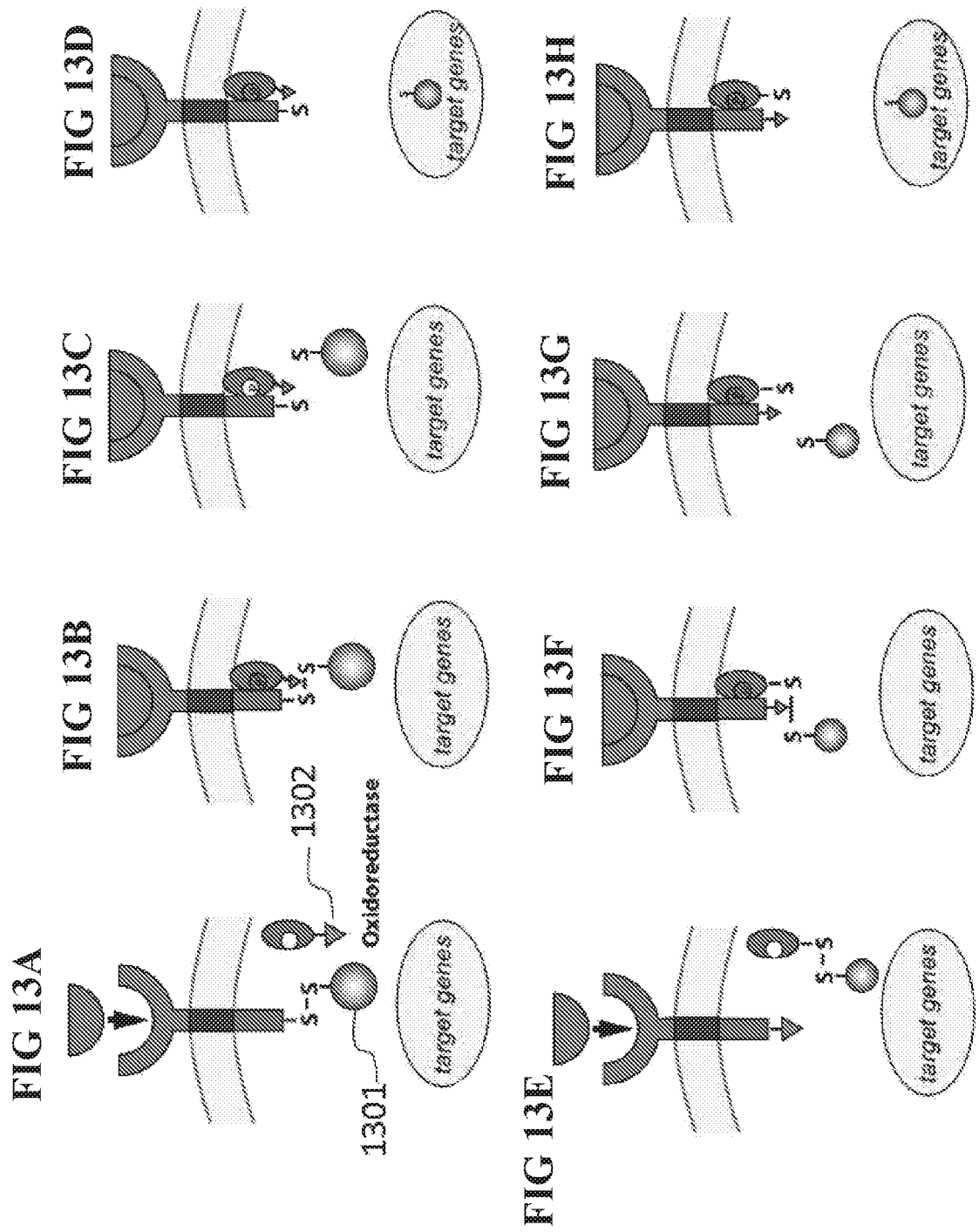
FIGS. 13A-D illustrate schematically a system in which the cleavage recognition site comprises a disulfide bond.
FIGS. 13E-H illustrate an alternative arrangement of a system in which the cleavage recognition site comprises a disulfide bond.

In some embodiments, the cleavage recognition site comprises a disulfide bond. The disulfide bond can link the actuator moiety to the chimeric receptor polypeptide. The disulfide bond can be formed between one or more cysteines of the actuator moiety and the receptor. The cysteines can be engineered into the actuator moiety or receptor. The cysteines can be a part of the native or wild-type sequence. The cysteines can be present in a linker peptide appended to the actuator moiety or the receptor. Cleavage of the disulfide bond can be facilitated by, for example, altering the redox conditions of the disulfide bond. Alteration of the redox conditions can lead to reduction of the disulfide bond to thiols and release of the actuator moiety. Cleavage of the disulfide bond can be facilitated by a cleavage moiety comprising a redox agent that can catalyze reduction of the disulfide bond. The redox agent can be an enzyme, or any derivative, variant or fragment thereof. The enzyme can be an oxidoreductase. Examples of oxidoreductases include protein-disulfide reductase, thioredoxins, glutaredoxins, thiol disulfide oxidoreductases (e.g., DsbA, BdbA-D, MdbA, and SdbA), and glutathione disulfide reductase. The redox agent can be from any suitable source including prokaryotes and eukaryotes. Cofactors (e.g., nicotinamide cofactors, flavins, and derivatives and analogs thereof) can be supplied for optimal activity of the enzyme. In an illustrative example shown in FIG. 13A, a chimeric receptor polypeptide comprises an actuator moiety 1301 linked by disulfide bond. The disulfide bond can be cleaved by a cleavage moiety 1302 comprising an enzyme such as an oxidoreductase, for example an oxidoreductase complexed and/or linked to an adaptor polypeptide as shown in FIG. 13B. Cleaving of the disulfide bond can release the actuator moiety as shown in FIG. 13C. The actuator moiety, upon release, can translocate to a cell nucleus where it is operable to regulate gene expression and/or activity or edit a nucleic acid sequence as shown in FIG. 13D. FIGS. 13E-H illustrate an alternative configuration wherein the actuator moiety is complexed and/or linked to the adaptor polypeptide and the cleavage moiety (e.g., oxidoreductase) is linked to the receptor.

In some embodiments, the chimeric transmembrane receptor polypeptide comprises at least one targeting sequence which directs transport of the receptor to a specific region of a cell. A targeting sequence can be used to direct transport of a polypeptide to which the targeting sequence is linked to a specific region of a cell. For example, a targeting sequence can direct the receptor to a cell nucleus utilizing a nuclear localization signal (NLS), outside of the nucleus (e.g., the cytoplasm) utilizing a nuclear export signal (NES), the mitochondria, the endoplasmic reticulum (ER), the Golgi, chloroplasts, apoplasts, peroxisomes, plasma membrane, or membrane of various organelles of a cell. In some embodiments, a targeting sequence comprises a nuclear export signal (NES) and directs a polypeptide outside of a nucleus, for example to the cytoplasm of a cell. A targeting sequence can direct a polypeptide to the cytoplasm utilizing various nuclear export signals. Nuclear export signals are generally short amino acid sequences of hydrophobic residues (e.g., at least about 2, 3, 4, or 5 hydrophobic residues) that target a protein for export from the cell nucleus to the cytoplasm through the nuclear pore complex using nuclear transport. Not all NES substrates can be constitutively exported from the nucleus. In some embodiments, a targeting sequence comprises a nuclear localization signal (NLS, e.g., a SV40 NLS) and directs a polypeptide to a cell nucleus. A targeting sequence can direct a polypeptide to a cell nucleus utilizing various nuclear localization signals (NLS). An NLS can be a monopartite sequence or a bipartite sequence.

Non-limiting examples of NLSs include an NLS sequence derived from: the NLS of the SV40 virus large T-antigen, having the amino acid sequence PKKKRKV (SEQ ID NO: 2); the NLS from nucleoplasmin (e.g. the nucleoplasmin bipartite NLS with the sequence KRPAATKKAGQAKKKK (SEQ ID NO: 3)); the c-myc NLS having the amino acid sequence PAAKRVKLD (SEQ ID NO: 4) or RQRRNELKRSP (SEQ ID NO: 5); the hRNPA1 M9 NLS having the sequence NQSSNFGPMKGGNFG-GRSSGPYGGGGQYFAKPRNQGGY (SEQ ID NO: 6); the sequence RIVIRIZFKNKGKDTAELRRRRVEVS-VELRKAKKDEQILKRRNV (SEQ ID NO: 7) of the IBB domain from importin-alpha; the sequences VSRKRPRP (SEQ ID NO: 8) and PPKKARED (SEQ ID NO: 9) of the myoma T protein; the sequence PQPKKKPL (SEQ ID NO: 10) of human p53; the sequence SALIKKKKKMAP (SEQ ID NO: 11) of mouse c-abl IV; the sequences DRLRR (SEQ ID NO: 12) and PKQKKRK (SEQ ID NO: 13) of the influenza virus NS1; the sequence RKLKKKIKKL (SEQ ID NO: 14) of the Hepatitis virus delta antigen; the sequence REKKKFLKRR (SEQ ID NO: 15) of the mouse Mx1 protein; the sequence KRKGDEVDGVDEVAKKKSKK (SEQ ID NO: 16) of the human poly(ADP-ribose) polymerase; and the sequence RKCLQAGMNLEARKTKK (SEQ ID NO: 17) of the steroid hormone receptors (human) glucocorticoid.

In some embodiments, a targeting sequence comprises a membrane targeting peptide and directs a polypeptide to a plasma membrane or membrane of a cellular organelle. A membrane-targeting sequence can provide for transport of the chimeric transmembrane receptor polypeptide to a cell surface membrane or other cellular membrane. Molecules in association with cell membranes contain certain regions that facilitate membrane association, and such regions can be incorporated into a membrane targeting sequence. For example, some proteins contain sequences at the N-terminus or C-terminus that are acylated, and these acyl moieties facilitate membrane association. Such sequences can be recognized by acyltransferases and often conform to a particular sequence motif. Certain acylation motifs are capable of being modified with a single acyl moiety (often followed by several positively charged residues (e.g. human c-Src) to improve association with anionic lipid head groups) and others are capable of being modified with multiple acyl moieties. For example the N-terminal sequence of the protein tyrosine kinase Src can comprise a single myristoyl moiety. Dual acylation regions are located within the N-terminal regions of certain protein kinases, such as a subset of Src family members (e.g., Yes, Fyn, Lck) and G-protein alpha subunits. Such dual acylation regions often are located within the first eighteen amino acids of such proteins, and conform to the sequence motif Met-Gly-Cys-Xaa-Cys (SEQ ID NO: 18), where the Met is cleaved, the Gly is N-acylated and one of the Cys residues is S-acylated. The Gly often is myristoylated and a Cys can be palmitoylated. Acylation regions conforming to the sequence motif Cys-Ala-Ala-Xaa (so called "CAAX boxes"), which can modified with C15 or C10 isoprenyl moieties, from the C-terminus of G-protein gamma subunits and other proteins also can be utilized. These and other acylation motifs include, for example, those discussed in Gauthier-Campbell et al., Molecular Biology of the Cell 15: 2205-2217 (2004); Glabati et al., Biochem. J. 303: 697-700 (1994) and Zlakine et al., J. Cell Science 110: 673-679 (1997), and can be incorporated in a targeting sequence to induce membrane localization.

In certain embodiments, a native sequence from a protein containing an acylation motif is incorporated into a targeting sequence. For example, in some embodiments, an N-terminal portion of Lck, Fyn or Yes or a G-protein alpha subunit, such as the first twenty-five N-terminal amino acids or fewer from such proteins (e.g., about 5 to about 20 amino acids, about 10 to about 19 amino acids, or about 15 to about 19 amino acids of the native sequence with optional mutations), may be incorporated within the N-terminus of a chimeric polypeptide. In certain embodiments, a C-terminal sequence of about 25 amino acids or less from a G-protein gamma subunit containing a CAAX box motif sequence (e.g., about 5 to about 20 amino acids, about 10 to about 18 amino acids, or about 15 to about 18 amino acids of the native sequence with optional mutations) can be linked to the C-terminus of a chimeric polypeptide.

Any membrane-targeting sequence can be employed. In some embodiments, such sequences include, but are not limited to myristoylation-targeting sequence, palmitoylation-targeting sequence, prenylation sequences (i.e., farnesylation, geranyl-geranylation, CAAX Box), protein-protein interaction motifs or transmembrane sequences (utilizing signal peptides) from receptors. Examples include those discussed in, for example, ten Klooster, J. P. et al, Biology of the Cell (2007) 99, 1-12; Vincent, S., et al., Nature Biotechnology 21:936-40, 1098 (2003).

Additional protein domains exist that can increase protein retention at various membranes. For example, an ~120 amino acid pleckstrin homology (PH) domain is found in over 200 human proteins that are typically involved in intracellular signaling. PH domains can bind various phosphatidylinositol (PI) lipids within membranes (e.g. PI (3,4,5)-P3, PI (3,4)-P2, PI (4,5)-P2) and thus can play a key role in recruiting proteins to different membrane or cellular compartments. Often the phosphorylation state of PI lipids is regulated, such as by PI-3 kinase or PTEN, and thus, interaction of membranes with PH domains may not be as stable as by acyl lipids.

In some embodiments, a targeting sequence directing a polypeptide to a cellular membrane can utilize a membrane anchoring signal sequence. Various membrane-anchoring sequences are available. For example, membrane anchoring signal sequences of various membrane bound proteins can be used. Sequences can include those from: 1) class I integral membrane proteins such as IL-2 receptor beta-chain and insulin receptor beta chain; 2) class II integral membrane proteins such as neutral endopeptidase; 3) type III proteins such as human cytochrome P450 NF25; and 4) type IV proteins such as human P-glycoprotein.

In some embodiments, the chimeric receptor polypeptide is linked to a polypeptide folding domain which can assist in protein folding. In some embodiments, an actuator moiety is linked to a cell-penetrating domain. For example, the cell-penetrating domain can be derived from the HIV-1 TAT protein, the TLM cell-penetrating motif from human hepatitis B virus, MPG, Pep-1, VP22, a cell penetrating peptide from Herpes simplex virus, or a polyarginine peptide sequence. The cell-penetrating domain can be located at the N-terminus, the C-terminus, or anywhere within the actuator moiety.

Figure 5:
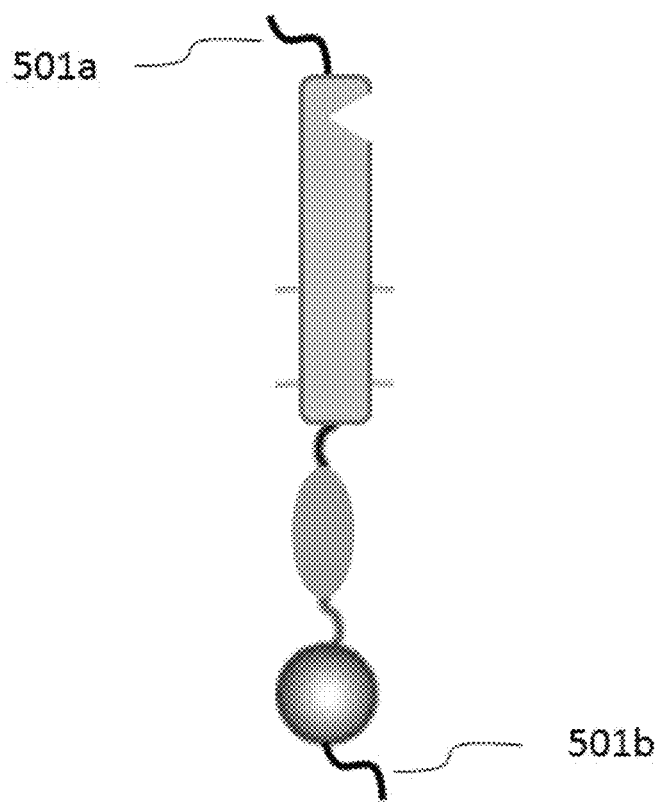
FIG. 5 shows an exemplary chimeric transmembrane receptor polypeptide comprising at least one targeting sequence.

The targeting sequence can be linked to any appropriate region of the chimeric receptor polypeptide, for example at the N-terminus, the C-terminus, or in an internal region of the receptor. In some embodiments, at least two targeting sequences are linked to the receptor. In an exemplary chimeric receptor polypeptide shown in FIG. 5, a first targeting sequence 501a can be linked to the extracellular region of the receptor and a second targeting sequence 501b can be linked to the intracellular region of the receptor, such as to the GMP. When a receptor is linked to multiple targeting sequences, for example targeting sequences directed to different locations of a cell, the final localization of the receptor can be determined by the relative strengths of the targeting sequences. For example, a receptor having both a targeting sequence comprising an NES and a targeting sequence comprising an NLS can localize to the cytoplasm if the NES is stronger than NLS. Alternatively, if the NLS is stronger than the NES, the receptor can localize to the nucleus even though both a nuclear localization signal and nuclear export signal are present on the receptor. A targeting sequence can comprise multiple copies of, for example, each a NLS and NES, to fine-tune the degree of the cellular localization.

In some cases, a targeting sequence is linked to the actuator moiety. Following release of the actuator moiety from the GMP by cleavage of the cleavage recognition site, the targeting sequence can direct the actuator moiety to a cellular location that is different from the receptor. For example, a chimeric transmembrane receptor can comprise a first targeting sequence directing the receptor to a plasma membrane and the actuator moiety can separately comprise a second targeting sequence directing localization to a cell nucleus. Initially, the actuator moiety (forming a portion of the receptor) can be localized to a plasma membrane due to the first targeting sequence. Following release of the actuator moiety from the GMP by cleavage of the cleavage recognition site, the actuator moiety can be localized to a cell nucleus via targeting by the second targeting sequence. In some embodiments, the actuator moiety translocates to a cell nucleus after cleavage of the cleavage recognition site.

Binding of the chimeric adaptor polypeptide to a chimeric transmembrane receptor polypeptide when the receptor polypeptide has undergone modification upon binding to an antigen can bring the cleavage moiety in proximity to the cleavage recognition site. Cleavage of the recognition site can release the actuator moiety from the GMP. Following release, the actuator moiety is operable to complex with a target polynucleotide, for example in the cell cytoplasm or a cell nucleus. Complexing of the actuator moiety with a target polynucleotide can regulate the expression and/or activity of at least one gene or edit a nucleic acid sequence.

Figure 6A:
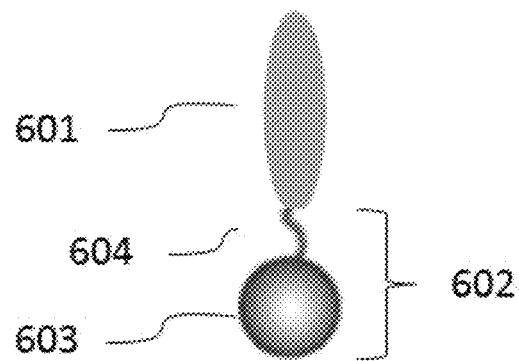
FIG. 6A shows an exemplary chimeric adaptor polypeptide comprising a receptor binding moiety and gene modulating polypeptide (GMP).

In another exemplary configuration, the GMP forms a portion of the chimeric adaptor polypeptide and the cleavage moiety forms a portion of the intracellular region of the chimeric transmembrane receptor polypeptide. A chimeric adaptor polypeptide of an exemplary configuration can comprise (a) receptor binding moiety that binds a receptor that has undergone modification upon binding to an antigen, the receptor comprising an intracellular region comprising an immune cell signaling domain; and (b) a gene modulating polypeptide (GMP) linked to the receptor binding moiety, wherein the GMP comprises an actuator moiety linked to a cleavage recognition site; wherein only upon binding of the receptor binding moiety to the modified receptor, the actuator moiety is released from the GMP by cleavage of the cleavage recognition site. As shown in FIG. 6A, an exemplary chimeric adaptor polypeptide can comprise a receptor binding moiety 601 linked to a GMP 602. A GMP can comprise an actuator moiety 603 linked to a cleavage recognition site 604.

A receptor binding moiety of a chimeric adaptor polypeptide can be any protein, derivative thereof, variant thereof, or fragment thereof, which can bind a receptor. The receptor binding moiety can bind, for example, a chimeric transmembrane receptor that has undergone receptor modification in response to antigen binding. The receptor binding moiety can comprise a binding domain of a binding partner (e.g., protein) that is recruited to a receptor which has undergone a receptor modification. In some embodiments, receptor modification comprises a conformational change in at least one region of the receptor. In some embodiments, receptor modification comprises a chemical modification, such as phosphorylation or dephosphorylation. In some embodiments, receptor modification comprises modification at multiple modification sites, and each modification site is effective to bind an adaptor polypeptide. The receptor binding moiety, in some cases, binds the immune cell signaling domain. The receptor binding moiety can bind, for example, a primary signaling domain and/or a co-stimulatory domain. When the receptor comprises an ITAM or ITIM domain, a receptor binding moiety can comprise a binding partner (e.g., protein) recruited to a phosphorylated ITAM or ITIM, or any derivative, variant or fragment thereof.

Binding partners (e.g., proteins) capable of binding phosphorylated substrates, such as phosphorylated ITAMs and/or ITIMs include, but are not limited to, molecules such as Src homology 2 (SH2) domain- and phosphotyrosine binding (PTB) domain-containing proteins. Examples of proteins containing an SH2 domain include ABL1, ABL2, BCAR3, BLK, BLNK, BMX, BTK, CHN2, CISH, CRK, CRKL, CSK, DAPP1, EAT-2, FER, FES, FGR, FRK, FYN, GADS, GRAP, GRAP2, GRB10, GRB14, GRB2, GRB7, HCK, HSH2D, INPP5D, INPPL1, ITK, JAK2, LCK, LCP2, LYN, MATK, NCK1, NCK2, PIK3P, PIK3R1, PIK3R2, PIK3R3, PLCG1, PLCG2, PTK6, PTPN11, PTPN6, RASA1, SAP, SH2B1, SH2B2, SH2B3, SH2D1A, SH2D1B, SH2D2A, SH2D3A, SH2D3C, SH2D4A, SH2D4B, SH2D5, SH2D6, SH3BP2, SHB, SHC1, SHC2, SHC3, SHC4, SHD, SHE, SHP1, SHP2, SLA, SLA2, SOCS1, SOCS2, SOCS3, SOCS4, SOCS5, SOCS6, SOCS7, SRC, SRMS, STAT1, STAT2, STAT3, STAT4, STAT5A, STAT5B, STATE, SUPT6H, SYK, TEC, TENC1, TNS, TNS1, TNS3, TNS4, TXK, VAV1, VAV2, VAV3, YES1, and ZAP70. Examples of proteins containing a PTB domain include APBA1, APBA2, APBA3, EPS8, EPS8L1, EPS8L2, EPS8L3, TENC1, TNS, TNS1, TNS3, TNS4, DOK1, DOK2, DOK3, DOK4, DOK5, DOK6, DOK7, FRS2, FRS3, IRS1, IRS2, IRS3, IRS4, SHC1, SHC2, SHC3, SHC4, TLN1, TLN2, and X11a. In some embodiments, a receptor binding moiety comprises a protein containing a SH2 domain and/or a PTB domain, or any derivative, variant or fragment thereof. In some embodiments, a receptor binding moiety comprises a receptor binding domain of ZAP70. In some embodiments, a receptor binding moiety comprises a co-stimulatory molecule or any derivative, variant, or fragment thereof which is recruited to the modified receptor.

In some configurations, a chimeric adaptor polypeptide of a subject system can comprise a gene modulating polypeptide (GMP). A GMP, as described elsewhere herein, can comprise an actuator moiety linked to a cleavage recognition site. The actuator moiety can comprise a nuclease (e.g., DNA nuclease and/or RNA nuclease), modified nuclease (e.g., DNA nuclease and/or RNA nuclease) that is nuclease-deficient or has reduced nuclease activity compared to a wild-type nuclease, a variant thereof, a derivative thereof, or a fragment thereof as described elsewhere herein. The actuator moiety can regulate expression and/or activity of a gene or edit the sequence of a nucleic acid (e.g., gene and/or gene product). An actuator moiety can regulate expression or activity of a gene and/or edit a nucleic acid sequence, whether exogenous or endogenous. In some embodiments, the actuator moiety comprises a DNA nuclease such as an engineered (e.g., programmable or targetable) DNA nuclease to induce genome editing of a target DNA sequence. In some embodiments, the actuator moiety comprises a RNA nuclease such as an engineered (e.g., programmable or targetable) RNA nuclease to induce editing of a target RNA sequence. In some embodiments, the actuator moiety has reduced or minimal nuclease activity. An actuator moiety having reduced or minimal nuclease activity can regulate expression and/or activity of a gene by physical obstruction of a target polynucleotide or recruitment of additional factors effective to suppress or enhance expression of the target polynucleotide. In some embodiments, the actuator moiety comprises a nuclease-null DNA binding protein derived from a DNA nuclease that can induce transcriptional activation or repression of a target DNA sequence. In some embodiments, the actuator moiety comprises a nuclease-null RNA binding protein derived from a RNA nuclease that can induce transcriptional activation or repression of a target RNA sequence. In some embodiments, an actuator moiety comprises a Cas protein which lacks cleavage activity.

Any suitable nuclease can be used in an actuator moiety. Suitable nucleases include, but are not limited to, CRISPR-associated (Cas) proteins or Cas nucleases including type I CRISPR-associated (Cas) polypeptides, type II CRISPR-associated (Cas) polypeptides, type III CRISPR-associated (Cas) polypeptides, type IV CRISPR-associated (Cas) polypeptides, type V CRISPR-associated (Cas) polypeptides, and type VI CRISPR-associated (Cas) polypeptides; zinc finger nucleases (ZFN); transcription activator-like effector nucleases (TALEN); meganucleases; RNA-binding proteins (RBP); CRISPR-associated RNA binding proteins; recombinases; flippases; transposases; Argonaute proteins; any derivative thereof; any variant thereof; and any fragment thereof.

Figure 6B:
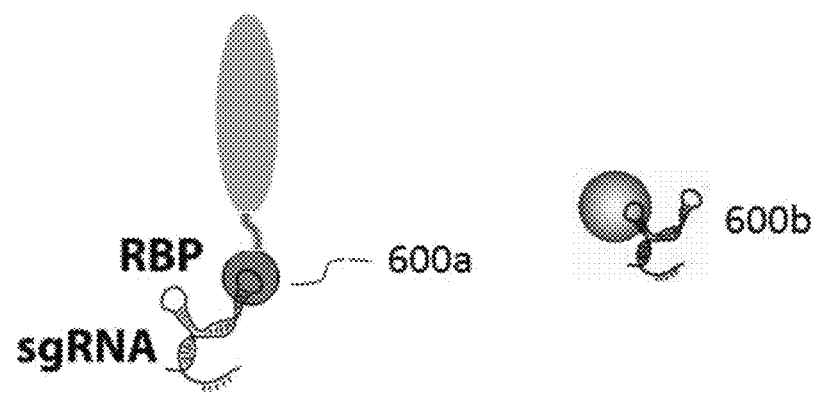
FIG. 6B shows an exemplary chimeric adaptor polypeptide including an actuator moiety comprising an RNA-binding protein optionally complexed to a guide nucleic acid (e.g., sgRNA).

In some embodiments, the actuator moiety comprises a Cas protein that forms a complex with a guide nucleic acid, such as a guide RNA. In some embodiments, the actuator moiety comprises a RNA-binding protein (RBP) optionally complexed with a guide nucleic acid, such as a guide RNA, which is able to form a complex with a Cas protein. FIG. 6B shows an exemplary chimeric adaptor polypeptide in which the actuator moiety comprises an RNA-binding protein 600a optionally complexed with a guide nucleic acid. Upon release from the RNA-binding protein (RBP), for example by dissociation of the guide nucleic acid from the RBP or cleavage of the cleavage recognition site, the guide nucleic acid can form a complex with a Cas protein 600b which is operable to regulate gene expression and/or activity or edit a nucleic acid sequence. In some embodiments, the actuator moiety comprises a nuclease-null DNA binding protein derived from a DNA nuclease that can induce transcriptional activation or repression of a target DNA sequence. In some embodiments, the actuator moiety comprises a nuclease-null RNA binding protein derived from a RNA nuclease that can induce transcriptional activation or repression of a target RNA sequence. In some embodiments, an actuator moiety can comprise a Cas protein which lacks cleavage activity.

Figure 7:
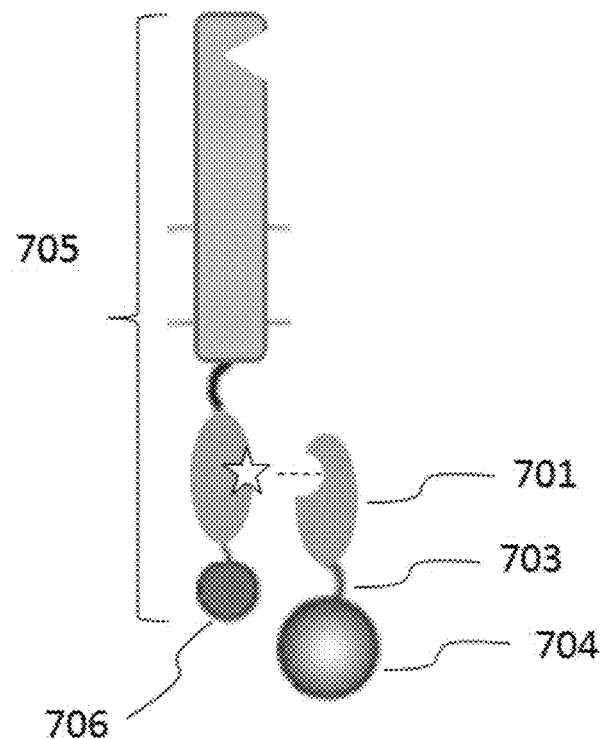
FIG. 7 shows an exemplary system comprising a chimeric adaptor polypeptide comprising a receptor binding moiety and gene modulating polypeptide (GMP) and a chimeric transmembrane receptor polypeptide comprising a cleavage moiety.

In some embodiments, the cleavage recognition site is flanked by the receptor binding moiety and the actuator moiety. The actuator moiety can be released from the GMP by cleavage of the cleavage recognition site by a cleavage moiety. The cleavage moiety can recognize and/or cleave a cleavage recognition site, for example, when in proximity to the cleavage recognition site. A cleavage moiety can comprise a polypeptide sequence. The cleavage moiety, in some configurations, forms a portion of the chimeric transmembrane receptor polypeptide. The cleavage moiety can form the N-terminus, C-terminus or an internal portion of the receptor. The cleavage moiety can be complexed to the N-terminus, C-terminus, or an internal portion of the receptor. In an exemplary configuration shown in FIG. 7, the cleavage recognition site 703 is flanked by the receptor binding moiety 701 and the actuator moiety 704, and the cleavage moiety 706 forms a portion of a chimeric transmembrane receptor polypeptide 705.

FIGS. 8A-D illustrate schematically the release of an actuator moiety from a GMP. FIG. 8A shows the binding of an antigen to a transmembrane chimeric receptor polypeptide. The transmembrane chimeric receptor polypeptide comprises an extracellular region having an antigen interacting domain 805 and an intracellular region comprising a cleavage moiety 806. The cleavage moiety can be complexed with the receptor or linked, for example by a peptide bond and/or peptide linker, to the receptor. The GMP forms a portion of the chimeric adaptor polypeptide. The GMP, linked to the receptor binding moiety 801, includes an actuator moiety 802a linked to a cleavage recognition site 802b. In response to antigen binding, the receptor is modified by phosphorylation 803 in the intracellular region of the receptor (FIG. 8B). Following receptor modification (e.g., phosphorylation), the chimeric adaptor polypeptide is recruited to the receptor as shown in FIG. 8C. The receptor comprises a cleavage moiety 806. When in proximity to the cleavage recognition site, the cleavage moiety can cleave the recognition site to release the actuator moiety from the GMP as shown in FIG. 8D. Upon release, the actuator moiety can enter the nucleus to regulate the expression and/or activity of a target gene or edit a nucleic acid sequence. FIGS. 8E-H show an analogous system wherein receptor modification comprises a conformational change. In some embodiments, the chimeric adaptor protein is tethered to the membrane (e.g., as a membrane bound protein).

Figure 9:
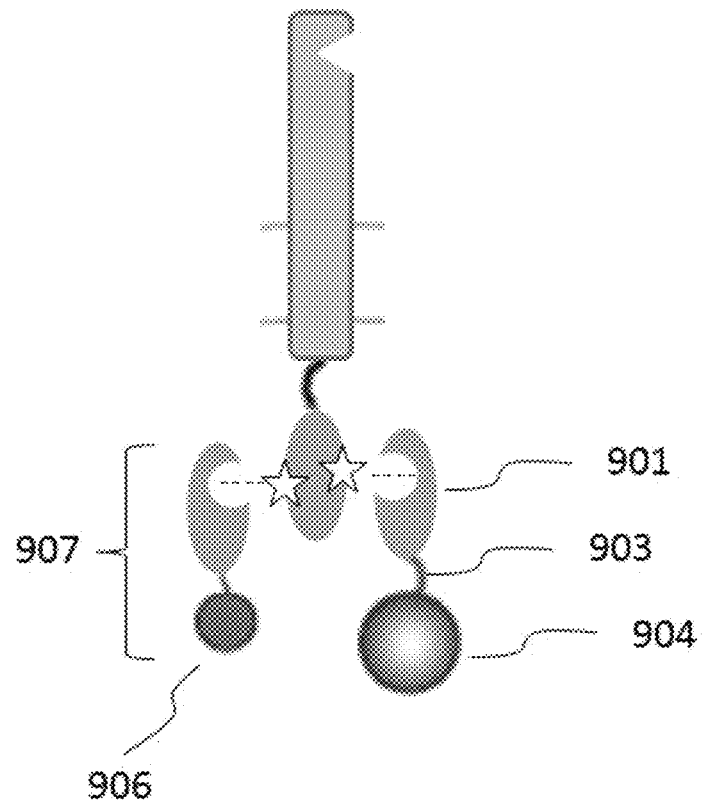
FIG. 9 shows an exemplary system comprising a chimeric adaptor polypeptide comprising a receptor binding moiety and gene modulating polypeptide (GMP), a second adaptor polypeptide comprising a cleavage moiety, and a chimeric transmembrane receptor polypeptide.

In other configurations, the cleavage moiety is complexed to a second adaptor polypeptide which binds the chimeric transmembrane receptor polypeptide when the receptor polypeptide has undergone modification upon binding to an antigen. In an exemplary configuration shown in FIG. 9, the cleavage recognition site 903 is flanked by the receptor binding moiety 901 and the actuator moiety 904, and the cleavage moiety 906 forms a portion a second adaptor polypeptide 907.

Figure 10:
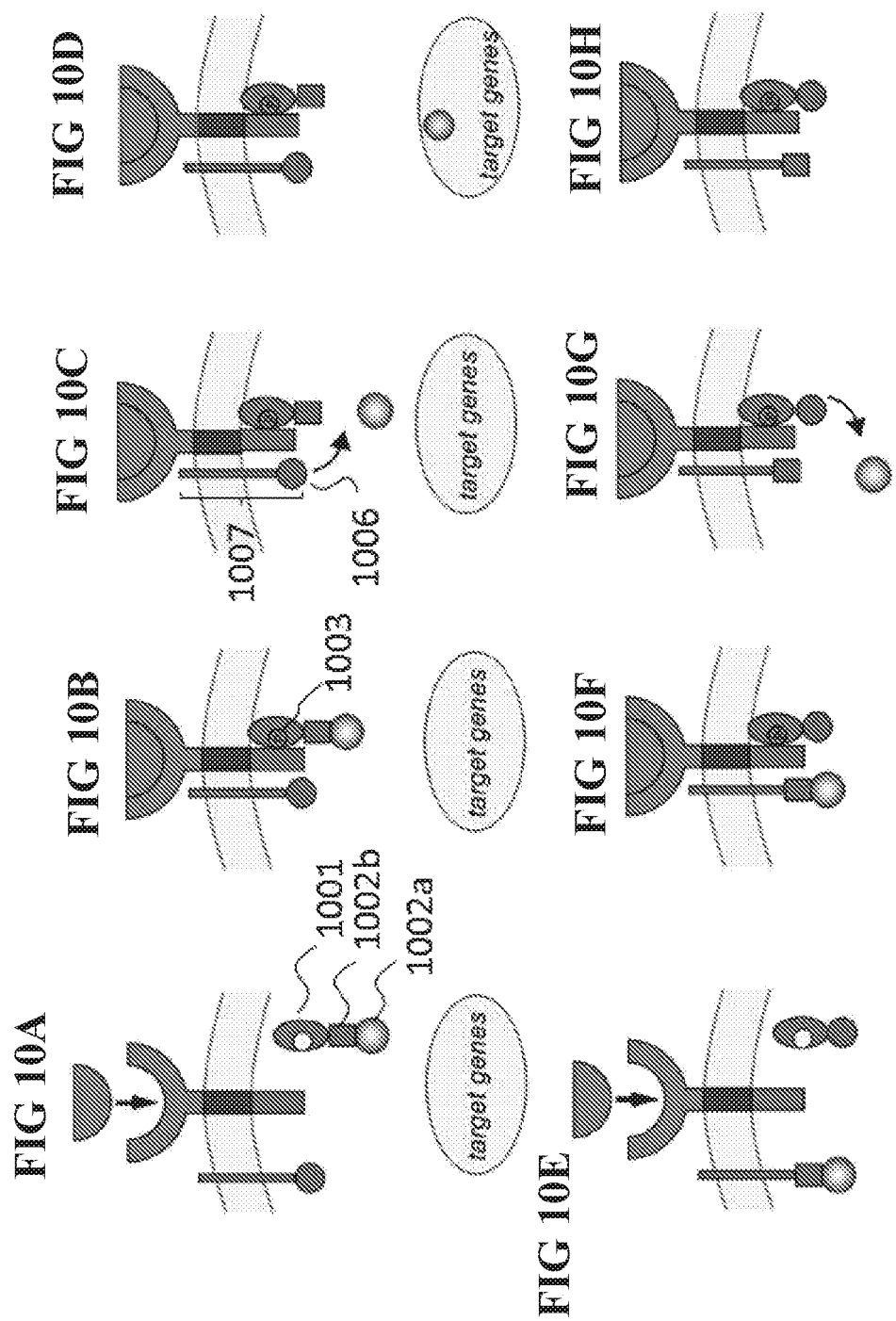
FIGS. 10A-D illustrate schematically the release of an actuator moiety from a GMP in a system comprising at least two adaptor polypeptides and a receptor which undergoes phosphorylation.
FIGS. 10E-H illustrate schematically the release of an actuator moiety from a GMP in a system comprising at least two adaptor polypeptides and a receptor in an alternative configuration.

FIGS. 10A-D illustrate schematically the release of an actuator moiety from a GMP. FIG. 10A shows the binding of an antigen to a transmembrane chimeric receptor polypeptide. The transmembrane chimeric receptor polypeptide comprises an extracellular region having an antigen interacting domain and an intracellular region. The GMP, comprising an actuator moiety linked to a cleavage recognition site, forms a portion of a chimeric adaptor polypeptide. The cleavage recognition site 1002b is flanked by the receptor binding moiety 1001 and the actuator moiety 1002a. In response to antigen binding, the receptor is modified by phosphorylation 1003 in the intracellular region (FIG. 10B). Following receptor modification (e.g., phosphorylation), the chimeric adaptor polypeptide is recruited to the receptor as shown in FIG. 10B. A second adaptor polypeptide 1007 comprising a cleavage moiety 1006 is also recruited to the modified receptor (FIG. 10C). The cleavage moiety may be complexed with the second adaptor polypeptide or linked, for example by a peptide bond and/or peptide linker, to the adaptor. When in proximity to the cleavage recognition site, the cleavage moiety can cleave the recognition site to release the actuator moiety from the GMP as shown in FIG. 10D. Upon release, the actuator moiety can enter the nucleus to regulate the expression and/or activity of a target gene or edit a nucleic acid sequence. FIGS. 10E-H show a system having an alternative configuration wherein the chimeric adaptor polypeptide comprises the cleavage moiety and the second adaptor polypeptide comprises the actuator moiety. In some embodiments, the chimeric adaptor polypeptide is tethered to the membrane (e.g., as a membrane bound protein). In some embodiments, the second adaptor polypeptide is tethered to the membrane (e.g., as a membrane bound protein).

Figure 18:
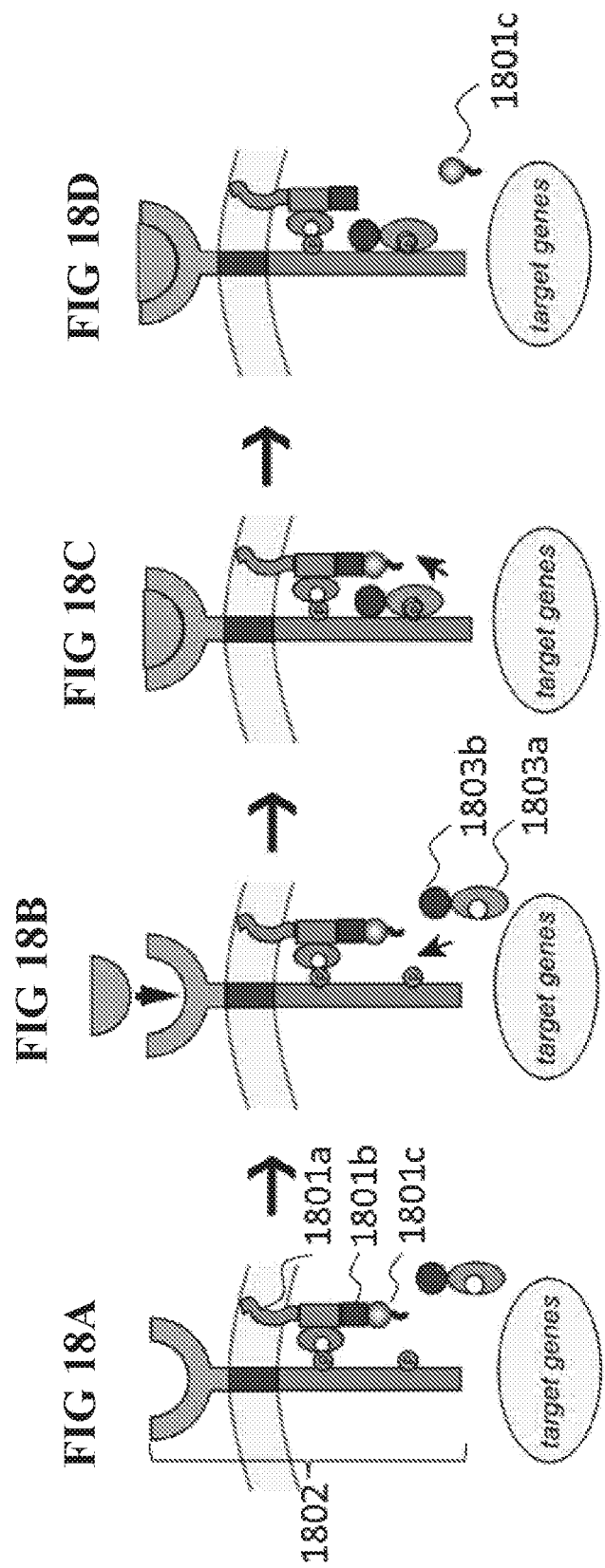
FIGS. 18 A-D illustrate schematically the release of an actuator moiety from a GMP in a system comprising at least two adaptor polypeptides.

FIGS. 18A-D illustrate schematically the release of an actuator moiety in a system comprising a first membrane-tethered adaptor and a second cytoplasmic adaptor. FIG. 18A shows the association of a first membrane-tethered adaptor comprising a membrane tethering domain 1801a (e.g., CAAX), a protease recognition site 1801b (e.g., TEV), and an actuator moiety 1801c with a chimeric transmembrane receptor 1802. The chimeric transmembrane receptor can function as a scaffold and includes at least two adaptor binding sites (e.g., EGFR or receptor tyrosine kinase (RTK)). One adaptor binding site can be associated with a membrane-tethered adaptor as shown in FIG. 18B. The association of the membrane-tethered adaptor, in some cases, is dependent on antigen binding to the receptor. In some systems, the membrane-tethered adaptor is located in proximity to the receptor and association may not depend on antigen binding to the receptor. As shown in FIGS. 18B and 18C, antigen interaction with the receptor can conditionally recruit a second adaptor protein comprising a cytoplasmic receptor binding moiety 1803a and protease 1803b, to the other adaptor binding site of the receptor. The second adaptor protein comprising the protease, when recruited to the transmembrane receptor, can cleave the protease recognition site 1801b of the membrane-tethered molecule, thereby releasing the actuator moiety 1801c as shown in FIG. 18D.

In some embodiments, the cleavage moiety only cleaves at the recognition site when in proximity to the cleavage recognition site. In some embodiments, the cleavage recognition site comprises a polypeptide sequence that is a recognition sequence of a protease (e.g., a peptide cleavage domain). The cleavage moiety comprises protease activity which recognizes the polypeptide sequence. A cleavage moiety comprising protease activity can comprise any protease including, but not limited to, a protease described elsewhere herein, or any derivative, variant or fragment thereof. In some embodiments, the cleavage recognition site comprises multiple cleavage recognition sequences, and each cleavage recognition sequence can be recognized by the same or different cleavage moiety comprising protease activity (e.g., protease).

In some embodiments, the cleavage recognition site comprises a first portion of an intein sequence that reacts with the second portion of the intein sequence to release the actuator moiety. A heterologous split intein system can be used to facilitate release of the actuator moiety from the chimeric adaptor polypeptide. The actuator moiety can be covalently linked to the first portion of the intein sequence. The actuator moiety can be linked via its N-terminus or C-terminus to the first portion of the intein sequence. The cleavage moiety can comprise the second portion of the intein sequence. The first portion or second portion of the intein sequence can be the N-terminal intein, the C-terminal intein, or any other suitable portion of an intein that can facilitate release of the actuator moiety. The intein sequences can be from any suitable source. The first and second portion can be from the same or different sources (e.g., organism, protein). In an illustrative example, an actuator moiety can be covalently linked (e.g., at its N-terminus or C-terminus) via a peptide bond to a first portion of the intein sequence, which comprises an N-terminal intein. The actuator moiety-N-terminal intein fusion can be contacted with a second portion of the intein sequence comprising a C-terminal intein. This contacting of the first and second portion of the intein sequences can result in a site specific cleavage (e.g., at a site between the actuator moiety and the N-terminal intein), thereby releasing the actuator moiety. In another illustrative example, an actuator moiety can be covalently linked (e.g., at its N-terminus or C-terminus) via a peptide bond to a first portion of the intein comprising a C-terminal intein. The actuator moiety-C-terminal intein fusion can be contacted with a second portion of the intein sequence comprising an N-terminal intein. This contacting of the first and second portion of the inteins can result in a site-specific cleavage (e.g., at a suitable site between the actuator moiety and the C-terminal intein), thereby releasing the actuator moiety.

In some embodiments, the cleavage recognition site comprises a disulfide bond. The disulfide bond can link the actuator moiety to the receptor binding moiety in a chimeric adaptor polypeptide. The disulfide bond can be formed between one or more cysteines of the actuator moiety and the receptor binding moiety. The cysteines can be engineered into the actuator moiety or receptor binding moiety. The cysteines can be a part of the native or wild-type sequence of the actuator moiety or receptor binding moiety. The cysteines can be present in a linker peptide appended to the actuator moiety or the receptor binding moiety. Cleavage of the disulfide bond can be facilitated by, for example, altering the redox conditions of the disulfide bond. Alteration of the redox conditions can lead to reduction of the disulfide bond to thiols and release of the actuator moiety. Cleavage of the disulfide bond can be facilitated by a cleavage moiety comprising a redox agent that can lead to reduction of the disulfide bond. The redox agent can be an enzyme, or any derivative, variant or fragment thereof. The enzyme can be an oxidoreductase. Examples of oxidoreductases include protein-disulfide reductase, thioredoxins, glutaredoxins, thiol disulfide oxidoreductases (e.g., DsbA, BdbA-D, MdbA, SdbA), and glutathione disulfide reductase. The redox agent can be from any suitable source including prokaryotes and eukaryotes. Cofactors (e.g, nicotinamide cofactors, flavins, and derivatives and analogs thereof) can be supplied for optimal activity of the enzyme.

In some embodiments, the chimeric adaptor polypeptide comprises at least one targeting sequence which directs transport of the adaptor to a specific region of a cell. For example, a targeting sequence can direct the adaptor to a cell nucleus utilizing a nuclear localization signal (NLS), outside of a cell nucleus (e.g., to the cytoplasm) utilizing a nuclear export signal (NES), the mitochondria, the endoplasmic reticulum (ER), the Golgi, chloroplasts, apoplasts, peroxisomes, plasma membrane, or membrane of various organelles of a cell. In some embodiments, a targeting sequence comprises a nuclear export signal (NES) and directs the chimeric adaptor polypeptide outside of a cell nucleus. In some embodiments, a targeting sequence comprises a nuclear localization signal (NLS) and directs the adaptor to a cell nucleus. A targeting sequence can direct the adaptor to a cell nucleus utilizing various nuclear localization signals (NLS). In some embodiments, a targeting sequence comprises a membrane targeting peptide and directs the adaptor to a plasma membrane or membrane of a cellular organelle. A targeting sequence can direct the adaptor to a membrane utilizing a membrane anchoring signal sequence as previously described. Various membrane-anchoring sequences are available.

Figure 11:
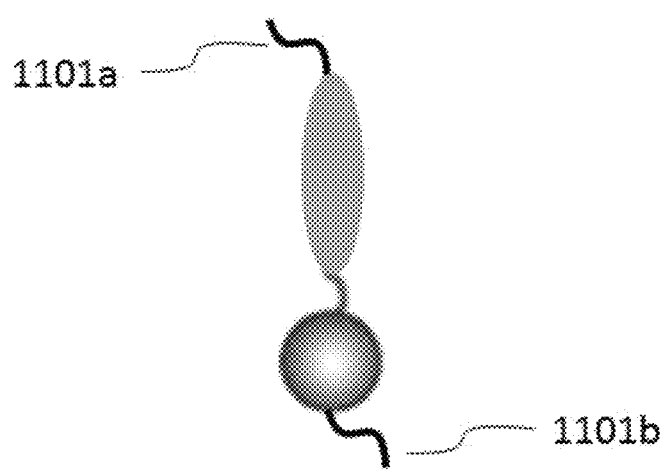
FIG. 11 shows an exemplary chimeric adaptor polypeptide comprising at least one targeting sequence.

The targeting sequence can be linked to any appropriate region of the chimeric adaptor polypeptide, for example at the N-terminus or the C-terminus of the polypeptide or in an internal region of the adaptor. In some embodiments, at least two targeting sequences are linked to the adaptor. For example, as shown in FIG. 11, a first targeting sequence 1101a can be linked to the receptor binding moiety of the adaptor and a second targeting sequence 1101b can be linked to the GMP of the adaptor, for example to the actuator moiety. When an adaptor is linked to multiple targeting sequences, for example targeting sequences directed to different locations of a cell, the final localization of the adaptor can be determined by the relative strengths of the targeting sequences. For example, an adaptor having both a targeting sequence comprising an NES and a targeting sequence comprising an NLS can localize to the cytosol if the NES is stronger than the NLS. Alternatively, if the NLS is stronger than the NES, the adaptor can localize to the nucleus even though both a nuclear localization signal and nuclear export signal are present on the adaptor. A targeting sequence can comprise multiple copies of, for example, each a NLS and NES, to fine-tune the degree of the cellular localization.

In some cases, a targeting sequence is linked to the actuator moiety. Following release of the actuator moiety from the GMP by cleavage of the cleavage recognition site, the targeting sequence can direct the actuator moiety to a cellular location that is different from the adaptor. For example, a chimeric adaptor polypeptide can comprise a first targeting sequence directing the adaptor to the cell cytoplasm and the actuator moiety can separately comprise a second targeting sequence directing localization to a cell nucleus. Initially, the actuator moiety (forming a portion of the adaptor) can localize to the cell cytoplasm due to the first targeting sequence. Following release of the actuator moiety from the GMP by cleavage of the cleavage recognition site, the actuator moiety can localize to a cell nucleus via targeting by the second targeting sequence. In some embodiments, the actuator moiety translocates to a cell nucleus after cleavage of the cleavage recognition sequence.

In some embodiments, a targeting sequence comprises a membrane targeting peptide and directs a polypeptide to a plasma membrane or membrane of a cellular organelle. A membrane-targeting sequence can provide for transport of the chimeric transmembrane receptor polypeptide to a cell surface membrane or other cellular membrane. Any suitable membrane target sequence previously described herein may be used.

In some embodiments, the chimeric adaptor polypeptide is linked to a polypeptide folding domain which can assist in protein folding. In some embodiments, an actuator moiety can be linked to a cell-penetrating domain. For example, the cell-penetrating domain can be derived from the HIV-1 TAT protein, the TLM cell-penetrating motif from human hepatitis B virus, MPG, Pep-1, VP22, a cell penetrating peptide from Herpes simplex virus, or a polyarginine peptide sequence. The cell-penetrating domain can be located at the N-terminus, the C-terminus, or anywhere within the actuator moiety.

The actuator moiety of a subject system, upon release from a chimeric adaptor polypeptide or chimeric transmembrane receptor polypeptide, can bind to a target polynucleotide to regulate expression and/or activity of the target polynucleotide by physical obstruction of the target polynucleotide or recruitment of additional factors effective to suppress or enhance expression of the target polynucleotide. In some embodiments, the actuator moiety comprises a transcriptional activator effective to increase expression of the target polynucleotide. The actuator moiety can comprise a transcriptional repressor effective to decrease expression of the target polynucleotide. In some embodiments, the actuator moiety is operable to edit a nucleic acid sequence.

In some embodiments, the target polynucleotide comprises genomic DNA. In some embodiments, the target polynucleotide comprises a region of a plasmid, for example a plasmid carrying an exogenous gene. In some embodiments, the target polynucleotide comprises RNA, for example mRNA. In some embodiments, the target polynucleotide comprises an endogenous gene or gene product. The actuator moiety can include one or more copies of a nuclear localization signal that allows the actuator to translocate into a cell nucleus upon cleavage from the GMP.

Figure 19:
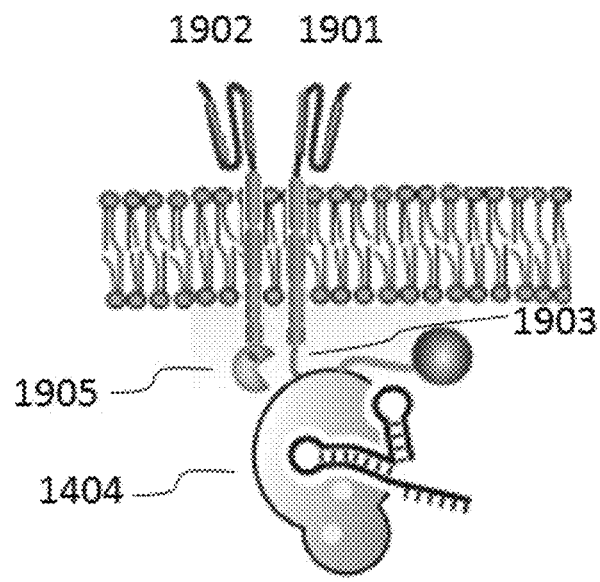
FIG. 19 shows an illustration of a system wherein the GMP forms a portion of a first chimeric transmembrane receptor polypeptide and the cleavage moiety forms a portion of a second chimeric transmembrane receptor polypeptide.

In another exemplary configuration, the GMP forms a portion of a chimeric transmembrane receptor polypeptide and the cleavage moiety forms a portion of a chimeric transmembrane polypeptide. In some embodiments, the chimeric transmembrane polypeptide having the cleavage moiety comprises an antigen interacting domain and can similarly be referred to as a transmembrane receptor polypeptide. This transmembrane receptor polypeptide, in some cases, comprises an immune cell signaling domain. In some embodiments, the antigen interacting domain binds the same antigen as that of the chimeric transmembrane receptor polypeptide comprising the GMP. In some embodiments, the antigen interacting domain binds a different antigen than that of the chimeric transmembrane receptor polypeptide comprising the GMP. In some embodiments, the chimeric transmembrane polypeptide does not comprise an antigen interacting domain and can be referred to as a transmembrane protein. The GMP, as previously described, can comprise an actuator moiety linked to a cleavage recognition sequence. A chimeric transmembrane receptor polypeptide comprising a cleavage moiety can cluster and/or interact with the chimeric transmembrane polypeptide (e.g., receptor or non-receptor) comprising a GMP in response to binding of an antigen to the chimeric transmembrane receptor polypeptide. Clustering and/or an interaction between the two polypeptides can bring the GMP in proximity to the cleavage moiety, allowing for cleavage of the cleavage recognition site by the cleavage moiety. A transmembrane protein comprising the cleavage moiety can cluster and/or interact with a chimeric transmembrane receptor polypeptide comprising the GMP upon binding of a ligand to the extracellular region of the chimeric transmembrane receptor polypeptide. In some embodiments, the chimeric transmembrane polypeptide comprises a molecule of the T-cell receptor complex, or any derivative, variant or fragment thereof. In some embodiments, the chimeric transmembrane polypeptide (e.g., receptor or non-receptor) comprises a molecule, or any derivative, variant or fragment, thereof, which is capable of clustering and/or oligomerizing with another transmembrane polypeptide (e.g., receptor or non-receptor). FIG. 19 provides an illustration of a system wherein the GMP forms a portion of a first chimeric transmembrane receptor polypeptide 1901 and the cleavage moiety forms a portion of a second chimeric transmembrane receptor polypeptide 1902. Upon antigen binding to the extracellular antigen binding domains of the first and second receptor polypeptides, the first and second chimeric transmembrane receptor polypeptides can cluster, bringing the cleavage moiety 1905 in proximity to the cleavage recognition site 1903. The cleavage moiety is able to cleave and release the actuator moiety 1904 (e.g., a Cas9 optionally complexed with a sgRNA, e.g., a dCas9) from the receptor.

Systems and compositions of the present disclosure are useful for a variety of applications. For example, systems and methods of the present disclosure are useful in methods of regulating gene expression and/or cellular activity. In an aspect, the systems and compositions disclosed herein are utilized in methods of regulating gene expression and/or cellular activity in an immune cell. Immune cells regulated using a subject system can be useful in a variety of applications, including, but not limited to, immunotherapy to treat diseases and disorders. Diseases and disorders that can be treated using modified immune cells of the present disclosure include inflammatory conditions, cancer, and infectious diseases. In some embodiments, immunotherapy is used to treat cancer.

A subject system can be introduced in a variety of immune cells, including any cell that is involved in an immune response. In some embodiments, immune cells comprise granulocytes such as asophils, eosinophils, and neutrophils; mast cells; monocytes which can develop into macrophages; antigen-presenting cells such as dendritic cells; and lymphocytes such as natural killer cells (NK cells), B cells, and T cells. In some embodiments, an immune cell is an immune effector cell. An immune effector cell refers to an immune cell that can perform a specific function in response to a stimulus. In some embodiments, an immune cell is an immune effector cell which can induce cell death. In some embodiments, the immune cell is a lymphocyte. In some embodiments, the lymphocyte is a NK cell. In some embodiments the lymphocyte is a T cell. In some embodiments, the T cell is an activated T cell. T cells include both naive and memory cells (e.g. central memory or $T_{CM}$, effector memory or $T_{EM}$ and effector memory RA or $T_{EMRA}$), effector cells (e.g. cytotoxic T cells or CTLs or Tc cells), helper cells (e.g. Th1, Th2, Th3, Th9, Th17, TFH), regulatory cells (e.g. Treg, and Tr1 cells), natural killer T cells (NKT cells), tumor infiltrating lymphocytes (TILs), lymphocyte-activated killer cells (LAKs), αβ T cells, γδ T cells, and similar unique classes of the T cell lineage. T cells can be divided into two broad categories: CD8+ T cells and CD4+ T cells, based on which protein is present on the cell's surface. T cells expressing a subject system can carry out multiple functions, including killing infected cells and activating or recruiting other immune cells. CD8+ T cells are referred to as cytotoxic T cells or cytotoxic T lymphocytes (CTLs). CTLs expressing a subject system can be involved in recognizing and removing virus-infected cells and cancer cells. CTLs have specialized compartments, or granules, containing cytotoxins that cause apoptosis, e.g., programmed cell death. CD4+ T cells can be subdivided into four sub-sets—Th1, Th2, Th17, and Treg, with "Th" referring to "T helper cell," although additional sub-sets may exist. Th1 cells can coordinate immune responses against intracellular microbes, especially bacteria. They can produce and secrete molecules that alert and activate other immune cells, like bacteria-ingesting macrophages. Th2 cells are involved in coordinating immune responses against extracellular pathogens, like helminths (parasitic worms), by alerting B cells, granulocytes, and mast cells. Th17 cells can produce interleukin 17 (IL-17), a signaling molecule that activates immune and non-immune cells. Th17 cells are important for recruiting neutrophils.

In an aspect, the present disclosure provides an immune cell expressing a subject system (e.g., at least one of a receptor polypeptide, an adaptor polypeptide, an gene modulating polypeptide GMP, and cleavage moiety as descried herein). In some embodiments, the immune cell is a lymphocyte. Subject systems, when expressed in an immune cell, can be useful for conditionally regulating certain activities of immune cells. Immune cells, such as lymphocytes, expressing a subject system can be involved in cell mediated immunity to eliminate diseased cells and/or pathogens.

In some embodiments, a lymphocyte of the present disclosure is characterized in that the actuator moiety is released form the GMP by cleavage at the cleavage recognition site only when the chimeric transmembrane receptor polypeptide is bound to an antigen. When the actuator moiety is released from the GMP, the actuator moiety is operable to complex with a target polynucleotide in the lymphocyte. Complexing of the actuator moiety with the target polynucleotide in the lymphocyte can result in up-regulated or increased expression of a target polynucleotide (e.g., gene) in the lymphocyte. In some embodiments, the actuator moiety regulates expression and/or activity of target polynucleotide comprising an endogenous gene or gene product. The endogenous gene or gene product can be involved in an immune response. For example, the actuator moiety can result in increased expression of an endogenous gene such as a cytokine. Increased expression of cytokines can contribute to an effective immune response and/or reduce negative therapeutic effects associated with an immune response.

In some embodiments, the actuator moiety regulates expression and/or activity of a cytokine. Methods of altering cytokine expression can be useful in regulating an immune cell and/or modulating an immune response, for example altering the activation of T cells, altering the level of NK cell activation, and various other immune cell activities in immunotherapy. Regulation of the expression of a cytokine can be accomplished by various mechanisms. In some embodiments, the actuator moiety regulates expression and/or activity of a cytokine from a target polynucleotide or edits a nucleic acid sequence, for example a nucleic acid sequence of genomic DNA encoding for the cytokine. In some embodiments, the actuator moiety regulates expression and/or activity of a cytokine receptor from a target polynucleotide or edits a nucleic acid sequence, for example a nucleic acid sequence of genomic DNA encoding for the cytokine receptor. The target polynucleotide regulated and/or edited by the actuator moiety can comprise an endogenous gene or gene product, for example an endogenous cytokine or cytokine receptor gene (e.g., DNA) or gene product (e.g., RNA). The actuator moiety, in some embodiments, alters the expression of the cytokine or cytokine receptor (e.g., up-regulate and/or down-regulate). In some embodiments, the actuator moiety edits the nucleic acid sequence encoding the cytokine or cytokine receptor. Editing the nucleic acid sequence can generate non-functional gene products, for example protein products that are truncated and/or out of frame.

Cytokines refer to proteins (e.g., chemokines, interferons, lymphokines, interleukins, and tumor necrosis factors) released by cells which can affect cell behavior. Cytokines are produced by a broad range of cells, including immune cells such as macrophages, B lymphocytes, T lymphocytes and mast cells, as well as endothelial cells, fibroblasts, and various stromal cells. A given cytokine can be produced by more than one type of cell. Cytokines can be involved in producing systemic or local immunomodulatory effects.

Certain cytokines can function as pro-inflammatory cytokines. Pro-inflammatory cytokines refer to cytokines involved in inducing or amplifying an inflammatory reaction. Pro-inflammatory cytokines can work with various cells of the immune system, such as neutrophils and leukocytes, to generate an immune response. Certain cytokines can function as anti-inflammatory cytokines. Anti-inflammatory cytokines refer to cytokines involved in the reduction of an inflammatory reaction. Anti-inflammatory cytokines, in some cases, can regulate a pro-inflammatory cytokine response. Some cytokines can function as both pro- and anti-inflammatory cytokines.

In some embodiments, the expression of a cytokine having pro-inflammatory functions can be up-regulated in an immune cell. Up-regulating the expression of a cytokine having pro-inflammatory functions can be useful, for example, to stimulate an immune response against a target cell in immunotherapy. However, excessive amounts of pro-inflammatory cytokines can, in some cases, cause detrimental effects, such as chronic systemic elevations in the body. In some embodiments, the expression of a cytokine having pro-inflammatory functions is down-regulated. Such down-regulation can decrease and/or minimize detrimental effects.

In some embodiments, the expression of a cytokine having anti-inflammatory functions can be up-regulated. Up-regulating the expression of a cytokine having anti-inflammatory functions can be useful, for example, to reduce and/or minimize an inflammatory response if an inflammatory response is causing a detrimental effect. In some embodiments, the expression of a cytokine having anti-inflammatory functions can be down-regulated. Such down-regulation can increase and/or enhance an inflammatory response where desired.

Examples of cytokines that are regulatable by systems and compositions of the present disclosure include, but are not limited to lymphokines, monokines, and traditional polypeptide hormones. Included among the cytokines are growth hormones such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; fibroblast growth factor; prolactin; placental lactogen; tumor necrosis factor-alpha; mullerian-inhibiting substance; mouse gonadotropin-associated peptide; inhibin; activin; vascular endothelial growth factor; integrin; thrombopoietin (TPO); nerve growth factors such as NGF-alpha; platelet-growth factor; transforming growth factors (TGFs) such as TGF-alpha, TGF-beta, TGF-beta1, TGF-beta2, and TGF-beta3; insulin-like growth factor-I and —II; erythropoietin (EPO); Flt-3L; stem cell factor (SCF); osteoinductive factors; interferons (IFNs) such as IFN-α, IFN-β, IFN-γ; colony stimulating factors (CSFs) such as macrophage-CSF (M-CSF); granulocyte-macrophage-CSF (GM-CSF); granulocyte-CSF (G-CSF); macrophage stimulating factor (MSP); interleukins (ILs) such as IL-1, IL-1a, IL-1b, IL-1RA, IL-18, IL-2, IL-3, IL-4, IL-5, IL-6, IL-7, IL-8, IL-9, IL-10, IL-11, IL-12, IL-13, IL-14, IL-15, IL-16, IL-17, IL-20; a tumor necrosis factor such as CD154, LT-beta, TNF-alpha, TNF-beta, 4-1BBL, APRIL, CD70, CD153, CD178, GITRL, LIGHT, OX40L, TALL-1, TRAIL, TWEAK, TRANCE; and other polypeptide factors including LIF, oncostatin M (OSM) and kit ligand (KL). Cytokine receptors refer to the receptor proteins which bind cytokines. Cytokine receptors may be both membrane-bound and soluble.

In some embodiments, the actuator moiety regulates expression and/or activity of an interleukin (IL-1) family member (e.g., ligand), an IL-1 receptor family member, an interleukin-6 (IL-6) family member (e.g., ligand), an IL-6 receptor, an interleukin-10 (IL-10) family member (e.g., ligand), an IL-10 receptor, an interleukin-12 (IL-12) family member (e.g., ligand), an IL-12 receptor, an interleukin-17 (IL-17) family member (e.g., ligand), or an IL-17 receptor.

In some embodiments, the actuator moiety regulates expression and/or activity of a cytokine including, but not limited to, an interleukin-1 (IL-1) family member or related protein; a tumor necrosis factor (TNF) family member or related protein; an interferon (IFN) family member or related protein; an interleukin-6 (IL-6) family member or related protein; and a chemokine or related protein. In some embodiments, the actuator moiety regulates expression and/ or activity of a cytokine selected from IL18, IL18BP, IL1A, IL1B, IL1F10, IL1F3/IL1RA, IL1F5, IL1F6, IL1F7, IL1F8, IL1RL2, IL1F9, IL33, BAFF/BLyS/TNFSF138, 4-1BBL, CD153/CD30L/TNFSF8, CD40LG, CD70, Fas Ligand/ FASLG/CD95L/CD178, EDA-A1, TNFSF14/LIGHT/ CD258, TNFA, LTA/TNFB/TNFSF1, LTB/TNFC, CD70/ CD27L/TNFSF7, TNFSF10/TRAIL/APO-2L(CD253), RANKL/OPGL/TNFSF11(CD254), TNFSF12, TNF-alpha/ TNFA, TNFSF13, TL1A/TNFSF15, OX-40L/TNFSF4/ CD252, CD40L/CD154/TNFSF5, IFNA1, IFNA10, IFNA13, IFNA14, IFNA2, IFNA4, IFNA7, IFNB1, IFNE, IFNG, IFNZ, IFNA8, IFNA5/IFNaG, IFNω/IFNW1, CLCF1, CNTF, IL11, IL31, IL6, Leptin, LIF, OSM, CCL1/ TCA3, CCL11, CCL12/MCP-5, CCL13/MCP-4, CCL14, CCL15, CCL16, CCL17/TARC, CCL18, CCL19, CCL2/ MCP-1, CCL20, CCL21, CCL22/MDC, CCL23, CCL24, CCL25, CCL26, CCL27, CCL28, CCL3, CCL3L3, CCL4, CCL4L1/LAG-1, CCL5, CCL6, CCL7, CCL8, CCL9, CX3CL1, CXCL1, CXCL10, CXCL11, CXCL12, CXCL13, CXCL14, CXCL15, CXCL16, CXCL17, CXCL2/MIP-2, CXCL3, CXCL4, CXCL5, CXCL6, CXCL7/Ppbp, CXCL9, IL8/CXCL8, XCL1, XCL2, FAM19A1, FAM19A2, FAM19A3, FAM19A4, and FAM19A5.

In some embodiments, the actuator moiety regulates expression and/or activity of a cytokine receptor including, but not limited to, an interleukin-1 (IL-1) receptor family member or related protein; a tumor necrosis factor (TNF) receptor family member or related protein; an interferon (IFN) receptor family member or related protein; an interleukin-6 (IL-6) receptor family member or related protein; and a chemokine receptor or related protein. In some embodiments, the actuator moiety regulates expression and/ or activity of a cytokine receptor selected from IL18R1, IL18RAP, IL1R1, IL1R2, IL1R3, IL1R8, IL1R9, IL1RL1, SIGIRR, 4-1BB, BAFFR, TNFRSF7, CD40, CD95, DcR3, TNFRSF21, EDA2R, EDAR, PGLYRP1, TNFRSF19L, TNFR1, TNFR2, TNFRSF11A, TNFRSF11B, TNFRSF12A, TNFRSF13B, TNFRSF14, TNFRSF17, TNFRSF18, TNFRSF19, TNFRSF25, LTBR, TNFRSF4, TNFRSF8, TRAILR1, TRAILR2, TRAILR3, TRAILR4, IFNAR1, IFNAR2, IFNGR1, IFNGR2, CNTFR, IL11RA, IL6R, LEPR, LIFR, OSMR, IL31RA, CCR1, CCR2, CCR3, CCR4, CCR5, CCR6, CCR7, CCR8, CCRL1, CXCR3, CXCR4, CXCR5, CXCR6, CXCR7, CXCR1, CXCR2, ARMCX, BCA-1/CXCL1, CCL1, CCL12/MCP-, CCL13/ MCP-, CCL15/MIP-5/MIP-1 delt, CCL16/HCC-4/NCC, CCL17/TAR, CCL18/PARC/MIP-, CCL19/MIP-3, CCL2/ MCP-, CCL20/MIP-3 alpha/MIP3, CCL21/6Ckin, CCL22/ MD, CCL23/MIP, CCL24/Eotaxin-2/MPIF-, CCL25, CCL26/Eotaxin-, CCL27, CCL3, CCL4, CCL4L1/LAG, CCL5, CCL6, CCL8/MCP-, CXCL10/Crg, CXCL12/SDF-1, CXCL14, CXCL15, CXCL16/SR-, CXCL2/MIP-, CXCL3/GRO, CXCL4, CXCL6/GCP-, CXCL9, FAM19A4, Fractalkine, I-309/CCL1/TCA-, IL-8, MCP-3, NAP-2/ PPBP, XCL2, CCR1, CCR2, CCR3, CCR4, CCR5, CCR6, CCR7, CCR8, CCRL1, CXCR3, CXCR4, CXCR5, CXCR6, CXCR7/RDC-1, IL8Ra/CXCR1, and IL8Rb/CXCR2.

In some embodiments, the actuator moiety regulates expression and/or activity of an activin (e.g., activin βA, activin βB, activin βC and activin βE); an inhibin (e.g., inhibin-A and inhibin-B); an activin receptor (e.g., activin type 1 receptor, activin type 2 receptor); a bone morphogenetic protein (e.g., BMP1, BMP2, BMP3, BMP4, BMP5, BMP6, BMP7, BMP8a, BMP8b, BMP10, and BMP15); a BMP receptor; a growth differentiation factor (e.g., GDF1, GDF2, GDF3, GDF4, GDF5, GDF6, GDF7, GDF8, GDF9, GDF10, GDF11, and GDF15); glial cell-derived neurotrophic factor family ligand (e.g., glial cell line-derived neurotrophic factor (GDNF), neurturin (NRTN), artemin (ARTN), and persephin (PSPN)); a GDNF family receptor; and c-MPL/CD110/TPOR.

Cytokine production can be evaluated using a variety of methods. Cytokine production can be evaluated by assaying cell culture media (e.g., in vitro production) in which the modified immune cells are grown or sera (e.g., in vivo production) obtained from a subject having the modified immune cells for the presence of one or more cytokines. Cytokine levels can be quantified in various suitable units, including concentration, using any suitable assay. In some embodiments, cytokine protein is detected. In some embodiments, mRNA transcripts of cytokines are detected. Examples of cytokine assays include enzyme-linked immunosorbent assays (ELISA), immunoblot, immunofluorescence assays, radioimmunoassays, antibody arrays which allow various cytokines in a sample to be detected in parallel, bead-based arrays, quantitative PCR, microarray, etc. Other suitable methods may include proteomics approaches (2-D gels, MS analysis etc).

In some embodiments, the endogenous gene or gene product encodes for an immune regulatory protein. Immune regulatory proteins include proteins such as immune checkpoint receptors which, when bound to their cognate ligands, can enhance and/or suppress immune cell signals, including but not limited to activation signals and inhibition signals of immune cells. The actuator may, in some cases, alter the expression of the regulatory protein (e.g., up-regulate and/or down-regulate). In some embodiments, the actuator edits the nucleic acid sequence encoding for a regulatory protein. In some embodiments, the endogenous gene or gene product encodes for a molecule such as A2AR, B7.1, B7-H3/CD276, B7-H4/B7S1/B7x/Vtcn1, B7-H6, BTLA/CD272, CCR4, CD122, 4-1BB/CD137, CD27, CD28, CD40, CD47, CD70, CISH, CTLA-4/CD152, DR3, GITR, ICOS/CD278, IDO, KIR, LAG-3, OX40/CD134, PD-1/CD279, PD2, PD-L1, PD-L2, TIM-3, and VISTA/Dies1/Gi24/PD-1H (C10orf54).

In some embodiments, the target polynucleotide comprises a heterologous gene or gene product. The heterologous gene or gene product can encode for a protein such as an additional chimeric transmembrane receptor polypeptide. In some embodiments, the additional chimeric transmembrane receptor polypeptide comprises (a) an extracellular region comprising an additional antigen interacting domain that specifically binds an additional antigen; and (b) a co-stimulatory domain. The additional antigen interacting domain can bind any suitable antigen. The additional antigen interacting domain can bind an antigen previously described. The additional antigen interacting domain can bind the same antigen or a different antigen as the chimeric receptor polypeptide. The additional antigen interacting domain can comprise any suitable antigen interacting domain. The additional antigen interacting domain can be any antigen interacting domain described elsewhere herein. For example, the additional antigen interacting domain can comprise a monoclonal antibody, a polyclonal antibody, a recombinant antibody, a human antibody, a humanized antibody, a Fab, a Fab', a F(ab')$_2$, an Fv, a single chain antibody (e.g., scFv), a minibody, a diabody, a single-domain antibody ("sdAb" or "nanobodies" or "camelids"), or an Fc binding domain. In some embodiments, the additional antigen interacting domain comprises an antibody mimetic.

The additional chimeric transmembrane receptor polypeptide can comprise a co-stimulatory domain. A co-stimulatory domain can be any co-stimulatory domain previously described. A co-stimulatory domain can provide co-stimulatory signals. Such co-stimulatory signals can, in some cases, provide a proliferative and/or survival signal in an immune cell expressing a subject system. In some embodiments, both the immune cell signaling domain of the chimeric transmembrane receptor polypeptide and the additional chimeric transmembrane receptor polypeptide contain at least one co-stimulatory domain. Expression of an additional chimeric transmembrane receptor comprising a co-stimulatory domain can provide sufficient cellular signaling to yield a persistent and/or adequate immune response.

In some embodiments, the immune cell signaling domain of the chimeric transmembrane receptor polypeptide does not include a co-stimulatory domain while the additional chimeric transmembrane receptor polypeptide comprises at least one co-stimulatory domain. Binding of a first antigen to the extracellular region of the chimeric transmembrane receptor polypeptide can result in cleavage of the cleavage recognition site to release the actuator moiety. The actuator moiety can then complex with a target polynucleotide, for example a polynucleotide encoding for an additional chimeric transmembrane receptor polypeptide, and regulate expression of the additional chimeric transmembrane receptor polypeptide. The additional chimeric transmembrane receptor polypeptide comprises (i) an additional antigen interacting domain which specifically binds an antigen different from the first antigen and a (ii) co-stimulatory domain which can contribute to an efficient immune response of the immune cell. As the co-stimulatory domain is located on the additional chimeric transmembrane receptor polypeptide, an effective immune response may not be produced until both receptors have been bound to an antigen. In this way, regulation of the immune cell is conditional upon the presence of two antigens, thereby increasing the specificity of immune cell regulation (e.g., activation and/or deactivation). In some embodiments, the placement of co-stimulatory domains (e.g., on the chimeric transmembrane receptor polypeptide, on the additional chimeric transmembrane receptor polypeptide and/or on both receptors) affect the specificity of conditional immune cell regulation. For example, an immune cell can express a system comprising a chimeric transmembrane receptor polypeptide having an extracellular region comprising antigen interacting domain and an intracellular region comprising an immune cell signaling domain linked to an actuator moiety via a cleavage recognition site. As many cell types express overlapping antigens (e.g., cell surface proteins, etc), conditional activation dependent on the presence of at least two antigens can increase the threshold for immune cell activation.

In an aspect, the disclosure provides a method for conditional regulation of a lymphocyte. In some embodiments, the method comprises contacting or exposing a lymphocyte disclosed herein with an antigen that binds specifically to the antigen interacting domain of the receptor. The contacting effects an activation or deactivation of immune cell activity, thereby conditionally regulating the lymphocyte. In some embodiments, the immune cell activity is selected from the group consisting of: clonal expansion of the lymphocyte; cytokine release by the lymphocyte; cytotoxicity of the lymphocyte; proliferation of the lymphocyte; differentiation, dedifferentiation or transdifferentiation of the lymphocyte; movement and/or trafficking of the lymphocyte; exhaustion and/or reactivation of the lymphocyte; and release of other intercellular molecules, metabolites, chemical compounds, or combinations thereof by the lymphocyte.

In some examples, the systems and compositions of the present disclosure, when expressed in an immune, can be used for killing a target cell. In an aspect, an immune cell or population of immune cells expressing a subject system can induce death of a target cell. Killing of a target cell can be useful for a variety of applications, including, but not limited to, treating a disease or disorder in which a cell population is desired to be eliminated or its proliferation desired to be inhibited. In some embodiments, a method of inducing death of a target cell comprises exposing the target cell to an immune cell or population of immune cells expressing a system disclosed herein. In some embodiments, the immune cell is a lymphocyte, such as a T cell or NK cell. Upon exposing the target cell to the lymphocyte, the receptor expressed by the lymphocyte can bind a membrane bound antigen of the target cell or a non-membrane bound antigen of the target cell, and the exposing effects an activation of cytotoxicity of the lymphocyte, thereby inducing death of the target cell.

Lymphocytes, such as cytotoxic T cells expressing a subject system can induce apoptosis of target cells. A subject system, when expressed in an immune cell such as a T cell, can be used to regulate clonal expansion of the T cell, expression of activation markers on the cell surface, differentiation into effector cells, induction of cytotoxicity or cytokine secretion, induction of apoptosis, and combinations thereof. A subject system expressed in cytotoxic T cells can alter the (i) release of cytotoxins such as perforin, granzymes, and granulysin and/or (ii) induction of apoptosis via Fas-Fas ligand interaction between the T cells and target cells, thereby triggering the destruction of target cells. A subject system, when expressed in a natural killer (NK) cell, can mediate killing of a target cell by the NK cell. Natural killer (NK) cells, when activated, can target and kill aberrant cells, such as virally infected and tumorigenic cells. A subject system can regulate the production and/or release of cytotoxic molecules stored within secretory lysosomes of NK cells which can result in specific killing of a target cell. In some embodiments, (i) an antigen-specific cytotoxic T cell (e.g., lymphocyte) expressing a subject system can induce apoptosis in cells displaying epitopes of a foreign antigen on their surface, such as virus-infected cells, cells with intracellular bacteria, and cancer cells displaying tumor antigens; (ii) macrophages and natural killer cells (NK cells) expressing a subject system can destroy pathogens; and/or (iii) other immune cells expressing a subject system can secrete a variety of cytokines to facilitate additional immune responses.

Activation of cytotoxicity of immune cells such as T cells and NK cells refers to induced changes in the biologic state by which the cells become cytotoxic. Such changes include altered expression of activation markers, production of cytokines, and proliferation. These changes can be produced by primary stimulatory signals. Co-stimulatory signals can amplify the magnitude of the primary signals and suppress cell death following initial stimulation resulting in a more durable activation state and thus a higher cytotoxic capacity. Cytotoxicity can refer to antibody-dependent cellular cytotoxicity.

In an immune cell expressing a system disclosed herein, the receptor can undergo receptor modification in response to antigen binding. The receptor modification can comprise a conformational change and/or chemical modification. A chemical modification can comprise, for example, phosphorylation or dephosphorylation at at least one amino acid residue of the receptor. In some embodiments, receptor modification comprises modification at multiple modification sites, and each modification is effective to bind an adaptor protein. Upon binding of the antigen interacting domain of the chimeric transmembrane receptor polypeptide on an immune cell to an antigen (either membrane bound or non-membrane bound) of the target cell, the actuator moiety is released from the GMP to effect the activation or deactivation of an immune cell activity, for example cytotoxicity of the lymphocyte.

The actuator moiety released from the GMP can effect the activation of cytotoxicity of the lymphocyte by regulating expression of a target polynucleotide such as DNA (e.g., genomic DNA and/or cDNA) and RNA (e.g., mRNA). In some embodiments, the actuator moiety regulates expression of a target polynucleotide by physical obstruction of the target polynucleotide or recruitment of additional factors effective to suppress or enhance gene expression form the target polynucleotide. In some embodiments, the actuator moiety comprises a transcriptional activator effective to increase expression of the target polynucleotide. In some embodiments, the actuator moiety comprises a transcriptional repressor effective to decrease expression of the target polynucleotide.

In some embodiments, the target polynucleotide comprises genomic DNA, such as a region of the genome. In some embodiments, the target polynucleotide comprises a region a plasmid, for example a plasmid carrying an exogenous gene. In some embodiments, the target polynucleotide comprises RNA. The actuator moiety can include one or more copies of a nuclear localization signal sequence that allows the domain to translocate into the nucleus upon cleavage from the GMP.

A variety of target cells can be killed using the systems and methods of the subject disclosure. A target cell to which this method can be applied includes a wide variety of cell types. A target cell can be in vitro. A target cell can be in vivo. A target cell can be ex vivo. A target cell can be an isolated cell. A target cell can be a cell inside of an organism. A target cell can be an organism. A target cell can be a cell in a cell culture. A target cell can be one of a collection of cells. A target cell can be a mammalian cell or derived from a mammalian cell. A target cell can be a rodent cell or derived from a rodent cell. A target cell can be a human cell or derived from a human cell. A target cell can be a prokaryotic cell or derived from a prokaryotic cell. A target cell can be a bacterial cell or can be derived from a bacterial cell. A target cell can be an archaeal cell or derived from an archaeal cell. A target cell can be a eukaryotic cell or derived from a eukaryotic cell. A target cell can be a pluripotent stem cell. A target cell can be a plant cell or derived from a plant cell. A target cell can be an animal cell or derived from an animal cell. A target cell can be an invertebrate cell or derived from an invertebrate cell. A target cell can be a vertebrate cell or derived from a vertebrate cell. A target cell can be a microbe cell or derived from a microbe cell. A target cell can be a fungi cell or derived from a fungi cell. A target cell can be from a specific organ or tissue.

A target cell can be a stem cell or progenitor cell. Target cells can include stem cells (e.g., adult stem cells, embryonic stem cells, induced pluripotent stem (iPS) cells) and progenitor cells (e.g., cardiac progenitor cells, neural progenitor cells, etc.). Target cells can include mammalian stem cells and progenitor cells, including rodent stem cells, rodent progenitor cells, human stem cells, human progenitor cells, etc. Clonal cells can comprise the progeny of a cell. A target cell can comprise a target nucleic acid. A target cell can be in a living organism. A target cell can be a genetically modified cell. A target cell can be a host cell.

A target cell can be a totipotent stem cell, however, in some embodiments of this disclosure, the term "cell" may be used but may not refer to a totipotent stem cell. A target cell can be a plant cell, but in some embodiments of this disclosure, the term "cell" may be used but may not refer to a plant cell. A target cell can be a pluripotent cell. For example, a target cell can be a pluripotent hematopoietic cell that can differentiate into other cells in the hematopoietic cell lineage but may not be able to differentiate into any other non-hematopoietic cell. A target cell may be able to develop into a whole organism. A target cell may or may not be able to develop into a whole organism. A target cell may be a whole organism.

A target cell can be a primary cell. For example, cultures of primary cells can be passaged 0 times, 1 time, 2 times, 4 times, 5 times, 10 times, 15 times or more. Cells can be unicellular organisms. Cells can be grown in culture.

A target cell can be a diseased cell. A diseased cell can have altered metabolic, gene expression, and/or morphologic features. A diseased cell can be a cancer cell, a diabetic cell, and a apoptotic cell. A diseased cell can be a cell from a diseased subject. Exemplary diseases can include blood disorders, cancers, metabolic disorders, eye disorders, organ disorders, musculoskeletal disorders, cardiac disease, and the like.

If the target cells are primary cells, they may be harvested from an individual by any method. For example, leukocytes may be harvested by apheresis, leukocytapheresis, density gradient separation, etc. Cells from tissues such as skin, muscle, bone marrow, spleen, liver, pancreas, lung, intestine, stomach, etc. can be harvested by biopsy. An appropriate solution may be used for dispersion or suspension of the harvested cells. Such solution can generally be a balanced salt solution, (e.g. normal saline, phosphate-buffered saline (PBS), Hank's balanced salt solution, etc.), conveniently supplemented with fetal calf serum or other naturally occurring factors, in conjunction with an acceptable buffer at low concentration. Buffers can include HEPES, phosphate buffers, lactate buffers, etc. Cells may be used immediately, or they may be stored (e.g., by freezing). Frozen cells can be thawed and can be capable of being reused. Cells can be frozen in a DMSO, serum, medium buffer (e.g., 10% DMSO, 50% serum, 40% buffered medium), and/or some other such common solution used to preserve cells at freezing temperatures.

Non-limiting examples of cells which can be target cells include, but are not limited to, lymphoid cells, such as B cell, T cell (Cytotoxic T cell, Natural Killer T cell, Regulatory T cell, T helper cell), Natural killer cell, cytokine induced killer (CIK) cells (see e.g. US20080241194); myeloid cells, such as granulocytes (Basophil granulocyte, Eosinophil granulocyte, Neutrophil granulocyte/Hypersegmented neutrophil), Monocyte/Macrophage, Red blood cell (Reticulocyte), Mast cell, Thrombocyte/Megakaryocyte, Dendritic cell; cells from the endocrine system, including thyroid (Thyroid epithelial cell, Parafollicular cell), parathyroid (Parathyroid chief cell, Oxyphil cell), adrenal (Chromaffin cell), pineal (Pinealocyte) cells; cells of the nervous system, including glial cells (Astrocyte, Microglia), Magnocellular neurosecretory cell, Stellate cell, Boettcher cell, and pituitary (Gonadotrope, Corticotrope, Thyrotrope, Somatotrope, Lactotroph); cells of the Respiratory system, including Pneumocyte (Type I pneumocyte, Type II pneumocyte), Clara cell, Goblet cell, Dust cell; cells of the circulatory system, including Myocardiocyte, Pericyte; cells of the digestive system, including stomach (Gastric chief cell, Parietal cell), Goblet cell, Paneth cell, G cells, D cells, ECL cells, I cells, K cells, S cells; enteroendocrine cells, including enterochromaffin cell, APUD cell, liver (Hepatocyte, Kupffer cell), Cartilage/bone/muscle; bone cells, including Osteoblast, Osteocyte, Osteoclast, teeth (Cementoblast, Ameloblast); cartilage cells, including Chondroblast, Chondrocyte; skin cells, including Trichocyte, Keratinocyte, Melanocyte (Nevus cell); muscle cells, including Myocyte; urinary system cells, including Podocyte, Juxtaglomerular cell, Intraglomerular mesangial cell/Extraglomerular mesangial cell, Kidney proximal tubule brush border cell, Macula densa cell; reproductive system cells, including Spermatozoon, Sertoli cell, Leydig cell, Ovum; and other cells, including Adipocyte, Fibroblast, Tendon cell, Epidermal keratinocyte (differentiating epidermal cell), Epidermal basal cell (stem cell), Keratinocyte of fingernails and toenails, Nail bed basal cell (stem cell), Medullary hair shaft cell, Cortical hair shaft cell, Cuticular hair shaft cell, Cuticular hair root sheath cell, Hair root sheath cell of Huxley's layer, Hair root sheath cell of Henle's layer, External hair root sheath cell, Hair matrix cell (stem cell), Wet stratified barrier epithelial cells, Surface epithelial cell of stratified squamous epithelium of cornea, tongue, oral cavity, esophagus, anal canal, distal urethra and vagina, basal cell (stem cell) of epithelia of cornea, tongue, oral cavity, esophagus, anal canal, distal urethra and vagina, Urinary epithelium cell (lining urinary bladder and urinary ducts), Exocrine secretory epithelial cells, Salivary gland mucous cell (polysaccharide-rich secretion), Salivary gland serous cell (glycoprotein enzyme-rich secretion), Von Ebner's gland cell in tongue (washes taste buds), Mammary gland cell (milk secretion), Lacrimal gland cell (tear secretion), Ceruminous gland cell in ear (wax secretion), Eccrine sweat gland dark cell (glycoprotein secretion), Eccrine sweat gland clear cell (small molecule secretion). Apocrine sweat gland cell (odoriferous secretion, sex-hormone sensitive), Gland of Moll cell in eyelid (specialized sweat gland), Sebaceous gland cell (lipid-rich sebum secretion), Bowman's gland cell in nose (washes olfactory epithelium), Brunner's gland cell in duodenum (enzymes and alkaline mucus), Seminal vesicle cell (secretes seminal fluid components, including fructose for swimming sperm), Prostate gland cell (secretes seminal fluid components), Bulbourethral gland cell (mucus secretion), Bartholin's gland cell (vaginal lubricant secretion), Gland of Littre cell (mucus secretion), Uterus endometrium cell (carbohydrate secretion), Isolated goblet cell of respiratory and digestive tracts (mucus secretion), Stomach lining mucous cell (mucus secretion), Gastric gland zymogenic cell (pepsinogen secretion), Gastric gland oxyntic cell (hydrochloric acid secretion), Pancreatic acinar cell (bicarbonate and digestive enzyme secretion), Paneth cell of small intestine (lysozyme secretion), Type II pneumocyte of lung (surfactant secretion), Clara cell of lung, Hormone secreting cells, Anterior pituitary cells, Somatotropes, Lactotropes, Thyrotropes, Gonadotropes, Corticotropes, Intermediate pituitary cell, Magnocellular neurosecretory cells, Gut and respiratory tract cells, Thyroid gland cells, thyroid epithelial cell, parafollicular cell, Parathyroid gland cells, Parathyroid chief cell, Oxyphil cell, Adrenal gland cells, chromaffin cells, Leydig cell of testes, Theca interna cell of ovarian follicle, Corpus luteum cell of ruptured ovarian follicle, Granulosa lutein cells, Theca lutein cells, Juxtaglomerular cell (renin secretion), Macula densa cell of kidney, Metabolism and storage cells, Barrier function cells (Lung, Gut, Exocrine Glands and Urogenital Tract), Kidney, Type I pneumocyte (lining air space of lung), Pancreatic duct cell (centroacinar cell), Nonstriated duct cell (of sweat gland, salivary gland, mammary gland, etc.), Duct cell (of seminal vesicle, prostate gland, etc.), Epithelial cells lining closed internal body cavities, Ciliated cells with propulsive function, Extracellular matrix secretion cells, Contractile cells; Skeletal muscle cells, stem cell, Heart muscle cells, Blood and immune system cells, Erythrocyte (red blood cell), Megakaryocyte (platelet precursor), Monocyte, Connective tissue macrophage (various types), Epidermal Langerhans cell, Osteoclast (in bone), Dendritic cell (in lymphoid tissues), Microglial cell (in central nervous system), Neutrophil granulocyte, Eosinophil granulocyte, Basophil granulocyte, Mast cell, Helper T cell, Suppressor T cell, Cytotoxic T cell, Natural Killer T cell, B cell, Natural killer cell, Reticulocyte, Stem cells and committed progenitors for the blood and immune system (various types), Pluripotent stem cells, Totipotent stem cells, Induced pluripotent stem cells, adult stem cells, Sensory transducer cells, Autonomic neuron cells, Sense organ and peripheral neuron supporting cells, Central nervous system neurons and glial cells, Lens cells, Pigment cells, Melanocyte, Retinal pigmented epithelial cell, Germ cells, Oogonium/Oocyte, Spermatid, Spermatocyte, Spermatogonium cell (stem cell for spermatocyte), Spermatozoon, Nurse cells, Ovarian follicle cell, Sertoli cell (in testis), Thymus epithelial cell, Interstitial cells, and Interstitial kidney cells.

Of particular interest are cancer cells. In some embodiments, the target cell is a cancer cell. Non-limiting examples of cancer cells include cells of cancers including Acanthoma, Acinic cell carcinoma, Acoustic neuroma, Acral lentiginous melanoma, Acrospiroma, Acute eosinophilic leukemia, Acute lymphoblastic leukemia, Acute megakaryoblastic leukemia, Acute monocytic leukemia, Acute myeloblastic leukemia with maturation, Acute myeloid dendritic cell leukemia, Acute myeloid leukemia, Acute promyelocytic leukemia, Adamantinoma, Adenocarcinoma, Adenoid cystic carcinoma, Adenoma, Adenomatoid odontogenic tumor, Adrenocortical carcinoma, Adult T-cell leukemia, Aggressive NK-cell leukemia, AIDS-Related Cancers, AIDS-related lymphoma, Alveolar soft part sarcoma, Ameloblastic fibroma, Anal cancer, Anaplastic large cell lymphoma, Anaplastic thyroid cancer, Angioimmunoblastic T-cell lymphoma, Angiomyolipoma, Angiosarcoma, Appendix cancer, Astrocytoma, Atypical teratoid rhabdoid tumor, Basal cell carcinoma, Basal-like carcinoma, B-cell leukemia, B-cell lymphoma, Bellini duct carcinoma, Biliary tract cancer, Bladder cancer, Blastoma, Bone Cancer, Bone tumor, Brain Stem Glioma, Brain Tumor, Breast Cancer, Brenner tumor, Bronchial Tumor, Bronchioloalveolar carcinoma, Brown tumor, Burkitt's lymphoma, Cancer of Unknown Primary Site, Carcinoid Tumor, Carcinoma, Carcinoma in situ, Carcinoma of the penis, Carcinoma of Unknown Primary Site, Carcinosarcoma, Castleman's Disease, Central Nervous System Embryonal Tumor, Cerebellar Astrocytoma, Cerebral Astrocytoma, Cervical Cancer, Cholangiocarcinoma, Chondroma, Chondrosarcoma, Chordoma, Choriocarcinoma, Choroid plexus papilloma, Chronic Lymphocytic Leukemia, Chronic monocytic leukemia, Chronic myelogenous leukemia, Chronic Myeloproliferative Disorder, Chronic neutrophilic leukemia, Clear-cell tumor, Colon Cancer, Colorectal cancer, Craniopharyngioma, Cutaneous T-cell lymphoma, Degos disease, Dermatofibrosarcoma protuberans, Dermoid cyst, Desmoplastic small round cell tumor, Diffuse large B cell lymphoma, Dysembryoplastic neuroepithelial tumor, Embryonal carcinoma, Endodermal sinus tumor, Endometrial cancer, Endometrial Uterine Cancer, Endometrioid tumor, Enteropathy-associated T-cell lymphoma, Ependymoblastoma, Ependymoma, Epithelioid sarcoma, Erythroleukemia, Esophageal cancer, Esthesioneuroblastoma, Ewing Family of Tumor, Ewing Family Sarcoma, Ewing's sarcoma, Extracranial Germ Cell Tumor, Extragonadal Germ Cell Tumor, Extrahepatic Bile Duct Cancer, Extramammary Paget's disease, Fallopian tube cancer, Fetus in fetu, Fibroma, Fibrosarcoma, Follicular lymphoma, Follicular thyroid cancer, Gallbladder Cancer, Gallbladder cancer, Ganglioglioma, Ganglioneuroma, Gastric Cancer, Gastric lymphoma, Gastrointestinal cancer, Gastrointestinal Carcinoid Tumor, Gastrointestinal Stromal Tumor, Gastrointestinal stromal tumor, Germ cell tumor, Germinoma, Gestational choriocarcinoma, Gestational Trophoblastic Tumor, Giant cell tumor of bone, Glioblastoma multiforme, Glioma, Gliomatosis cerebri, *Glomus* tumor, Glucagonoma, Gonadoblastoma, Granulosa cell tumor, Hairy Cell Leukemia, Hairy cell leukemia, Head and Neck Cancer, Head and neck cancer, Heart cancer, Hemangioblastoma, Hemangiopericytoma, Hemangiosarcoma, Hematological malignancy, Hepatocellular carcinoma, Hepatosplenic T-cell lymphoma, Hereditary breast-ovarian cancer syndrome, Hodgkin Lymphoma, Hodgkin's lymphoma, Hypopharyngeal Cancer, Hypothalamic Glioma, Inflammatory breast cancer, Intraocular Melanoma, Islet cell carcinoma, Islet Cell Tumor, Juvenile myelomonocytic leukemia, Kaposi Sarcoma, Kaposi's sarcoma, Kidney Cancer, Klatskin tumor, Krukenberg tumor, Laryngeal Cancer, Laryngeal cancer, Lentigo maligna melanoma, Leukemia, Leukemia, Lip and Oral Cavity Cancer, Liposarcoma, Lung cancer, Luteoma, Lymphangioma, Lymphangiosarcoma, Lymphoepithelioma, Lymphoid leukemia, Lymphoma, Macroglobulinemia, Malignant Fibrous Histiocytoma, Malignant fibrous histiocytoma, Malignant Fibrous Histiocytoma of Bone, Malignant Glioma, Malignant Mesothelioma, Malignant peripheral nerve sheath tumor, Malignant rhabdoid tumor, Malignant triton tumor, MALT lymphoma, Mantle cell lymphoma, Mast cell leukemia, Mediastinal germ cell tumor, Mediastinal tumor, Medullary thyroid cancer, Medulloblastoma, Medulloblastoma, Medulloepithelioma, Melanoma, Melanoma, Meningioma, Merkel Cell Carcinoma, Mesothelioma, Mesothelioma, Metastatic Squamous Neck Cancer with Occult Primary, Metastatic urothelial carcinoma, Mixed Mullerian tumor, Monocytic leukemia, Mouth Cancer, Mucinous tumor, Multiple Endocrine Neoplasia Syndrome, Multiple Myeloma, Multiple myeloma, Mycosis Fungoides, Mycosis fungoides, Myelodysplastic Disease, Myelodysplastic Syndromes, Myeloid leukemia, Myeloid sarcoma, Myeloproliferative Disease, Myxoma, Nasal Cavity Cancer, Nasopharyngeal Cancer, Nasopharyngeal carcinoma, Neoplasm, Neurinoma, Neuroblastoma, Neuroblastoma, Neurofibroma, Neuroma, Nodular melanoma, Non-Hodgkin Lymphoma, Non-Hodgkin lymphoma, Nonmelanoma Skin Cancer, Non-Small Cell Lung Cancer, Ocular oncology, Oligoastrocytoma, Oligodendroglioma, Oncocytoma, Optic nerve sheath meningioma, Oral Cancer, Oral cancer, Oropharyngeal Cancer, Osteosarcoma, Osteosarcoma, Ovarian Cancer, Ovarian cancer, Ovarian Epithelial Cancer, Ovarian Germ Cell Tumor, Ovarian Low Malignant Potential Tumor, Paget's disease of the breast, Pancoast tumor, Pancreatic Cancer, Pancreatic cancer, Papillary thyroid cancer, Papillomatosis, Paraganglioma, Paranasal Sinus Cancer, Parathyroid Cancer, Penile Cancer, Perivascular epithelioid cell tumor, Pharyngeal Cancer, Pheochromocytoma, Pineal Parenchymal Tumor of Intermediate Differentiation, Pineoblastoma, Pituicytoma, Pituitary adenoma, Pituitary tumor, Plasma Cell Neoplasm, Pleuropulmonary blastoma, Polyembryoma, Precursor T-lymphoblastic lymphoma, Primary central nervous system lymphoma, Primary effusion lymphoma, Primary Hepatocellular Cancer, Primary Liver Cancer, Primary peritoneal cancer, Primitive neuroectodermal tumor, Prostate cancer, Pseudomyxoma peritonei, Rectal Cancer, Renal cell carcinoma, Respiratory Tract Carcinoma Involving the NUT Gene on Chromosome 15, Retinoblastoma, Rhabdomyoma, Rhabdomyosarcoma, Richter's transformation, Sacrococcygeal teratoma, Salivary Gland Cancer, Sarcoma, Schwannomatosis, Sebaceous gland carcinoma, Secondary neoplasm, Seminoma, Serous tumor, Sertoli-Leydig cell tumor, Sex cord-stromal tumor, Sezary Syndrome, Signet ring cell carcinoma, Skin Cancer, Small blue round cell tumor, Small cell carcinoma, Small Cell Lung Cancer, Small cell lymphoma, Small intestine cancer, Soft tissue sarcoma, Somatostatinoma, Soot wart, Spinal Cord Tumor, Spinal tumor, Splenic marginal zone lymphoma, Squamous cell carcinoma, Stomach cancer, Superficial spreading melanoma, Supratentorial Primitive Neuroectodermal Tumor, Surface epithelial-stromal tumor, Synovial sarcoma, T-cell acute lymphoblastic leukemia, T-cell large granular lymphocyte leukemia, T-cell leukemia, T-cell lymphoma, T-cell prolymphocytic leukemia, Teratoma, Terminal lymphatic cancer, Testicular cancer, Thecoma, Throat Cancer, Thymic Carcinoma, Thymoma, Thyroid cancer, Transitional Cell Cancer of Renal Pelvis and Ureter, Transitional cell carcinoma, Urachal cancer, Urethral cancer, Urogenital neoplasm, Uterine sarcoma, Uveal melanoma, Vaginal Cancer, Verner Morrison syndrome, Verrucous carcinoma, Visual Pathway Glioma, Vulvar Cancer, Waldenstrom's macroglobulinemia, Warthin's tumor, Wilms' tumor, and combinations thereof. In some embodiments, the targeted cancer cell represents a subpopulation within a cancer cell population, such as a cancer stem cell. In some embodiments, the cancer is of a hematopoietic lineage, such as a lymphoma. The antigen can be a tumor associated antigen.

In some embodiments, the target cells form a tumor. A tumor treated with the methods herein can result in stabilized tumor growth (e.g., one or more tumors do not increase more than 1%, 5%, 10%, 15%, or 20% in size, and/or do not metastasize). In some embodiments, a tumor is stabilized for at least about 1, 2, 3, 4, 5, 6, 7, 8, 9, 10, 11, 12, or more weeks. In some embodiments, a tumor is stabilized for at least about 1, 2, 3, 4, 5, 6, 7, 8, 9, 10, 11, 12, or more months. In some embodiments, a tumor is stabilized for at least about 1, 2, 3, 4, 5, 6, 7, 8, 9, 10, or more years. In some embodiments, the size of a tumor or the number of tumor cells is reduced by at least about 5%, 10%, 15%, 20%, 25, 30%, 35%, 40%, 45%, 50%, 55%, 60%, 65%, 70%, 75%, 80%, 85%, 90%, 95% or more. In some embodiments, the tumor is completely eliminated, or reduced below a level of detection. In some embodiments, a subject remains tumor free (e.g. in remission) for at least about 1, 2, 3, 4, 5, 6, 7, 8, 9, 10, 11, 12, or more weeks following treatment. In some embodiments, a subject remains tumor free for at least about 1, 2, 3, 4, 5, 6, 7, 8, 9, 10, 11, 12, or more months following treatment. In some embodiments, a subject remains tumor free for at least about 1, 2, 3, 4, 5, 6, 7, 8, 9, 10, or more years after treatment.

Death of target cells can be determined by any suitable method, including, but not limited to, counting cells before and after treatment, or measuring the level of a marker associated with live or dead cells (e.g. live or dead target cells). Degree of cell death can be determined by any suitable method. In some embodiments, degree of cell death is determined with respect to a starting condition. For example, an individual can have a known starting amount of target cells, such as a starting cell mass of known size or circulating target cells at a known concentration. In such cases, degree of cell death can be expressed as a ratio of surviving cells after treatment to the starting cell population. In some embodiments, degree of cell death can be determined by a suitable cell death assay. A variety of cell death assays are available, and can utilize a variety of detection methodologies. Examples of detection methodologies include, without limitation, the use of cell staining, microscopy, flow cytometry, cell sorting, and combinations of these.

When a tumor is subject to surgical resection following completion of a therapeutic period, the efficacy of treatment in reducing tumor size can be determined by measuring the percentage of resected tissue that is necrotic (i.e., dead). In some embodiments, a treatment is therapeutically effective if the necrosis percentage of the resected tissue is greater than about 20% (e.g., at least about 30%, 40%, 50%, 60%, 70%, 80%, 90%, or 100%). In some embodiments, the necrosis percentage of the resected tissue is 100%, that is, no living tumor tissue is present or detectable.

Exposing a target cell to an immune cell or population of immune cells disclosed herein can be conducted either in vitro or in vivo. Exposing a target cell to an immune cell or population of immune cells generally refers to bringing the target cell in contact with the immune cell and/or in sufficient proximity such that an antigen of a target cell (e.g., membrane bound or non-membrane bound) can bind to the antigen interacting domain of the chimeric transmembrane receptor polypeptide expressed in the immune cell. Exposing a target cell to an immune cell or population of immune cells in vitro can be accomplished by co-culturing the target cells and the immune cells. Target cells and immune cells can be co-cultured, for example, as adherent cells or alternatively in suspension. Target cells and immune cells can be co-cultured in various suitable types of cell culture media, for example with supplements, growth factors, ions, etc. Exposing a target cell to an immune cell or population of immune cells in vivo can be accomplished, in some cases, by administering the immune cells to a subject, for example a human subject, and allowing the immune cells to localize to the target cell via the circulatory system. In some cases, an immune cell can be delivered to the immediate area where a target cell is localized, for example, by direct injection.

Exposing can be performed for any suitable length of time, for example at least 1 minute, at least 5 minutes, at least 10 minutes, at least 30 minutes, at least 1 hour, at least 2 hours, at least 3 hours, at least 4 hours, at least 5 hours, at least 6 hours, at least 7 hours, at least 8 hours, at least 12 hours, at least 16 hours, at least 20 hours, at least 24 hours, at least 2 days, at least 3 days, at least 4 days, at least 5 days, at least 6 days, at least 1 week, at least 2 weeks, at least 3 weeks, at least 1 month or longer.

In some embodiments, cells expressing a system provided herein induce death of a target cell in an in vitro cell death assay. In an aspect, the present disclosure provides a method of inducing death of a target cell comprising exposing the target cell to a lymphocyte expressing a system comprising (a) a chimeric transmembrane receptor polypeptide comprising a ligand binding domain, an immune cell signaling domain, and a gene modulating polypeptide (GMP), the GMP comprising an actuator moiety linked to a cleavage recognition site; and (b) a chimeric adaptor polypeptide comprising a receptor binding moiety linked to a cleavage moiety capable of cleaving the cleavage recognition site when in proximity to the cleavage recognition site, wherein the receptor binding moiety binds the receptor polypeptide upon a receptor modification resulting from binding of the ligand binding domain to the ligand. Upon exposing the target cell to the lymphocyte, the ligand binding domain can bind a ligand present on the target cell to yield (i) activation of cytotoxicity of the lymphocyte via the immune cell signaling domain and (ii) modulation of expression and activity of an immune regulatory protein by the actuator moiety. In response to binding of the ligand to the ligand binding domain, the receptor can undergo the receptor modification, and the chimeric adaptor polypeptide can bind the modified transmembrane receptor. The actuator moiety can be released from the GMP by cleavage at the cleavage recognition site by the cleavage moiety and the released actuator moiety can modulated expression and activity of the immune regulatory protein. In some cases, modulationg of expression and activity of the immune regulatory protein enhances cytotoxicity of the lymphocyte. In some cases, modulation of expression and activity of the immune regulator protein decrease hypercytokinemia of the lymphocyte.

In some embodiments, the lymphocyte exhibits an enhanced ability to induce death of the target cell compared to a control lymphocyte. The control lymphocyte can be a lymphocyte in which expression and/or activity of the immune regulatory protein is not modulated. In some embodiments, the control lymphocyte is a lymphocyte lacking a system of the present disclosure. For example, the control lymphocyte may be an unmodified lymphocyte or a lymphocyte transfected and/or transduced with an empty plasmid vector. In some embodiments, the control lymphocyte is a lymphocyte expressing an incomplete system of the present disclosure, e.g., lacking one or more components of a system provided herein. For example, the control lymphocyte may express a system lacking at least one of a chimeric transmembrane receptor polypeptide and a chimeric adaptor polypeptide. In some cases, the control lymphocyte may express both a chimeric transmembrane receptor polypeptide and a chimeric adaptor polypeptide, but the chimeric transmembrane receptor polypeptide may lack at least one of the ligand binding domain, the immune cell signaling domain, the actuator moiety, and the cleavage recognition site. In some cases, the control lymphocyte may express both a chimeric transmembrane receptor polypeptide and a chimeric adaptor polypeptide, but the chimeric adaptor polypeptide may lack at least one of the receptor binding moiety and the cleavage moiety. In some embodiments, the control lymphocyte is a lymphocyte expressing a system of the present disclosure, but at least one of the components of the system is non-functional. For example, the control lymphocyte may express a system provided herein, but at least one of the chimeric transmembrane receptor polypeptide and the chimeric adaptor polypeptide may be non-functional. In some cases, the control lymphocyte may express a system in which the ligand binding domain of the transmembrane receptor is unable to bind a ligand, the immune cell signaling domain of the transmembrane receptor lacks signaling activity, the actuator moiety is unable to modulate expression and/or activity of the regulatory protein, and/or the cleavage recognition site is unable to be cleaved by a cleavage moiety. In some cases, the control lymphocyte may express a system in which the receptor binding moiety of the chimeric adaptor polypeptide is unable to bind the receptor, e.g., in response to binding of the ligand to the ligand binding domain, and/or the cleavage moiety is unable to cleave the cleavage recognition site. In an example, the cleavage moiety of a control lymphocyte may lack cleavage activity. In another example, the cleavage recognition site of a control lymphocyte is unable to be cleaved by the cleavage moiety. In another example, the receptor binding moiety is unable to bind the receptor polypeptide. In another example, an actuator moiety is unable to modulate expression and/or activity of the immune regulatory protein. This may occur if, for example, the actuator moiety comprises a polynucleotide-guided endonuclease but the system lacks a guide polynucleotide. For instance, in a control lymphocyte, the actuator moiety may comprise a Cas protein lacking a guideRNA (gRNA). In some cases, the control lymphocyte may comprise an actuator moiety complexed with a non-targeting gRNA or non-specific gRNA.

In some cases, the enhanced ability to induce death of the target cell is at least a 1.1-fold, 1.2-fold, 1.3-fold, 1.4-fold, 1.5-fold, 1.6-fold, 1.7-fold, 1.8-fold, 1.9-fold, 2.0-fold, 2.5-fold, 3.0-fold, 3.5-fold, 4.0-fold, 5-fold, 10-fold, 100-fold, or 1000-fold increase in induced cell death. The degree of induced cell death can be determined at any suitable time point, for example, at least 4 hours, 6 hours, 8 hours, 12 hours, 16 hours, 24 hours, 36 hours, 48 hours, or 52 hours after contacting the lymphocyte to the target cell.

In some embodiments, the ligand binding domain comprises a single-chain variable fragment (scFv). In some embodiments, the immune cell signaling domain comprises an immunoreceptor tyrosine-based activation motif (ITAM). In some cases, the ITAM is a CD3 ITAM. In some embodiments, the immune cell signaling domain comprises a co-stimulatory domain, for example signaling domains from 4-1BB and/or OX40. In some cases, the receptor binding moiety comprises a LAT protein or a fragment derived therefrom.

In some embodiments, the actuator moiety comprises a polynucleotide-guided endonuclease. In some cases, the polynucleotide-guided endonuclease is an RNA-guided endonuclease, such as Cas9, Cpf1, or C2c2. In some cases, the RNA-guided endonuclease substantially lacks nuclease activity.

In some embodiments, the cleavage moiety comprises a TEV protease. In some embodiments, the cleavage recognition site comprises a TEV cleavage site.

In some embodiments, the immune regulatory protein is programmed cell death protein 1 (PD-1).

In various embodiments of the aspects herein, a plurality of actuator moieties are used simultaneously in the same cell. In some embodiments, an actuator moiety comprising a Cas protein can be used simultaneously with a second actuator moiety comprising a zinc finger nuclease (ZFN), transcription activator-like effector nuclease (TALEN), meganuclease, RNA-binding protein (RBP), CRISPR-associated RNA binding protein, recombinase, flippase, transposase, or Argonaute protein. In some embodiments, an actuator moiety comprising a ZFN can be used simultaneously with a second actuator moiety comprising a Cas protein, transcription activator-like effector nuclease (TALEN), meganuclease, RNA-binding protein (RBP), CRISPR-associated RNA binding protein, recombinase, flippase, transposase, or Argonaute protein. In some embodiments, an actuator moiety comprising a TALEN can be used simultaneously with a second actuator moiety comprising a Cas protein, a zinc finger nuclease (ZFN), meganuclease, RNA-binding protein (RBP), CRISPR-associated RNA binding protein, recombinase, flippase, transposase, or Argonaute protein. In some embodiments, an actuator moiety comprising a meganuclease can be used simultaneously with a second actuator moiety comprising a Cas protein, a zinc finger nuclease (ZFN), transcription activator-like effector nuclease (TALEN), RNA-binding protein (RBP), CRISPR-associated RNA binding protein, recombinase, flippase, transposase, or Argonaute protein. In some embodiments, an actuator moiety comprising a RNA-binding protein (RBP) can be used simultaneously with a second actuator moiety comprising a Cas protein, a zinc finger nuclease (ZFN), transcription activator-like effector nuclease (TALEN), meganuclease, CRISPR-associated RNA binding protein, recombinase, flippase, transposase, or Argonaute protein. In some embodiments, an actuator moiety comprising a CRISPR-associated RNA binding protein can be used simultaneously with a second actuator moiety comprising a Cas protein, a zinc finger nuclease (ZFN), transcription activator-like effector nuclease (TALEN), meganuclease, RNA-binding protein (RBP), recombinase, flippase, transposase, or Argonaute protein. In some embodiments, an actuator moiety comprising a recombinase can be used simultaneously with a second actuator moiety comprising a Cas protein, a zinc finger nuclease (ZFN), transcription activator-like effector nuclease (TALEN), meganuclease, RNA-binding protein (RBP), CRISPR-associated RNA binding protein, flippase, transposase, or Argonaute protein. In some embodiments, an actuator moiety comprising a flippase can be used simultaneously with a second actuator moiety comprising a Cas protein, a zinc finger nuclease (ZFN), transcription activator-like effector nuclease (TALEN), meganuclease, RNA-binding protein (RBP), CRISPR-associated RNA binding protein, recombinase, transposase, or Argonaute protein. In some embodiments, an actuator moiety comprising a transposase can be used simultaneously with a second actuator moiety comprising a Cas protein, a zinc finger nuclease (ZFN), transcription activator-like effector nuclease (TALEN), meganuclease, RNA-binding protein (RBP), CRISPR-associated RNA binding protein, recombinase, flippase, or Argonaute protein. In some embodiments, an actuator moiety comprising a Argonaute protein can be used simultaneously with a second actuator moiety comprising a Cas protein, a zinc finger nuclease (ZFN), transcription activator-like effector nuclease (TALEN), meganuclease, RNA-binding protein (RBP), CRISPR-associated RNA binding protein, recombinase, flippase, or transposase.

In some embodiments, a plurality of actuator moieties is used simultaneously in the same cell to simultaneously modulate transcription at different locations on the same target DNA or on different target DNAs. In some embodiments, the actuator moiety comprises a Cas nuclease. The plurality of CRISPR/Cas complexes can use a single source or type of Cas protein with a plurality of guide nucleic acids to target different nucleic acids. Alternatively, the plurality of CRISPR/Cas complexes can use orthologous Cas proteins (e.g., dead Cas9 proteins from different organisms such as *S. pyogenes*, *S. aureus*, *S. thermophilus*, *L. innocua*, and *N. meningitides*) to target multiple nucleic acids.

In some embodiments, a plurality of actuator moieties are used to regulate the expression and/or activity of at least two target polynucleotides or edit the nucleic acid sequence of at least two target polynucleotides. The at least two target polynucleotides may comprise the same or different gene or gene product. In some embodiments, the expression of at least two cytokines are up-regulated, down-regulated, or a combination thereof. In some embodiments, the expression of at least two immune regulatory proteins are up-regulated, down-regulated, or a combination thereof. In some embodiments, the expression of a cytokine and an immune regulatory protein are altered. For example, expression of both the cytokine and the immune regulatory protein are increased. Expression of both the cytokine and the immune regulatory protein can be decreased. The expression of the cytokine can be increased while the expression of the immune regulatory protein can be decreased, or vice versa.

In some embodiments, the expression of an endogenous gene and an exogenous gene are altered. For example, the expression of an endogenous gene such as a cytokine or immune regulatory protein can be altered in addition to altering expression of an exogenous gene comprising an additional chimeric receptor. Regulating the expression of target polynucleotides discussed herein can be multiplexed in any desired variety of combinations.

In some embodiments, a plurality of guide nucleic acids can be used simultaneously in the same cell to simultaneously modulate transcription at different locations on the same target DNA or on different target DNAs. In some embodiments, two or more guide nucleic acids target the same gene or transcript or locus. In some embodiments, two or more guide nucleic acids target different unrelated loci. In some embodiments, two or more guide nucleic acids target different, but related loci.

The two or more guide nucleic acids can be simultaneously present on the same expression vector. The two or more guide nucleic acids can be under the same transcriptional control. In some embodiments, two or more (e.g., 3 or more, 4 or more, 5 or more, 10 or more, 15 or more, 20 or more, 25 or more, 30 or more, 35 or more, 40 or more, 45 or more, or 50 or more) guide nucleic acids are simultaneously expressed in a target cell (from the same or different vectors). The expressed guide nucleic acids can be differently recognized by dead Cas proteins (e.g., dCas9 proteins from different bacteria, such as *S. pyogenes, S. aureus, S. thermophilus, L. innocua*, and *N. meningitides*).

To express multiple guide nucleic acids, an artificial guide nucleic acid processing system mediated by an endonuclease (e.g., Csy4 endoribonuclease can be used for processing guide RNAs) can be utilized. For example, multiple guide RNAs can be concatenated into a tandem array on a precursor transcript (e.g., expressed from a U6 promoter), and separated by Csy4-specific RNA sequence. Co-expressed Csy4 protein can cleave the precursor transcript into multiple guide RNAs. Since all guide RNAs are processed from a precursor transcript, their concentrations can be normalized for similar dCas9-binding.

Promoters that can be used with the methods and compositions of the disclosure include, for example, promoters active in a eukaryotic, mammalian, non-human mammalian or human cell. The promoter can be an inducible or constitutively active promoter. Alternatively or additionally, the promoter can be tissue or cell specific.

Non-limiting examples of suitable eukaryotic promoters (i.e. promoters functional in a eukaryotic cell) can include those from cytomegalovirus (CMV) immediate early, herpes simplex virus (HSV) thymidine kinase, early and late SV40, long terminal repeats (LTRs) from retrovirus, human elongation factor-1 promoter (EF1), a hybrid construct comprising the cytomegalovirus (CMV) enhancer fused to the chicken beta-active promoter (CAG), murine stem cell virus promoter (MSCV), phosphoglycerate kinase-1 locus promoter (PGK) and mouse metallothionein-I. The promoter can be a fungi promoter. The promoter can be a plant promoter. A database of plant promoters can be found (e.g., PlantProm). The expression vector may also contain a ribosome binding site for translation initiation and a transcription terminator. The expression vector may also include appropriate sequences for amplifying expression.

In some embodiments, a target polynucleotide can comprise one or more disease-associated genes and polynucleotides as well as signaling biochemical pathway-associated genes and polynucleotides. Examples of target polynucleotides include a sequence associated with a signaling biochemical pathway, e.g., a signaling biochemical pathway-associated gene or polynucleotide. Examples of target polynucleotides include a disease associated gene or polynucleotide. A "disease-associated" gene or polynucleotide refers to any gene or polynucleotide which is yielding transcription or translation products at an abnormal level or in an abnormal form in cells derived from a disease-affected tissue compared with tissue(s) or cells of a non-disease control. In some embodiments, it is a gene that becomes expressed at an abnormally high level. In some embodiments, it is a gene that becomes expressed at an abnormally low level. The altered expression can correlate with the occurrence and/or progression of the disease. A disease-associated gene also refers to a gene possessing mutation(s) or genetic variation that is directly responsible or is in linkage disequilibrium with a gene(s) that is response for the etiology of a disease. The transcribed or translated products may be known or unknown, and may be at a normal or abnormal level.

Examples of disease-associated genes and polynucleotides are available from McKusick-Nathans Institute of Genetic Medicine, Johns Hopkins University (Baltimore, Md.) and National Center for Biotechnology Information, National Library of Medicine (Bethesda, Md.), available on the World Wide Web. Exemplary genes associated with certain diseases and disorders are provided in Tables 4 and 5. Examples of signaling biochemical pathway-associated genes and polynucleotides are listed in Table 6.

Mutations in these genes and pathways can result in production of improper proteins or proteins in improper amounts which affect function.

TABLE 4

| DISEASE/DISORDERS | GENE(S) |
|---|---|
| Neoplasia | PTEN; ATM; ATR; EGFR; ERBB2; ERBB3; ERBB4; Notch1; Notch2; Notch3; Notch4; AKT; AKT2; AKT3; HIF; HIF1a; HIF3a; Met; HRG; Bcl2; PPAR alpha; PPAR gamma; WT1 (Wilms Tumor); FGF Receptor Family members (5 members: 1, 2, 3, 4, 5); CDKN2a; APC; RB (retinoblastoma); MEN1; VHL; BRCA1; BRCA2; AR (Androgen Receptor); TSG101; IGF; IGF Receptor; Igf1 (4 variants); Igf2 (3 variants); Igf 1 Receptor; Igf 2 Receptor; Bax; Bcl2; caspases family (9 members: 1, 2, 3, 4, 6, 7, 8, 9, 12); Kras; Apc |
| Age-related Macular Degeneration | Abcr; Ccl2; Cc2; cp (ceruloplasmin); Timp3; cathepsinD; Vldlr; Ccr2 |
| Schizophrenia | Neuregulin1 (Nrg1); Erb4 (receptor for Neuregulin); Complexin1 (Cplx1); Tph1 Tryptophan hydroxylase; Tph2 Tryptophan hydroxylase 2; Neurexin 1; GSK3; GSK3a; GSK3b |

TABLE 4-continued

| DISEASE/DISORDERS | GENE(S) |
|---|---|
| Disorders | 5-HTT (Slc6a4); COMT; DRD (Drd1a); SLC6A3; DAOA; DTNBP1; Dao (Dao1) |
| Trinucleotide Repeat Disorders | HTT (Huntington's Dx); SBMA/SMAX1/AR (Kennedy's Dx); FXN/X25 (Friedrich's Ataxia); ATX3 (Machado-Joseph's Dx); ATXN1 and ATXN2 (spinocerebellar ataxias); DMPK (myotonic dystrophy); Atrophin-1 and Atn1 (DRPLA Dx); CBP (Creb-BP - global instability); VLDLR (Alzheimer's); Atxn7; Atxn10 |
| Fragile X Syndrome | FMR2; FXR1; FXR2; mGLUR5 |
| Secretase Related Disorders | APH-1 (alpha and beta); Presenilin (Psen1); nicastrin (Ncstn); PEN-2 |
| Others | Nos1; Parp1; Nat1; Nat2 |
| Prion - related disorders | Prp |
| ALS | SOD1; ALS2; STEX; FUS; TARDBP; VEGF (VEGF-a; VEGF-b; VEGF-c) |
| Drug addiction | Prkce (alcohol); Drd2; Drd4; ABAT (alcohol); GRIA2; Grm5; Grin1; Htr1b; Grin2a; Drd3; Pdyn; Gria1 (alcohol) |
| Autism | Mecp2; BZRAP1; MDGA2; Sema5A; Neurexin 1; Fragile X (FMR2 (AFF2); FXR1; FXR2; Mglur5) |
| Alzheimer's Disease | E1; CHIP; UCH; UBB; Tau; LRP; PICALM; Clusterin; PS1; SORL1; CR1; Vldlr; Uba1; Uba3; CHIP28 (Aqp1, Aquaporin 1); Uchl1; Uchl3; APP |
| Inflammation | IL-10; IL-1 (IL-1a; IL-1b); IL-13; IL-17 (IL-17a (CTLA8); IL-17b; IL-17c; IL-17d; IL-17f); II-23; Cx3cr1; ptpn22; TNFa; NOD2/CARD15 for IBD; IL-6; IL-12 (IL-12a; IL-12b); CTLA4; Cx3cl1 |
| Parkinson's Disease | x-Synuclein; DJ-1; LRRK2; Parkin; PINK1 |

TABLE 5

| | |
|---|---|
| Blood and coagulation diseases and disorders | Anemia (CDAN1, CDA1, RPS19, DBA, PKLR, PK1, NT5C3, UMPH1, PSN1, RHAG, RH50A, NRAMP2, SPTB, ALAS2, ANH1, ASB, ABCB7, ABC7, ASAT); Bare lymphocyte syndrome (TAPBP, TPSN, TAP2, ABCB3, PSF2, RING11, MHC2TA, C2TA, RFX5, RFXAP, RFX5), Bleeding disorders (TBXA2R, P2RX1, P2X1); Factor H and factor H-like 1 (HF1, CFH, HUS); Factor V and factor VIII (MCFD2); Factor VII deficiency (F7); Factor X deficiency (F10); Factor XI deficiency (F11); Factor XII deficiency (F12, HAF); Factor XIIIA deficiency (F13A1, F13A); Factor XIIIB deficiency (F13B); Fanconi anemia (FANCA, FACA, FA1, FA, FAA, FAAP95, FAAP90, FLJ34064, FANCB, FANCC, FACC, BRCA2, FANCD1, FANCD2, FANCD, FACD, FAD, FANCE, FACE, FANCF, XRCC9, FANCG, BRIP1, BACH1, FANCJ, PHF9, FANCL, FANCM, KIAA1596); Hemophagocytic lymphohistiocytosis disorders (PRF1, HPLH2, UNC13D, MUNC13-4, HPLH3, HLH3, FHL3); Hemophilia A (F8, F8C, HEMA); Hemophilia B (F9, HEMB), Hemorrhagic disorders (PI, ATT, F5); Leukocyde deficiencies and disorders (ITGB2, CD18, LCAMB, LAD, EIF2B1, EIF2BA, EIF2B2, EIF2B3, EIF2B5, LVWM, CACH, CLE, EIF2B4); Sickle cell anemia (HBB); Thalassemia (HBA2, HBB, HBD, LCRB, HBA1). |
| Cell dysregulation and oncology diseases and disorders | B-cell non-Hodgkin lymphoma (BCL7A, BCL7); Leukemia (TAL1 TCL5, SCL, TAL2, FLT3, NBS1, NBS, ZNFN1A1, IK1, LYF1, HOXD4, HOX4B, BCR, CML, PHL, ALL, ARNT, KRAS2, RASK2, GMPS, AF10, ARHGEF12, LARG, KIAA0382, CALM, CLTH, CEBPA, CEBP, CHIC2, BTL, FLT3, KIT, PBT, LPP, NPM1, NUP214, D9S46E, CAN, CAIN, RUNX1, CBFA2, AML1, WHSC1L1, NSD3, FLT3, AF1Q, NPM1, NUMA1, ZNF145, PLZF, PML, MYL, STAT5B, AF10, CALM, CLTH, ARL11, ARLTS1, P2RX7, P2X7, BCR, CML, PHL, ALL, GRAF, NF1, VRNF, WSS, NFNS, PTPN11, PTP2C, SHP2, NS1, BCL2, CCND1, PRAD1, BCL1, TCRA, GATA1, GF1, ERYF1, NFE1, ABL1, NQO1, DIA4, NMOR1, NUP214, D9S46E, CAN, CAIN). |
| Inflammation and immune related diseases and disorders | AIDS (KIR3DL1, NKAT3, NKB1, AMB11, KIR3DS1, IFNG, CXCL12, SDF1); Autoimmune lymphoproliferative syndrome (TNFRSF6, APT1, FAS, CD95, ALPS1A); Combined immunodeficiency, (IL2RG, SCIDX1, SCIDX, IMD4); HIV-1 (CCL5, SCYA5, D17S136E, TCP228), HIV susceptibility or infection (IL10, CSIF, CMKBR2, CCR2, CMKBR5, CCCKR5 (CCR5)); Immunodeficiencies (CD3E, CD3G, AICDA, AID, HIGM2, TNFRSF5, CD40, UNG, DGU, HIGM4, TNFSF5, CD40LG, HIGM1, IGM, FOXP3, IPEX, AIID, XPID, PIDX, TNFRSF14B, TACI); Inflammation (IL-10, IL-1 (IL-1a, IL-1b), IL-13, IL-17 (IL-17a (CTLA8), IL-17b, IL-17c, IL-17d, IL-17f), II-23, Cx3cr1, ptpn22, TNFa, NOD2/CARD15 for IBD, IL-6, IL-12 (IL-12a, IL-12b), CTLA4, Cx3cl1); Severe combined immunodeficiencies (SCIDs)(JAK3, JAKL, DCLRE1C, ARTEMIS, SCIDA, RAG1, RAG2, ADA, PTPRC, CD45, LCA, IL7R, CD3D, T3D, IL2RG, SCIDX1, SCIDX, IMD4). |

TABLE 5-continued

| | |
|---|---|
| Metabolic, liver, kidney and protein diseases and disorders | Amyloid neuropathy (TTR, PALB); Amyloidosis (APOA1, APP, AAA, CVAP, AD1, GSN, FGA, LYZ, TTR, PALB); Cirrhosis (KRT18, KRT8, CIRH1A, NAIC, TEX292, KIAA1988); Cystic fibrosis (CFTR, ABCC7, CF, MRP7); Glycogen storage diseases (SLC2A2, GLUT2, G6PC, G6PT, G6PT1, GAA, LAMP2, LAMPB, AGL, GDE, GBE1, GYS2, PYGL, PFKM); Hepatic adenoma, 142330 (TCF1, HNF1A, MODY3), Hepatic failure, early onset, and neurologic disorder (SCOD1, SCO1), Hepatic lipase deficiency (LIPC), Hepatoblastoma, cancer and carcinomas (CTNNB1, PDGFRL, PDGRL, PRLTS, AXIN1, AXIN, CTNNB1, TP53, P53, LFS1, IGF2R, MPRI, MET, CASP8, MCH5; Medullary cystic kidney disease (UMOD, HNFJ, FJHN, MCKD2, ADMCKD2); Phenylketonuria (PAH, PKU1, QDPR, DHPR, PTS); Polycystic kidney and hepatic disease (FCYT, PKHD1, ARPKD, PKD1, PKD2, PKD4, PKDTS, PRKCSH, G19P1, PCLD, SEC63). |
| Muscular/Skeletal diseases and disorders | Becker muscular dystrophy (DMD, BMD, MYF6), Duchenne Muscular Dystrophy (DMD, BMD); Emery-Dreifuss muscular dystrophy (LMNA, LMN1, EMD2, FPLD, CMD1A, HGPS, LGMD1B, LMNA, LMN1, EMD2, FPLD, CMD1A); Facioscapulohumeral muscular dystrophy (FSHMD1A, FSHD1A); Muscular dystrophy (FKRP, MDC1C, LGMD2I, LAMA2, LAMM, LARGE, KIAA0609, MDC1D, FCMD, TTID, MYOT, CAPN3, CANP3, DYSF, LGMD2B, SGCG, LGMD2C, DMDA1, SCG3, SGCA, ADL, DAG2, LGMD2D, DMDA2, SGCB, LGMD2E, SGCD, SGD, LGMD2F, CMD1L, TCAP, LGMD2G, CMD1N, TRIM32, HT2A, LGMD2H, FKRP, MDC1C, LGMD2I, TTN, CMD1G, TMD, LGMD2J, POMT1, CAV3, LGMD1C, SEPN1, SELN, RSMD1, PLEC1, PLTN, EBS1); Osteopetrosis (LRP5, BMND1, LRP7, LR3, OPPG, VBCH2, CLCN7, CLC7, OPTA2, OSTM1, GL, TCIRG1, TIRC7, OC116, OPTB1); Muscular atrophy (VAPB, VAPC, ALS8, SMN1, SMA1, SMA2, SMA3, SMA4, BSCL2, SPG17, GARS, SMAD1, CMT2D, HEXB, IGHMBP2, SMUBP2, CATF1, SMARD1). |
| Neurological and neuronal diseases and disorders | ALS (SOD1, ALS2, STEX, FUS, TARDBP, VEGF (VEGF-a, VEGF-b, VEGF-c); Alzheimer disease (APP, AAA, CVAP, AD1, APOE, AD2, PSEN2, AD4, STM2, APBB2, FE65L1, NOS3, PLAU, URK, ACE, DCP1, ACE1, MPO, PACIP1, PAXIP1L, PTIP, A2M, BLMH, BMH, PSEN1, AD3); Autism (Mecp2, BZRAP1, MDGA2, Sema5A, Neurexin 1, GLO1, MECP2, RTT, PPMX, MRX16, MRX79, NLGN3, NLGN4, KIAA1260, AUTSX2); Fragile X Syndrome (FMR2, FXR1, FXR2, mGLUR5); Huntington's disease and disease like disorders (HD, IT15, PRNP, PRIP, JPH3, JP3, HDL2, TBP, SCA17); Parkinson disease (NR4A2, NURR1, NOT, TINUR, SNCAIP, TBP, SCA17, SNCA, NACP, PARK1, PARK4, DJ1, PARK7, LRRK2, PARK8, PINK1, PARK6, UCHL1, PARK5, SNCA, NACP, PARK1, PARK4, PRKN, PARK2, PDJ, DBH, NDUFV2); Rett syndrome (MECP2, RTT, PPMX, MRX16, MRX79, CDKL5, STK9, MECP2, RTT, PPMX, MRX16, MRX79, x-Synuclein, DJ-1); Schizophrenia (Neuregulin1 (Nrg1), Erb4 (receptor for Neuregulin), Complexin1 (Cplx1), Tph1 Tryptophan hydroxylase, Tph2, Tryptophan hydroxylase 2, Neurexin 1, GSK3, GSK3a, GSK3b, 5-HTT (Slc6a4), COMT, DRD (Drd1a), SLC6A3, DAOA, DTNBP1, Dao (Dao1)); Secretase Related Disorders (APH-1 (alpha and beta), Presenilin (Psen1), nicastrin, (Ncstn), PEN-2, Nos1, Parp1, Nat1, Nat2); Trinucleotide Repeat Disorders (HTT (Huntington's Dx), SBMA/SMAX1/AR (Kennedy's Dx), FXN/X25 (Friedrich's Ataxia), ATX3 (Machado-Joseph's Dx), ATXN1 and ATXN2 (spinocerebellar ataxias), DMPK (myotonic dystrophy), Atrophin-1 and Atn1 (DRPLA Dx), CBP (Creb-BP - global instability), VLDLR (Alzheimer's), Atxn7, Atxn10). |
| Ocular diseases and disorders | Age-related macular degeneration (Abcr, Ccl2, Cc2, cp (ceruloplasmin), Timp3, cathepsinD, Vldlr, Ccr2); Cataract (CRYAA, CRYA1, CRYBB2, CRYB2, PITX3, BFSP2, CP49, CP47, CRYAA, CRYA1, PAX6, AN2, MGDA, CRYBA1, CRYB1, CRYGC, CRYG3, CCL, LIM2, MP19, CRYGD, CRYG4, BFSP2, CP49, CP47, HSF4, CTM, HSF4, CTM, MIP, AQP0, CRYAB, CRYA2, CTPP2, CRYBB1, CRYGD, CRYG4, CRYBB2, CRYB2, CRYGC, CRYG3, CCL, CRYAA, CRYA1, GJA8, CX50, CAE1, GJA3, CX46, CZP3, CAE3, CCM1, CAM, KRIT1); Corneal clouding and dystrophy (APOA1, TGFBI, CSD2, CDGG1, CSD, BIGH3, CDG2, TACSTD2, TROP2, M1S1, VSX1, RINX, PPCD, PPD, KTCN, COL8A2, FECD, PPCD2, PIP5K3, CFD); Cornea plana congenital (KERA, CNA2); Glaucoma (MYOC, TIGR, GLC1A, JOAG, GPOA, OPTN, GLC1E, FIP2, HYPL, NRP, CYP1B1, GLC3A, OPA1, NTG, NPG, CYP1B1, GLC3A); Leber congenital amaurosis (CRB1, RP12, CRX, CORD2, CRD, RPGRIP1, LCA6, CORD9, RPE65, RP20, AIPL1, LCA4, GUCY2D, GUC2D, LCA1, CORD6, RDH12, LCA3); Macular dystrophy (ELOVL4, ADMD, STGD2, STGD3, RDS, RP7, PRPH2, PRPH, AVMD, AOFMD, VMD2). |

TABLE 6

| CELLULAR FUNCTION | GENES |
| --- | --- |
| PI3K/AKT Signaling | PRKCE; ITGAM; ITGA5; IRAK1; PRKAA2; EIF2AK2; PTEN; EIF4E; PRKCZ; GRK6; MAPK1; TSC1; PLK1; AKT2; IKBKB; PIK3CA; CDK8; CDKN1B; NFKB2; BCL2; PIK3CB; PPP2R1A; MAPK8; BCL2L1; MAPK3; TSC2; ITGA1; KRAS; EIF4EBP1; RELA; PRKCD; NOS3; PRKAA1; MAPK9; CDK2; PPP2CA; PIM1; ITGB7; YWHAZ; ILK; TP53; RAF1; IKBKG; RELB; DYRK1A; CDKN1A; ITGB1; MAP2K2; JAK1; AKT1; JAK2; PIK3R1; CHUK; PDPK1; PPP2R5C; CTNNB1; MAP2K1; NFKB1; PAK3; ITGB3; CCND1; GSK3A; FRAP1; SFN; ITGA2; TTK; CSNK1A1; BRAF; GSK3B; AKT3; FOXO1; SGK; HSP90AA1; RPS6KB1 |
| ERK/MAPK Signaling | PRKCE; ITGAM; ITGA5; HSPB1; IRAK1; PRKAA2; EIF2AK2; RAC1; RAP1A; TLN1; EIF4E; ELK1; GRK6; MAPK1; RAC2; PLK1; AKT2; PIK3CA; CDK8; CREB1; PRKCI; PTK2; FOS; RPS6KA4; PIK3CB; PPP2R1A; PIK3C3; MAPK8; MAPK3; ITGA1; ETS1; KRAS; MYCN; EIF4EBP1; PPARG; PRKCD; PRKAA1; MAPK9; SRC; CDK2; PPP2CA; PIM1; PIK3C2A; ITGB7; YWHAZ; PPP1CC; KSR1; PXN; RAF1; FYN; DYRK1A; ITGB1; MAP2K2; PAK4; PIK3R1; STAT3; PPP2R5C; MAP2K1; PAK3; ITGB3; ESR1; ITGA2; MYC; TTK; CSNK1A1; CRKL; BRAF; ATF4; PRKCA; SRF; STAT1; SGK |
| Glucocorticoid Receptor Signaling | RAC1; TAF4B; EP300; SMAD2; TRAF6; PCAF; ELK1; MAPK1; SMAD3; AKT2; IKBKB; NCOR2; UBE2I; PIK3CA; CREB1; FOS; HSPA5; NFKB2; BCL2; MAP3K14; STAT5B; PIK3CB; PIK3C3; MAPK8; BCL2L1; MAPK3; TSC22D3; MAPK10; NRIP1; KRAS; MAPK13; RELA; STAT5A; MAPK9; NOS2A; PBX1; NR3C1; PIK3C2A; CDKN1C; TRAF2; SERPINE1; NCOA3; MAPK14; TNF; RAF1; IKBKG; MAP3K7; CREBBP; CDKN1A; MAP2K2; JAK1; IL8; NCOA2; AKT1; JAK2; PIK3R1; CHUK; STAT3; MAP2K1; NFKB1; TGFBR1; ESR1; SMAD4; CEBPB; JUN; AR; AKT3; CCL2; MMP1; STAT1; IL6; HSP90AA1 |
| Axonal Guidance Signaling | PRKCE; ITGAM; ROCK1; ITGA5; CXCR4; ADAM12; IGF1; RAC1; RAP1A; E1F4E; PRKCZ; NRP1; NTRK2; ARHGEF7; SMO; ROCK2; MAPK1; PGF; RAC2; PTPN11; GNAS; AKT2; PIK3CA; ERBB2; PRKCI; PTK2; CFL1; GNAQ; PIK3CB; CXCL12; PIK3C3; WNT11; PRKD1; GNB2L1; ABL1; MAPK3; ITGA1; KRAS; RHOA; PRKCD; PIK3C2A; ITGB7; GLI2; PXN; VASP; RAF1; FYN; ITGB1; MAP2K2; PAK4; ADAM17; AKT1; PIK3R1; GLI1; WNT5A; ADAM10; MAP2K1; PAK3; ITGB3; CDC42; VEGFA; ITGA2; EPHA8; CRKL; RND1; GSK3B; AKT3; PRKCA |
| Ephrin Receptor Signaling | PRKCE; ITGAM; ROCK1; ITGA5; CXCR4; IRAK1; PRKAA2; EIF2AK2; RAC1; RAP1A; GRK6; ROCK2; MAPK1; PGF; RAC2; PTPN11; GNAS; PLK1; AKT2; DOK1; CDK8; CREB1; PTK2; CFL1; GNAQ; MAP3K14; CXCL12; MAPK8; GNB2L1; ABL1; MAPK3; ITGA1; KRAS; RHOA; PRKCD; PRKAA1; MAPK9; SRC; CDK2; PIM1; ITGB7; PXN; RAF1; FYN; DYRK1A; ITGB1; MAP2K2; PAK4; AKT1; JAK2; STAT3; ADAM10; MAP2K1; PAK3; ITGB3; CDC42; VEGFA; ITGA2; EPHA8; TTK; CSNK1A1; CRKL; BRAF; PTPN13; ATF4; AKT3; SGK |
| Actin Cytoskeleton Signaling | ACTN4; PRKCE; ITGAM; ROCK1; ITGA5; IRAK1; PRKAA2; EIF2AK2; RAC1; INS; ARHGEF7; GRK6; ROCK2; MAPK1; RAC2; PLK1; AKT2; PIK3CA; CDK8; PTK2; CFL1; PIK3CB; MYH9; DIAPH1; PIK3C3; MAPK8; F2R; MAPK3; SLC9A1; ITGA1; KRAS; RHOA; PRKCD; PRKAA1; MAPK9; CDK2; PIM1; PIK3C2A; ITGB7; PPP1CC; PXN; VIL2; RAF1; GSN; DYRK1A; ITGB1; MAP2K2; PAK4; PIP5K1A; PIK3R1; MAP2K1; PAK3; ITGB3; CDC42; APC; ITGA2; TTK; CSNK1A1; CRKL; BRAF; VAV3; SGK |
| Huntington's Disease Signaling | PRKCE; IGF1; EP300; RCOR1; PRKCZ; HDAC4; TGM2; MAPK1; CAPNS1; AKT2; EGFR; NCOR2; SP1; CAPN2; PIK3CA; HDAC5; CREB1; PRKC1; HSPA5; REST; GNAQ; PIK3CB; PIK3C3; MAPK8; IGF1R; PRKD1; GNB2L1; BCL2L1; CAPN1; MAPK3; CASP8; HDAC2; HDAC7A; PRKCD; HDAC11; MAPK9; HDAC9; PIK3C2A; HDAC3; TP53; CASP9; CREBBP; AKT1; PIK3R1; PDPK1; CASP1; APAF1; FRAP1; CASP2; JUN; BAX; ATF4; AKT3; PRKCA; CLTC; SGK; HDAC6; CASP3 |

TABLE 6-continued

| CELLULAR FUNCTION | GENES |
|---|---|
| Apoptosis Signaling | PRKCE; ROCK1; BID; IRAK1; PRKAA2; EIF2AK2; BAK1; BIRC4; GRK6; MAPK1; CAPNS1; PLK1; AKT2; IKBKB; CAPN2; CDK8; FAS; NFKB2; BCL2; MAP3K14; MAPK8; BCL2L1; CAPN1; MAPK3; CASP8; KRAS; RELA; PRKCD; PRKAA1; MAPK9; CDK2; PIM1; TP53; TNF; RAF1; IKBKG; RELB; CASP9; DYRK1A; MAP2K2; CHUK; APAF1; MAP2K1; NFKB1; PAK3; LMNA; CASP2; BIRC2; TTK; CSNK1A1; BRAF; BAX; PRKCA; SGK; CASP3; BIRC3; PARP1 |
| B Cell Receptor Signaling | RAC1; PTEN; LYN; ELK1; MAPK1; RAC2; PTPN11; AKT2; IKBKB; PIK3CA; CREB1; SYK; NFKB2; CAMK2A; MAP3K14; PIK3CB; PIK3C3; MAPK8; BCL2L1; ABL1; MAPK3; ETS1; KRAS; MAPK13; RELA; PTPN6; MAPK9; EGR1; PIK3C2A; BTK; MAPK14; RAF1; IKBKG; RELB; MAP3K7; MAP2K2; AKT1; PIK3R1; CHUK; MAP2K1; NFKB1; CDC42; GSK3A; FRAP1; BCL6; BCL10; JUN; GSK3B; ATF4; AKT3; VAV3; RPS6KB1 |
| Leukocyte Extravasation Signaling | ACTN4; CD44; PRKCE; ITGAM; ROCK1; CXCR4; CYBA; RAC1; RAP1A; PRKCZ; ROCK2; RAC2; PTPN11; MMP14; PIK3CA; PRKCI; PTK2; PIK3CB; CXCL12; PIK3C3; MAPK8; PRKD1; ABL1; MAPK10; CYBB; MAPK13; RHOA; PRKCD; MAPK9; SRC; PIK3C2A; BTK; MAPK14; NOX1; PXN; VIL2; VASP; ITGB1; MAP2K2; CTNND1; PIK3R1; CTNNB1; CLDN1; CDC42; F11R; ITK; CRKL; VAV3; CTTN; PRKCA; MMP1; MMP9 |
| Integrin Signaling | ACTN4; ITGAM; ROCK1; ITGA5; RAC1; PTEN; RAP1A; TLN1; ARHGEF7; MAPK1; RAC2; CAPNS1; AKT2; CAPN2; PIK3CA; PTK2; PIK3CB; PIK3C3; MAPK8; CAV1; CAPN1; ABL1; MAPK3; ITGA1; KRAS; RHOA; SRC; PIK3C2A; ITGB7; PPP1CC; ILK; PXN; VASP; RAF1; FYN; ITGB1; MAP2K2; PAK4; AKT1; PIK3R1; TNK2; MAP2K1; PAK3; ITGB3; CDC42; RND3; ITGA2; CRKL; BRAF; GSK3B; AKT3 |
| Acute Phase Response Signaling | IRAK1; SOD2; MYD88; TRAF6; ELK1; MAPK1; PTPN11; AKT2; IKBKB; PIK3CA; FOS; NFKB2; MAP3K14; PIK3CB; MAPK8; RIPK1; MAPK3; IL6ST; KRAS; MAPK13; IL6R; RELA; SOCS1; MAPK9; FTL; NR3C1; TRAF2; SERPINE1; MAPK14; TNF; RAF1; PDK1; IKBKG; RELB; MAP3K7; MAP2K2; AKT1; JAK2; PIK3R1; CHUK; STAT3; MAP2K1; NFKB1; FRAP1; CEBPB; JUN; AKT3; IL1R1; IL6 |
| PTEN Signaling | ITGAM; ITGA5; RAC1; PTEN; PRKCZ; BCL2L11; MAPK1; RAC2; AKT2; EGFR; IKBKB; CBL; PIK3CA; CDKN1B; PTK2; NFKB2; BCL2; PIK3CB; BCL2L1; MAPK3; ITGA1; KRAS; ITGB7; ILK; PDGFRB; INSR; RAF1; IKBKG; CASP9; CDKN1A; ITGB1; MAP2K2; AKT1; PIK3R1; CHUK; PDGFRA; PDPK1; MAP2K1; NFKB1; ITGB3; CDC42; CCND1; GSK3A; ITGA2; GSK3B; AKT3; FOXO1; CASP3; RPS6KB1 |
| p53 Signaling | PTEN; EP300; BBC3; PCAF; FASN; BRCA1; GADD45A; BIRC5; AKT2; PIK3CA; CHEK1; TP53INP1; BCL2; PIK3CB; PIK3C3; MAPK8; THBS1; ATR; BCL2L1; E2F1; PMAIP1; CHEK2; TNFRSF10B; TP73; RB1; HDAC9; CDK2; PIK3C2A; MAPK14; TP53; LRDD; CDKN1A; HIPK2; AKT1; PIK3R1; RRM2B; APAF1; CTNNB1; SIRT1; CCND1; PRKDC; ATM; SFN; CDKN2A; JUN; SNAI2; GSK3B; BAX; AKT3 |
| Aryl Hydrocarbon Receptor Signaling | HSPB1; EP300; FASN; TGM2; RXRA; MAPK1; NQO1; NCOR2; SP1; ARNT; CDKN1B; FOS; CHEK1; SMARCA4; NFKB2; MAPK8; ALDH1A1; ATR; E2F1; MAPK3; NRIP1; CHEK2; RELA; TP73; GSTP1; RB1; SRC; CDK2; AHR; NFE2L2; NCOA3; TP53; TNF; CDKN1A; NCOA2; APAF1; NFKB1; CCND1; ATM; ESR1; CDKN2A; MYC; JUN; ESR2; BAX; IL6; CYP1B1; HSP90AA1 |
| Xenobiotic Metabolism Signaling | PRKCE; EP300; PRKCZ; RXRA; MAPK1; NQO1; NCOR2; PIK3CA; ARNT; PRKCI; NFKB2; CAMK2A; PIK3CB; PPP2R1A; PIK3C3; MAPK8; PRKD1; ALDH1A1; MAPK3; NRIP1; KRAS; MAPK13; PRKCD; GSTP1; MAPK9; NOS2A; ABCB1; AHR; PPP2CA; FTL; NFE2L2; PIK3C2A; PPARGC1A; MAPK14; TNF; RAF1; CREBBP; MAP2K2; PIK3R1; PPP2R5C; MAP2K1; NFKB1; KEAP1; PRKCA; EIF2AK3; IL6; CYP1B1; HSP90AA1 |

TABLE 6-continued

| CELLULAR FUNCTION | GENES |
|---|---|
| SAPK/JNK Signaling | PRKCE; IRAK1; PRKAA2; EIF2AK2; RAC1; ELK1; GRK6; MAPK1; GADD45A; RAC2; PLK1; AKT2; PIK3CA; FADD; CDK8; PIK3CB; PIK3C3; MAPK8; RIPK1; GNB2L1; IRS1; MAPK3; MAPK10; DAXX; KRAS; PRKCD; PRKAA1; MAPK9; CDK2; PIM1; PIK3C2A; TRAF2; TP53; LCK; MAP3K7; DYRK1A; MAP2K2; PIK3R1; MAP2K1; PAK3; CDC42; JUN; TTK; CSNK1A1; CRKL; BRAF; SGK |
| PPAr/RXR Signaling | PRKAA2; EP300; INS; SMAD2; TRAF6; PPARA; FASN; RXRA; MAPK1; SMAD3; GNAS; IKBKB; NCOR2; ABCA1; GNAQ; NFKB2; MAP3K14; STAT5B; MAPK8; IRS1; MAPK3; KRAS; RELA; PRKAA1; PPARGC1A; NCOA3; MAPK14; INSR; RAF1; IKBKG; RELB; MAP3K7; CREBBP; MAP2K2; JAK2; CHUK; MAP2K1; NFKB1; TGFBR1; SMAD4; JUN; IL1R1; PRKCA; IL6; HSP90AA1; ADIPOQ |
| NF-KB Signaling | IRAK1; EIF2AK2; EP300; INS; MYD88; PRKCZ; TRAF6; TBK1; AKT2; EGFR; IKBKB; PIK3CA; BTRC; NFKB2; MAP3K14; PIK3CB; PIK3C3; MAPK8; RIPK1; HDAC2; KRAS; RELA; PIK3C2A; TRAF2; TLR4; PDGFRB; TNF; INSR; LCK; IKBKG; RELB; MAP3K7; CREBBP; AKT1; PIK3R1; CHUK; PDGFRA; NFKB1; TLR2; BCL10; GSK3B; AKT3; TNFAIP3; IL1R1 |
| Neuregulin Signaling | ERBB4; PRKCE; ITGAM; ITGA5; PTEN; PRKCZ; ELK1; MAPK1; PTPN11; AKT2; EGFR; ERBB2; PRKCI; CDKN1B; STAT5B; PRKD1; MAPK3; ITGA1; KRAS; PRKCD; STAT5A; SRC; ITGB7; RAF1; ITGB1; MAP2K2; ADAM17; AKT1; PIK3R1; PDPK1; MAP2K1; ITGB3; EREG; FRAP1; PSEN1; ITGA2; MYC; NRG1; CRKL; AKT3; PRKCA; HSP90AA1; RPS6KB1 |
| Wnt & Beta catenin Signaling | CD44; EP300; LRP6; DVL3; CSNK1E; GJA1; SMO; AKT2; PIN1; CDH1; BTRC; GNAQ; MARK2; PPP2R1A; WNT11; SRC; DKK1; PPP2CA; SOX6; SFRP2; ILK; LEF1; SOX9; TP53; MAP3K7; CREBBP; TCF7L2; AKT1; PPP2R5C; WNT5A; LRP5; CTNNB1; TGFBR1; CCND1; GSK3A; DVL1; APC; CDKN2A; MYC; CSNK1A1; GSK3B; AKT3; SOX2 |
| Insulin Receptor | PTEN; INS; EIF4E; PTPN1; PRKCZ; MAPK1; TSC1; PTPN11; AKT2; CBL; PIK3CA; PRKCI; PIK3CB; PIK3C3; MAPK8; IRS1; MAPK3; TSC2; KRAS; EIF4EBP1; SLC2A4; PIK3C2A; PPP1CC; INSR; RAF1; FYN; MAP2K2; JAK1; AKT1; JAK2; PIK3R1; PDPK1; MAP2K1; GSK3A; FRAP1; CRKL; GSK3B; AKT3; FOXO1; SGK; RPS6KB1 |
| IL-6 Signaling | HSPB1; TRAF6; MAPKAPK2; ELK1; MAPK1; PTPN11; IKBKB; FOS; NFKB2; MAP3K14; MAPK8; MAPK3; MAPK10; IL6ST; KRAS; MAPK13; IL6R; RELA; SOCS1; MAPK9; ABCB1; TRAF2; MAPK14; TNF; RAF1; IKBKG; RELB; MAP3K7; MAP2K2; IL8; JAK2; CHUK; STAT3; MAP2K1; NFKB1; CEBPB; JUN; IL1R1; SRF; IL6 |
| Hepatic Cholestasis | PRKCE; IRAK1; INS; MYD88; PRKCZ; TRAF6; PPARA; RXRA; IKBKB; PRKCI; NFKB2; MAP3K14; MAPK8; PRKD1; MAPK10; RELA; PRKCD; MAPK9; ABCB1; TRAF2; TLR4; TNF; INSR; IKBKG; RELB; MAP3K7; IL8; CHUK; NR1H2; TJP2; NFKB1; ESR1; SREBF1; FGFR4; JUN; IL1R1; PRKCA; IL6 |
| IGF-1 Signaling | IGF1; PRKCZ; ELK1; MAPK1; PTPN11; NEDD4; AKT2; PIK3CA; PRKCI; PTK2; FOS; PIK3CB; PIK3C3; MAPK8; IGF1R; IRS1; MAPK3; IGFBP7; KRAS; PIK3C2A; YWHAZ; PXN; RAF1; CASP9; MAP2K2; AKT1; PIK3R1; PDPK1; MAP2K1; IGFBP2; SFN; JUN; CYR61; AKT3; FOXO1; SRF; CTGF; RPS6KB1 |
| NRF2-Mediated Oxidative Stress Response | PRKCE; EP300; SOD2; PRKCZ; MAPK1; SQSTM1; NQO1; PIK3CA; PRKCI; FOS; PIK3CB; PIK3C3; MAPK8; PRKD1; MAPK3; KRAS; PRKCD; GSTP1; MAPK9; FTL; NFE2L2; PIK3C2A; MAPK14; RAF1; MAP3K7; CREBBP; MAP2K2; AKT1; PIK3R1; MAP2K1; PPIB; JUN; KEAP1; GSK3B; ATF4; PRKCA; EIF2AK3; HSP90AA1 |
| Hepatic Fibrosis/Hepatic Stellate Cell Activation | EDN1; IGF1; KDR; FLT1; SMAD2; FGFR1; MET; PGF; SMAD3; EGFR; FAS; CSF1; NFKB2; BCL2; MYH9; IGF1R; IL6R; RELA; TLR4; PDGFRB; TNF; RELB; IL8; PDGFRA; NFKB1; TGFBR1; SMAD4; VEGFA; BAX; IL1R1; CCL2; HGF; MMP1; STAT1; IL6; CTGF; MMP9 |

TABLE 6-continued

| CELLULAR FUNCTION | GENES |
|---|---|
| PPAR Signaling | EP300; INS; TRAF6; PPARA; RXRA; MAPK1; IKBKB; NCOR2; FOS; NFKB2; MAP3K14; STAT5B; MAPK3; NRIP1; KRAS; PPARG; RELA; STAT5A; TRAF2; PPARGC1A; PDGFRB; TNF; INSR; RAF1; IKBKG; RELB; MAP3K7; CREBBP; MAP2K2; CHUK; PDGFRA; MAP2K1; NFKB1; JUN; IL1R1; HSP90AA1 |
| Fc Epsilon RI Signaling | PRKCE; RAC1; PRKCZ; LYN; MAPK1; RAC2; PTPN11; AKT2; PIK3CA; SYK; PRKCI; PIK3CB; PIK3C3; MAPK8; PRKD1; MAPK3; MAPK10; KRAS; MAPK13; PRKCD; MAPK9; PIK3C2A; BTK; MAPK14; TNF; RAF1; FYN; MAP2K2; AKT1; PIK3R1; PDPK1; MAP2K1; AKT3; VAV3; PRKCA |
| G-Protein Coupled Receptor Signaling | PRKCE; RAP1A; RGS16; MAPK1; GNAS; AKT2; IKBKB; PIK3CA; CREB1; GNAQ; NFKB2; CAMK2A; PIK3CB; PIK3C3; MAPK3; KRAS; RELA; SRC; PIK3C2A; RAF1; IKBKG; RELB; FYN; MAP2K2; AKT1; PIK3R1; CHUK; PDPK1; STAT3; MAP2K1; NFKB1; BRAF; ATF4; AKT3; PRKCA |
| Inositol Phosphate Metabolism | PRKCE; IRAK1; PRKAA2; EIF2AK2; PTEN; GRK6; MAPK1; PLK1; AKT2; PIK3CA; CDK8; PIK3CB; PIK3C3; MAPK8; MAPK3; PRKCD; PRKAA1; MAPK9; CDK2; PIM1; PIK3C2A; DYRK1A; MAP2K2; PIP5K1A; PIK3R1; MAP2K1; PAK3; ATM; TTK; CSNK1A1; BRAF; SGK |
| PDGF Signaling | EIF2AK2; ELK1; ABL2; MAPK1; PIK3CA; FOS; PIK3CB; PIK3C3; MAPK8; CAV1; ABL1; MAPK3; KRAS; SRC; PIK3C2A; PDGFRB; RAF1; MAP2K2; JAK1; JAK2; PIK3R1; PDGFRA; STAT3; SPHK1; MAP2K1; MYC; JUN; CRKL; PRKCA; SRF; STAT1; SPHK2 |
| VEGF Signaling | ACTN4; ROCK1; KDR; FLT1; ROCK2; MAPK1; PGF; AKT2; PIK3CA; ARNT; PTK2; BCL2; PIK3CB; PIK3C3; BCL2L1; MAPK3; KRAS; HIF1A; NOS3; PIK3C2A; PXN; RAF1; MAP2K2; ELAVL1; AKT1; PIK3R1; MAP2K1; SFN; VEGFA; AKT3; FOXO1; PRKCA |
| Natural Killer Cell Signaling | PRKCE; RAC1; PRKCZ; MAPK1; RAC2; PTPN11; KIR2DL3; AKT2; PIK3CA; SYK; PRKCI; PIK3CB; PIK3C3; PRKD1; MAPK3; KRAS; PRKCD; PTPN6; PIK3C2A; LCK; RAF1; FYN; MAP2K2; PAK4; AKT1; PIK3R1; MAP2K1; PAK3; AKT3; VAV3; PRKCA |
| Cell Cycle: G1/S Checkpoint Regulation | HDAC4; SMAD3; SUV39H1; HDAC5; CDKN1B; BTRC; ATR; ABL1; E2F1; HDAC2; HDAC7A; RB1; HDAC11; HDAC9; CDK2; E2F2; HDAC3; TP53; CDKN1A; CCND1; E2F4; ATM; RBL2; SMAD4; CDKN2A; MYC; NRG1; GSK3B; RBL1; HDAC6 |
| T Cell Receptor Signaling | RAC1; ELK1; MAPK1; IKBKB; CBL; PIK3CA; FOS; NFKB2; PIK3CB; PIK3C3; MAPK8; MAPK3; KRAS; RELA; PIK3C2A; BTK; LCK; RAF1; IKBKG; RELB; FYN; MAP2K2; PIK3R1; CHUK; MAP2K1; NFKB1; ITK; BCL10; JUN; VAV3 |
| Death Receptor Signaling | CRADD; HSPB1; BID; BIRC4; TBK1; IKBKB; FADD; FAS; NFKB2; BCL2; MAP3K14; MAPK8; RIPK1; CASP8; DAXX; TNFRSF10B; RELA; TRAF2; TNF; IKBKG; RELB; CASP9; CHUK; APAF1; NFKB1; CASP2; BIRC2; CASP3; BIRC3 |
| FGF Signaling | RAC1; FGFR1; MET; MAPKAPK2; MAPK1; PTPN11; AKT2; PIK3CA; CREB1; PIK3CB; PIK3C3; MAPK8; MAPK3; MAPK13; PTPN6; PIK3C2A; MAPK14; RAF1; AKT1; PIK3R1; STAT3; MAP2K1; FGFR4; CRKL; ATF4; AKT3; PRKCA; HGF |
| GM-CSF Signaling | LYN; ELK1; MAPK1; PTPN11; AKT2; PIK3CA; CAMK2A; STAT5B; PIK3CB; PIK3C3; GNB2L1; BCL2L1; MAPK3; ETS1; KRAS; RUNX1; PIM1; PIK3C2A; RAF1; MAP2K2; AKT1; JAK2; PIK3R1; STAT3; MAP2K1; CCND1; AKT3; STAT1 |
| Amyotrophic Lateral Sclerosis Signaling | BID; IGF1; RAC1; BIRC4; PGF; CAPNS1; CAPN2; PIK3CA; BCL2; PIK3CB; PIK3C3; BCL2L1; CAPN1; PIK3C2A; TP53; CASP9; PIK3R1; RAB5A; CASP1; APAF1; VEGFA; BIRC2; BAX; AKT3; CASP3; BIRC3 |
| JAK/Stat Signaling | PTPN1; MAPK1; PTPN11; AKT2; PIK3CA; STAT5B; PIK3CB; PIK3C3; MAPK3; KRAS; SOCS1; STAT5A; PTPN6; PIK3C2A; RAF1; CDKN1A; MAP2K2; JAK1; AKT1; JAK2; PIK3R1; STAT3; MAP2K1; FRAP1; AKT3; STAT1 |
| Nicotinate and Nicotinamide Metabolism | PRKCE; IRAK1; PRKAA2; EIF2AK2; GRK6; MAPK1; PLK1; AKT2; CDK8; MAPK8; MAPK3; PRKCD; PRKAA1; PBEF1; MAPK9; CDK2; PIM1; DYRK1A; MAP2K2; MAP2K1; PAK3; NT5E; TTK; CSNK1A1; BRAF; SGK |

TABLE 6-continued

| CELLULAR FUNCTION | GENES |
| --- | --- |
| Chemokine Signaling | CXCR4; ROCK2; MAPK1; PTK2; FOS; CFL1; GNAQ; CAMK2A; CXCL12; MAPK8; MAPK3; KRAS; MAPK13; RHOA; CCR3; SRC; PPP1CC; MAPK14; NOX1; RAF1; MAP2K2; MAP2K1; JUN; CCL2; PRKCA |
| IL-2 Signaling | ELK1; MAPK1; PTPN11; AKT2; PIK3CA; SYK; FOS; STAT5B; PIK3CB; PIK3C3; MAPK8; MAPK3; KRAS; SOCS1; STAT5A; PIK3C2A; LCK; RAF1; MAP2K2; JAK1; AKT1; PIK3R1; MAP2K1; JUN; AKT3 |
| Synaptic Long Term Depression | PRKCE; IGF1; PRKCZ; PRDX6; LYN; MAPK1; GNAS; PRKCI; GNAQ; PPP2R1A; IGF1R; PRKD1; MAPK3; KRAS; GRN; PRKCD; NOS3; NOS2A; PPP2CA; YWHAZ; RAF1; MAP2K2; PPP2R5C; MAP2K1; PRKCA |
| Estrogen Receptor Signaling | TAF4B; EP300; CARM1; PCAF; MAPK1; NCOR2; SMARCA4; MAPK3; NRIP1; KRAS; SRC; NR3C1; HDAC3; PPARGC1A; RBM9; NCOA3; RAF1; CREBBP; MAP2K2; NCOA2; MAP2K1; PRKDC; ESR1; ESR2 |
| Protein Ubiquitination Pathway | TRAF6; SMURF1; BIRC4; BRCA1; UCHL1; NEDD4; CBL; UBE2I; BTRC; HSPA5; USP7; USP10; FBXW7; USP9X; STUB1; USP22; B2M; BIRC2; PARK2; USP8; USP1; VHL; HSP90AA1; BIRC3 |
| IL-10 Signaling | TRAF6; CCR1; ELK1; IKBKB; SP1; FOS; NFKB2; MAP3K14; MAPK8; MAPK13; RELA; MAPK14; TNF; IKBKG; RELB; MAP3K7; JAK1; CHUK; STAT3; NFKB1; JUN; IL1R1; IL6 |
| VDR/RXR Activation | PRKCE; EP300; PRKCZ; RXRA; GADD45A; HES1; NCOR2; SP1; PRKC1; CDKN1B; PRKD1; PRKCD; RUNX2; KLF4; YY1; NCOA3; CDKN1A; NCOA2; SPP1; LRP5; CEBPB; FOXO1; PRKCA |
| TGF-beta Signaling | EP300; SMAD2; SMURF1; MAPK1; SMAD3; SMAD1; FOS; MAPK8; MAPK3; KRAS; MAPK9; RUNX2; SERPINE1; RAF1; MAP3K7; CREBBP; MAP2K2; MAP2K1; TGFBR1; SMAD4; JUN; SMAD5 |
| Toll-like Receptor Signaling | IRAK1; EIF2AK2; MYD88; TRAF6; PPARA; ELK1; IKBKB; FOS; NFKB2; MAP3K14; MAPK8; MAPK13; RELA; TLR4; MAPK14; IKBKG; RELB; MAP3K7; CHUK; NFKB1; TLR2; JUN |
| p38 MAPK Signaling | HSPB1; IRAK1; TRAF6; MAPKAPK2; ELK1; FADD; FAS; CREB1; DDIT3; RPS6KA4; DAXX; MAPK13; TRAF2; MAPK14; TNF; MAP3K7; TGFBR1; MYC; ATF4; IL1R1; SRF; STAT1 |
| Neurotrophin/TRK Signaling | NTRK2; MAPK1; PTPN11; PIK3CA; CREB1; FOS; PIK3CB; PIK3C3; MAPK8; MAPK3; KRAS; PIK3C2A; RAF1; MAP2K2; AKT1; PIK3R1; PDPK1; MAP2K1; CDC42; JUN; ATF4 |
| FXR/RXR Activation | INS; PPARA; FASN; RXRA; AKT2; SDC1; MAPK8; APOB; MAPK10; PPARG; MTTP; MAPK9; PPARGC1A; TNF; CREBBP; AKT1; SREBF1; FGFR4; AKT3; FOXO1 |
| Synaptic Long Term Potentiation | PRKCE; RAP1A; EP300; PRKCZ; MAPK1; CREB1; PRKCI; GNAQ; CAMK2A; PRKD1; MAPK3; KRAS; PRKCD; PPP1CC; RAF1; CREBBP; MAP2K2; MAP2K1; ATF4; PRKCA |
| Calcium Signaling | RAP1A; EP300; HDAC4; MAPK1; HDAC5; CREB1; CAMK2A; MYH9; MAPK3; HDAC2; HDAC7A; HDAC11; HDAC9; HDAC3; CREBBP; CALR; CAMKK2; ATF4; HDAC6 |
| EGF Signaling | ELK1; MAPK1; EGFR; PIK3CA; FOS; PIK3CB; PIK3C3; MAPK8; MAPK3; PIK3C2A; RAF1; JAK1; PIK3R1; STAT3; MAP2K1; JUN; PRKCA; SRF; STAT1 |
| Hypoxia Signaling in the Cardiovascular System | EDN1; PTEN; EP300; NQO1; UBE2I; CREB1; ARNT; HIF1A; SLC2A4; NOS3; TP53; LDHA; AKT1; ATM; VEGFA; JUN; ATF4; VHL; HSP90AA1 |
| LPS/IL-1 Mediated Inhibition of RXR Function | IRAK1; MYD88; TRAF6; PPARA; RXRA; ABCA1; MAPK8; ALDH1A1; GSTP1; MAPK9; ABCB1; TRAF2; TLR4; TNF; MAP3K7; NR1H2; SREBF1; JUN; IL1R1 |
| LXR/RXR Activation | FASN; RXRA; NCOR2; ABCA1; NFKB2; IRF3; RELA; NOS2A; TLR4; TNF; RELB; LDLR; NR1H2; NFKB1; SREBF1; IL1R1; CCL2; IL6; MMP9 |
| Amyloid Processing | PRKCE; CSNK1E; MAPK1; CAPNS1; AKT2; CAPN2; CAPN1; MAPK3; MAPK13; MAPT; MAPK14; AKT1; PSEN1; CSNK1A1; GSK3B; AKT3; APP |
| IL-4 Signaling | AKT2; PIK3CA; PIK3CB; PIK3C3; IRS1; KRAS; SOCS1; PTPN6; NR3C1; PIK3C2A; JAK1; AKT1; JAK2; PIK3R1; FRAP1; AKT3; RPS6KB1 |
| Cell Cycle: G2/M DNA Damage Checkpoint Regulation | EP300; PCAF; BRCA1; GADD45A; PLK1; BTRC; CHEK1; ATR; CHEK2; YWHAZ; TP53; CDKN1A; PRKDC; ATM; SFN; CDKN2A |

TABLE 6-continued

| CELLULAR FUNCTION | GENES |
| --- | --- |
| Nitric Oxide Signaling in the Cardiovascular System | KDR; FLT1; PGF; AKT2; PIK3CA; PIK3CB; PIK3C3; CAV1; PRKCD; NOS3; PIK3C2A; AKT1; PIK3R1; VEGFA; AKT3; HSP90AA1 |
| Purine Metabolism | NME2; SMARCA4; MYH9; RRM2; ADAR; EIF2AK4; PKM2; ENTPD1; RAD51; RRM2B; TJP2; RAD51C; NT5E; POLD1; NME1 |
| cAMP-mediated Signaling | RAP1A; MAPK1; GNAS; CREB1; CAMK2A; MAPK3; SRC; RAF1; MAP2K2; STAT3; MAP2K1; BRAF; ATF4 |
| Mitochondrial Dysfunction | SOD2; MAPK8; CASP8; MAPK10; MAPK9; CASP9; PARK7; PSEN1; PARK2; APP; CASP3 |
| Notch Signaling | HES1; JAG1; NUMB; NOTCH4; ADAM17; NOTCH2; PSEN1; NOTCH3; NOTCH1; DLL4 |
| Endoplasmic Reticulum Stress Pathway | HSPA5; MAPK8; XBP1; TRAF2; ATF6; CASP9; ATF4; EIF2AK3; CASP3 |
| Pyrimidine Metabolism | NME2; AICDA; RRM2; EIF2AK4; ENTPD1; RRM2B; NT5E; POLD1; NME1 |
| Parkinson's Signaling | UCHL1; MAPK8; MAPK13; MAPK14; CASP9; PARK7; PARK2; CASP3 |
| Cardiac & Beta Adrenergic Signaling | GNAS; GNAQ; PPP2R1A; GNB2L1; PPP2CA; PPP1CC; PPP2R5C |
| Glycolysis/Gluconeogenesis | HK2; GCK; GPI; ALDH1A1; PKM2; LDHA; HK1 |
| Interferon Signaling | IRF1; SOCS1; JAK1; JAK2; IFITM1; STAT1; IFIT3 |
| Sonic Hedgehog Signaling | ARRB2; SMO; GLI2; DYRK1A; GLI1; GSK3B; DYRK1B |
| Glycerophospholipid Metabolism | PLD1; GRN; GPAM; YWHAZ; SPHK1; SPHK2 |
| Phospholipid Degradation | PRDX6; PLD1; GRN; YWHAZ; SPHK1; SPHK2 |
| Tryptophan Metabolism | SIAH2; PRMT5; NEDD4; ALDH1A1; CYP1B1; SIAH1 |
| Lysine Degradation | SUV39H1; EHMT2; NSD1; SETD7; PPP2R5C |
| Nucleotide Excision Repair Pathway | ERCC5; ERCC4; XPA; XPC; ERCC1 |
| Starch and Sucrose Metabolism | UCHL1; HK2; GCK; GPI; HK1 |
| Aminosugars Metabolism | NQO1; HK2; GCK; HK1 |
| Arachidonic Acid Metabolism | PRDX6; GRN; YWHAZ; CYP1B1 |
| Circadian Rhythm Signaling | CSNK1E; CREB1; ATF4; NR1D1 |
| Coagulation System | BDKRB1; F2R; SERPINE1; F3 |
| Dopamine Receptor Signaling | PPP2R1A; PPP2CA; PPP1CC; PPP2R5C |
| Glutathione Metabolism | IDH2; GSTP1; ANPEP; IDH1 |
| Glycerolipid Metabolism | ALDH1A1; GPAM; SPHK1; SPHK2 |
| Linoleic Acid Metabolism | PRDX6; GRN; YWHAZ; CYP1B1 |
| Methionine Metabolism | DNMT1; DNMT3B; AHCY; DNMT3A |
| Pyruvate Metabolism | GLO1; ALDH1A1; PKM2; LDHA |
| Arginine and Proline Metabolism | ALDH1A1; NOS3; NOS2A |
| Eicosanoid Signaling | PRDX6; GRN; YWHAZ |
| Fructose and Mannose Metabolism | HK2; GCK; HK1 |
| Galactose Metabolism | HK2; GCK; HK1 |
| Stilbene, Coumarine and Lignin Biosynthesis | PRDX6; PRDX1; TYR |
| Antigen Presentation Pathway | CALR; B2M |
| Biosynthesis of Steroids | NQO1; DHCR7 |
| Butanoate Metabolism | ALDH1A1; NLGN1 |
| Citrate Cycle | IDH2; IDH1 |
| Fatty Acid Metabolism | ALDH1A1; CYP1B1 |
| Glycerophospholipid Metabolism | PRDX6; CHKA |
| Histidine Metabolism | PRMT5; ALDH1A1 |
| Inositol Metabolism | ERO1L; APEX1 |
| Metabolism of Xenobiotics by Cytochrome p450 | GSTP1; CYP1B1 |
| Methane Metabolism | PRDX6; PRDX1 |
| Phenylalanine Metabolism | PRDX6; PRDX1 |
| Propanoate Metabolism | ALDH1A1; LDHA |
| Selenoamino Acid Metabolism | PRMT5; AHCY |
| Sphingolipid Metabolism | SPHK1; SPHK2 |
| Aminophosphonate Metabolism | PRMT5 |
| Androgen and Estrogen Metabolism | PRMT5 |
| Ascorbate and Aldarate Metabolism | ALDH1A1 |
| Bile Acid Biosynthesis | ALDH1A1 |
| Cysteine Metabolism | LDHA |
| Fatty Acid Biosynthesis | FASN |
| Glutamate Receptor Signaling | GNB2L1 |
| NRF2-mediated Oxidative Stress Response | PRDX1 |

TABLE 6-continued

| CELLULAR FUNCTION | GENES |
| --- | --- |
| Pentose Phosphate Pathway | GPI |
| Pentose and Glucuronate Interconversions | UCHL1 |
| Retinol Metabolism | ALDH1A1 |
| Riboflavin Metabolism | TYR |
| Tyrosine Metabolism | PRMT5, TYR |
| Ubiquinone Biosynthesis | PRMT5 |
| Valine, Leucine and Isoleucine Degradation | ALDH1A1 |
| Glycine, Serine and Threonine Metabolism | CHKA |
| Lysine Degradation | ALDH1A1 |
| Pain/Taste | TRPM5; TRPA1 |
| Pain | TRPM7; TRPC5; TRPC6; TRPC1; Cnr1; cnr2; Grk2; Trpa1; Pomc; Cgrp; Crf; Pka; Era; Nr2b; TRPM5; Prkaca; Prkacb; Prkar1a; Prkar2a |
| Mitochondrial Function | AIF; CytC; SMAC (Diablo); Aifm-1; Aifm-2 |
| Developmental Neurology | BMP-4; Chordin (Chrd); Noggin (Nog); WNT (Wnt2; Wnt2b; Wnt3a; Wnt4; Wnt5a; Wnt6; Wnt7b; Wnt8b; Wnt9a; Wnt9b; Wnt10a; Wnt10b; Wnt16); beta-catenin; Dkk-1; Frizzled related proteins; Otx-2; Gbx2; FGF-8; Reelin; Dab1; unc-86 (Pou4fl or Brn3a); Numb; Reln |

A target polynucleotide of the various embodiments of the aspects herein can be DNA or RNA (e.g., mRNA). The target polynucleotide can be single-stranded or double-stranded. The target polynucleotide can be genomic DNA. The target polynucleotide can be any polynucleotide endogenous or exogenous to a cell. For example, the target polynucleotide can by a polynucleotide residing in the nucleus of a eukaryotic cell. The target polynucleotide can be a sequence coding a gene product (e.g., a protein) or a non-coding sequence (e.g., a regulatory polynucleotide).

The target polynucleotide sequence can comprise a target nucleic acid or a protospacer sequence (i.e. sequence recognized by the spacer region of a guide nucleic acid) of 20 nucleotides in length. The protospacer can be less than 20 nucleotides in length. The protospacer can be at least 5, 10, 15, 16, 17, 18, 19, 20, 21, 22, 23, 24, 25, 30 or more nucleotides in length. The protospacer sequence can be at most 5, 10, 15, 16, 17, 18, 19, 20, 21, 22, 23, 24, 25, 30 or more nucleotides in length. The protospacer sequence can be 16, 17, 18, 19, 20, 21, 22, or 23 bases immediately 5' of the first nucleotide of the PAM. The protospacer sequence can be 16, 17, 18, 19, 20, 21, 22, or 23 bases immediately 3' of the last nucleotide of the PAM sequence. The protospacer sequence can be 20 bases immediately 5' of the first nucleotide of the PAM sequence. The protospacer sequence can be 20 bases immediately 3' of the last nucleotide of the PAM. The target nucleic acid sequence can be 5' or 3' of the PAM.

A protospacer sequence can include a nucleic acid sequence present in a target polynucleotide to which a nucleic acid-targeting segment of a guide nucleic acid can bind. For example, a protospacer sequence can include a sequence to which a guide nucleic acid is designed to have complementarity. A protospacer sequence can comprise any polynucleotide, which can be located, for example, in the nucleus or cytoplasm of a cell or within an organelle of a cell, such as a mitochondrion or chloroplast. A protospacer sequence can include cleavage sites for Cas proteins. A protospacer sequence can be adjacent to cleavage sites for Cas proteins.

The Cas protein can bind the target polynucleotide at a site within or outside of the sequence to which the nucleic acid-targeting sequence of the guide nucleic acid can bind. The binding site can include the position of a nucleic acid at which a Cas protein can produce a single-strand break or a double-strand break.

Site-specific binding of a target nucleic acid by a Cas protein can occur at locations determined by base-pairing complementarity between the guide nucleic acid and the target nucleic acid. Site-specific binding of a target nucleic acid by a Cas protein can occur at locations determined by a short motif, called the protospacer adjacent motif (PAM), in the target nucleic acid. The PAM can flank the protospacer, for example at the 3' end of the protospacer sequence. For example, the binding site of Cas9 can be about 1 to about 25, or about 2 to about 5, or about 19 to about 23 base pairs (e.g., 3 base pairs) upstream or downstream of the PAM sequence. The binding site of Cas (e.g., Cas9) can be 3 base pairs upstream of the PAM sequence. The binding site of Cas (e.g., Cpf1) can be 19 bases on the (+) strand and 23 base on the (−) strand.

Different organisms can comprise different PAM sequences. Different Cas proteins can recognize different PAM sequences. For example, in *S. pyogenes*, the PAM can comprise the sequence 5'-XRR-3', where R can be either A or G, where X is any nucleotide and X is immediately 3' of the target nucleic acid sequence targeted by the spacer sequence. The PAM sequence of *S. pyogenes* Cas9 (SpyCas9) can be 5'-XGG-3', where X is any DNA nucleotide and is immediately 3' of the protospacer sequence of the non-complementary strand of the target DNA. The PAM of Cpf1 can be 5'-TTX-3', where X is any DNA nucleotide and is immediately 5' of the CRISPR recognition sequence.

The target sequence for the guide nucleic acid can be identified by bioinformatics approaches, for example, locating sequences within the target sequence adjacent to a PAM sequence. The optimal target sequence for the guide nucleic acid can be identified by experimental approaches, for example, testing a number of guide nucleic acid sequences to identify the sequence with the highest on-target activity and lowest off-target activity. The location of a target sequence can be determined by the desired experimental outcome. For example, a target protospacer can be located in a promoter in order to activate or repress a target gene. A target protospacer can be within a coding sequence, such as a 5' constitutively expressed exon or sequences encoding a known domain. A target protospacer can be a unique sequence within the genome in order to mitigate off-target effects. Many publicly available algorithms for determining and ranking potential target protospacers are known in the art and can be used.

In some aspects, systems disclosed herein can regulate the expression of at least one gene associated with a genetic disease or medical condition. A wide range of genetic diseases which are further described on the website of the National Institutes of Health under the topic subsection Genetic Disorders (website at health.nih.gov/topic/GeneticDisorders).

As will be apparent, it is envisaged that the present system can be used to target any polynucleotide sequence of interest. However, the genes exemplified are not exhaustive.

In various embodiments of the aspects herein, subject systems can be used for selectively modulating transcription (e.g., reduction or increase) of a target nucleic acid in a host cell (e.g., immune cell). Selective modulation of transcription of a target nucleic acid can reduce or increase transcription of the target nucleic acid, but may not substantially modulate transcription of a non-target nucleic acid or off-target nucleic acid, e.g., transcription of a non-target nucleic acid may be modulated by less than 1%, less than 5%, less than 10%, less than 20%, less than 30%, less than 40%, or less than 50% compared to the level of transcription of the non-target nucleic acid in the absence of an actuator moiety, such as a guide nucleic acid/enzymatically inactive or enzymatically reduced Cas protein complex. For example, selective modulation (e.g., reduction or increase) of transcription of a target nucleic acid can reduce or increase transcription of the target nucleic acid by at least about 10%, at least about 20%, at least about 30%, at least about 40%, at least about 50%, at least about 60%, at least about 70%, at least about 80%, at least about 90%, or greater than 90%, compared to the level of transcription of the target nucleic acid in the absence of an actuator moiety, such as a guide nucleic acid/enzymatically inactive or enzymatically reduced Cas protein complex.

In some embodiments, the disclosure provides methods for increasing transcription of a target nucleic acid. The transcription of a target nucleic acid can increase by at least about 1.1 fold, at least about 1.2 fold, at least about 1.3 fold, at least about 1.4 fold, at least about 1.5 fold, at least about 1.6 fold, at least about 1.7 fold, at least about 1.8 fold, at least about 1.9 fold, at least about 2 fold, at least about 2.5 fold, at least about 3 fold, at least about 3.5 fold, at least about 4 fold, at least about 4.5 fold, at least about 5 fold, at least about 6 fold, at least about 7 fold, at least about 8 fold, at least about 9 fold, at least about 10 fold, at least about 12 fold, at least about 15 fold, at least about 20-fold, at least about 50-fold, at least about 70-fold, or at least about 100-fold compared to the level of transcription of the target DNA in the absence of an actuator moiety, such as a guide nucleic acid/enzymatically inactive or enzymatically reduced Cas protein complex. Selective increase of transcription of a target nucleic acid increases transcription of the target nucleic acid, but may not substantially increase transcription of a non-target DNA, e.g., transcription of a non-target nucleic acid is increased, if at all, by less than about 5-fold, less than about 4-fold, less than about 3-fold, less than about 2-fold, less than about 1.8-fold, less than about 1.6-fold, less than about 1.4-fold, less than about 1.2-fold, or less than about 1.1-fold compared to the level of transcription of the non-targeted DNA in the absence of an actuator moiety, such as a guide nucleic acid/enzymatically inactive or enzymatically reduced Cas protein complex.

In some embodiments, the disclosure provides methods for decreasing transcription of a target nucleic acid. The transcription of a target nucleic acid can decrease by at least about 1.1 fold, at least about 1.2 fold, at least about 1.3 fold, at least about 1.4 fold, at least about 1.5 fold, at least about 1.6 fold, at least about 1.7 fold, at least about 1.8 fold, at least about 1.9 fold, at least about 2 fold, at least about 2.5 fold, at least about 3 fold, at least about 3.5 fold, at least about 4 fold, at least about 4.5 fold, at least about 5 fold, at least about 6 fold, at least about 7 fold, at least about 8 fold, at least about 9 fold, at least about 10 fold, at least about 12 fold, at least about 15 fold, at least about 20-fold, at least about 50-fold, at least about 70-fold, or at least about 100-fold compared to the level of transcription of the target DNA in the absence of an actuator moiety, such as a guide nucleic acid/enzymatically inactive or enzymatically reduced Cas protein complex. Selective decrease of transcription of a target nucleic acid decreases transcription of the target nucleic acid, but may not substantially decrease transcription of a non-target DNA, e.g., transcription of a non-target nucleic acid is decreased, if at all, by less than about 5-fold, less than about 4-fold, less than about 3-fold, less than about 2-fold, less than about 1.8-fold, less than about 1.6-fold, less than about 1.4-fold, less than about 1.2-fold, or less than about 1.1-fold compared to the level of transcription of the non-targeted DNA in the absence of an actuator moiety, such as a guide nucleic acid/enzymatically inactive or enzymatically reduced Cas protein complex.

Transcription modulation can be achieved by fusing the actuator moiety, such as an enzymatically inactive Cas protein, to a heterologous sequence. The heterologous sequence can be a suitable fusion partner, e.g., a polypeptide that provides an activity that indirectly increases, decreases, or otherwise modulates transcription by acting directly on the target nucleic acid or on a polypeptide (e.g., a histone or other DNA-binding protein) associated with the target nucleic acid. Non-limiting examples of suitable fusion partners include a polypeptide that provides for methyltransferase activity, demethylase activity, acetyltransferase activity, deacetylase activity, kinase activity, phosphatase activity, ubiquitin ligase activity, deubiquitinating activity, adenylation activity, deadenylation activity, SUMOylating activity, deSUMOylating activity, ribosylation activity, deribosylation activity, myristoylation activity, or demyristoylation activity.

A suitable fusion partner can include a polypeptide that directly provides for increased transcription of the target nucleic acid. For example, a transcription activator or a fragment thereof, a protein or fragment thereof that recruits a transcription activator, or a small molecule/drug-responsive transcription regulator. A suitable fusion partner can include a polypeptide that directly provides for decreased transcription of the target nucleic acid. For example, a transcription repressor or a fragment thereof, a protein or fragment thereof that recruits a transcription repressor, or a small molecule/drug-responsive transcription regulator.

The heterologous sequence or fusion partner can be fused to the C-terminus, N-terminus, or an internal portion (i.e., a portion other than the N- or C-terminus) of the actuator moiety, for example a dead Cas protein. Non-limiting examples of fusion partners include transcription activators, transcription repressors, histone lysine methyltransferases (KMT), Histone Lysine Demethylates, Histone lysine acetyltransferases (KAT), Histone lysine deacetylase, DNA methylases (adenosine or cytosine modification), CTCF, periphery recruitment elements (e.g., Lamin A, Lamin B), and protein docking elements (e.g., FKBP/FRB).

Non-limiting examples of transcription activators include GAL4, VP16, VP64, and p65 subdomain (NFkappaB).

Non-limiting examples of transcription repressors include Kruippel associated box (KRAB or SKD), the Mad mSIN3 interaction domain (SID), and the ERF repressor domain (ERD).

Non-limiting examples of histone lysine methyltransferases (KMT) include members from KMT1 family (e.g., SUV39H1, SUV39H2, G9A, ESET/SETDB1, Clr4, Su(var)3-9), KMT2 family members (e.g., hSET1A, hSET1B, MLL 1 to 5, ASH1, and homologs (Trx, Trr, Ash1)), KMT3 family (SYMD2, NSD1), KMT4 (DOT1L and homologs), KMT5 family (Pr-SET7/8, SUV4-20H1, and homologs), KMT6 (EZH2), and KMT8 (e.g., RIZ1).

Non-limiting examples of Histone Lysine Demethylates (KDM) include members from KDM1 family (LSD1/BHC110, Splsd1/Swm1/Saf110, Su(var)3-3), KDM3 family (JHDM2a/b), KDM4 family (JMJD2A/JHDM3A, JMJD2B, JMJD2C/GASC1, JMJD2D, and homologs (Rph1)), KDM5 family (JARID1A/RBP2, JARID1B/PLU-1, JARIDIC/SMCX, JARID1D/SMCY, and homologs (Lid, Jhn2, Jmj2)), and KDM6 family (e.g., UTX, JMJD3).

Non-limiting examples of KAT include members of KAT2 family (hGCN5, PCAF, and homologs (dGCN5/PCAF, Gcn5), KAT3 family (CBP, p300, and homologs (dCBP/NEJ)), KAT4, KAT5, KAT6, KAT7, KAT8, and KAT13.

In some embodiments, an actuator moiety comprising a dead Cas protein or dead Cas fusion protein is targeted by a guide nucleic acid to a specific location (i.e., sequence) in the target nucleic acid and exerts locus-specific regulation such as blocking RNA polymerase binding to a promoter (e.g., which can selectively inhibit transcription activator function), and/or modifying the local chromatin status (e.g., when a fusion sequence is used that can modify the target nucleic acid or modifies a polypeptide associated with the target nucleic acid). In some cases, the changes are transient (e.g., transcription repression or activation). In some cases, the changes are inheritable (e.g., when epigenetic modifications are made to the target DNA or to proteins associated with the target DNA, e.g., nucleosomal histones).

In some embodiments, a guide nucleic acid can comprise a protein binding segment to recruit a heterologous polypeptide to a target nucleic acid to modulate transcription of a target nucleic acid. Non-limiting examples of the heterologous polypeptide include a polypeptide that provides for methyltransferase activity, demethylase activity, acetyltransferase activity, deacetylase activity, kinase activity, phosphatase activity, ubiquitin ligase activity, deubiquitinating activity, adenylation activity, deadenylation activity, SUMOylating activity, deSUMOylating activity, ribosylation activity, deribosylation activity, myristoylation activity, or demyristoylation activity. The guide nucleic acid can comprise a protein binding segment to recruit a transcriptional activator, transcriptional repressor, or fragments thereof.

In some embodiments, gene expression modulation is achieved by using a guide nucleic acid designed to target a regulatory element of a target nucleic acid, for example, transcription response element (e.g., promoters, enhancers), upstream activating sequences (UAS), and/or sequences of unknown or known function that are suspected of being able to control expression of the target DNA.

In various embodiments of the aspects herein, the disclosure provides a guide nucleic acid. A guide nucleic acid (e.g., guide RNA) can bind to a Cas protein and target the Cas protein to a specific location within a target polynucleotide. A guide nucleic acid can comprise a nucleic acid-targeting segment and a Cas protein binding segment.

A guide nucleic acid can refer to a nucleic acid that can hybridize to another nucleic acid, for example, the target polynucleotide in the genome of a cell. A guide nucleic acid can be RNA, for example, a guide RNA. A guide nucleic acid can be DNA. A guide nucleic acid can comprise DNA and RNA. A guide nucleic acid can be single stranded. A guide nucleic acid can be double-stranded. A guide nucleic acid can comprise a nucleotide analog. A guide nucleic acid can comprise a modified nucleotide. The guide nucleic acid can be programmed or designed to bind to a sequence of nucleic acid site-specifically.

A guide nucleic acid can comprise one or more modifications to provide the nucleic acid with a new or enhanced feature. A guide nucleic acid can comprise a nucleic acid affinity tag. A guide nucleic acid can comprise synthetic nucleotide, synthetic nucleotide analog, nucleotide derivatives, and/or modified nucleotides.

The guide nucleic acid can comprise a nucleic acid-targeting region (e.g., a spacer region), for example, at or near the 5' end or 3' end, that is complementary to a protospacer sequence in a target polynucleotide. The spacer of a guide nucleic acid can interact with a protospacer in a sequence-specific manner via hybridization (i.e., base pairing). The protospacer sequence can be located 5' or 3' of protospacer adjacent motif (PAM) in the target polynucleotide. The nucleotide sequence of a spacer region can vary and determines the location within the target nucleic acid with which the guide nucleic acid can interact. The spacer region of a guide nucleic acid can be designed or modified to hybridize to any desired sequence within a target nucleic acid.

A guide nucleic acid can comprise two separate nucleic acid molecules, which can be referred to as a double guide nucleic acid. A guide nucleic acid can comprise a single nucleic acid molecule, which can be referred to as a single guide nucleic acid (e.g., sgRNA). In some embodiments, the guide nucleic acid is a single guide nucleic acid comprising a fused CRISPR RNA (crRNA) and a transactivating crRNA (tracrRNA). In some embodiments, the guide nucleic acid is a single guide nucleic acid comprising a crRNA. In some embodiments, the guide nucleic acid is a single guide nucleic acid comprising a crRNA but lacking a tracrRNA. In some embodiments, the guide nucleic acid is a double guide nucleic acid comprising non-fused crRNA and tracrRNA. An exemplary double guide nucleic acid can comprise a crRNA-like molecule and a tracrRNA-like molecule. An exemplary single guide nucleic acid can comprise a crRNA-like molecule. An exemplary single guide nucleic acid can comprise a fused crRNA-like and tracrRNA-like molecules.

A crRNA can comprise the nucleic acid-targeting segment (e.g., spacer region) of the guide nucleic acid and a stretch of nucleotides that can form one half of a double-stranded duplex of the Cas protein-binding segment of the guide nucleic acid.

A tracrRNA can comprise a stretch of nucleotides that forms the other half of the double-stranded duplex of the Cas protein-binding segment of the gRNA. A stretch of nucleotides of a crRNA can be complementary to and hybridize with a stretch of nucleotides of a tracrRNA to form the double-stranded duplex of the Cas protein-binding domain of the guide nucleic acid.

The crRNA and tracrRNA can hybridize to form a guide nucleic acid. The crRNA can also provide a single-stranded nucleic acid targeting segment (e.g., a spacer region) that hybridizes to a target nucleic acid recognition sequence (e.g., protospacer). The sequence of a crRNA, including spacer region, or tracrRNA molecule can be designed to be specific to the species in which the guide nucleic acid is to be used.

In some embodiments, the nucleic acid-targeting region of a guide nucleic acid can be between 18 to 72 nucleotides in length. The nucleic acid-targeting region of a guide nucleic acid (e.g., spacer region) can have a length of from about 12 nucleotides to about 100 nucleotides. For example, the nucleic acid-targeting region of a guide nucleic acid (e.g., spacer region) can have a length of from about 12 nucleotides (nt) to about 80 nt, from about 12 nt to about 50 nt, from about 12 nt to about 40 nt, from about 12 nt to about 30 nt, from about 12 nt to about 25 nt, from about 12 nt to about 20 nt, from about 12 nt to about 19 nt, from about 12 nt to about 18 nt, from about 12 nt to about 17 nt, from about 12 nt to about 16 nt, or from about 12 nt to about 15 nt. Alternatively, the DNA-targeting segment can have a length of from about 18 nt to about 20 nt, from about 18 nt to about 25 nt, from about 18 nt to about 30 nt, from about 18 nt to about 35 nt, from about 18 nt to about 40 nt, from about 18 nt to about 45 nt, from about 18 nt to about 50 nt, from about 18 nt to about 60 nt, from about 18 nt to about 70 nt, from about 18 nt to about 80 nt, from about 18 nt to about 90 nt, from about 18 nt to about 100 nt, from about 20 nt to about 25 nt, from about 20 nt to about 30 nt, from about 20 nt to about 35 nt, from about 20 nt to about 40 nt, from about 20 nt to about 45 nt, from about 20 nt to about 50 nt, from about 20 nt to about 60 nt, from about 20 nt to about 70 nt, from about 20 nt to about 80 nt, from about 20 nt to about 90 nt, or from about 20 nt to about 100 nt. The length of the nucleic acid-targeting region can be at least 5, 10, 15, 16, 17, 18, 19, 20, 21, 22, 23, 24, 25, 30 or more nucleotides. The length of the nucleic acid-targeting region (e.g., spacer sequence) can be at most 5, 10, 15, 16, 17, 18, 19, 20, 21, 22, 23, 24, 25, 30 or more nucleotides.

In some embodiments, the nucleic acid-targeting region of a guide nucleic acid (e.g., spacer) is 20 nucleotides in length. In some embodiments, the nucleic acid-targeting region of a guide nucleic acid is 19 nucleotides in length. In some embodiments, the nucleic acid-targeting region of a guide nucleic acid is 18 nucleotides in length. In some embodiments, the nucleic acid-targeting region of a guide nucleic acid is 17 nucleotides in length. In some embodiments, the nucleic acid-targeting region of a guide nucleic acid is 16 nucleotides in length. In some embodiments, the nucleic acid-targeting region of a guide nucleic acid is 21 nucleotides in length. In some embodiments, the nucleic acid-targeting region of a guide nucleic acid is 22 nucleotides in length.

The nucleotide sequence of the guide nucleic acid that is complementary to a nucleotide sequence (target sequence) of the target nucleic acid can have a length of, for example, at least about 12 nt, at least about 15 nt, at least about 18 nt, at least about 19 nt, at least about 20 nt, at least about 25 nt, at least about 30 nt, at least about 35 nt or at least about 40 nt. The nucleotide sequence of the guide nucleic acid that is complementary to a nucleotide sequence (target sequence) of the target nucleic acid can have a length of from about 12 nucleotides (nt) to about 80 nt, from about 12 nt to about 50 nt, from about 12 nt to about 45 nt, from about 12 nt to about 40 nt, from about 12 nt to about 35 nt, from about 12 nt to about 30 nt, from about 12 nt to about 25 nt, from about 12 nt to about 20 nt, from about 12 nt to about 19 nt, from about 19 nt to about 20 nt, from about 19 nt to about 25 nt, from about 19 nt to about 30 nt, from about 19 nt to about 35 nt, from about 19 nt to about 40 nt, from about 19 nt to about 45 nt, from about 19 nt to about 50 nt, from about 19 nt to about 60 nt, from about 20 nt to about 25 nt, from about 20 nt to about 30 nt, from about 20 nt to about 35 nt, from about 20 nt to about 40 nt, from about 20 nt to about 45 nt, from about 20 nt to about 50 nt, or from about 20 nt to about 60 nt.

A protospacer sequence can be identified by identifying a PAM within a region of interest and selecting a region of a desired size upstream or downstream of the PAM as the protospacer. A corresponding spacer sequence can be designed by determining the complementary sequence of the protospacer region.

A spacer sequence can be identified using a computer program (e.g., machine readable code). The computer program can use variables such as predicted melting temperature, secondary structure formation, and predicted annealing temperature, sequence identity, genomic context, chromatin accessibility, % GC, frequency of genomic occurrence, methylation status, presence of SNPs, and the like.

The percent complementarity between the nucleic acid-targeting sequence (e.g., spacer sequence) and the target nucleic acid (e.g., protospacer) can be at least 60%, at least 70%, at least 75%, at least 80%, at least 85%, at least 90%, at least 95%, at least 97%, at least 98%, at least 99%, or 100%. The percent complementarity between the nucleic acid-targeting sequence and the target nucleic acid can be at least 60%, at least 70%, at least 75%, at least 80%, at least 85%, at least 90%, at least 95%, at least 97%, at least 98%, at least 99%, or 100% over about 20 contiguous nucleotides.

The Cas protein-binding segment of a guide nucleic acid can comprise two stretches of nucleotides (e.g., crRNA and tracrRNA) that are complementary to one another. The two stretches of nucleotides (e.g., crRNA and tracrRNA) that are complementary to one another can be covalently linked by intervening nucleotides (e.g., a linker in the case of a single guide nucleic acid). The two stretches of nucleotides (e.g., crRNA and tracrRNA) that are complementary to one another can hybridize to form a double stranded RNA duplex or hairpin of the Cas protein-binding segment, thus resulting in a stem-loop structure. The crRNA and the tracrRNA can be covalently linked via the 3' end of the crRNA and the 5' end of the tracrRNA. Alternatively, tracrRNA and the crRNA can be covalently linked via the 5' end of the tracrRNA and the 3' end of the crRNA.

The Cas protein binding segment of a guide nucleic acid can have a length of from about 10 nucleotides to about 100 nucleotides, e.g., from about 10 nucleotides (nt) to about 20 nt, from about 20 nt to about 30 nt, from about 30 nt to about 40 nt, from about 40 nt to about 50 nt, from about 50 nt to about 60 nt, from about 60 nt to about 70 nt, from about 70 nt to about 80 nt, from about 80 nt to about 90 nt, or from about 90 nt to about 100 nt. For example, the Cas protein-binding segment of a guide nucleic acid can have a length of from about 15 nucleotides (nt) to about 80 nt, from about 15 nt to about 50 nt, from about 15 nt to about 40 nt, from about 15 nt to about 30 nt or from about 15 nt to about 25 nt.

The dsRNA duplex of the Cas protein-binding segment of the guide nucleic acid can have a length from about 6 base pairs (bp) to about 50 bp. For example, the dsRNA duplex of the protein-binding segment can have a length from about 6 bp to about 40 bp, from about 6 bp to about 30 bp, from about 6 bp to about 25 bp, from about 6 bp to about 20 bp, from about 6 bp to about 15 bp, from about 8 bp to about 40 bp, from about 8 bp to about 30 bp, from about 8 bp to about 25 bp, from about 8 bp to about 20 bp or from about 8 bp to about 15 bp. For example, the dsRNA duplex of the Cas protein-binding segment can have a length from about from about 8 bp to about 10 bp, from about 10 bp to about 15 bp, from about 15 bp to about 18 bp, from about 18 bp to about 20 bp, from about 20 bp to about 25 bp, from about 25 bp to about 30 bp, from about 30 bp to about 35 bp, from about 35 bp to about 40 bp, or from about 40 bp to about 50 bp. In some embodiments, the dsRNA duplex of the Cas protein-binding segment can has a length of 36 base pairs. The percent complementarity between the nucleotide sequences that hybridize to form the dsRNA duplex of the protein-binding segment can be at least about 60%. For example, the percent complementarity between the nucleotide sequences that hybridize to form the dsRNA duplex of the protein-binding segment can be at least about 65%, at least about 70%, at least about 75%, at least about 80%, at least about 85%, at least about 90%, at least about 95%, at least about 98%, or at least about 99%. In some cases, the percent complementarity between the nucleotide sequences that hybridize to form the dsRNA duplex of the protein-binding segment is 100%.

The linker (e.g., that links a crRNA and a tracrRNA in a single guide nucleic acid) can have a length of from about 3 nucleotides to about 100 nucleotides. For example, the linker can have a length of from about 3 nucleotides (nt) to about 90 nt, from about 3 nucleotides (nt) to about 80 nt, from about 3 nucleotides (nt) to about 70 nt, from about 3 nucleotides (nt) to about 60 nt, from about 3 nucleotides (nt) to about 50 nt, from about 3 nucleotides (nt) to about 40 nt, from about 3 nucleotides (nt) to about 30 nt, from about 3 nucleotides (nt) to about 20 nt or from about 3 nucleotides (nt) to about 10 nt. For example, the linker can have a length of from about 3 nt to about 5 nt, from about 5 nt to about 10 nt, from about 10 nt to about 15 nt, from about 15 nt to about 20 nt, from about 20 nt to about 25 nt, from about 25 nt to about 30 nt, from about 30 nt to about 35 nt, from about 35 nt to about 40 nt, from about 40 nt to about 50 nt, from about 50 nt to about 60 nt, from about 60 nt to about 70 nt, from about 70 nt to about 80 nt, from about 80 nt to about 90 nt, or from about 90 nt to about 100 nt. In some embodiments, the linker of a DNA-targeting RNA is 4 nt.

Guide nucleic acids can include modifications or sequences that provide for additional desirable features (e.g., modified or regulated stability; subcellular targeting; tracking with a fluorescent label; a binding site for a protein or protein complex; and the like). Examples of such modifications include, for example, a 5' cap (e.g., a 7-methylguanylate cap (m7G)); a 3' polyadenylated tail (i.e., a 3' poly(A) tail); a riboswitch sequence (e.g., to allow for regulated stability and/or regulated accessibility by proteins and/or protein complexes); a stability control sequence; a sequence that forms a dsRNA duplex (i.e., a hairpin)); a modification or sequence that targets the RNA to a subcellular location (e.g., nucleus, mitochondria, chloroplasts, and the like); a modification or sequence that provides for tracking (e.g., direct conjugation to a fluorescent molecule, conjugation to a moiety that facilitates fluorescent detection, a sequence that allows for fluorescent detection, and so forth); a modification or sequence that provides a binding site for proteins (e.g., proteins that act on DNA, including transcriptional activators, transcriptional repressors, DNA methyl transferases, DNA demethylases, histone acetyltransferases, histone deacetylases, and combinations thereof.

A guide nucleic acid can comprise one or more modifications (e.g., a base modification, a backbone modification), to provide the nucleic acid with a new or enhanced feature (e.g., improved stability). A guide nucleic acid can comprise a nucleic acid affinity tag. A nucleoside can be a base-sugar combination. The base portion of the nucleoside can be a heterocyclic base. The two most common classes of such heterocyclic bases are the purines and the pyrimidines. Nucleotides can be nucleosides that further include a phosphate group covalently linked to the sugar portion of the nucleoside. For those nucleosides that include a pentofuranosyl sugar, the phosphate group can be linked to the 2', the 3', or the 5' hydroxyl moiety of the sugar. In forming guide nucleic acids, the phosphate groups can covalently link adjacent nucleosides to one another to form a linear polymeric compound. In turn, the respective ends of this linear polymeric compound can be further joined to form a circular compound; however, linear compounds are generally suitable. In addition, linear compounds may have internal nucleotide base complementarity and may therefore fold in a manner as to produce a fully or partially double-stranded compound. Within guide nucleic acids, the phosphate groups can commonly be referred to as forming the internucleoside backbone of the guide nucleic acid. The linkage or backbone of the guide nucleic acid can be a 3' to 5' phosphodiester linkage.

A guide nucleic acid can comprise a modified backbone and/or modified internucleoside linkages. Modified backbones can include those that retain a phosphorus atom in the backbone and those that do not have a phosphorus atom in the backbone.

Suitable modified guide nucleic acid backbones containing a phosphorus atom therein can include, for example, phosphorothioates, chiral phosphorothioates, phosphorodithioates, phosphotriesters, aminoalkylphosphotriesters, methyl and other alkyl phosphonates such as 3'-alkylene phosphonates, 5'-alkylene phosphonates, chiral phosphonates, phosphinates, phosphoramidates including 3'-amino phosphoramidate and aminoalkylphosphoramidates, phosphorodiamidates, thionophosphoramidates, thionoalkylphosphonates, thionoalkylphosphotriesters, selenophosphates, and boranophosphates having normal 3'-5' linkages, 2'-5' linked analogs, and those having inverted polarity wherein one or more internucleotide linkages is a 3' to 3', a 5' to 5' or a 2' to 2' linkage. Suitable guide nucleic acids having inverted polarity can comprise a single 3' to 3' linkage at the 3'-most internucleotide linkage (i.e. a single inverted nucleoside residue in which the nucleobase is missing or has a hydroxyl group in place thereof). Various salts (e.g., potassium chloride or sodium chloride), mixed salts, and free acid forms can also be included.

A guide nucleic acid can comprise one or more phosphorothioate and/or heteroatom internucleoside linkages, in particular —CH2-NH—O-CH2-, -CH2-N(CH3)-O—CH2- (i.e. a methylene (methylimino) or MMI backbone), —CH2-O—N(CH3)-CH2-, -CH2-N(CH3)-N(CH3)-CH2- and —O—N(CH3)-CH2-CH2-(wherein the native phosphodiester internucleotide linkage is represented as —O—P(=O)(OH)—O-CH2-).

A guide nucleic acid can comprise a morpholino backbone structure. For example, a nucleic acid can comprise a 6-membered morpholino ring in place of a ribose ring. In some of these embodiments, a phosphorodiamidate or other non-phosphodiester internucleoside linkage replaces a phosphodiester linkage.

A guide nucleic acid can comprise polynucleotide backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These can include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and CH2 component parts.

A guide nucleic acid can comprise a nucleic acid mimetic. The term "mimetic" can be intended to include polynucleotides wherein only the furanose ring or both the furanose ring and the internucleotide linkage are replaced with non-furanose groups, replacement of only the furanose ring can also be referred as being a sugar surrogate. The heterocyclic base moiety or a modified heterocyclic base moiety can be maintained for hybridization with an appropriate target nucleic acid. One such nucleic acid can be a peptide nucleic acid (PNA). In a PNA, the sugar-backbone of a polynucleotide can be replaced with an amide containing backbone, in particular an aminoethylglycine backbone. The nucleotides can be retained and are bound directly or indirectly to aza nitrogen atoms of the amide portion of the backbone. The backbone in PNA compounds can comprise two or more linked aminoethylglycine units which gives PNA an amide containing backbone. The heterocyclic base moieties can be bound directly or indirectly to aza nitrogen atoms of the amide portion of the backbone.

A guide nucleic acid can comprise linked morpholino units (i.e. morpholino nucleic acid) having heterocyclic bases attached to the morpholino ring. Linking groups can link the morpholino monomeric units in a morpholino nucleic acid. Non-ionic morpholino-based oligomeric compounds can have less undesired interactions with cellular proteins. Morpholino-based polynucleotides can be non-ionic mimics of guide nucleic acids. A variety of compounds within the morpholino class can be joined using different linking groups. A further class of polynucleotide mimetic can be referred to as cyclohexenyl nucleic acids (CeNA). The furanose ring normally present in a nucleic acid molecule can be replaced with a cyclohexenyl ring. CeNA DMT protected phosphoramidite monomers can be prepared and used for oligomeric compound synthesis using phosphoramidite chemistry. The incorporation of CeNA monomers into a nucleic acid chain can increase the stability of a DNA/RNA hybrid. CeNA oligoadenylates can form complexes with nucleic acid complements with similar stability to the native complexes. A further modification can include Locked Nucleic Acids (LNAs) in which the 2'-hydroxyl group is linked to the 4' carbon atom of the sugar ring thereby forming a 2'-C,4'-C-oxymethylene linkage thereby forming a bicyclic sugar moiety. The linkage can be a methylene (—CH2-), group bridging the 2' oxygen atom and the 4' carbon atom wherein n is 1 or 2. LNA and LNA analogs can display very high duplex thermal stabilities with complementary nucleic acid (Tm=+3 to +10° C.), stability towards 3'-exonucleolytic degradation and good solubility properties.

A guide nucleic acid can comprise one or more substituted sugar moieties. Suitable polynucleotides can comprise a sugar substituent group selected from: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted C1 to C10 alkyl or C2 to C10 alkenyl and alkynyl. Particularly suitable are O((CH2)nO)mCH3, O(CH2)nOCH3, O(CH2)nNH2, O(CH2)nCH3, O(CH2)nONH2, and O(CH2)nON((CH2)nCH3)2, where n and m are from 1 to about 10. A sugar substituent group can be selected from: C1 to C10 lower alkyl, substituted lower alkyl, alkenyl, alkynyl, alkaryl, aralkyl, O-alkaryl or O-aralkyl, SH, SCH3, OCN, Cl, Br, CN, CF3, OCF3, SOCH3, SO2CH3, ONO2, NO2, N3, NH2, heterocycloalkyl, heterocycloalkaryl, aminoalkylamino, polyalkylamino, substituted silyl, an RNA cleaving group, a reporter group, an intercalator, a group for improving the pharmacokinetic properties of an guide nucleic acid, or a group for improving the pharmacodynamic properties of an guide nucleic acid, and other substituents having similar properties. A suitable modification can include 2'-methoxyethoxy (2'-O-CH2 CH2OCH3, also known as 2'-O-(2-methoxyethyl) or 2'-MOE i.e., an alkoxyalkoxy group). A further suitable modification can include 2'-dimethylaminooxyethoxy, (i.e., a O(CH2)2ON(CH3)2 group, also known as 2'-DMAOE), and 2'-dimethylaminoethoxyethoxy (also known as 2'-O-dimethyl-amino-ethoxy-ethyl or 2'-DMAEOE), i.e., 2'-O-CH2-O-CH2-N(CH3)2.

Other suitable sugar substituent groups can include methoxy (—O—CH3), aminopropoxy (—OCH2 CH2 CH2NH2), allyl (—CH2-CH=CH2), —O-allyl (—O—CH2-CH=CH2) and fluoro (F). 2'-sugar substituent groups may be in the arabino (up) position or ribo (down) position. A suitable 2'-arabino modification is 2'-F. Similar modifications may also be made at other positions on the oligomeric compound, particularly the 3' position of the sugar on the 3' terminal nucleoside or in 2'-5' linked nucleotides and the 5' position of 5' terminal nucleotide. Oligomeric compounds may also have sugar mimetics such as cyclobutyl moieties in place of the pentofuranosyl sugar.

A guide nucleic acid may also include nucleobase (often referred to simply as "base") modifications or substitutions. As used herein, "unmodified" or "natural" nucleobases can include the purine bases, (e.g. adenine (A) and guanine (G)), and the pyrimidine bases, (e.g. thymine (T), cytosine (C) and uracil (U)). Modified nucleobases can include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—CH3) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine. Modified nucleobases can include tricyclic pyrimidines such as phenoxazine cytidine(1H-pyrimido(5,4-b)(1,4)benzoxazin-2(3H)-one), phenothiazine cytidine (1H-pyrimido(5,4-b)(1,4)benzothiazin-2(3H)-one), G-clamps such as a substituted phenoxazine cytidine (e.g. 9-(2-aminoethoxy)-H-pyrimido(5,4-(b) (1,4)benzoxazin-2 (3H)-one), carbazole cytidine (2H-pyrimido(4,5-b)indol-2-one), pyridoindole cytidine (H¬pyrido(3',2':4,5)pyrrolo(2,3-d)pyrimidin-2-one).

Heterocyclic base moieties can include those in which the purine or pyrimidine base is replaced with other heterocycles, for example 7-deaza-adenine, 7-deazaguanosine, 2-aminopyridine and 2-pyridone. Nucleobases can be useful for increasing the binding affinity of a polynucleotide compound. These can include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions can increase nucleic acid duplex stability by 0.6-1.2° C. and can be suitable base substitutions (e.g., when combined with 2'-O-methoxyethyl sugar modifications).

A modification of a guide nucleic acid can comprise chemically linking to the guide nucleic acid one or more moieties or conjugates that can enhance the activity, cellular distribution or cellular uptake of the guide nucleic acid. These moieties or conjugates can include conjugate groups covalently bound to functional groups such as primary or secondary hydroxyl groups. Conjugate groups can include, but are not limited to, intercalators, reporter molecules, polyamines, polyamides, polyethylene glycols, polyethers, groups that enhance the pharmacodynamic properties of oligomers, and groups that can enhance the pharmacokinetic properties of oligomers. Conjugate groups can include, but are not limited to, cholesterols, lipids, phospholipids, biotin, phenazine, folate, phenanthridine, anthraquinone, acridine, fluoresceins, rhodamines, coumarins, and dyes. Groups that enhance the pharmacodynamic properties include groups that improve uptake, enhance resistance to degradation, and/or strengthen sequence-specific hybridization with the target nucleic acid. Groups that can enhance the pharmacokinetic properties include groups that improve uptake, distribution, metabolism or excretion of a nucleic acid. Conjugate moieties can include but are not limited to lipid moieties such as a cholesterol moiety, cholic acid a thioether, (e.g., hexyl-S-tritylthiol), a thiocholesterol, an aliphatic chain (e.g., dodecandiol or undecyl residues), a phospholipid (e.g., di-hexadecyl-rac-glycerol or triethylammonium 1,2-di-O-hexadecyl-rac-glycero-3-H-phosphonate), a polyamine or a polyethylene glycol chain, or adamantane acetic acid, a palmityl moiety, or an octadecylamine or hexylamino-carbonyl-oxycholesterol moiety.

A modification may include a "Protein Transduction Domain" or PTD (i.e. a cell penetrating peptide (CPP)). The PTD can refer to a polypeptide, polynucleotide, carbohydrate, or organic or inorganic compound that facilitates traversing a lipid bilayer, micelle, cell membrane, organelle membrane, or vesicle membrane. A PTD can be attached to another molecule, which can range from a small polar molecule to a large macromolecule and/or a nanoparticle, and can facilitate the molecule traversing a membrane, for example going from extracellular space to intracellular space, or cytosol to within an organelle. A PTD can be covalently linked to the amino terminus of a polypeptide. A PTD can be covalently linked to the carboxyl terminus of a polypeptide. A PTD can be covalently linked to a nucleic acid. Exemplary PTDs can include, but are not limited to, a minimal peptide protein transduction domain; a polyarginine sequence comprising a number of arginines sufficient to direct entry into a cell (e.g., 3, 4, 5, 6, 7, 8, 9, 10, or 10-50 arginines), a VP22 domain, a Drosophila Antennapedia protein transduction domain, a truncated human calcitonin peptide, polylysine, and transportan, arginine homopolymer of from 3 arginine residues to 50 arginine residues. The PTD can be an activatable CPP (ACPP). ACPPs can comprise a polycationic CPP (e.g., Arg9 or "R9") connected via a cleavable linker to a matching polyanion (e.g., Glu9 or "E9"), which can reduce the net charge to nearly zero and thereby inhibits adhesion and uptake into cells. Upon cleavage of the linker, the polyanion can be released, locally unmasking the polyarginine and its inherent adhesiveness, thus "activating" the ACPP to traverse the membrane.

Guide nucleic acids can be provided in any form. For example, the guide nucleic acid can be provided in the form of RNA, either as two molecules (e.g., separate crRNA and tracrRNA) or as one molecule (e.g., sgRNA). The guide nucleic acid can be provided in the form of a complex with a Cas protein. The guide nucleic acid can also be provided in the form of DNA encoding the RNA. The DNA encoding the guide nucleic acid can encode a single guide nucleic acid (e.g., sgRNA) or separate RNA molecules (e.g., separate crRNA and tracrRNA). In the latter case, the DNA encoding the guide nucleic acid can be provided as separate DNA molecules encoding the crRNA and tracrRNA, respectively.

DNAs encoding guide nucleic acid can be stably integrated in the genome of the cell and, optionally, operably linked to a promoter active in the cell. DNAs encoding guide nucleic acids can be operably linked to a promoter in an expression construct.

Guide nucleic acids can be prepared by any suitable method. For example, guide nucleic acids can be prepared by in vitro transcription using, for example, T7 RNA polymerase. Guide nucleic acids can also be a synthetically produced molecule prepared by chemical synthesis.

A guide nucleic acid can comprise a sequence for increasing stability. For example, a guide nucleic acid can comprise a transcriptional terminator segment (i.e., a transcription termination sequence). A transcriptional terminator segment can have a total length of from about 10 nucleotides to about 100 nucleotides, e.g., from about 10 nucleotides (nt) to about 20 nt, from about 20 nt to about 30 nt, from about 30 nt to about 40 nt, from about 40 nt to about 50 nt, from about 50 nt to about 60 nt, from about 60 nt to about 70 nt, from about 70 nt to about 80 nt, from about 80 nt to about 90 nt, or from about 90 nt to about 100 nt. For example, the transcriptional terminator segment can have a length of from about 15 nucleotides (nt) to about 80 nt, from about 15 nt to about 50 nt, from about 15 nt to about 40 nt, from about 15 nt to about 30 nt or from about 15 nt to about 25 nt. The transcription termination sequence can be functional in a eukaryotic cell or a prokaryotic cell.

The various domains of chimeric receptor polypeptides and adaptor polypeptides disclosed herein (e.g., antigen interacting domains, immune cell signaling domains (e.g., primary signaling domains and co-stimulatory domains), receptor binding moiety, actuator moiety, cleavage moiety etc) can be linked by means of chemical bond, e.g., an amide bond or a disulfide bond; a small, organic molecule (e.g., a hydrocarbon chain); an amino acid sequence such as a peptide linker (e.g., an amino acid sequence about 3-200 amino acids in length), or a combination of a small, organic molecule and peptide linker. Peptide linkers can provide desirable flexibility to permit the desired expression, activity and/or conformational positioning of the chimeric polypeptide. The peptide linker can be of any appropriate length to connect at least two domains of interest and is preferably designed to be sufficiently flexible so as to allow the proper folding and/or function and/or activity of one or both of the domains it connects. The peptide linker can have a length of at least 3, 5, 10, 15, 20, 25, 30, 35, 40, 45, 50, 55, 60, 65, 70, 75, 80, 85, 90, 95, or 100 amino acids. In some embodiments, a peptide linker has a length between about 0 and 200 amino acids, between about 10 and 190 amino acids, between about 20 and 180 amino acids, between about 30 and 170 amino acids, between about 40 and 160 amino acids, between about 50 and 150 amino acids, between about 60 and 140 amino acids, between about 70 and 130 amino acids, between about 80 and 120 amino acids, between about 90 and 110 amino acids. In some embodiments, the linker sequence can comprise an endogenous protein sequence. In some embodiments, the linker sequence comprises glycine, alanine and/or serine amino acid residues. In some embodiments, a linker can contain motifs, e.g., multiple or repeating motifs, of GS, GGS, GGGGS, GGSG, or SGGG. The linker sequence can include any naturally occurring amino acids, non-naturally occurring amino acids, or combinations thereof.

In various embodiments of the aspects herein, a subject system is expressed in a cell or cell population. Cells, for example immune cells (e.g., lymphocytes including T cells and NK cells), can be obtained from a subject. Non-limiting examples of subjects include humans, dogs, cats, mice, rats, and transgenic species thereof. Examples of samples from a subject from which cells can be derived include, without limitation, skin, heart, lung, kidney, bone marrow, breast, pancreas, liver, muscle, smooth muscle, bladder, gall bladder, colon, intestine, brain, prostate, esophagus, thyroid, serum, saliva, urine, gastric and digestive fluid, tears, stool, semen, vaginal fluid, interstitial fluids derived from tumorous tissue, ocular fluids, sweat, mucus, earwax, oil, glandular secretions, spinal fluid, hair, fingernails, plasma, nasal swab or nasopharyngeal wash, spinal fluid, cerebral spinal fluid, tissue, throat swab, biopsy, placental fluid, amniotic fluid, cord blood, emphatic fluids, cavity fluids, sputum, pus, microbiota, meconium, breast milk, and/or other excretions or body tissues.

In various embodiments of the aspects herein, an immune cell comprises a lymphocyte. In some embodiments, the lymphocyte is a natural killer cell (NK cell). In some embodiments, the lymphocyte is a T cell. T cells can be obtained from a number of sources, including peripheral blood mononuclear cells, bone marrow, lymph node tissue, spleen tissue, umbilical cord, and tumors. In some embodiments, any number of T cell lines available can be used. Immune cells such as lymphocytes (e.g., cytotoxic lymphocytes) can preferably be autologous cells, although heterologous cells can also be used. T cells can be obtained from a unit of blood collected from a subject using any number of techniques, such as Ficoll separation. Cells from the circulating blood of an individual can be obtained by apheresis or leukapheresis. The apheresis product typically contains lymphocytes, including T cells, monocytes, granulocytes, B cells, other nucleated white blood cells, red blood cells, and platelets. The cells collected by apheresis can be washed to remove the plasma fraction and to place the cells in an appropriate buffer or media, such as phosphate buffered saline (PBS), for subsequent processing steps. After washing, the cells can be resuspended in a variety of biocompatible buffers, such as Ca-free, Mg-free PBS. Alternatively, the undesirable components of the apheresis sample can be removed and the cells directly resuspended in culture media. Samples can be provided directly by the subject, or indirectly through one or more intermediaries, such as a sample collection service provider or a medical provider (e.g. a physician or nurse). In some embodiments, isolating T cells from peripheral blood leukocytes can include lysing the red blood cells and separating peripheral blood leukocytes from monocytes by, for example, centrifugation through, e.g., a PERCOL™ gradient.

A specific subpopulation of T cells, such as CD4+ or CD8+ T cells, can be further isolated by positive or negative selection techniques. Negative selection of a T cell population can be accomplished, for example, with a combination of antibodies directed to surface markers unique to the cells negatively selected. One suitable technique includes cell sorting via negative magnetic immunoadherence, which utilizes a cocktail of monoclonal antibodies directed to cell surface markers present on the cells negatively selected. For example, to isolate CD4+ cells, a monoclonal antibody cocktail can include antibodies to CD14, CD20, CD11b, CD16, HLA-DR, and CD8. The process of negative selection can be used to produce a desired T cell population that is primarily homogeneous. In some embodiments, a composition comprises a mixture of two or more (e.g. 2, 3, 4, 5, or more) different kind of T-cells.

In some embodiments, the immune cell is a member of an enriched population of cells. One or more desired cell types can be enriched by any suitable method, non-limiting examples of which include treating a population of cells to trigger expansion and/or differentiation to a desired cell type, treatment to stop the growth of undesired cell type(s), treatment to kill or lyse undesired cell type(s), purification of a desired cell type (e.g. purification on an affinity column to retain desired or undesired cell types on the basis of one or more cell surface markers). In some embodiments, the enriched population of cells is a population of cells enriched in cytotoxic lymphocytes selected from cytotoxic T cells (also variously known as cytotoxic T lymphocytes, CTLs, T killer cells, cytolytic T cells, CD8+ T cells, and killer T cells), natural killer (NK) cells, and lymphokine-activated killer (LAK) cells.

For isolation of a desired population of cells by positive or negative selection, the concentration of cells and surface (e.g., particles such as beads) can be varied. In certain embodiments, it can be desirable to significantly decrease the volume in which beads and cells are mixed together (i.e., increase the concentration of cells), to ensure maximum contact of cells and beads. For example, a concentration of 2 billion cells/mL can be used. In some embodiments, a concentration of 1 billion cells/mL is used. In some embodiments, greater than 100 million cells/mL are used. A concentration of cells of 10, 15, 20, 25, 30, 35, 40, 45, or 50 million cells/mL can be used. In yet another embodiment, a concentration of cells from 75, 80, 85, 90, 95, or 100 million cells/mL can be used. In further embodiments, concentrations of 125 or 150 million cells/mL can be used. Using high concentrations can result in increased cell yield, cell activation, and cell expansion.

A cell, e.g., an immune cell, can be transiently or non-transiently transfected with one or more vectors described herein. A cell can be transfected as it naturally occurs in a subject. A cell can be taken or derived from a subject and transfected. A cell can be derived from cells taken from a subject, such as a cell line. In some embodiments, a cell transfected with one or more vectors described herein is used to establish a new cell line comprising one or more vector-derived sequences. In some embodiments, a cell transiently transfected with the various components of a subject system (such as by transient transfection of one or more vectors, or transfection with RNA), and modified through the activity of a CRISPR complex, is used to establish a new cell line comprising cells containing the modification but lacking any other exogenous sequence.

In an aspect, the present disclosure provides a population of immune cells, for example lymphocytes, in which individual immune cells express a system disclosed herein. The population of immune cells can be characterized in that upon exposing the population of immune cells to a target cell population in an in vitro cell death assay, the population of lymphocytes induces death of the target cells. In some cases, the population of lymphocytes induces death of at least 40%, 45%, 50%, 55%, 60%, 65%, 70%, 75%, 80%, 85%, 90%, or 95% of the target cells. In some cases, the population of lymphocytes induces death of the target cells within about 4 hours, 8 hours, 16 hours, 1 day, 2 days, 3 days, 4 days, 5 days, 6 days, 1 week, 2 weeks, 3 weeks, or 4 weeks. In some cases, the population of lymphocytes induces death of at least 10%, 15%, 20%, 25%, 30%, 35%, 40%, 45%, 50%, 55%, 60%, 65%, 70%, 75%, 80%, 85%, 90%, or 95% of the target cells withing about 1 day. In some cases, the population of lymphocytes induces death of at least 10%, 15%, 20%, 25%, 30%, 35%, 40%, 45%, 50%, 55%, 60%, 65%, 70%, 75%, 80%, 85%, 90%, or 95% of the target cells withing about 2 days. In some cases, the population of lymphocytes induces death of at least 10%, 15%, 20%, 25%, 30%, 35%, 40%, 45%, 50%, 55%, 60%, 65%, 70%, 75%, 80%, 85%, 90%, or 95% of the target cells withing about 5 days. In some cases, the population of lymphocytes induces death of at least 10%, 15%, 20%, 25%, 30%, 35%, 40%, 45%, 50%, 55%, 60%, 65%, 70%, 75%, 80%, 85%, 90%, or 95% of the target cells withing about 1 week. In some cases, the population of lymphocytes induces death of at least 10%, 15%, 20%, 25%, 30%, 35%, 40%, 45%, 50%, 55%, 60%, 65%, 70%, 75%, 80%, 85%, 90%, or 95% of the target cells withing about 2 weeks. In some cases, the population of lymphocytes induces death of at least 10%, 15%, 20%, 25%, 30%, 35%, 40%, 45%, 50%, 55%, 60%, 65%, 70%, 75%, 80%, 85%, 90%, or 95% of the target cells withing about 3 weeks. In some cases, the population of lymphocytes induces death of at least 10%, 15%, 20%, 25%, 30%, 35%, 40%, 45%, 50%, 55%, 60%, 65%, 70%, 75%, 80%, 85%, 90%, or 95% of the target cells withing about 4 weeks. In some cases, the population of lymphocytes induces death of at least 45% of the target cells withing about 1 day. In some cases, the population of lymphocytes induces death of at least 45% of the target cells withing about 2 days. The ratio of the number of lymphocyte cells in the population of lymphocytes to the number of target cells in the target cell population can be about 5 to 1, 4 to 1, 3 to 1, 2 to 1, 1 to 1, 1 to 2, 1 to 3, 1 to 4, 1 to 5, 1 to 10, 1 to 100, 1 to 1000 or less. In some embodiments, the amount of cell death induced by the lymphocytes is about or more than about 2-fold, 3-fold, 4-fold, 5-fold, 6-fold, 7-fold, 8-fold, 9-fold, 10-fold, 15-fold, 20-fold, 25-fold, 50-fold, 75-fold, 100-fold, 200-fold, 250-fold, 500-fold, 1000-fold or greater than the amount of cell death induced by a population of lymphocytes expressing a system lacking an actuator moiety capable of modulating expression and activity of an immune regulatory protein.

In an aspect, the present disclosure provides a population of immune cells, for example lymphocytes, in which individual immune cells express a system disclosed herein. The population of immune cells can be characterized in that upon exposing the population of immune cells to a target cell population, for example in an in vitro cell death assay, the population of lymphocytes induces death of the target cells. In some embodiments, individual lymphocytes of the population exhibit an enhanced ability to induce death of the target cell compared to a control lymphocyte. The control lymphocyte can be a lymphocyte in which expression and/or activity of the immune regulatory protein is not modulated. In some embodiments, the control lymphocyte is a lymphocyte lacking a system of the present disclosure. For example, the control lymphocyte may be an unmodified lymphocyte or a lymphocyte transfected and/or transduced with an empty plasmid vector. In some embodiments, the control lymphocyte is a lymphocyte expressing an incomplete system of the present disclosure, e.g., lacking one or more components of a system provided herein. For example, the control lymphocyte may express a system lacking at least one of a chimeric transmembrane receptor polypeptide and a chimeric adaptor polypeptide. In some cases, the control lymphocyte may express both a chimeric transmembrane receptor polypeptide and a chimeric adaptor polypeptide, but the chimeric transmembrane receptor polypeptide may lack at least one of the ligand binding domain, the immune cell signaling domain, the actuator moiety, and the cleavage recognition site. In some cases, the control lymphocyte may express both a chimeric transmembrane receptor polypeptide and a chimeric adaptor polypeptide, but the chimeric adaptor polypeptide may lack at least one of the receptor binding moiety and the cleavage moiety. In some embodiments, the control lymphocyte is a lymphocyte expressing a system of the present disclosure, but at least one of the components of the system is non-functional. For example, the control lymphocyte may express a system provided herein, but at least one of the chimeric transmembrane receptor polypeptide and the chimeric adaptor polypeptide may be non-functional. In some cases, the control lymphocyte may express a system in which the ligand binding domain of the transmembrane receptor is unable to bind a ligand, the immune cell signaling domain of the transmembrane receptor lacks signaling activity, the actuator moiety is unable to modulate expression and/or activity of the regulatory protein, and/or the cleavage recognition site is unable to be cleaved by a cleavage moiety. In some cases, the control lymphocyte may express a system in which the receptor binding moiety of the chimeric adaptor polypeptide is unable to bind the receptor, e.g., in response to binding of the ligand to the ligand binding domain, and/or the cleavage moiety is unable to cleave the cleavage recognition site. In an example, the cleavage moiety of a control lymphocyte may lack cleavage activity. In another example, the cleavage recognition site of a control lymphocyte is unable to be cleaved by the cleavage moiety. In another example, the receptor binding moiety is unable to bind the receptor polypeptide. In another example, an actuator moiety is unable to modulate expression and/or activity of the immune regulatory protein. This may occur if, for example, the actuator moiety comprises a polynucleotide-guided endonuclease but the system lacks a guide polynucleotide. For instance, in a control lymphocyte, the actuator moiety may comprise a Cas protein lacking a guideRNA (gRNA). In some cases, the control lymphocyte may comprise an actuator moiety complexed with a non-targeting gRNA or non-specific gRNA.

In some cases, the enhanced ability to induce death of the target cell is at least a 1.1-fold, 1.2-fold, 1.3-fold, 1.4-fold, 1.5-fold, 1.6-fold, 1.7-fold, 1.8-fold, 1.9-fold, 2.0-fold, 2.5-fold, 3.0-fold, 3.5-fold, 4.0-fold, 5-fold, 10-fold, 100-fold, or 1000-fold increase in induced cell death. The degree of induced cell death can be determined at any suitable time point, for example, at least 4 hours, 6 hours, 8 hours, 12 hours, 16 hours, 24 hours, 36 hours, 48 hours, or 52 hours after contacting the lymphocyte to the target cell.

Cell death may be determined by any suitable method, including, but not limited to, counting cells before and after exposing, or measuring the level of a marker associated with live or dead cells (e.g. live or dead target cells). Degree of cell death may be determined by any suitable method. In some embodiments, degree of cell death is determined with respect to a starting condition. In such cases, degree of cell death may be expressed as a ratio of surviving cells after treatment to the starting cell population. In some embodiments, degree of cell death may be determined by a suitable cell death assay. A variety of cell death assays are available, and may utilize a variety of detection methodologies. Example of detection methodologies include, without limitation, the use of cell staining, microscopy, flow cytometry, cell sorting, and combinations of these.

Any suitable method may be used to compare degree of cell death induced by one cell population with respect to another (e.g. expressing a system herein, with or without an actuator moiety capable of modulating the activity and expression of an immune regulatory protein).

Any suitable delivery method can be used for introducing compositions and molecules (e.g., polypeptides and/or nucleic acid encoding polypeptides) of the disclosure into a host cell, such as an immune cell. The various components of a subject system can be delivered simultaneously or temporally separated. In some embodiments, an actuator moiety comprising a Cas protein and/or chimeric receptor and/or adaptor, in combination with, and optionally complexed with, a guide sequence is delivered to a cell, e.g., an immune cell. The choice of method can be dependent on the type of cell being transformed and/or the circumstances under which the transformation is taking place (e.g., in vitro, ex vivo, or in vivo).

Cells expressing the various components of the system can be optionally enriched, for example by cell sorting. In some embodiments, various components of the system can be labeled with detectable tags, for example fluorescent tags (e.g., fluorescent proteins). Cells expressing the various components of the system can be sorted by detecting the tags, for example by flow cytometry. Different components of the system can be labeled with unique detectable tags, for example fluorescent tags having different fluorescent properties (e.g., wavelengths).

A method of delivery can involve contacting a target polynucleotide or introducing into a cell (or a population of cells such as immune cells) one or more nucleic acids comprising nucleotide sequences encoding the compositions of the disclosure (e.g., actuator moiety such as Cas protein or Cas chimera, chimeric receptor, chimeric adaptor, guide nucleic acid, etc). Suitable nucleic acids comprising nucleotide sequences encoding the compositions of the disclosure can include expression vectors, where an expression vector comprising a nucleotide sequence encoding one or more compositions of the disclosure (e.g., actuator moiety such as Cas protein or Cas chimera, chimeric receptor, chimeric adaptor, guide nucleic acid, etc) is a recombinant expression vector.

Non-limiting examples of delivery methods or transformation include, for example, viral or bacteriophage infection, transfection, conjugation, protoplast fusion, lipofection, electroporation, calcium phosphate precipitation, polyethyleneimine (PEI)-mediated transfection, DEAE-dextran mediated transfection, liposome-mediated transfection, particle gun technology, calcium phosphate precipitation, direct micro injection, and nanoparticle-mediated nucleic acid delivery.

In some aspects, the present disclosure provides methods comprising delivering one or more polynucleotides, or one or more vectors as described herein, or one or more transcripts thereof, and/or one or proteins transcribed therefrom, to a host cell. In some aspects, the disclosure further provides cells produced by such methods, and organisms (such as animals, plants, or fungi) comprising or produced from such cells. In some embodiments, a Cas protein and/or chimeric receptor and/or adaptor, in combination with, and optionally complexed with, a guide sequence is delivered to a cell.

Conventional viral and non-viral based gene transfer methods can be used to introduce nucleic acids in mammalian cells or target tissues. Such methods can be used to administer nucleic acids encoding compositions of the disclosure to cells in culture, or in a host organism. Non-viral vector delivery systems can include DNA plasmids, RNA (e.g. a transcript of a vector described herein), naked nucleic acid, and nucleic acid complexed with a delivery vehicle, such as a liposome. Viral vector delivery systems can include DNA and RNA viruses, which can have either episomal or integrated genomes after delivery to the cell.

Methods of non-viral delivery of nucleic acids can include lipofection, nucleofection, microinjection, biolistics, virosomes, liposomes, immunoliposomes, polycation or lipid:nucleic acid conjugates, naked DNA, artificial virions, and agent-enhanced uptake of DNA. Cationic and neutral lipids that are suitable for efficient receptor-recognition lipofection of polynucleotides can be used. Delivery can be to cells (e.g. in vitro or ex vivo administration) or target tissues (e.g. in vivo administration). The preparation of lipid:nucleic acid complexes, including targeted liposomes such as immunolipid complexes, can be used.

RNA or DNA viral based systems can be used to target specific cells in the body and trafficking the viral payload to the nucleus of the cell. Viral vectors can be administered directly (in vivo) or they can be used to treat cells in vitro, and the modified cells can optionally be administered (ex vivo). Viral based systems can include retroviral, lentivirus, adenoviral, adeno-associated and herpes simplex virus vectors for gene transfer. Integration in the host genome can occur with the retrovirus, lentivirus, and adeno-associated virus gene transfer methods, which can result in long term expression of the inserted transgene. High transduction efficiencies can be observed in many different cell types and target tissues.

The tropism of a retrovirus can be altered by incorporating foreign envelope proteins, expanding the potential target population of target cells. Lentiviral vectors are retroviral vectors that can transduce or infect non-dividing cells and produce high viral titers. Selection of a retroviral gene transfer system can depend on the target tissue. Retroviral vectors can comprise cis-acting long terminal repeats with packaging capacity for up to 6-10 kb of foreign sequence. The minimum cis-acting LTRs can be sufficient for replication and packaging of the vectors, which can be used to integrate the therapeutic gene into the target cell to provide permanent transgene expression. Retroviral vectors can include those based upon murine leukemia virus (MuLV), gibbon ape leukemia virus (GaLV), Simian Immuno deficiency virus (SIV), human immuno deficiency virus (HIV), and combinations thereof.

An adenoviral-based systems can be used. Adenoviral-based systems can lead to transient expression of the transgene. Adenoviral based vectors can have high transduction efficiency in cells and may not require cell division. High titer and levels of expression can be obtained with adenoviral based vectors. Adeno-associated virus ("AAV") vectors can be used to transduce cells with target nucleic acids, e.g., in the in vitro production of nucleic acids and peptides, and for in vivo and ex vivo gene therapy procedures.

Packaging cells can be used to form virus particles capable of infecting a host cell. Such cells can include 293 cells, (e.g., for packaging adenovirus), and Psi2 cells or PA317 cells (e.g., for packaging retrovirus). Viral vectors can be generated by producing a cell line that packages a nucleic acid vector into a viral particle. The vectors can contain the minimal viral sequences required for packaging and subsequent integration into a host. The vectors can contain other viral sequences being replaced by an expression cassette for the polynucleotide(s) to be expressed. The missing viral functions can be supplied in trans by the packaging cell line. For example, AAV vectors can comprise ITR sequences from the AAV genome which are required for packaging and integration into the host genome. Viral DNA can be packaged in a cell line, which can contain a helper plasmid encoding the other AAV genes, namely rep and cap, while lacking ITR sequences. The cell line can also be infected with adenovirus as a helper. The helper virus can promote replication of the AAV vector and expression of AAV genes from the helper plasmid. Contamination with adenovirus can be reduced by, e.g., heat treatment to which adenovirus is more sensitive than AAV. Additional methods for the delivery of nucleic acids to cells can be used, for example, as described in US20030087817, incorporated herein by reference.

A host cell can be transiently or non-transiently transfected with one or more vectors described herein. A cell can be transfected as it naturally occurs in a subject. A cell can be taken or derived from a subject and transfected. A cell can be derived from cells taken from a subject, such as a cell line. In some embodiments, a cell transfected with one or more vectors described herein is used to establish a new cell line comprising one or more vector-derived sequences. In some embodiments, a cell transiently transfected with the compositions of the disclosure (such as by transient transfection of one or more vectors, or transfection with RNA), and modified through the activity of a an actuator moiety such as a CRISPR complex, is used to establish a new cell line comprising cells containing the modification but lacking any other exogenous sequence.

Any suitable vector compatible with the host cell can be used with the methods of the disclosure. Non-limiting examples of vectors for eukaryotic host cells include pXT1, pSG5 (Stratagene™), pSVK3, pBPV, pMSG, and pSVLSV40 (Pharmacia™).

In some embodiments, a nucleotide sequence encoding a guide nucleic acid and/or Cas protein or chimera is operably linked to a control element, e.g., a transcriptional control element, such as a promoter. The transcriptional control element can be functional in either a eukaryotic cell, e.g., a mammalian cell, or a prokaryotic cell (e.g., bacterial or archaeal cell). In some embodiments, a nucleotide sequence encoding a guide nucleic acid and/or a Cas protein or chimera is operably linked to multiple control elements that allow expression of the nucleotide sequence encoding a guide nucleic acid and/or a Cas protein or chimera in prokaryotic and/or eukaryotic cells.

Depending on the host/vector system utilized, any of a number of suitable transcription and translation control elements, including constitutive and inducible promoters, transcription enhancer elements, transcription terminators, etc. may be used in the expression vector (e.g., U6 promoter, H1 promoter, etc.; see above) (see e.g., Bitter et al. (1987) Methods in Enzymology, 153:516-544).

In some embodiments, compositions of the disclosure (e.g., actuator moiety such as a Cas protein or Cas chimera, chimeric receptor, chimeric adaptor, guide nucleic acid, etc) can be provided as RNA. In such cases, the compositions of the disclosure (e.g., actuator moiety such as a Cas protein or Cas chimera, chimeric receptor, adaptor, guide nucleic acid, etc) can be produced by direct chemical synthesis or may be transcribed in vitro from a DNA. The compositions of the disclosure (e.g., actuator moiety such as a Cas protein or Cas chimera, chimeric receptor, adaptor, guide nucleic acid, etc) can be synthesized in vitro using an RNA polymerase enzyme (e.g., T7 polymerase, T3 polymerase, SP6 polymerase, etc.). Once synthesized, the RNA can directly contact a target DNA or can be introduced into a cell using any suitable technique for introducing nucleic acids into cells (e.g., microinjection, electroporation, transfection, etc).

Nucleotides encoding a guide nucleic acid (introduced either as DNA or RNA) and/or a Cas protein or chimera (introduced as DNA or RNA) can be provided to the cells using a suitable transfection technique; see, e.g. Angel and Yanik (2010) PLoS ONE 5(7): e11756, and the commercially available TransMessenger® reagents from Qiagen, Stemfect™ RNA Transfection Kit from Stemgent, and TransIT®-mRNA Transfection Kit from Minis Bio LLC. See also Beumer et al. (2008) Efficient gene targeting in *Drosophila* by direct embryo injection with zinc-finger nucleases. PNAS 105(50):19821-19826. Nucleic acids encoding the compositions of the disclosure (e.g., actuator moiety such as a Cas protein or Cas chimera, chimeric receptor, adaptor, guide nucleic acid, etc) may be provided on DNA vectors. Many vectors, e.g. plasmids, cosmids, minicircles, phage, viruses, etc., useful for transferring nucleic acids into target cells are available. The vectors comprising the nucleic acid(s) can be maintained episomally, e.g. as plasmids, minicircle DNAs, viruses such cytomegalovirus, adenovirus, etc., or they may be integrated into the target cell genome, through homologous recombination or random integration, e.g. retrovirus-derived vectors such as MMLV, HIV-1, and ALV.

An actuator moiety such as a Cas protein or chimera, chimeric receptor, and/or adaptor can be provided to cells as a polypeptide. Such a protein may optionally be fused to a polypeptide domain that increases solubility of the product. The domain may be linked to the polypeptide through a defined protease cleavage site, e.g. a TEV sequence, which is cleaved by TEV protease. The linker may also include one or more flexible sequences, e.g. from 1 to 10 glycine residues. In some embodiments, the cleavage of the fusion protein is performed in a buffer that maintains solubility of the product, e.g. in the presence of from 0.5 to 2 M urea, in the presence of polypeptides and/or polynucleotides that increase solubility, and the like. Domains of interest include endosomolytic domains, e.g. influenza HA domain; and other polypeptides that aid in production, e.g. IF2 domain, GST domain, GRPE domain, and the like. The polypeptide may be formulated for improved stability. For example, the peptides may be PEGylated, where the polyethyleneoxy group provides for enhanced lifetime in the blood stream.

The compositions of the disclosure (e.g., actuator moiety such as a Cas protein or Cas chimera, chimeric receptor, chimeric adaptor, guide nucleic acid, etc) may be fused to a polypeptide permeant domain to promote uptake by the cell. A number of permeant domains can be used in the non-integrating polypeptides of the present disclosure, including peptides, peptidomimetics, and non-peptide carriers. For example, a permeant peptide may be derived from the third alpha helix of *Drosophila melanogaster* transcription factor Antennapaedia, referred to as penetratin, which comprises the amino acid sequence RQIKIWFQNRRMKWKK. As another example, the permeant peptide can comprise the HIV-1 tat basic region amino acid sequence, which may include, for example, amino acids 49-57 of naturally-occurring tat protein. Other permeant domains include poly-arginine motifs, for example, the region of amino acids 34-56 of HIV-1 rev protein, nona-arginine, octa-arginine, and the like. (See, for example, Futaki et al. (2003) Curr Protein Pept Sci. 2003 April; 4(2): 87-9 and 446; and Wender et al. (2000) Proc. Natl. Acad. Sci. U.S.A 2000 Nov. 21; 97(24):13003-8; published U.S. Patent applications 20030220334; 20030083256; 20030032593; and 20030022831, herein specifically incorporated by reference for the teachings of translocation peptides and peptoids). The nona-arginine (R9) sequence can be used. (Wender et al. 2000; Uemura et al. 2002). The site at which the fusion is made may be selected in order to optimize the biological activity, secretion or binding characteristics of the polypeptide.

The compositions of the disclosure (e.g., an actuator moiety such as a Cas protein or Cas chimera, chimeric receptor, adaptor, guide nucleic acid, etc) may be produced in vitro or by eukaryotic cells or by prokaryotic cells, and it may be further processed by unfolding, e.g. heat denaturation, DTT reduction, etc. and may be further refolded.

The compositions of the disclosure (e.g., an actuator moiety such as a Cas protein or Cas chimera, chimeric receptor, adaptor, guide nucleic acid, etc) may be prepared by in vitro synthesis. Various commercial synthetic apparatuses can be used, for example, automated synthesizers by Applied Biosystems, Inc., Beckman, etc. By using synthesizers, naturally occurring amino acids can be substituted with unnatural amino acids. The particular sequence and the manner of preparation can be determined by convenience, economics, purity required, and the like.

The compositions of the disclosure (e.g., an actuator moiety such as a Cas protein or Cas chimera, chimeric receptor, adaptor, guide nucleic acid, etc) may also be isolated and purified in accordance with conventional methods of recombinant synthesis. A lysate may be prepared of the expression host and the lysate purified using HPLC, exclusion chromatography, gel electrophoresis, affinity chromatography, or other purification technique. The compositions can comprise, for example, at least 20% by weight of the desired product, at least about 75% by weight, at least about 95% by weight, and for therapeutic purposes, for example, at least about 99.5% by weight, in relation to contaminants related to the method of preparation of the product and its purification. The percentages can be based upon total protein.

The compositions of the disclosure (e.g., an actuator moiety such as a Cas protein or Cas chimera, chimeric receptor, adaptor, guide nucleic acid, etc), whether introduced as nucleic acids or polypeptides, can be provided to the cells for about 30 minutes to about 24 hours, e.g., 1 hour, 1.5 hours, 2 hours, 2.5 hours, 3 hours, 3.5 hours 4 hours, 5 hours, 6 hours, 7 hours, 8 hours, 12 hours, 16 hours, 18 hours, 20 hours, or any other period from about 30 minutes to about 24 hours, which can be repeated with a frequency of about every day to about every 4 days, e.g., every 1.5 days, every 2 days, every 3 days, or any other frequency from about every day to about every four days. The compositions may be provided to the subject cells one or more times, e.g. one time, twice, three times, or more than three times, and the cells allowed to incubate with the agent(s) for some amount of time following each contacting event e.g. 16-24 hours, after which time the media can be replaced with fresh media and the cells can be cultured further.

In cases in which two or more different targeting complexes are provided to the cell (e.g., two different guide nucleic acids that are complementary to different sequences within the same or different target DNA), the complexes may be provided simultaneously (e.g. as two polypeptides and/or nucleic acids), or delivered simultaneously. Alternatively, they may be provided consecutively, e.g. the targeting complex being provided first, followed by the second targeting complex, etc. or vice versa.

An effective amount of the compositions of the disclosure (e.g., actuator moiety such as Cas protein or Cas chimera, chimeric receptor, adaptor, guide nucleic acid, etc) can be provided to the target DNA or cells. An effective amount can be the amount to induce, for example, at least about a 2-fold change (increase or decrease) or more in the amount of target regulation observed between two homologous sequences relative to a negative control, e.g. a cell contacted with an empty vector or irrelevant polypeptide. An effective amount or dose can induce, for example, about 2-fold change, about 3-fold change, about 4-fold change, about a 7-fold, about 8-fold increase, about 10-fold, about 50-fold, about 100-fold, about 200-fold, about 500-fold, about 700-fold, about 1000-fold, about 5000-fold, or about 10.000-fold change in target gene regulation. The amount of target gene regulation may be measured by any suitable method.

Contacting the cells with a composition of the can occur in any culture media and under any culture conditions that promote the survival of the cells. For example, cells may be suspended in any appropriate nutrient medium that is convenient, such as Iscove's modified DMEM or RPMI 1640, supplemented with fetal calf serum or heat inactivated goat serum (about 5-10%), L-glutamine, a thiol, particularly 2-mercaptoethanol, and antibiotics, e.g. penicillin and streptomycin. The culture may contain growth factors to which the cells are responsive. Growth factors, as defined herein, are molecules capable of promoting survival, growth and/or differentiation of cells, either in culture or in the intact tissue, through specific effects on a transmembrane receptor. Growth factors can include polypeptides and non-polypeptide factors.

In numerous embodiments, the chosen delivery system is targeted to specific tissue or cell types. In some cases, tissue- or cell-targeting of the delivery system is achieved by binding the delivery system to tissue- or cell-specific markers, such as cell surface proteins. Viral and non-viral delivery systems can be customized to target tissue or cell-types of interest.

Pharmaceutical compositions containing molecules (e.g., polypeptides and/or nucleic acids encoding polypeptides) or immune cells described herein can be administered for prophylactic and/or therapeutic treatments. In therapeutic applications, the compositions can be administered to a subject already suffering from a disease or condition, in an amount sufficient to cure or at least partially arrest the symptoms of the disease or condition, or to cure, heal, improve, or ameliorate the condition. Amounts effective for this use can vary based on the severity and course of the disease or condition, previous therapy, the subject's health status, weight, and response to the drugs, and the judgment of the treating physician.

Multiple therapeutic agents can be administered in any order or simultaneously. If simultaneously, the multiple therapeutic agents can be provided in a single, unified form, or in multiple forms, for example, as multiple separate pills. The molecules can be packed together or separately, in a single package or in a plurality of packages. One or all of the therapeutic agents can be given in multiple doses. If not simultaneous, the timing between the multiple doses may vary to as much as about a month.

Molecules described herein can be administered before, during, or after the occurrence of a disease or condition, and the timing of administering the composition containing a compound can vary. For example, the pharmaceutical compositions can be used as a prophylactic and can be administered continuously to subjects with a propensity to conditions or diseases in order to prevent the occurrence of the disease or condition. The molecules and pharmaceutical compositions can be administered to a subject during or as soon as possible after the onset of the symptoms. The administration of the molecules can be initiated within the first 48 hours of the onset of the symptoms, within the first 24 hours of the onset of the symptoms, within the first 6 hours of the onset of the symptoms, or within 3 hours of the onset of the symptoms. The initial administration can be via any route practical, such as by any route described herein using any formulation described herein. A molecule can be administered as soon as is practicable after the onset of a disease or condition is detected or suspected, and for a length of time necessary for the treatment of the disease, such as, for example, from about 1 month to about 3 months. The length of treatment can vary for each subject.

A molecule can be packaged into a biological compartment. A biological compartment comprising the molecule can be administered to a subject. Biological compartments can include, but are not limited to, viruses (lentivirus, adenovirus), nanospheres, liposomes, quantum dots, nanoparticles, microparticles, nanocapsules, vesicles, polyethylene glycol particles, hydrogels, and micelles.

For example, a biological compartment can comprise a liposome. A liposome can be a self-assembling structure comprising one or more lipid bilayers, each of which can comprise two monolayers containing oppositely oriented amphipathic lipid molecules. Amphipathic lipids can comprise a polar (hydrophilic) headgroup covalently linked to one or two or more non-polar (hydrophobic) acyl or alkyl chains. Energetically unfavorable contacts between the hydrophobic acyl chains and a surrounding aqueous medium induce amphipathic lipid molecules to arrange themselves such that polar headgroups can be oriented towards the bilayer's surface and acyl chains are oriented towards the interior of the bilayer, effectively shielding the acyl chains from contact with the aqueous environment.

Examples of preferred amphipathic compounds used in liposomes can include phosphoglycerides and sphingolipids, representative examples of which include phosphatidylcholine, phosphatidylethanolamine, phosphatidylserine, phosphatidylinositol, phosphatidic acid, phoasphatidylglycerol, palmitoyloleoyl phosphatidylcholine, lysophosphatidylcholine, lysophosphatidylethanolamine, dimyristoylphosphatidylcholine (DMPC), dipalmitoylphosphatidylcholine (DPPC), dioleoylphosphatidylcholine, di stearoylphosphatidylcholine (DSPC), dilinoleoylphosphatidylcholine and egg sphingomyelin, or any combination thereof.

A biological compartment can comprise a nanoparticle. A nanoparticle can comprise a diameter of from about 40 nanometers to about 1.5 micrometers, from about 50 nanometers to about 1.2 micrometers, from about 60 nanometers to about 1 micrometer, from about 70 nanometers to about 800 nanometers, from about 80 nanometers to about 600 nanometers, from about 90 nanometers to about 400 nanometers, from about 100 nanometers to about 200 nanometers.

In some instances, as the size of the nanoparticle increases, the release rate can be slowed or prolonged and as the size of the nanoparticle decreases, the release rate can be increased.

The amount of albumin in the nanoparticles can range from about 5% to about 85% albumin (v/v), from about 10% to about 80%, from about 15% to about 80%, from about 20% to about 70% albumin (v/v), from about 25% to about 60%, from about 30% to about 50%, or from about 35% to about 40%. The pharmaceutical composition can comprise up to 30, 40, 50, 60, 70 or 80% or more of the nanoparticle. In some instances, the nucleic acid molecules of the disclosure can be bound to the surface of the nanoparticle.

A biological compartment can comprise a virus. The virus can be a delivery system for the pharmaceutical compositions of the disclosure. Exemplary viruses can include lentivirus, retrovirus, adenovirus, herpes simplex virus I or II, parvovirus, reticuloendotheliosis virus, and adeno-associated virus (AAV). Pharmaceutical compositions of the disclosure can be delivered to a cell using a virus. The virus can infect and transduce the cell in vivo, ex vivo, or in vitro. In ex vivo and in vitro delivery, the transduced cells can be administered to a subject in need of therapy.

Pharmaceutical compositions can be packaged into viral delivery systems. For example, the compositions can be packaged into virions by a HSV-1 helper virus-free packaging system.

Viral delivery systems (e.g., viruses comprising the pharmaceutical compositions of the disclosure) can be administered by direct injection, stereotaxic injection, intracerebroventricularly, by minipump infusion systems, by convection, catheters, intravenous, parenteral, intraperitoneal, and/or subcutaneous injection, to a cell, tissue, or organ of a subject in need. In some instances, cells can be transduced in vitro or ex vivo with viral delivery systems. The transduced cells can be administered to a subject having a disease. For example, a stem cell can be transduced with a viral delivery system comprising a pharmaceutical composition and the stem cell can be implanted in the patient to treat a disease. In some instances, the dose of transduced cells given to a subject can be about $1\times10^5$ cells/kg, about $5\times10^5$ cells/kg, about $1\times10^6$ cells/kg, about $2\times10^6$ cells/kg, about $3\times10^6$ cells/kg, about $4\times10^6$ cells/kg, about $5\times10^6$ cells/kg, about $6\times10^6$ cells/kg, about $7\times10^6$ cells/kg, about $8\times10^6$ cells/kg, about $9\times10^6$ cells/kg, about $1\times10^7$ cells/kg, about $5\times10^7$ cells/kg, about $1\times10^8$ cells/kg, or more in one single dose.

Introduction of the biological compartments into cells can occur by viral or bacteriophage infection, transfection, conjugation, protoplast fusion, lipofection, electroporation, calcium phosphate precipitation, polyethyleneimine (PEI)-mediated transfection, DEAE-dextran mediated transfection, liposome-mediated transfection, particle gun technology, calcium phosphate precipitation, direct micro-injection, nanoparticle-mediated nucleic acid delivery, and the like.

In some embodiments, immune cells expressing a subject system are administered. Immune cells expressing a subject system can be administered before, during, or after the occurrence of a disease or condition, and the timing of administering the immune cells can vary. For example, immune cells expressing a subject system can be used as a prophylactic and can be administered continuously to subjects with a propensity to conditions or diseases in order to prevent the occurrence of the disease or condition. The immune cells can be administered to a subject during or as soon as possible after the onset of the symptoms. The administration can be initiated within the first 48 hours of the onset of the symptoms, within the first 24 hours of the onset of the symptoms, within the first 6 hours of the onset of the symptoms, or within 3 hours of the onset of the symptoms. The initial administration can be via any suitable route, such as by any route described herein using any formulation described herein. Immune cells can be administered as soon as is practicable after the onset of a disease or condition is detected or suspected, and for a length of time necessary for the treatment of the disease, such as, for example, from about 1 month to about 3 months. The length of treatment can vary for each subject.

A molecule described herein (e.g., polypeptide and/or nucleic acid) can be present in a composition in a range of from about 1 mg to about 2000 mg; from about 5 mg to about 1000 mg, from about 10 mg to about 25 mg to 500 mg, from about 50 mg to about 250 mg, from about 100 mg to about 200 mg, from about 1 mg to about 50 mg, from about 50 mg to about 100 mg, from about 100 mg to about 150 mg, from about 150 mg to about 200 mg, from about 200 mg to about 250 mg, from about 250 mg to about 300 mg, from about 300 mg to about 350 mg, from about 350 mg to about 400 mg, from about 400 mg to about 450 mg, from about 450 mg to about 500 mg, from about 500 mg to about 550 mg, from about 550 mg to about 600 mg, from about 600 mg to about 650 mg, from about 650 mg to about 700 mg, from about 700 mg to about 750 mg, from about 750 mg to about 800 mg, from about 800 mg to about 850 mg, from about 850 mg to about 900 mg, from about 900 mg to about 950 mg, or from about 950 mg to about 1000 mg.

A molecule (e.g., polypeptide and/or nucleic acid) described herein can be present in a composition in an amount of about 1 mg, about 2 mg, about 3 mg, about 4 mg, about 5 mg, about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 125 mg, about 150 mg, about 175 mg, about 200 mg, about 250 mg, about 300 mg, about 350 mg, about 400 mg, about 450 mg, about 500 mg, about 550 mg, about 600 mg, about 650 mg, about 700 mg, about 750 mg, about 800 mg, about 850 mg, about 900 mg, about 950 mg, about 1000 mg, about 1050 mg, about 1100 mg, about 1150 mg, about 1200 mg, about 1250 mg, about 1300 mg, about 1350 mg, about 1400 mg, about 1450 mg, about 1500 mg, about 1550 mg, about 1600 mg, about 1650 mg, about 1700 mg, about 1750 mg, about 1800 mg, about 1850 mg, about 1900 mg, about 1950 mg, or about 2000 mg.

A molecule (e.g., polypeptide and/or nucleic acid) described herein can be present in a composition that provides at least 0.1, 0.5, 1, 1.5, 2, 2.5 3, 3.5, 4, 4.5, 5, 5.5, 6, 6.5, 10 or more units of activity/mg molecule. The activity can be regulation of gene expression. In some embodiments, the total number of units of activity of the molecule delivered to a subject is at least 25,000, 30,000, 35,000, 40,000, 45,000, 50,000, 60,000, 70,000, 80,000, 90,000, 110,000, 120,000, 130,000, 140,000, 150,000, 160,000, 170,000, 180,000, 190,000, 200,000, 210,000, 220,000, 230,000, or 250,000 or more units. In some embodiments, the total number of units of activity of the molecule delivered to a subject is at most 25,000, 30,000, 35,000, 40,000, 45,000, 50,000, 60,000, 70,000, 80,000, 90,000, 110,000, 120,000, 130,000, 140,000, 150,000, 160,000, 170,000, 180,000, 190,000, 200, 000, 210,000, 220,000, 230,000, or 250,000 or more units.

In some embodiments, at least about 10,000 units of activity is delivered to a subject, normalized per 50 kg body weight. In some embodiments, at least about 10,000, 15,000, 25,000, 30,000, 35,000, 40,000, 45,000, 50,000, 60,000, 70,000, 80,000, 90,000, 110,000, 120,000, 130,000, 140, 000, 150,000, 160,000, 170,000, 180,000, 190,000, 200,000, 210,000, 220,000, 230,000, or 250,000 units or more of activity of the molecule is delivered to the subject, normalized per 50 kg body weight. In some embodiments, a therapeutically effective dose comprises at least 5×105, 1×106, 2×106, 3×106, 4, 106, 5×106, 6×106, 7×106, 8×106, 9×106, 1×107, 1.1×107, 1.2×107, 1.5×107, 1.6×107, 1.7× 107, 1.8×107, 1.9×107, 2×107, 2.1×107, or 3×107 or more units of activity of the molecule. In some embodiments, a therapeutically effective dose comprises at most 5×105, 1×106, 2×106, 3×106, 4, 106, 5×106, 6×106, 7×106, 8×106, 9×106, 1×107, 1.1×107, 1.2×107, 1.5×107, 1.6×107, 1.7× 107, 1.8×107, 1.9×107, 2×107, 2.1×107, or 3×107 or more units of activity of the molecule.

In some embodiments, a therapeutically effective dose is at least about 10,000, 15,000, 20,000, 22,000, 24,000, 25,000, 30,000, 40,000, 50,000, 60,000, 70,000, 80,000, 90,000, 100,000, 125,000, 150,000, 200,000, or 500,000 units/kg body weight. In some embodiments, a therapeutically effective dose is at most about 10,000, 15,000, 20,000, 22,000, 24,000, 25,000, 30,000, 40,000, 50,000, 60,000, 70,000, 80,000, 90,000, 100,000, 125,000, 150,000, 200, 000, or 500,000 units/kg body weight.

In some embodiments, the activity of the molecule delivered to a subject is at least 10,000, 11,000, 12,000, 13,000, 14,000, 20,000, 21,000, 22,000, 23,000, 24,000, 25,000, 26,000, 27,000, 28,000, 30,000, 32,000, 34,000, 35,000, 36,000, 37,000, 40,000, 45,000, or 50,000 or more U/mg of molecule. In some embodiments, the activity of the molecule delivered to a subject is at most 10,000, 11,000, 12,000, 13,000, 14,000, 20,000, 21,000, 22,000, 23,000, 24,000, 25,000, 26,000, 27,000, 28,000, 30,000, 32,000, 34,000, 35,000, 36,000, 37,000, 40,000, 45,000, or 50,000 or more U/mg of molecule.

In various embodiments of the aspects herein, pharmacokinetic and pharmacodynamic data can be obtained. Various experimental techniques for obtaining such data are available. Appropriate pharmacokinetic and pharmacodynamic profile components describing a particular composition can vary due to variations in drug metabolism in human subjects. Pharmacokinetic and pharmacodynamic profiles can be based on the determination of the mean parameters of a group of subjects. The group of subjects includes any reasonable number of subjects suitable for determining a representative mean, for example, 5 subjects, 10 subjects, 15 subjects, 20 subjects, 25 subjects, 30 subjects, 35 subjects, or more. The mean can be determined by calculating the average of all subject's measurements for each parameter measured. A dose can be modulated to achieve a desired pharmacokinetic or pharmacodynamics profile, such as a desired or effective blood profile, as described herein.

The pharmacokinetic parameters can be any parameters suitable for describing a molecule. For example, the Cmax can be, for example, not less than about 25 ng/mL; not less than about 50 ng/mL; not less than about 75 ng/mL; not less than about 100 ng/mL; not less than about 200 ng/mL; not less than about 300 ng/mL; not less than about 400 ng/mL; not less than about 500 ng/mL; not less than about 600 ng/mL; not less than about 700 ng/mL; not less than about 800 ng/mL; not less than about 900 ng/mL; not less than about 1000 ng/mL; not less than about 1250 ng/mL; not less than about 1500 ng/mL; not less than about 1750 ng/mL; not less than about 2000 ng/mL; or any other Cmax appropriate for describing a pharmacokinetic profile of a molecule described herein.

The Tmax of a molecule described herein can be, for example, not greater than about 0.5 hours, not greater than about 1 hours, not greater than about 1.5 hours, not greater than about 2 hours, not greater than about 2.5 hours, not greater than about 3 hours, not greater than about 3.5 hours, not greater than about 4 hours, not greater than about 4.5 hours, not greater than about 5 hours, or any other Tmax appropriate for describing a pharmacokinetic profile of a molecule described herein.

The AUC(0-inf) of a molecule described herein can be, for example, not less than about 50 ng·hr/mL, not less than about 100 ng/hr/mL, not less than about 150 ng/hr/mL, not less than about 200 ng·hr/mL, not less than about 250 ng/hr/mL, not less than about 300 ng/hr/mL, not less than about 350 ng/hr/mL, not less than about 400 ng/hr/mL, not less than about 450 ng/hr/mL, not less than about 500 ng/hr/mL, not less than about 600 ng/hr/mL, not less than about 700 ng/hr/mL, not less than about 800 ng/hr/mL, not less than about 900 ng/hr/mL, not less than about 1000 ng·hr/mL, not less than about 1250 ng/hr/mL, not less than about 1500 ng/hr/mL, not less than about 1750 ng/hr/mL, not less than about 2000 ng/hr/mL, not less than about 2500 ng/hr/mL, not less than about 3000 ng/hr/mL, not less than about 3500 ng/hr/mL, not less than about 4000 ng/hr/mL, not less than about 5000 ng/hr/mL, not less than about 6000 ng/hr/mL, not less than about 7000 ng/hr/mL, not less than about 8000 ng/hr/mL, not less than about 9000 ng/hr/mL, not less than about 10,000 ng/hr/mL, or any other AUC(0-inf) appropriate for describing a pharmacokinetic profile of a molecule described herein.

The plasma concentration of a molecule described herein about one hour after administration can be, for example, not less than about 25 ng/mL, not less than about 50 ng/mL, not less than about 75 ng/mL, not less than about 100 ng/mL, not less than about 150 ng/mL, not less than about 200 ng/mL, not less than about 300 ng/mL, not less than about 400 ng/mL, not less than about 500 ng/mL, not less than about 600 ng/mL, not less than about 700 ng/mL, not less than about 800 ng/mL, not less than about 900 ng/mL, not less than about 1000 ng/mL, not less than about 1200 ng/mL, or any other plasma concentration of a molecule described herein.

The pharmacodynamic parameters can be any parameters suitable for describing pharmaceutical compositions of the disclosure. For example, the pharmacodynamic profile can exhibit decreases in factors associated with inflammation after, for example, about 2 hours, about 4 hours, about 8 hours, about 12 hours, or about 24 hours.

In various embodiments of the aspects herein, methods of the disclosure are performed in a subject. A subject can be a human. A subject can be a mammal (e.g., rat, mouse, cow, dog, pig, sheep, horse). A subject can be a vertebrate or an invertebrate. A subject can be a laboratory animal. A subject can be a patient. A subject can be suffering from a disease. A subject can display symptoms of a disease. A subject may not display symptoms of a disease, but still have a disease. A subject can be under medical care of a caregiver (e.g., the subject is hospitalized and is treated by a physician). A subject can be a plant or a crop.

EXAMPLES

Various aspects of the disclosure are further illustrated by the following non-limiting examples.

Example 1: Altering Cytokine Expression Via a Chimeric Transmembrane Receptor

Figure 14:
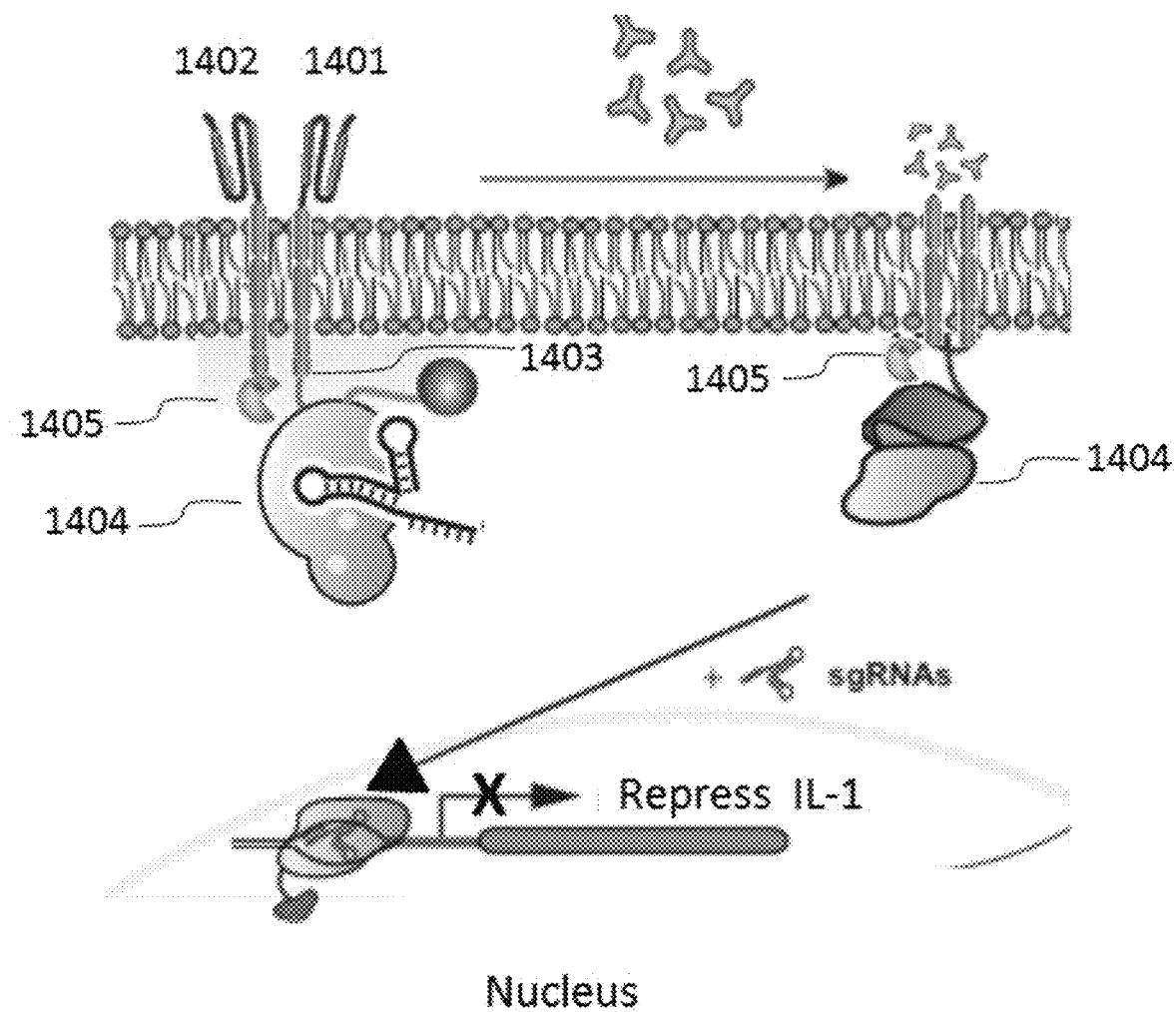
FIG. 14 illustrates the use of a system disclosed herein for repression of IL-1 in a lymphocyte.

As depicted in FIG. 14, a system comprising a chimeric transmembrane receptor polypeptide 1401 and a chimeric adaptor polypeptide 1402 are used to alter cytokine expression an immune cell. Components of the system are expressed in a lymphocyte, such as a T cell. The chimeric transmembrane receptor polypeptide is produced to include an extracellular region comprising a single-chain Fv (scFv, e.g., antigen interacting domain) which binds HER2. The intracellular region of the chimeric transmembrane receptor polypeptide comprises an immune cell signaling domain 1403 linked to a gene modulating polypeptide (GMP). The immune cell signaling domain comprises a CD3 ζ signaling domain as the primary signaling domain and co-stimulatory domain from CD28. The GMP comprises an actuator moiety 1404 (e.g., dCas9) linked to a restriction recognition site (e.g., protease sequence). The chimeric adaptor polypeptide comprises a cleavage moiety 1405. The receptor binding moiety can bind or cluster with a modified chimeric transmembrane receptor polypeptide. When the cleavage moiety is brought in proximity to the cleavage recognition site by receptor and adaptor interaction, the cleavage recognition site can be cleaved by the cleavage moiety, thereby releasing the actuator moiety from the membrane tethered receptor. The actuator moiety translocates to the nucleus and regulates expression of interleukin-1 (IL-1) from genomic DNA (e.g., target polynucleotide). The actuator moiety can regulate expression of IL-1 by regulating transcription via physical obstruction or editing the nucleic acid sequence encoding for IL-1 such that the gene products are defective or completely removing the gene sequence. Decreasing expression of IL-1 from a lymphocyte may decrease toxicity associated CRS in immunotherapy. A dCas9 actuator moiety can complex with a single guide RNA (sgRNA), either before or after release from the GMP. In an alternative configuration, the chimeric transmembrane receptor comprises the cleavage moiety and the chimeric adaptor polypeptide comprises the GMP.

Example 2: Altering Cytokine Expression Via an Antibody-Coupled Chimeric Transmembrane Receptor As depicted in FIG. 14, a system comprising a chimeric transmembrane receptor polypeptide 1401 and a chimeric adaptor polypeptide 1402 are used to alter cytokine expression an immune cell. Components of the system are expressed in a lymphocyte, such as a T cell. The chimeric transmembrane receptor polypeptide is produced to include an extracellular region comprising an Fc binding domain of an Fc receptor (e.g., antigen interacting domain) which binds an anti-HER2 antibody (e.g., antigen). The intracellular region of the chimeric transmembrane receptor polypeptide comprises an immune cell signaling domain 1403 linked to a gene modulating polypeptide (GMP). The immune cell signaling domain comprises a CD3 ζ signaling domain as the primary signaling domain and co-stimulatory domain from CD28. The GMP comprises an actuator moiety 1404 (e.g., dCas9) linked to a restriction recognition site (e.g., protease sequence). The chimeric adaptor polypeptide comprises a cleavage moiety 1405. The receptor binding moiety can bind or cluster with a modified chimeric transmembrane receptor polypeptide. When the cleavage moiety is brought in proximity to the cleavage recognition site by receptor and adaptor interaction, the cleavage recognition site can be cleaved by the cleavage moiety, thereby releasing the actuator moiety from the membrane tethered receptor. The actuator moiety translocates to the nucleus and regulates expression of interleukin-1 (IL-1) from genomic DNA (e.g., target polynucleotide). The actuator moiety can regulate expression of IL-1 by regulating transcription via physical obstruction or editing the nucleic acid sequence encoding for IL-1 such that the gene products are defective or completely removing the gene sequence. Decreasing expression of IL-1 from a lymphocyte may decrease toxicity associated CRS in immunotherapy. A dCas9 actuator moiety can complex with a single guide RNA (sgRNA), either before or after release from the GMP. In an alternative configuration, the chimeric transmembrane receptor comprises the cleavage moiety and the chimeric adaptor polypeptide comprises the GMP.

Example 3: Altering PD-1 Expression Via a Chimeric Transmembrane Receptor

Figure 15:
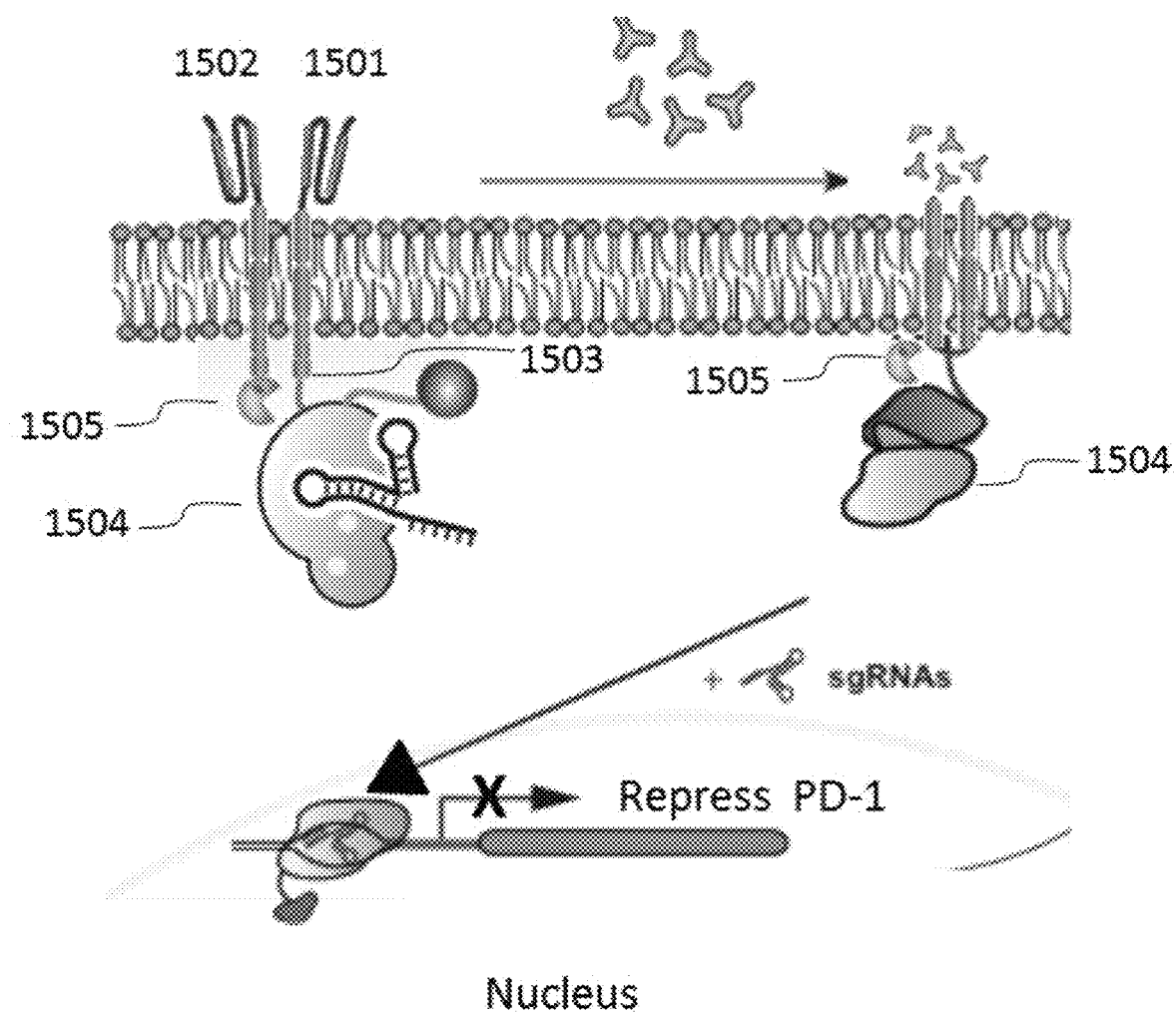
FIG. 15 illustrates the use of a system disclosed herein for repression of PD-1 in a lymphocyte.

As depicted in FIG. 15, a system comprising a chimeric transmembrane receptor polypeptide 1501 and a chimeric adaptor polypeptide 1502 are used to alter expression of PD-1 in an immune cell. Components of the system are expressed in a lymphocyte, such as a T cell. The chimeric transmembrane receptor polypeptide is produced to include an extracellular region comprising a single-chain Fv (scFv, e.g., antigen interacting domain) which binds HER2. The intracellular region of the chimeric transmembrane receptor polypeptide comprises an immune cell signaling domain 1503 linked to a gene modulating polypeptide (GMP). The immune cell signaling domain comprises a CD3 ζ signaling domain as the primary signaling domain and co-stimulatory domain from CD28. The GMP comprises an actuator moiety 1504 (e.g., dCas9) linked to a restriction recognition site (e.g., protease sequence). The chimeric adaptor polypeptide comprises a cleavage moiety 1505. The receptor binding moiety can bind or cluster with a modified chimeric transmembrane receptor polypeptide. When the cleavage moiety is brought in proximity to the cleavage recognition site by receptor and adaptor interaction, the cleavage recognition site can be cleaved by the cleavage moiety, thereby releasing the actuator moiety from the membrane tethered receptor. The actuator moiety translocates to the nucleus and regulates expression of PD-1 from genomic DNA (e.g., target polynucleotide). The actuator moiety can regulate expression of PD-1 by regulating transcription via physical obstruction or edit the nucleic acid sequence encoding for PD-1 such that the gene products are defective or completely removing the gene sequence. Decreasing expression of PD-1 from a lymphocyte may increase the effectiveness of immunotherapy. A dCas9 actuator moiety can complex with a single guide RNA (sgRNA), either before or after release from the GMP. In an alternative configuration, the chimeric transmembrane receptor comprises the cleavage moiety and the chimeric adaptor polypeptide comprises the GMP.

Example 4: Altering PD-1 Expression Via an Antibody-Coupled Chimeric Transmembrane Receptor As depicted in FIG. 15, a system comprising a chimeric transmembrane receptor polypeptide 1501 and a chimeric adaptor polypeptide 1502 are used to alter expression of PD-1 in an immune cell. Components of the system are expressed in a lymphocyte, such as a T cell. The chimeric transmembrane receptor polypeptide is produced to include an extracellular region comprising an Fc binding domain of an Fc receptor (e.g., antigen interacting domain) which binds an anti-HER2 antibody (e.g., antigen). The intracellular region of the chimeric transmembrane receptor polypeptide comprises an immune cell signaling domain 1503 linked to a gene modulating polypeptide (GMP). The immune cell signaling domain comprises a CD3 ζ signaling domain as the primary signaling domain and co-stimulatory domain from CD28. The GMP comprises an actuator moiety 1504 (e.g., dCas9) linked to a restriction recognition site (e.g., protease sequence). The chimeric adaptor polypeptide comprises a cleavage moiety 1505. The receptor binding moiety can bind or cluster with a modified chimeric transmembrane receptor polypeptide. When the cleavage moiety is brought in proximity to the cleavage recognition site by receptor and adaptor interaction, the cleavage recognition site can be cleaved by the cleavage moiety, thereby releasing the actuator moiety from the membrane tethered receptor. The actuator moiety translocates to the nucleus and regulates expression of PD-1 from genomic DNA (e.g., target polynucleotide). The actuator moiety can regulate expression of PD-1 by regulating transcription via physical obstruction or edit the nucleic acid sequence encoding for PD-1 such that the gene products are defective or completely removing the gene sequence. Decreasing expression of PD-1 from a lymphocyte may increase the effectiveness of immunotherapy. A dCas9 actuator moiety can complex with a single guide RNA (sgRNA), either before or after release from the GMP. In an alternative configuration, the chimeric transmembrane receptor comprises the cleavage moiety and the chimeric adaptor polypeptide comprises the GMP.

Figure 16:
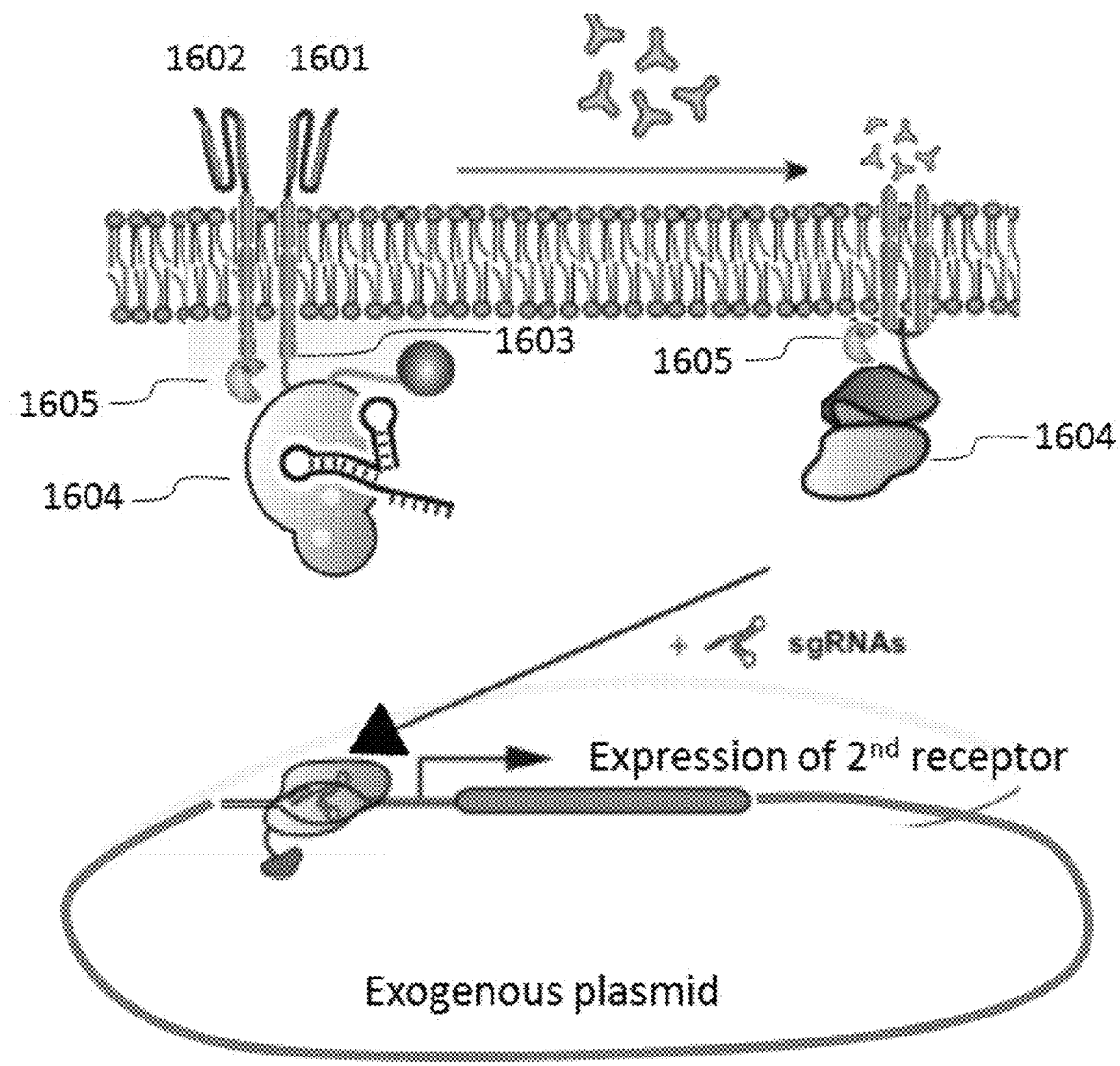
FIG. 16 illustrates the use of a system disclosed herein for expression of a second chimeric receptor from an exogenous plasmid in an immune cell.

Example 5: Expression of an Additional Chimeric Transmembrane Receptor Polypeptide Via Chimeric Transmembrane Receptor Polypeptide As depicted in FIG. 16, a system comprising a chimeric transmembrane receptor polypeptide 1601 and a chimeric adaptor polypeptide 1602 are used to express a second receptor polypeptide from a plasmid. Components of the system are expressed in a lymphocyte, such as a T cell. The chimeric transmembrane receptor polypeptide is produced to include an extracellular region comprising a single-chain Fv (scFv, e.g., antigen interacting domain) which binds HER2. The intracellular region of the chimeric transmembrane receptor polypeptide comprises an immune cell signaling domain 1603 linked to a gene modulating polypeptide (GMP). The immune cell signaling domain comprises a CD3 ζ signaling domain as the primary signaling domain and co-stimulatory domain from CD28. The GMP comprises an actuator moiety 1604 (e.g., dCas9) linked to a restriction recognition site (e.g., protease sequence). The chimeric adaptor polypeptide comprises a cleavage moiety 1605. The receptor binding moiety can bind or cluster with a modified chimeric transmembrane receptor polypeptide. When the cleavage moiety is brought in proximity to the cleavage recognition site by receptor and adaptor interaction, the cleavage recognition site can be cleaved by the cleavage moiety, thereby releasing the actuator moiety from the membrane tethered receptor. The actuator moiety translocates to an exogenous plasmid (e.g., target polynucleotide) delivered to the cell and regulates expression of a second receptor polypeptide. The actuator moiety can comprise a transcriptional activator which enhances transcription from the exogenous plasmid. A dCas9 actuator moiety can complex with a single guide RNA (sgRNA), either before or after release from the GMP. In an alternative configuration, the chimeric transmembrane receptor comprises the cleavage moiety and the chimeric adaptor polypeptide comprises the GMP.

Example 6: Expression of an Additional Chimeric Transmembrane Receptor Polypeptide Via Antibody-Coupled Chimeric Transmembrane Receptor Polypeptide As depicted in FIG. 16, a system comprising a chimeric transmembrane receptor polypeptide 1601 and a chimeric adaptor polypeptide 1602 are used to express a second receptor polypeptide from a plasmid. Components of the system are expressed in a lymphocyte, such as a T cell. The chimeric transmembrane receptor polypeptide is produced to include an extracellular region comprising an Fc binding domain of an Fc receptor (e.g., antigen interacting domain) which binds an anti-HER2 antibody (e.g., antigen). The intracellular region of the chimeric transmembrane receptor polypeptide comprises an immune cell signaling domain 1603 linked to a gene modulating polypeptide (GMP). The immune cell signaling domain comprises a CD3 signaling domain as the primary signaling domain and co-stimulatory domain from CD28. The GMP comprises an actuator moiety 1604 (e.g., dCas9) linked to a restriction recognition site (e.g., protease sequence). The chimeric adaptor polypeptide comprises a cleavage moiety 1605. The receptor binding moiety can bind or cluster with a modified chimeric transmembrane receptor polypeptide. When the cleavage moiety is brought in proximity to the cleavage recognition site by receptor and adaptor interaction, the cleavage recognition site can be cleaved by the cleavage moiety, thereby releasing the actuator moiety from the membrane tethered receptor. The actuator moiety translocates to an exogenous plasmid (e.g., target polynucleotide) delivered to the cell and regulates expression of a second receptor polypeptide. The actuator moiety can comprise a transcriptional activator which enhances transcription from the exogenous plasmid. A dCas9 actuator moiety can complex with a single guide RNA (sgRNA), either before or after release from the GMP. In an alternative configuration, the chimeric transmembrane receptor comprises the cleavage moiety and the chimeric adaptor polypeptide comprises the GMP.

Example 7: dCas9-KRAB Domain is Cleaved from Chimeric Receptors in the Presence of TEV Protease In the presence of TEV protease, chimeric receptor polypeptides comprising dCas9-KRAB expressed in mammalian cells were cleaved at a TEV cleavable sequence (tcs). In this example, TEV protease was co-expressed with one of pre T-cell antigen receptor alpha (PTCRA) linked to dCas9-KRAB (PTCRA-dCas9-KRAB), GPCR receptor CXCR2 linked to dCas9-KRAB (CXCR2-dCas9-KRAB), interleukin 6 receptor (IL6R) linked to dCas9-KRAB (IL6R-dCas9-KRAB), or CD19-targeted chimeric antigen receptor (CAR) linked to dCas9-KRAB (CAR-dCas9-KRAB) in HEK293T cells, and cell lysate was analyzed by Western blot for the presence of cleavage products.

Mammalian cell expression vectors for each chimeric receptor was generated by molecular cloning. The PTCRA-dCas9-KRAB construct included PTCRA linked to a TEV cleavable sequence (tcs), dCas9, KRAB, and C-Myc-DDK (PTCRA-dCas9-KRAB). The CXCR2 construct included CXCR2 linked to a TEV cleavable sequence (tcs), dCas9, KRAB, and C-Myc-DDK (CXCR2-dCas9-KRAB). The IL6R construct included IL6R linked to a TEV cleavable sequence (tcs), dCas9, KRAB, and C-Myc-DDK (IL6R-dCas9-KRAB). The CAR construct included CAR linked to a TEV cleavable sequence (tcs), dCas9, KRAB, and C-Myc-DDK (CAR-dCas9-KRAB). The TEV protease was provided in an inducible expression system (tet-on) to allow for regulation of TEV expression by doxycycline (DOX); this included a tet-on-TEV plasmid and a rtTA expressing plasmid.

For each chimeric receptor, the mammalian cell expression vector was co-transfected with tet-on-TEV and rtTA plasmids in HEK293T cells. Cells transfected with 'free' dCas9-KRAB or no DNA were used as controls. Briefly, HEK293T cells were transfected at 50-70% confluency using Minis transfection reagent. 24 hours after transfection, doxycycline (DOX) was added to cell culture media to initiate the high expression of TEV protease. Using the inducible expression system, the addition of doxycycline (DOX) results in the high expression of TEV protease while the absence of DOX results in low expression of TEV protease. Cell samples were collected in RIPA buffer supplemented with protease inhibitors 48 hours after transfection and assayed by Western blot.

For Western blot analysis, cell lysate was prepared using NuPAGE LDS Sample Buffer (4×) NuPAGE Reducing Agent (10×), run on pre-cast protein gels and then transferred to nitrocellulose membranes. The membranes were probed with anti-Cas9 and anti-ACTB (control) antibodies.

Figure 20:
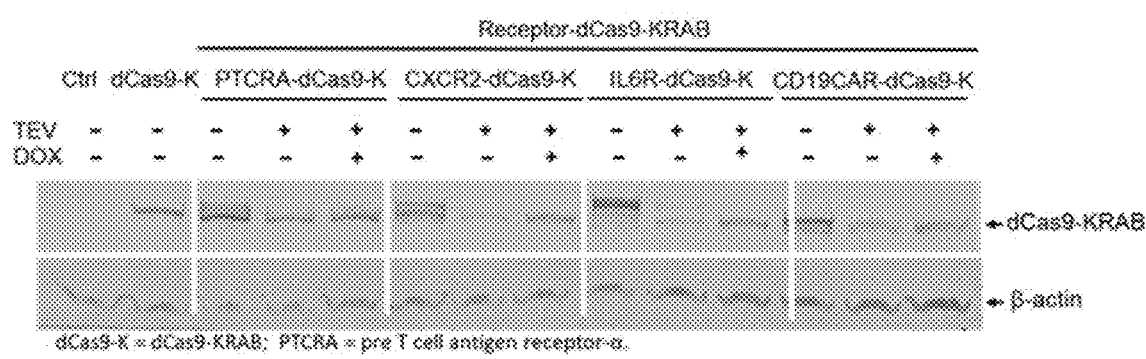
FIG. 20 shows dCas9-KRAB domain is cleaved from chimeric receptors in the presence of protease by Western blot analysis.

Western blot analysis indicates cleavage of the chimeric receptors at the tcs in the presence or absence of DOX. The presence of smaller protein bands corresponding to cleaved dCas9-KRAB in FIG. 20 indicates cleavage of dCas9-KRAB from chimeric receptors in the presence of TEV protease (low' and 'high' TEV).

Example 8: dCas9-KRAB is Cleaved from CAR-dCas9-KRAB in the Presence of Adaptor-TEV Protease In the presence of various adaptor-TEV protease fusions, CAR-dCas9-KRAB polypeptides were cleaved at a TEV cleavable sequence (tcs). In this example, TEV protease was fused to various transmembrane and cytoplasmic adaptor proteins which can be recruited to an activated CAR. Cytoplasmic adaptor proteins tested include ZAP70, LCP-2, GADS, and GRB2. Transmembrane adaptors tested include LCK and LAT. The various adaptor-TEV protease constructs were provided in an inducible expression system (tet-on) to allow for the regulation of TEV expression by doxycycline (DOX); this included a tet-on adaptor-TEV plasmid and a rtTA expressing plasmid.

For each adaptor protein, expression vector for CAR-dCas9-KRAB, as described in Example 7, was co-expressed with tet-on adaptor-TEV and rtTA plasmids in HEK293T cells. Cells transfected with 'free' dCas9-KBAB or CAR-dCas9-KRAB without co-transfection of adaptor-TEV were used as controls. Briefly, HEK293T cells were transfected at 50-70% confluency using Minis transfection reagent. 24 hours after transfection, doxycycline (DOX) was added to cell culture media to initiate the high expression of adaptor-TEV. Using the inducible expression system, the addition of doxycycline (DOX) results in the high expression of adaptor-TEV protease while the absence of DOX results in low expression of adaptor-TEV protease. Cell samples were collected in RIPA buffer supplemented with protease inhibitors 48 hours after transfection and assayed by Western blot.

For Western blot analysis, cell lysate was prepared using NuPAGE LDS Sample Buffer (4×) NuPAGE Reducing Agent (10×), run on pre-cast protein gels and then transferred to nitrocellulose membranes. The membranes were probed with anti-Cas9 and anti-ACTB (control) antibodies.

Figure 21:
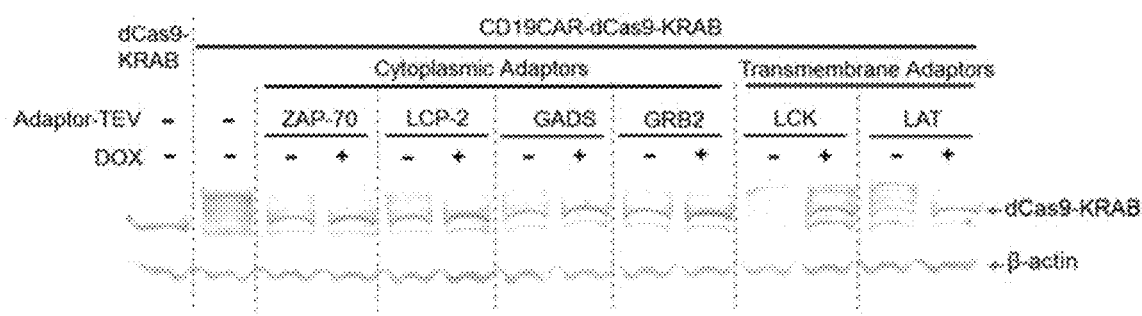
FIG. 21 shows dCas9-KRAB domain is cleaved from chimeric receptors in the presence of adaptor-protease by Western blot analysis.

Cleavage of the chimeric receptors at the tcs was observed for both transmembrane and cytoplasmic adaptor-TEV fusions in the presence of low and high DOX. The presence of smaller protein bands corresponding to cleaved dCas9-KRAB in FIG. 21 indicates cleavage of dCas9-KRAB from chimeric receptors in the presence of adaptor-TEV protease (low and high TEV). For cytoplasmic adaptors, low expression of adaptor-TEV was sufficient for cleavage. For transmembrane adaptors, high expression of adaptor-TEV (+DOX) resulted in higher levels of cleavage.

Example 9: Ligand-Binding Induced Chimeric Receptor Cleavage

Ligand-induced receptor cleavage of chimeric receptor polypeptides is assayed in Jurkat cells and primary human T cells. Chimeric receptor polypeptides binding CD19 antigen and chimeric adaptor polypeptides are expressed in Jurkat cells or primary human T cells to generate engineered Jurkat cells and engineered T cells. Receptor cleavage is observed in engineered Jurkat cells and engineered T cells when cells are presented with CD19 antigen.

CD19 binding CAR-dCas9-KRAB (CD19-CAR-dCas9-KRAB) lentivirus and adaptor-TEV lentivirus are packaged in 293T cells. Lentiviral transduction is used to generate engineered Jurkat cells and engineered T cells co-expressing CD19-CAR-dCas9-KRAB and adaptor-TEV polypeptides (e.g., ZAP70-TEV, LCP2-TEV, GADS-TEV, GRB2-TEV, PIK3R-TEV, LCK-TEV, LAT-TEV and NCK-TEV). Lentiviral transduction is verified by flow cytometry (CD19-CAR-dCas9-KRAB) and Western blot (adaptor-TEV). Following transduction and verification of polypeptide expression, engineered Jurkat cells and engineered T cells are (separately) co-cultured with CD19+ leukemia cell line NALM-6 cells, CD19+ Burkitt lymphoma Daudi cells, or CD19+ Burkitt lymphoma Raji cells. As control, engineered Jurkat cells and T cells are (separately) co-cultured with CD19-cells (not expressing CD19). Binding of CD19 to the extracellular domain of CD19-CAR-dCas9-KRAB activates CAR signaling, and recruits adaptor-TEV polypeptides (e.g., ZAP70-TEV, LCP2-TEV, GADS-TEV, GRB2-TEV, PIK3R-TEV, LCK-TEV, LAT-TEV and NCK-TEV) to the intracellular domain of the chimeric receptor polypeptide where cleavage occurs. After co-culture, engineered Jurkat cells and engineered T cells are lysed for Western blot analysis to detect the presence of free dCas9-KRAB (cleaved from receptor) in the presence of CD19+ cells or CD19-cells as described in Example 7. CD19-activated cleavage levels are compared to basal levels of receptor cleavage in engineered Jurkat cells and engineered T-cells co-cultured with CD19-cells.

Cleavage of the chimeric receptor polypeptides is expected to be higher in engineered Jurkat cells or engineered T cells co-cultured with CD19+ cells.

Example 10: Transcriptional Regulation (Down-Regulation) Resulting from Chimeric Receptor Cleavage Changes in gene expression levels resulting from ligand dependent cleavage of chimeric receptor polypeptides and resulting release of dCas9-KRAB for transcriptional regulation is assayed in engineered Jurkat cells and engineered T cells. As described in Example 9, engineered Jurkat cells and engineered T cells co-express CD19-CAR-dCas9-KRAB and adaptor-TEV and additionally express targeting RNAs (sgRNAs). Targeting RNAs are specific for PD-1 (sgPD-1) or IL-6 (sgIL-6). CD19 binding CAR-dCas9-KRAB (CD19-CAR-dCas9-KRAB) lentivirus, adaptor-TEV lentivirus, and sgRNA targeting PD-1 or IL-6 lentivirus are packaged in 293T cells. Lentiviral transduction is used to generate engineered Jurkat cells and engineered T cells co-expressing CD19-CAR-dCas9-KRAB, an adaptor-TEV polypeptide (e.g., ZAP70-TEV, LCP2-TEV, GADS-TEV, GRB2-TEV, PIK3R-TEV, LCK-TEV, LAT-TEV and NCK-TEV), and a sgRNA (e.g., sgPD-1, sgIL-6, or sgNT "non-targeting"). Lentiviral transduction is verified by flow cytometry (CD19-CAR-dCas9-KRAB) and Western blot (adaptor-TEV). Following transduction, engineered Jurkat cells and engineered T cells are (separately) co-cultured with CD19+ leukemia cell line NALM-6 cells, CD19+ Burkitt lymphoma Daudi cells, or CD19+ Burkitt lymphoma Raji cells. As control, engineered Jurkat cells and engineered T cells are co-cultured with CD19-cells. Binding of CD19 to the extracellular domain of the chimeric receptor activates CAR signaling, and recruits adaptor-TEV polypeptides (e.g., ZAP70-TEV, LCP2-TEV, GADS-TEV, GRB2-TEV, PIK3R-TEV, LCK-TEV, LAT-TEV and NCK-TEV) to the intracellular domain of CAR-dCas9-KRAB fusion protein where cleavage can occur. After co-culture, engineered Jurkat cells and engineered T cells are lysed for Western blot analysis to detect the presence of free dCas9-KRAB (cleaved from receptor) in the presence of CD19+ cells or CD19-cells as described in Example 7.

Ligand dependent receptor cleavage is verified by Western blot analysis as described in Example 8. Changes in gene expression levels of PD-1 and IL-6 resulting from the release of dCas9-KRAB and subsequent targeting of dCas9-KRAB complexed with sgRNA is analyzed by qPCR. PD-1 (protein) surface expression is analyzed by flow cytometry. IL-6 (protein) secretion is analyzed by ELISA.

Changes in transcriptional regulation of PD-1 and IL-6 expression are expected in response to CD19 and CD19CAR-dCas9-KRAB binding. Down-regulation of PD-1 and IL-6 is expected in engineered Jurkat cells and primary human T-cells expressing CD19CAR-dCas9-KRAB, adaptor-TEV and sgRNA. Engineered Jurkat and T-cells expressing non-targeting RNA, e.g., sgNT, co-cultured with CD19+ leukemia and lymphoma cells are expected to show minimal changes in transcriptional regulation over baseline as sgNT is not expected to target the dCas9-KRAB for transcriptional regulation.

Example 11: Transcriptional Regulation (Up-Regulation) Resulting from Chimeric Receptor Cleavage Changes in gene expression levels resulting from ligand dependent cleavage of chimeric receptor polypeptides and resulting release of dCas9-KRAB for transcriptional regulation is assayed in engineered Jurkat cells and engineered T cells. As described in Example 9, engineered Jurkat cells and engineered T cells co-express CD19-CAR-dCas9-VPR and adaptor-TEV and additionally express targeting RNAs (sgRNAs). Targeting RNAs are specific for PD-1 (sgPD-1) or IL-6 (sgIL-6). CD19 binding CAR-dCas9-VPR (CD19-CAR-dCas9-VPR) lentivirus, adaptor-TEV lentivirus, and sgRNA targeting PD-1 or IL-6 lentivirus are packaged in 293T cells. Lentiviral transduction is used to generate engineered Jurkat cells and engineered T cells co-expressing CD19-CAR-dCas9-VPR, an adaptor-TEV polypeptide (e.g., ZAP70-TEV, LCP2-TEV, GADS-TEV, GRB2-TEV, PIK3R-TEV, LCK-TEV, LAT-TEV and NCK-TEV), and a sgRNA (e.g., sgPD-1, sgIL-6, or sgNT "non-targeting"). Lentiviral transduction is verified by flow cytometry (CD19-CAR-dCas9-VPR) and Western blot (adaptor-TEV). Following transduction, engineered Jurkat cells and engineered T cells are (separately) co-cultured with CD19+ leukemia cell line NALM-6 cells, CD19+ Burkitt lymphoma Daudi cells, or CD19+ Burkitt lymphoma Raji cells. As control, engineered Jurkat cells and engineered T cells are co-cultured with CD19-cells. Binding of CD19 to the extracellular domain of the chimeric receptor activates CAR signaling, and recruits adaptor-TEV polypeptides (e.g., ZAP70-TEV, LCP2-TEV, GADS-TEV, GRB2-TEV, PIK3R-TEV, LCK-TEV, LAT-TEV and NCK-TEV) to the intracellular domain of CAR-dCas9-VPR fusion protein where cleavage can occur. After co-culture, engineered Jurkat cells and engineered T cells are lysed for Western blot analysis to detect the presence of free dCas9-VPR (cleaved from receptor) in the presence of CD19+ cells or CD19-cells as described in Example 7.

Ligand dependent receptor cleavage is verified by Western blot analysis as described in Example 8. Changes in gene expression levels of PD-1 and IL-6 resulting from the release of dCas9-VPR and subsequent targeting of dCas9-VPR complexed with sgRNA is analyzed by qPCR. PD-1 (protein) surface expression is analyzed by flow cytometry. IL-6 (protein) secretion is analyzed by ELISA.

Changes in transcriptional regulation of PD-1 and IL-6 expression are expected in response to CD19 and CD19CAR-dCas9-VPR binding. Up-regulation of PD-1 and IL-6 is expected in engineered Jurkat cells and primary human T-cells expressing CD19CAR-dCas9-VPR, adaptor-TEV and sgRNA. Engineered Jurkat and T-cells expressing non-targeting RNA, e.g., sgNT, co-cultured with CD19+ leukemia and lymphoma cells are expected to show minimal changes in transcriptional regulation over baseline as sgNT is not expected to target the dCas9-VPR for transcriptional regulation.

Example 12: Demonstration of Ligand-Dependent dCas9-KRAB Cleavage in T Cells

Figure 22A:
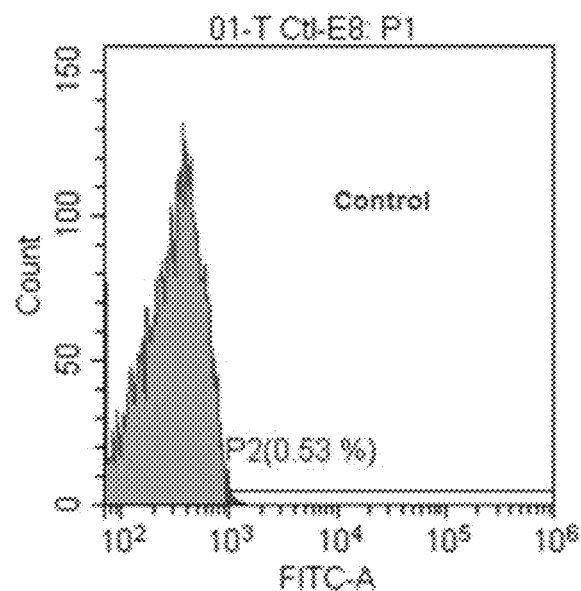
FIGS. 22A-22B depict flow cytometry results of control (FIG. 22A) and CD19-CAR-dCas9-KRAB expressing T cell (FIG. 22B), with FITC detecting GFP signal from CD19-CAR-dCas9-KRAB expression.
Figure 22B:
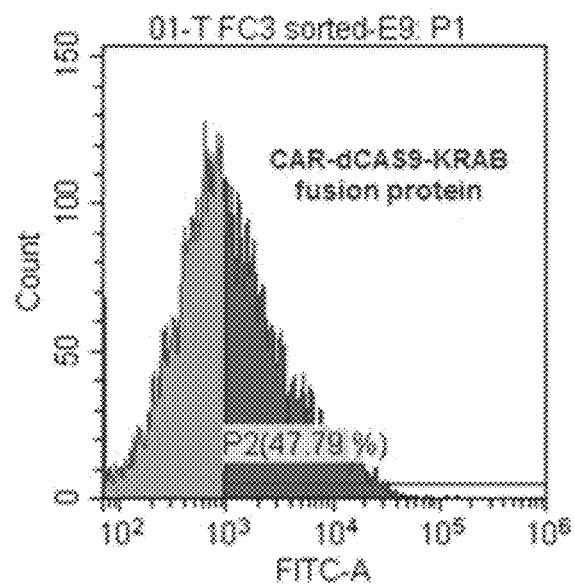
Figure 23A:
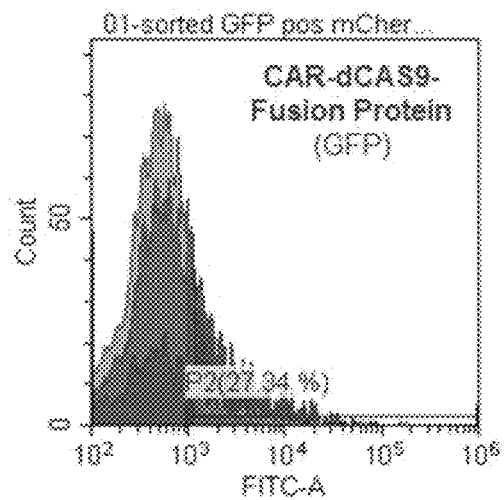
Figure 23B:
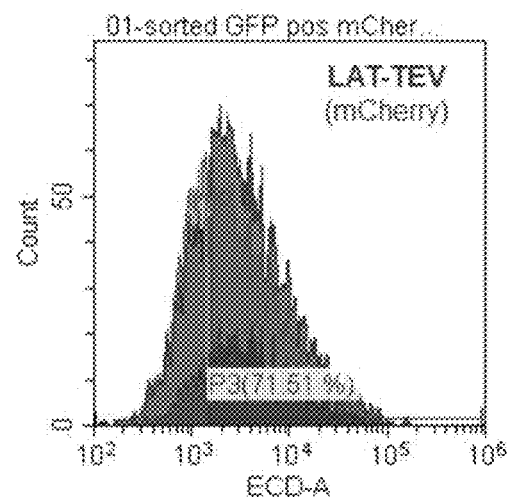
Figure 23C:
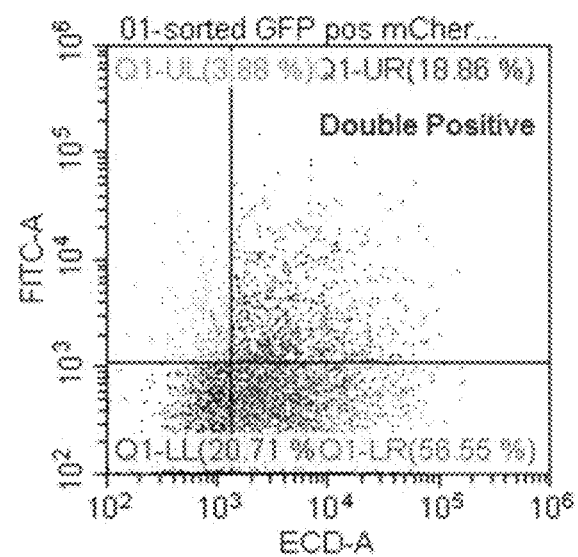

CD3/CD28 microbeads were used to activate primary human T cells isolated from hPBMCs (human peripheral blood mononuclear cells). CD19 binding CAR-dCas9-KRAB (CD19-CAR-dCas9-KRAB) lentivirus was transduced into the primary human T cells. The transduced T cells were screened and positively transduced cells were isolated by fluorescence-activated cell sorting (FACS) (FIGS. 22A-22B). Approximately 48% of transduced T cells were CD19-CAR-dCas9-KRAB positive T cells based on FITC (GFP) signal detection. Adaptor-TEV lentivirus (e.g., LAT-TEV), was transduced into the CD19-CAR-dCas9-KRAB positive T cells. FACS was used to confirm expression of CD19-CAR-dCas9-KRAB (GFP) and LAT-TEV (mCherry). Approximately 27% of transduced T cells were CD19-CAR-dCas9-KRAB positive T cells based on FITC (GFP) signal detection (FIG. 23A), and approximately 72% of transduced T cells were LAT-TEV positive T cells based on ECD (mCherry) signal detection (FIG. 23B). Approximately 19% of transduced cells were double positive for both CD19-CAR-dCas9-KRAB and LAT-TEV (FIG. 23C).

Figure 24:
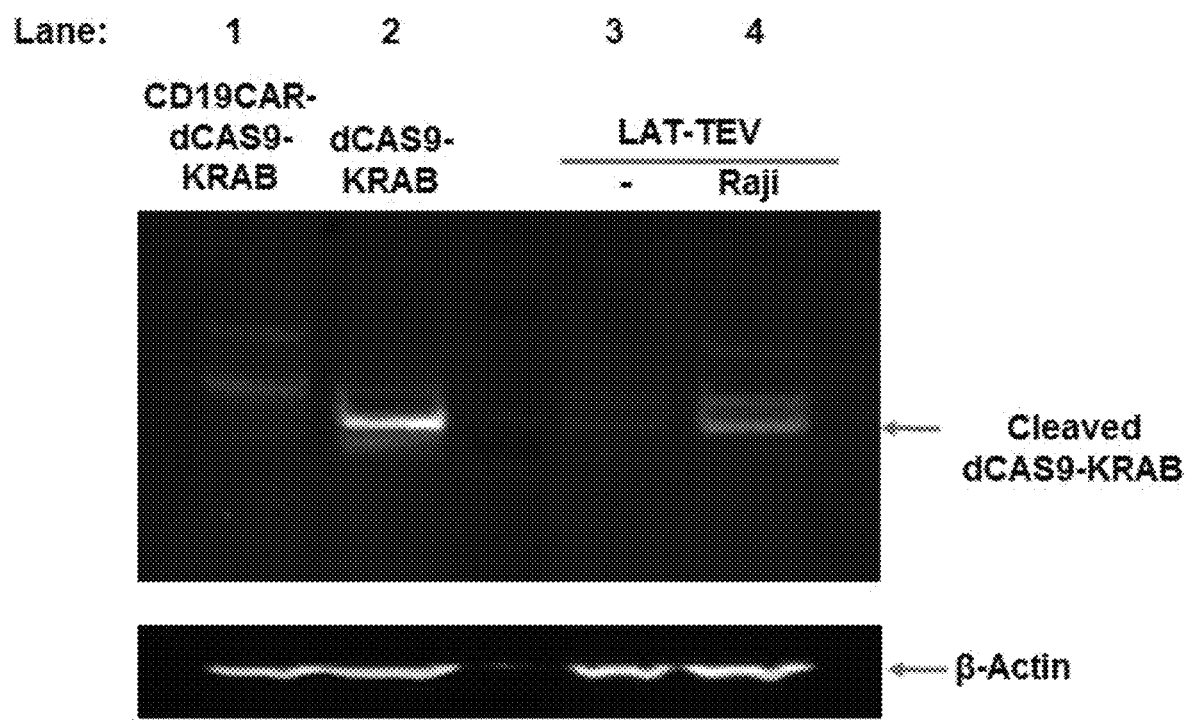
FIG. 24 depicts an western blot detecting cleaved dCas9-KRAB in samples of uncleaved CD19 CAR-dCas9-KRAB (lane 1), cleaved dCas9-KRAB (lane 2), CD19 CAR-dCas9-KRAB and LAT-TEV co-expressing T cells incubated alone (lane 3), or CD19 CAR-dCas9-KRAB and LAT-TEV co-expressing T cells that were incubated and activated with Raji cells (lane 4), and a beta-actin loading control.

The double positive T cells were isolated and incubated with CD19+ Raji cells or no Raji cells (control) for 24 hours. Raji cells are a CD19 positive human B cell lymphoma cell line. After the 24 hour incubation, cells were lysated and analyzed by western blot. Increased ligand-dependent dCas9-KRAB cleavage by LAT-TEV was observed in cells incubated with Raji cells (FIG. 24, fourth lane) compared to cells not incubated with Raji cells (FIG. 24, third lane). FIG. 24 also includes non-cleaved CD19-CAR-dCas9-KRAB (lane 1) and cleaved dCas9-KRAB (lane 2) as controls. The lower panel of FIG. 24 is a loading control of beta actin.

Example 13: Screening PD-1 sgRNA in Primary Human T Cells

CD3/CD28 beads were used to activate primary human T cells. dCas9-KRAB lentivirus and rtTA lentivirus were co-transduced into the activated T cell. The transduced cells were then transfected with different PD-1 targeting sgRNAs or a control sg RNA. Finally, the cells were analyzed by flow cytometry to determine PD-1 expression levels.

Figure 25A:
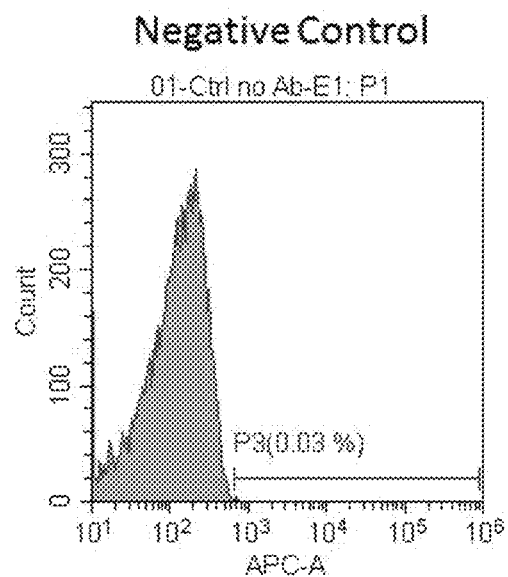
FIGS. 25A, 25B, 25C, and 25D depict flow cytometry data using ECD to detect dCas9-KRAB expression and APC to detect PD-1 expression.
Figure 25B:
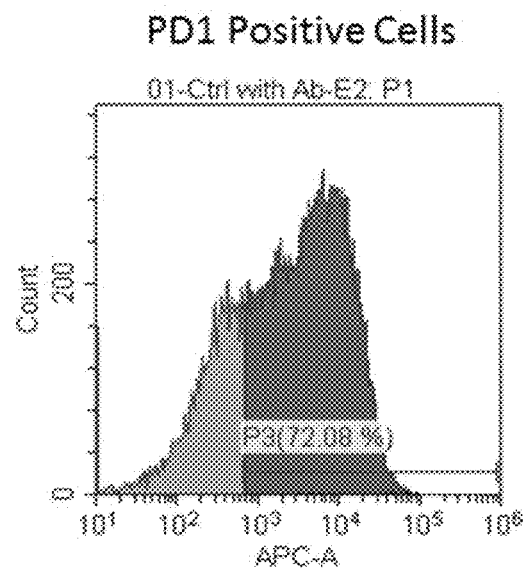
Figure 25C:
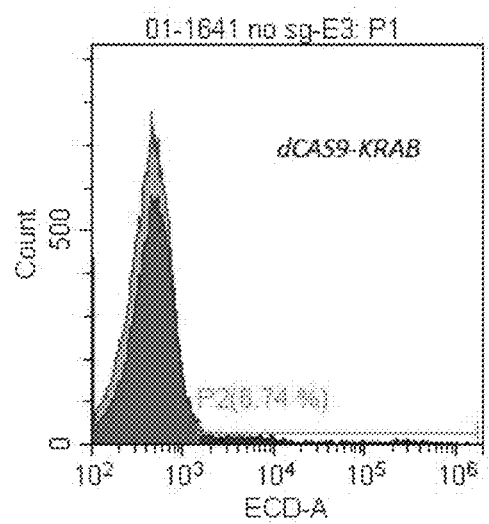
Figure 25D:
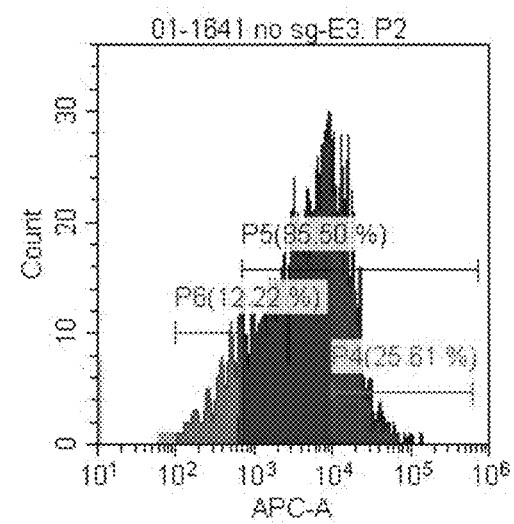

In the first experiment six different sgRNAs targeting PD-1 were tested and the results are summarized in Table 7. Cell populations were categorized based on their PD-1 expression level, either no or insignificant levels of expression (PD-1 Neg), a positive level of expression (PD-1 Pos), or a high level of expression (PD-1 High Pos). The percent decrease in expression signal was then calculated compared to a control (Ctl) for both the positive population (PD-1 down %) and the high PD-1 positive population (PD-1 High down %). FIG. 25A depicts negative control cells that were not labeled with an anti-PD-1 antibody and FIG. 25B depicts positive control cells that were labeled with an anti-PD-1 antibody, which was detected in the APC channel. FIG. 25C and FIG. 25D are control cells that were transfected with dCas9-KRAB, but not with a sgRNA, and in the absence (FIG. 25C) or presence (FIG. 25D) of an anti-PD-1 antibody. FIG. 25D depicts the three categories of PD-1 Neg (P6 window on the left), PD-1 Pos (P5 window in middle), and PD-1 High Pos (P4 window on the right). ECD was used to detect dCas9-KRAB expression and APC was used to detect PD-1 expression.

Figure 27A:
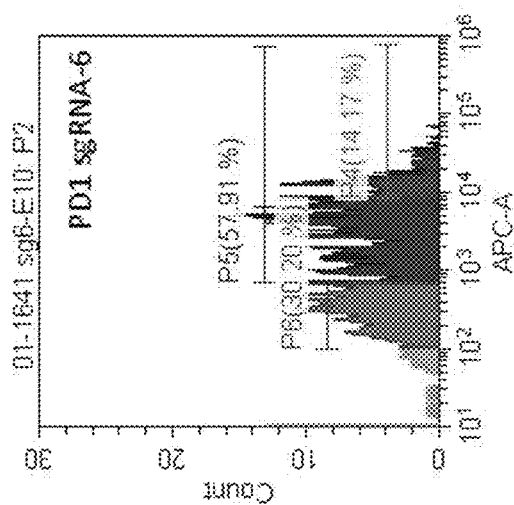
FIGS. 27A, 27B, and 27C depict flow cytometry data using ECD to detect dCas9-KRAB expression and APC to detect PD-1 expression.
Figure 27B:
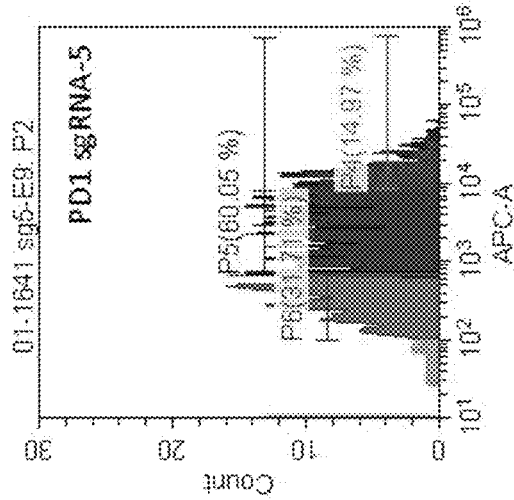
Figure 27C:
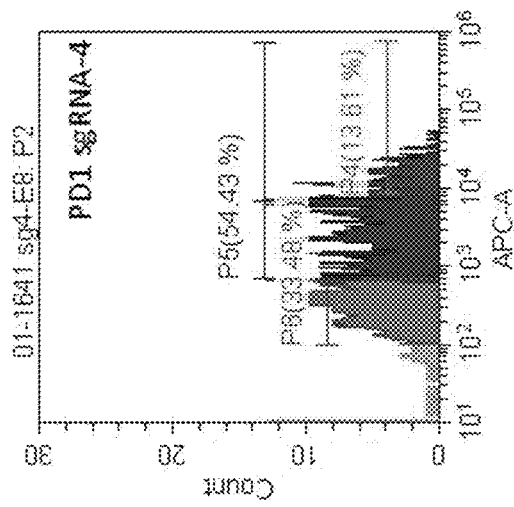

In the first experiment, cells were transfected with dCas9-KRAB and a PD-1-targeted sgRNA and analyzed by FACS to determine the level of PD-1 expression reduction. These results are depicted in FIGS. 26A-F and FIGS. 27A-C, which depict control cells with no sgRNA (FIGS. 26A (without anti-PD-1 antibody) and 26B (with anti-PD-1 antibody)), PD-1 sgRNA-0 (FIG. 26C), PD-1 sgRNA-1 (FIG. 26D), PD-1 sgRNA-2 (FIG. 26E), PD-1 sgRNA-3 (FIG. 26F), PD-1 sgRNA-4 (FIG. 27A), PD-1 sgRNA-5 (FIG. 27B), and PD-1 sgRNA-6 (FIG. 27C). In each case, the cells were categorized as PD-1 Neg (P6 window on the left), PD-1 Pos (P5 window in middle), and PD-1 High Pos (P4 window on the right). Again, a summary of the average cells in each category, as well as the percent decrease compared to the control for this experiment are summarized in Table 7. In this case, sgRNA-3 and sgRNA-4 resulted in the greatest decrease in PD-1 expression.

TABLE 7

| PD-1 sgRNA | PD-1 Neg (%) | PD-1 Pos (%) | PD-1 High Pos (%) | PD-1 down % | PD-1 High down % |
| --- | --- | --- | --- | --- | --- |
| Ctl | 13.21 | 85.5 | 32.25 | | |
| PD-1 sgRNA0 | 28.54 | 68.34 | 19.16 | 20.07 | 40.59 |
| PD-1 sgRNA1 | 27.14 | 68.27 | 17.52 | 20.15 | 45.67 |
| PD-1 sgRNA2 | 34.47 | 60.05 | 14.63 | 29.77 | 54.64 |
| PD-1 sgRNA3 | 36.2 | 55.9 | 13.8 | 34.62 | 57.21 |
| PD-1 sgRNA4 | 38.55 | 54.43 | 13.61 | 36.34 | 57.80 |
| PD-1 sgRNA5 | 34.83 | 60.05 | 14.97 | 29.77 | 53.58 |
| PD-1 sgRNA6 | 34.75 | 57.91 | 14.17 | 32.27 | 56.06 |

Figure 28A:
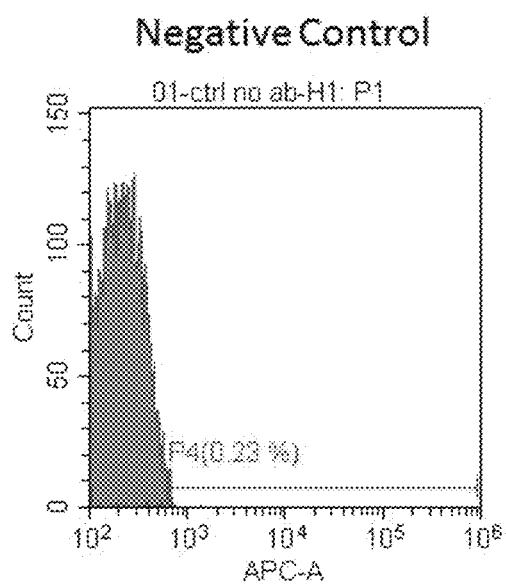
FIGS. 28A and 28B depict flow cytometry data using ECD to detect dCas9-KRAB expression and APC to detect PD-1 expression.
Figure 28B:
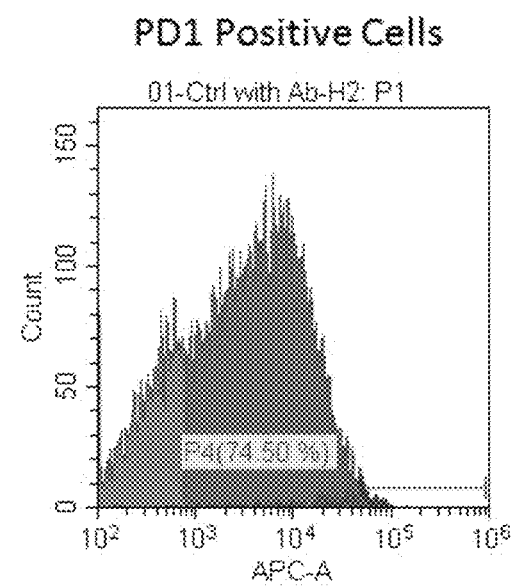
Figure 30A:
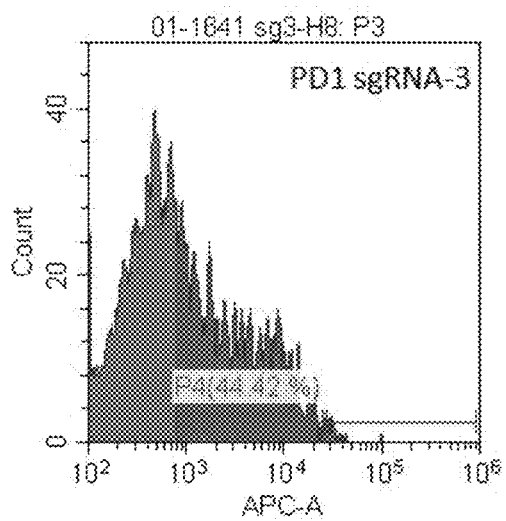
FIGS. 30A, 30B, 30C, and 30D depict flow cytometry data using ECD to detect dCas9-KRAB expression and APC to detect PD-1 expression.
Figure 30B:
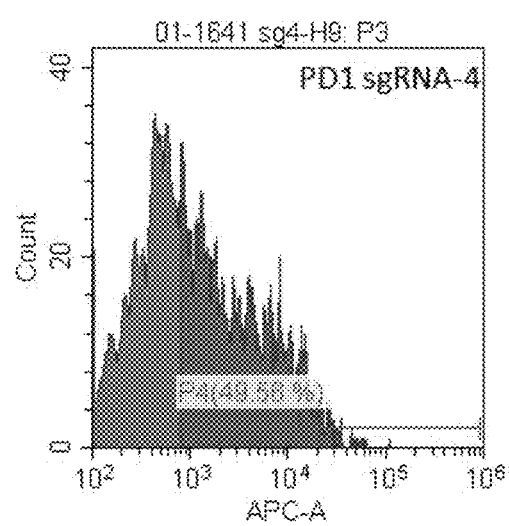
Figure 30C:
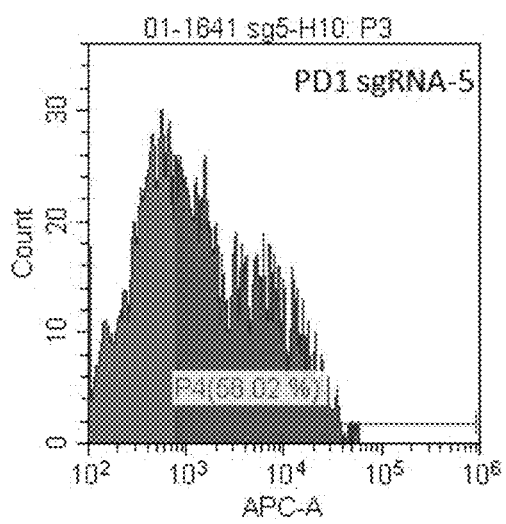
Figure 30D:
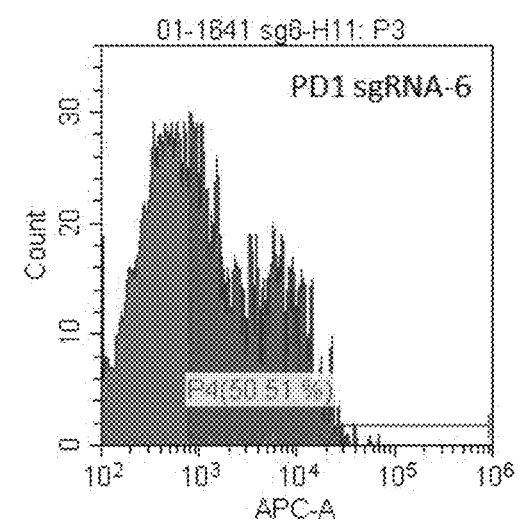

The experiment described above was repeated, and this time cells were counted and classified as either PD-1 Negative (PD-1 Neg) or PD-1 Positive (PD-1 Pos). The results from this experiement are summarized in Table 8. PD-1 expression levels in negative and positive controls are depicted in FIGS. 28A and 28B. PD-1 expression levels in control cells with dCas9-KRAB, without sgRNA, and without anti-PD-1 antibody is shown in FIG. 29A, with dCas9-KRAB, without sgRNAs, and with anti-PD-1 antibody is shown in FIG. 29B, with dCas9-KRAB, with a control sgRNA, and with anti-PD-1 antibody is shown in FIG. 29C, with dCas9-KRAB, with PD-1 sgRNA-0, and with anti- PD-1 antibody is shown in FIG. 29D, with dCas9-KRAB, with PD-1 sgRNA-1, and with anti-PD-1 antibody is shown in FIG. 29E, with dCas9-KRAB, with PD-1 sgRNA-2, and with anti-PD-1 antibody is shown in FIG. 29F, with dCas9-KRAB, with PD-1 sgRNA-3, and with anti-PD-1 antibody is shown in FIG. 30A, with dCas9-KRAB, with PD-1 sgRNA-4, and with anti-PD-1 antibody is shown in FIG. 30B, with dCas9-KRAB, with PD-1 sgRNA-5, and with anti-PD-1 antibody is shown in FIG. 30C, and with dCas9-KRAB, with PD-1 sgRNA-6, and with anti-PD-1 antibody is shown in FIG. 30D. In each case, the cells were categorized as PD-1 Neg or PD-1 Pos (P4 window on right). ECD was used to detect dCas9-KRAB expression and APC was used to detect PD-1 expression. Again, a summary of the average cells in each category, as well as the percent decrease compared to the control for this experiment are summarized in Table 8. sgRNA-3 and sgRNA-4 were selected for use in further experiments.

TABLE 8

| PD-1 sgRNA | PD-1 Neg (%) | PD-1 Pos (%) | PD-1 down % |
|---|---|---|---|
| Ctl | 23.03 | 76.44 | |
| Ctl sgRNA | 25.8 | 73.63 | 3.68 |
| PD-1 sgRNA1 | 36.19 | 62.93 | 17.67 |
| PD-1 sgRNA2 | 42.72 | 50.97 | 33.32 |
| PD-1 sgRNA3 | 53.54 | 44.42 | 41.89 |
| PD-1 sgRNA4 | 48.63 | 49.56 | 35.16 |
| PD-1 sgRNA5 | 42.76 | 56.02 | 26.71 |
| PD-1 sgRNA6 | 47.94 | 50.51 | 33.92 |

Example 14: Screen of PD-1 sgRNA Lentiviruses in Primary Human T Cells

CD3/CD28 beads were used to activate primary human T cells. dCas9-KRAB lentivirus, rtTA lentivirus, and PD-1 sgRNA lentivirus were co-transduced into the activated T cell.

Figures 31A, 31B, 31C, 31D:
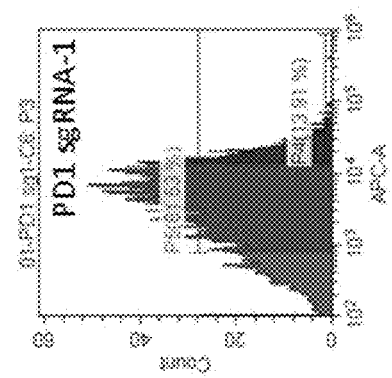
FIGS. 31A, 31B, 31C, 31D, 31E, 31F, 31G, and 31H depict flow cytometry data using ECD to detect dCas9-KRAB expression and APC to detect PD-1 expression.
Figures 31E, 31F, 31G, 31H:
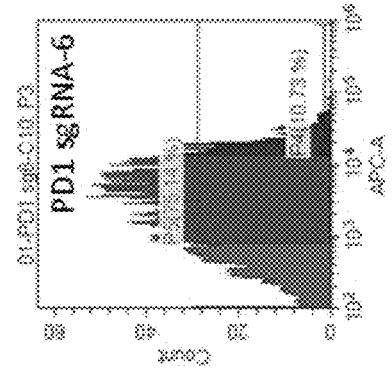

The cells were analyzed by flow cytometry to determine PD-1 expression levels. Cells were counted and classified as either PD-1 Positive (PD-1 Pos) or PD-1 High Positive (PD-1 High Pos). The results from this experiment are summarized in Table 9 and included controls cells with no sgRNA (FIGS. 31A-31B), a control sgRNA (FIG. 31C), PD-1 sgRNA-1 (FIG. 31D), PD-1 sgRNA-2 (FIG. 31E), PD-1 sgRNA-3 (FIG. 31F), PD-1 sgRNA-4 (FIG. 31G), and PD-1 sgRNA-6 (FIG. 31H). In each case, the cells were counted as PD-1 Pos (P5 window on left) or PD-1 High Pos (P4 window on right). ECD was used to detect dCas9-KRAB expression and APC was used to detect PD-1 expression. Again, a summary of the average cells in each category, as well as the percent decrease compared to the control for this experiment are summarized in Table 9. In this case, sgRNA-2, sgRNA-3, and sgRNA-4 resulted in the greatest decrease in PD-1 expression.

TABLE 9

| PD-1 sgRNA | PD-1 Pos (%) | PD-1 High Pos (%) | PD-1 down % | PD-1 High down % |
|---|---|---|---|---|
| Ctl | 81 | 13.4 | | |
| Ctl sgRNA | 79.77 | 13.75 | 1.52 | −2.61 |
| PD-1 sgRNA1 | 81.53 | 13.91 | −0.65 | −3.81 |
| PD-1 sgRNA2 | 72.03 | 9.93 | 11.07 | 25.90 |
| PD-1 sgRNA3 | 71.63 | 9.42 | 11.57 | 29.70 |
| PD-1 sgRNA4 | 73.06 | 10.06 | 9.80 | 24.93 |
| PD-1 sgRNA6 | 75.14 | 10.73 | 7.23 | 19.93 |

Figure 32A:
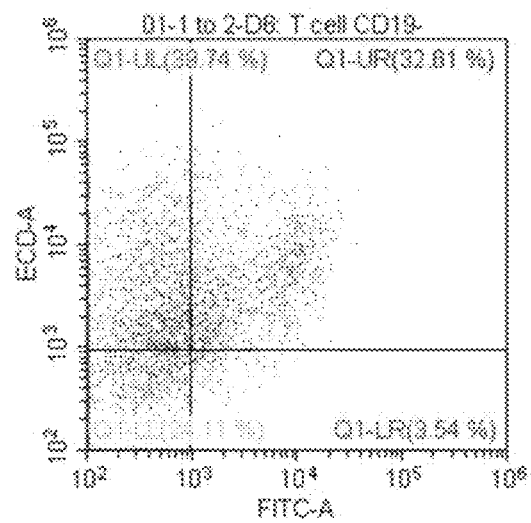
FIGS. 32A and 32B depict flow cytometry data using FITC to detect CD19 CAR-dCas9-KRAB expression and ECD to detect LAT-TEV expression.
Figure 32B:
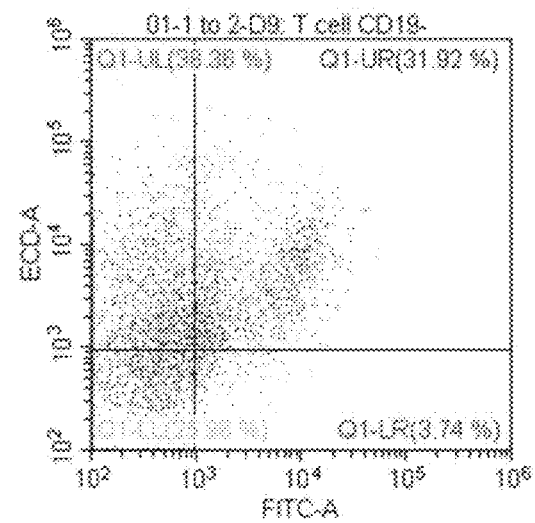
Figure 33A:
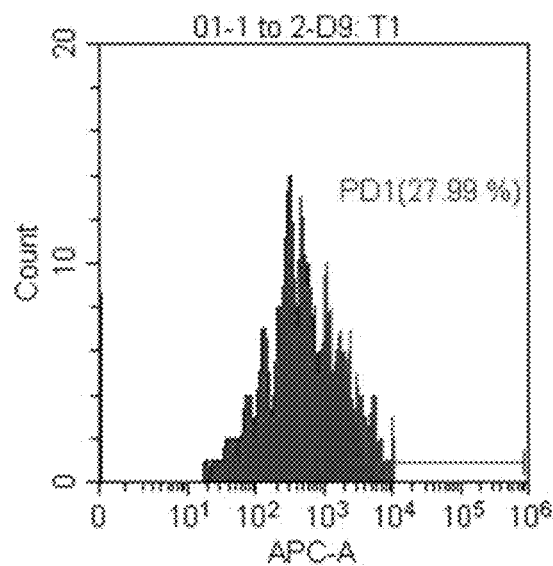
FIGS. 33A and 33B depict flow cytometry data using APC to detect PD-1 expression.

Example 15: Demonstration of Ligand-Dependant PD-1 Downregulation by CD19-CAR-dCas9-KRAB/PD-1 sgRNAs in Primary T Cells and Cell Killing T cells were isolated and transduced with LAT-TEV lentivirus and CD19-CAR-dCas9-KRAB fusion protein lentivirus. Cells expressing both LAT-TEV and CD19-CAR-dCas9-KRAB can be optionally enriched, for example by cell sorting. In this example, cells were sorted based on co-expression of LAT-TEV (ECD, FIGS. 32A-32B) and CD19-CAR-dCas9-KRAB (FITC, FIGS. 32A-32B). Cells expressing both lentiviral payloads were then transduced with #2, #3, and #4 PD-1 sgRNA lentiviruses. The transduced T cells were then co-cultured with Raji cells (lymphoma cells expressing CD19) in order to activate the CD19-CAR, leading to ligand dependent cleavage of dCas9-KRAB from the CAR fusion protein. T cells were analyzed for PD-1 expression levels (FIGS. 33A-33B) and cell killing efficiency. Approximately 17% of cells transduced with the PD-1 sgRNAs #2, #3, and #4 expressed detectable levels of PD-1 (FIG. 33B), compared to approximately 28% of the cells that were transduced with control sgRNA (FIG. 33A).

For the cell killing assay, 1) T cells expressing CD19-CAR-dCas9-KRAB, LAT-TEV and PD-1 sgRNAs #2, #3, and #4, 2) T cells expressing CD19-CAR-dCas9-KRAB, LAT-TEV and control sgRNAs, or 3) control T cells were incubated with Raji cells expressing PD-L1 for one day or two days. The ratio of T cells versus Raji-PD-L1 cells was 5:1 or 1:2 as indicated in Table 10. The cells were stained with anti-CD19 antibody and analyzed by flow cytometry to detect remaining Raji-PD-L1 cells. Cells were analyzed by flow cytometery after 4 hours, 1 day, or 2 days of incubation. APC-A750 was used to detect CD19 on the surface of Raji-PD-L1 cells.

TABLE 10

| | Ratio | Ratio |
|---|---|---|
| Control T cells:Raji-PD-L1 cells | 5:1 | 1:2 |
| CD19-CAR-T cells with control sgRNAs:Raji-PD-L1 cells | 5:1 | 1:2 |
| CD19-CAR-T cells with PD-1 sgRNAs:Raji-PD-L1 cells | 5:1 | 1:2 |

CD19-CAR-T cells with control sgRNAs = transduced T cells expressing CD19-CAR-dCas9-KRAB, LAT-TEV and control sgRNAs
CD19-CAR-T cells with PD-1 sgRNAs = transduced T cells expressing CD19-CAR-dCas9-KRAB, LAT-TEV and PD-1 sgRNAs T cells versus Raji-PD-L1 cells at a 5:1 ratio analyzed after 4 hour incubation are depicted in FIG. 34A (Control T cells vs Raji-PD-L1 cells), FIG. 34B (CD19-CAR-T cells with control sgRNAs vs Raji-PD-L1 cells), and FIG. 34C (CD19-CAR T cells with PD-1 sgRNAs vs Raji-PD-L1 cells).

T cells versus Raji-PD-L1 cells at a 5:1 ratio analyzed after 1 day incubation are depicted in FIG. 35A (Control T cells vs Raji-PD-L1 cells), FIG. 35B (CD19-CAR-T cells with control sgRNAs vs Raji-PD-L1 cells), and FIG. 35C (CD19-CAR T cells with PD-1 sgRNAs vs Raji-PD-L1 cells).

T cells versus Raji-PD-L1 cells at a 5:1 ratio analyzed after 2 days incubation are depicted in FIG. 36A (Control T cells vs Raji-PD-L1 cells), FIG. 36B (CD19-CAR-T cells with control sgRNAs vs Raji-PD-L1 cells), and FIG. 36C (CD19-CAR T cells with PD-1 sgRNA vs Raji-PD-L1 cells)

T cells versus Raji-PD-L1 cells at a 1:2 ratio analyzed after 4 hour incubation are depicted in FIG. 37A (Control T cells vs Raji-PD-L1 cells), FIG. 37B (CD19-CAR-T cells with control sgRNAs vs Raji-PD-L1 cells), and FIG. 37C (CD19-CAR T cells with PD-1 sgRNAs vs Raji-PD-L1 cells)

T cells versus Raji-PD-L1 cells at a 1:2 ratio analyzed after 1 day incubation are depicted in FIG. 38A (Control T cells vs Raji-PD-L1 cells), FIG. 38B (CD19-CAR-T cells with control sgRNAs vs Raji-PD-L1 cells), and FIG. 38C (CD19-CAR T cells with PD-1 sgRNAs vs Raji-PD-L1 cells)

T cells versus Raji-PD-L1 cells at a 1:2 ratio analyzed after 2 days incubation are depicted in FIG. 39A (Control T cells vs Raji-PD-L1 cells), FIG. 39B (CD19-CAR-T cells with control sgRNAs vs Raji-PD-L1 cells), and FIG. 39C (CD19-CAR T cells with PD-1 sgRNAs vs Raji-PD-L1 cells)

Figure 40A:
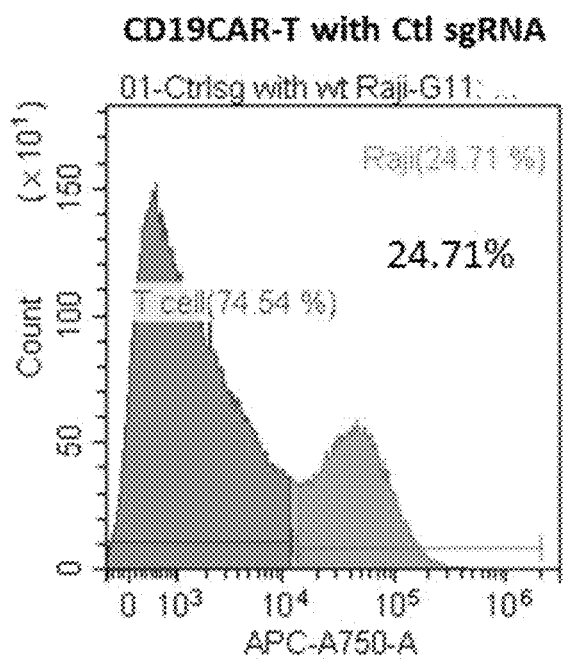
FIGS. 40A and 40B depict flow cytometry data using APC-A750 to detect CD19 expression after the indicated T cells were incubated with Raji cells at a 1 to 1 ratio for 5 days.
Figure 40B:
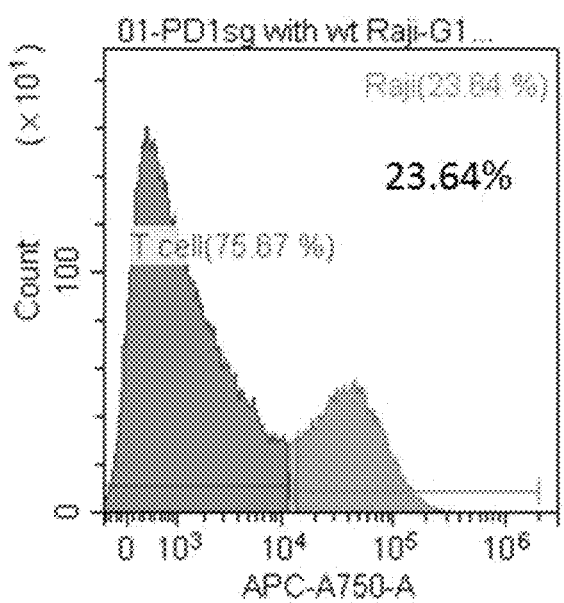

T cells versus Raji-PD-L1 cells at a 1:1 ratio analyzed after 5 days incubation are depicted in FIG. 40A (Control T cells vs Raji-PD-L1 cells), FIG. 40B (CD19-CAR-T cells with control sgRNAs vs Raji-PD-L1 cells), and FIG. 40C (CD19-CAR T cells with PD-1 sgRNAs vs Raji-PD-L1 cells).

Figure 33B:
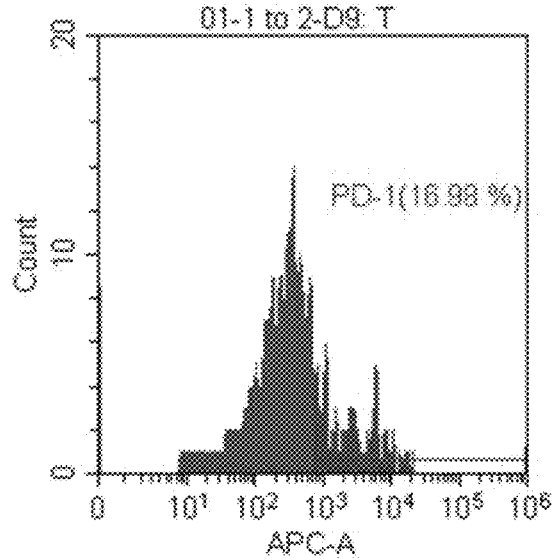

These data demonstrated successful dCas9-KRAB cleavage in engineered CD19-CAR T cells with PD-1 sgRNA treated with CD19+ Raji cells (FIG. 24). These data also demonstrated PD-1 down-regulation by dCas9-KRAB and PD-1 sgRNAs in the engineered T cells treated with Raji cells (FIGS. 33A & 33B). These data also demonstrated that the CD19-CAR T cells with PD-1 sgRNAs (with PD-1 downregulation) are more effective than control CD19-CAR T cells with control sgRNAs (without PD-1 downregulation) in killing Raji lymphoma cells expressing PD-L1 (FIGS. 34-39). CD19-CART cells expressing PD-1 sgRNAs and CD19-CAR T cells expressing control sgRNAs have similar activities in killing Raji lymphoma cells that do not express PD-L1 (FIG. 40).

Example 16: Jurkat Cell Engineering with Ligand-Dependant dCas9-KRAB Cleavage

Figure 41A:
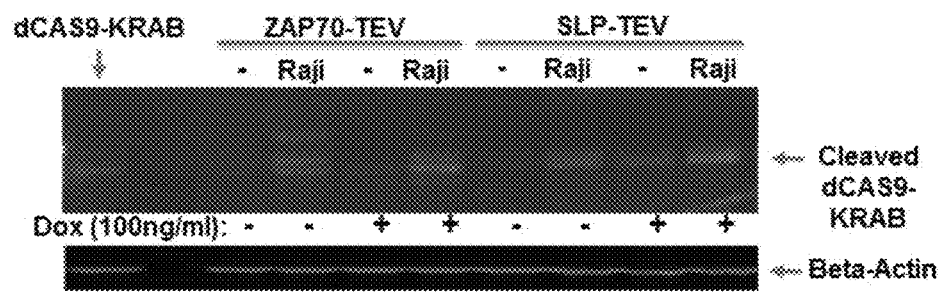
FIGS. 41A, 41B, and 41C depict western blot for cleaved dCas9-KRAB in the indicated samples and using beta-actin as a loading control.
Figure 41B:
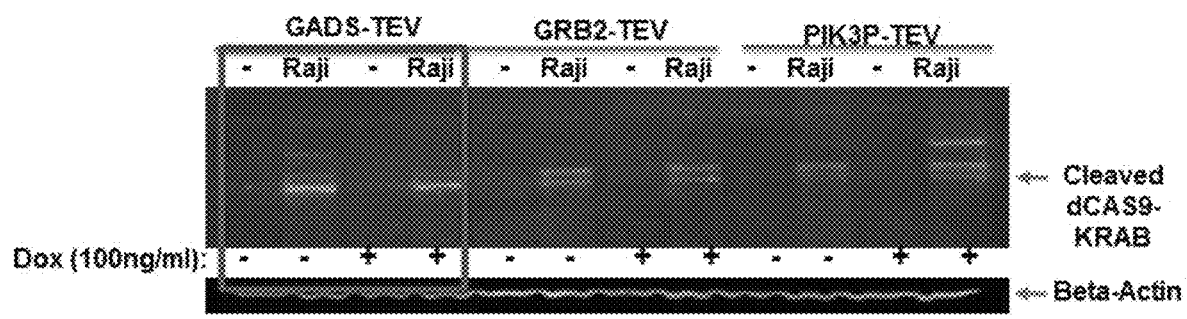
Figure 41C:
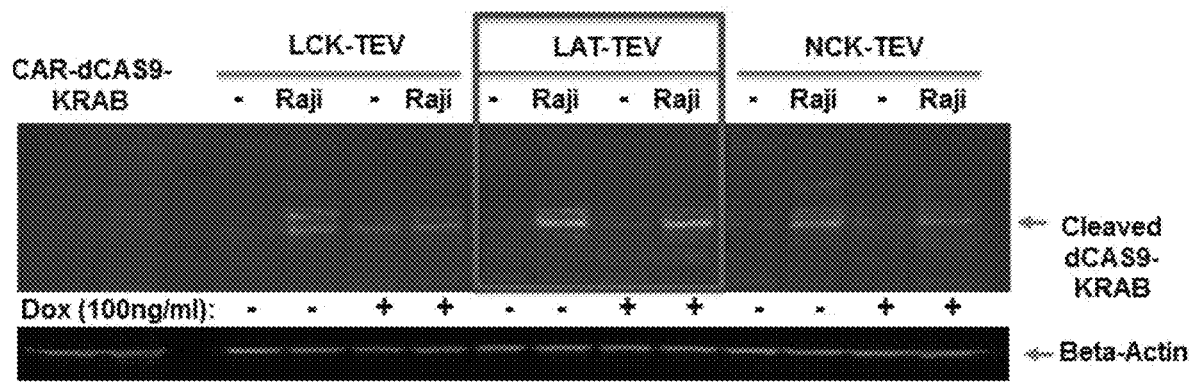

Lentiviruses encoding one of eight adaptors fused to TEV were cotransduced into Jurkat cells along with an rtTA lentivirus and a third lentivirus encoding CD19 CAR-dCas9-KRAB fusion protein. The CD19 CAR-dCas9-KRAB fusion protein also comprised CD28 and CD3-zeta signaling domains. The transduced cells were then activated with Raji cells and subjected to western blot to detect dCas9-KRAB cleavage. FIG. 41A depicts western blot of cleaved dCas9-KRAB, and cells co-expressing CD19 CAR-dCas9-KRAB fusion protein and ZAP70-TEV or SLP-TEV. FIG. 41B depicts western blot of cells co-expressing CD19 CAR-dCas9-KRAB fusion protein and GADS-TEV, GRB2-TEV, or PIK3P-TEV. FIG. 41C depicts western blot of uncleaved CAR-dCas9-KRAB, and cells co-expressing CD19 CAR-dCas9-KRAB fusion protein and LCK-TEV, LAT-TEV, or NCK-TEV. In each case, the cells were either incubated with Raji cells (Raji) or not (−) prior to being harvested for western blot analysis. Additionally, the cells were kept in the presence (+) or absence (−) of doxycycline at a concentration of 100 ng/mL prior to western blot analysis. Beta-actin was used as a loading control. These data demonstrate dCas9-KRAB cleavage in engineered CD19 CAR-dCAS9-KRAB/adaptor-TEV positive Jurkat cells when activated with CD19+ Raji lymphoma cells. In the depicted example experiment, GADS-TEV and LAT-TEV showed the most cleavage of dCas9-KRAB.

Example 17: Ligand-Dependent CXCR4 Down-Regulation by dCas9-KRAB

Figure 42A:
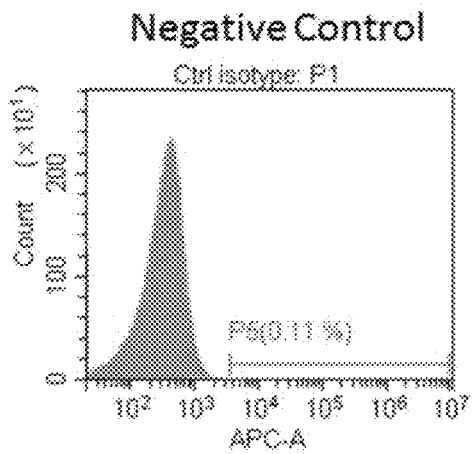
FIGS. 42A, 42B, 42C, and 42D depict flow cytometry data using APC to detect CXCR4 expression.
Figure 42B:
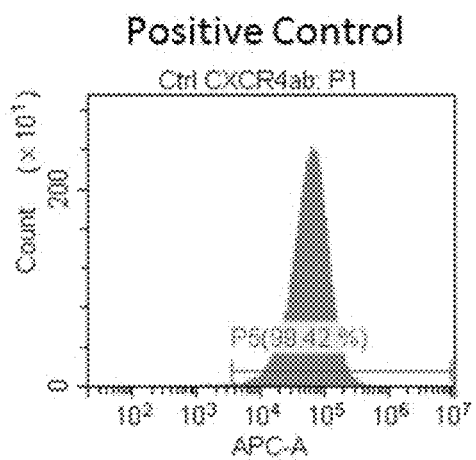
Figure 42C:
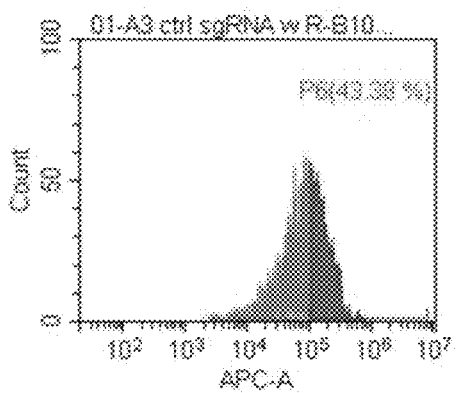
Figure 42D:
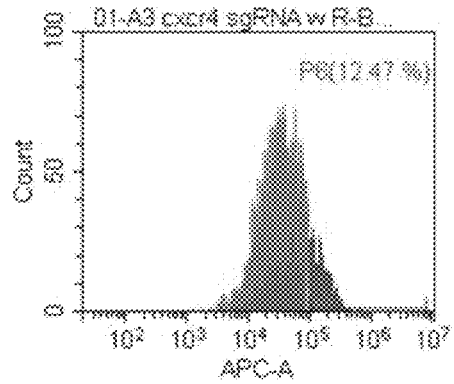
Figure 43A:
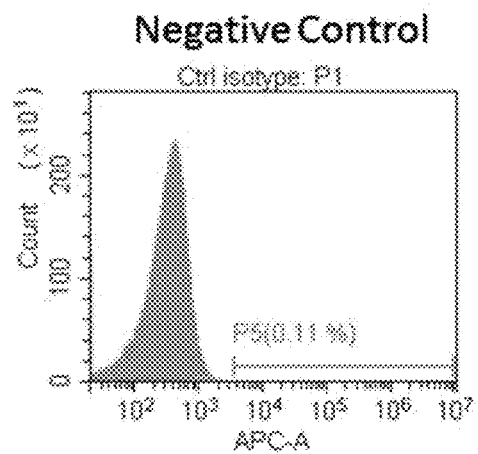
FIGS. 43A, 43B, 43C, and 43D depict flow cytometry data using APC to detect CXCR4 expression.
Figure 43B:
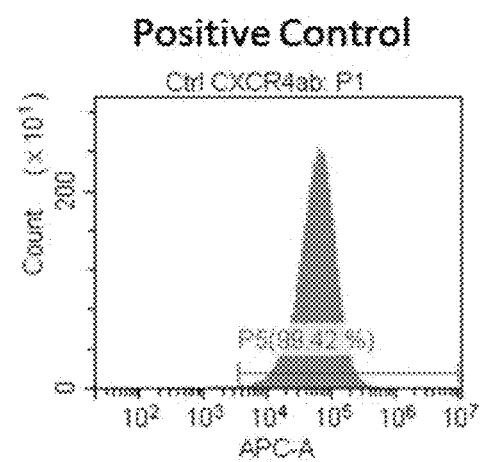
Figure 43C:
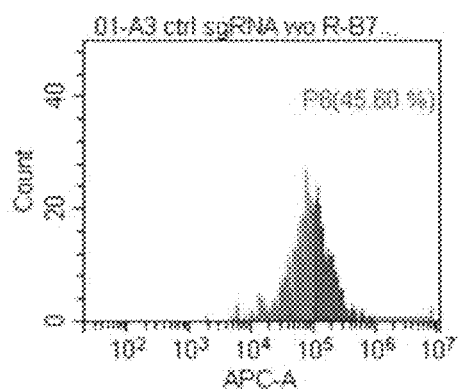
Figure 43D:
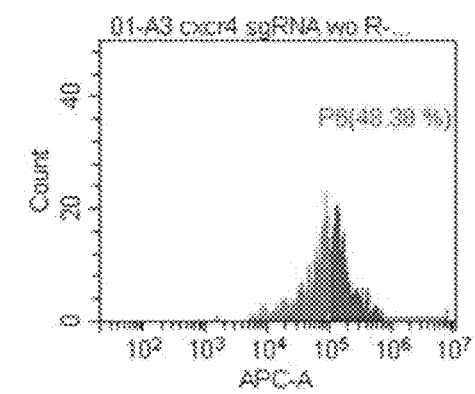
Figure 45A:
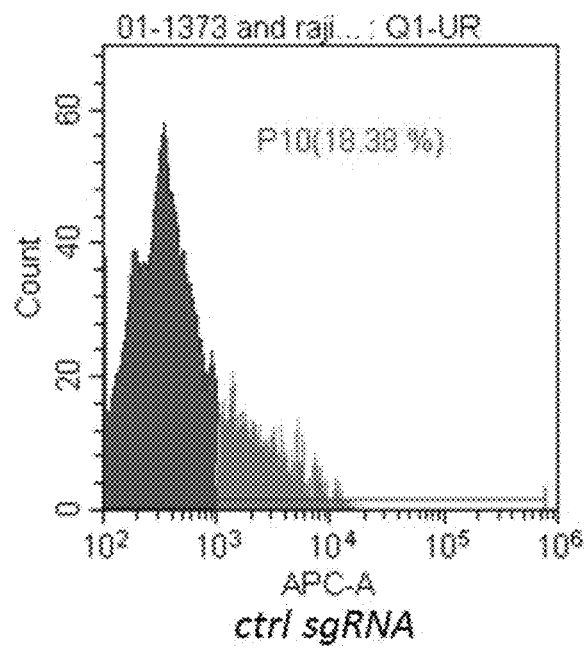
FIGS. 45A, 45B, 45C, 45D, 45E, 45F, 45G, and 45H depict flow cytometry data using APC-A750 to detect PD-1.
Figure 45C:
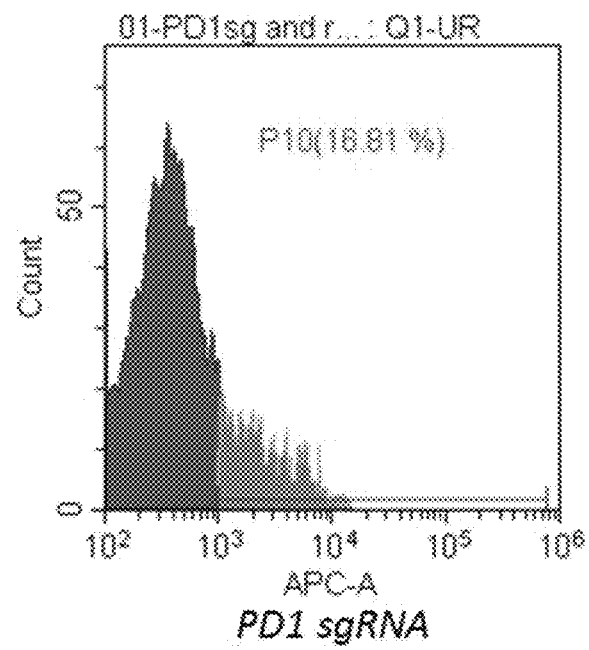
Figure 45B:
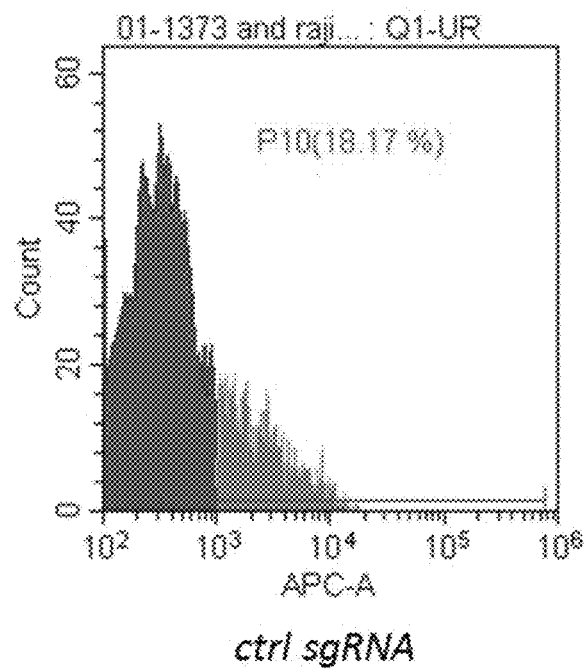
Figure 45D:
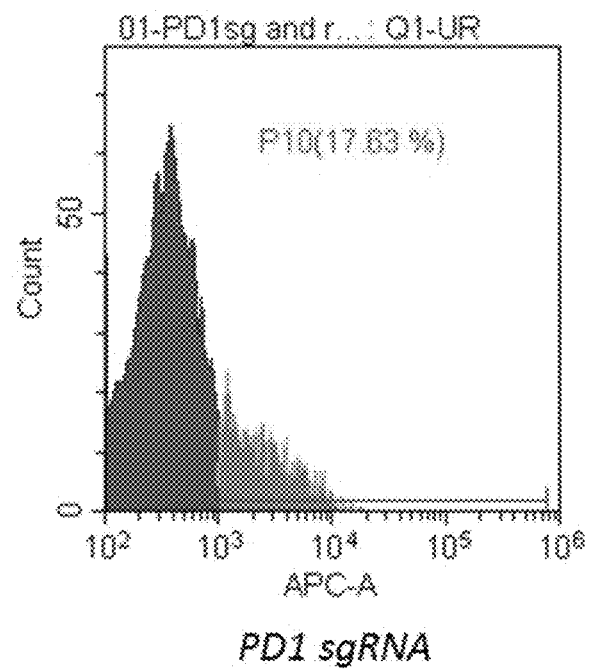
Figure 45E:
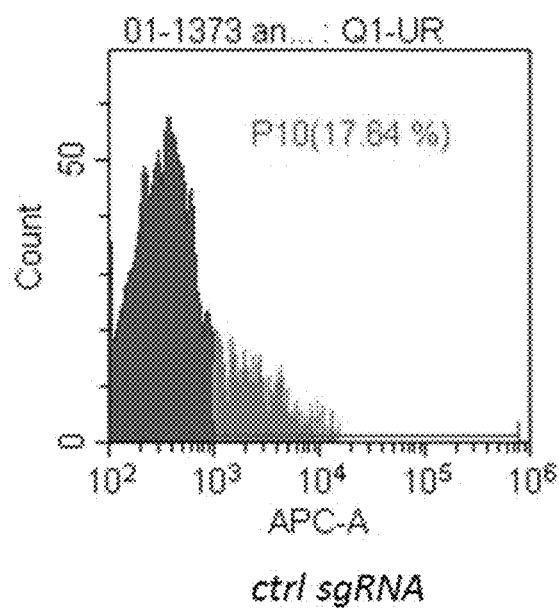
Figure 45G:
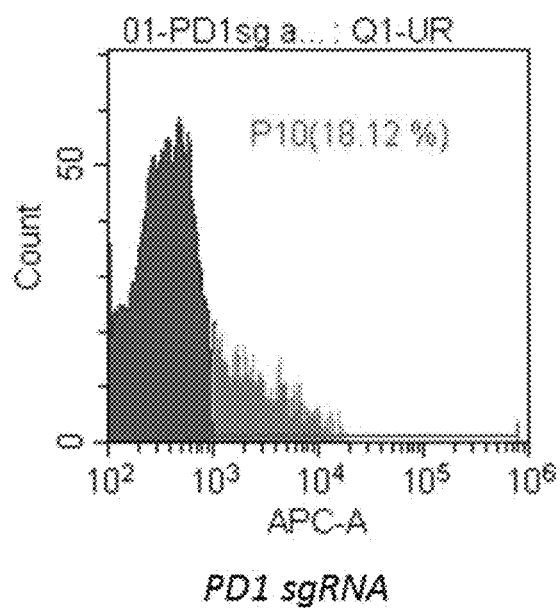
Figure 45F:
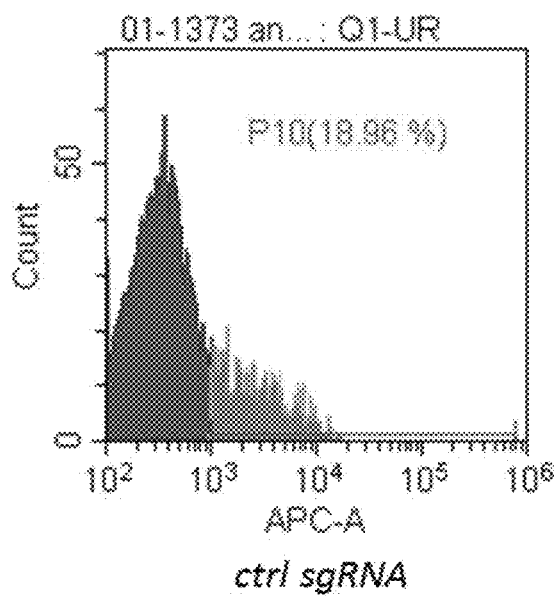
Figure 45H:
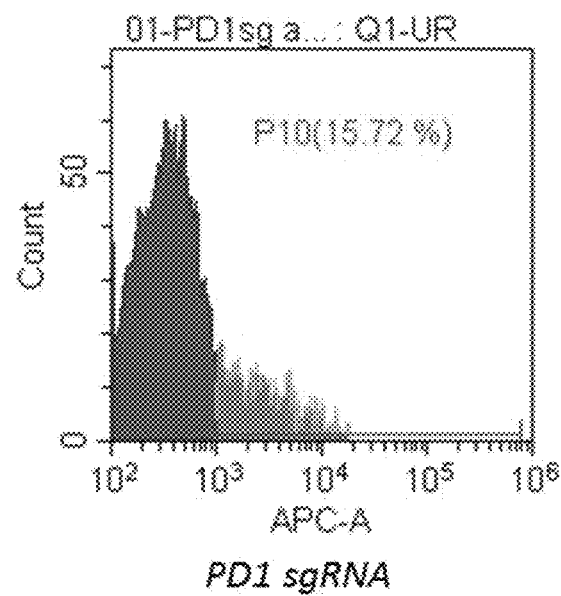

GADS-TEV lentivirus, rtTA lentivirus, CD19 CAR-dCas9-KRAB fusion protein lentivirus, and CXCR4-targeting sgRNA lentivirus (or a control sgRNA lentivirus) were co-transduced into Jurkat cells, which were subsequently activated by Raji cells. Activated cells were then tested for CXCR4 down-regulation by flow cytometer. Unlabeled cells were used as a negative control (FIG. 42A and FIG. 43A). Cells labeled with anti-CXCR4 were used as a positive control (FIG. 42B and FIG. 43B). Cells transduced with control sgRNA and activated with Raji cells are depicted in FIG. 42C. Cells transduced with CXCR4 sgRNA and activated with Raji cells are depicted in FIG. 42D. Cells transduced with control sgRNA and not activated with Raji cells are depicted in FIG. 43C. Cells transduced with CXCR4 sgRNA and not activated with Raji cells are depicted in FIG. 43D. These data demonstrate CXCR4 down-regulation by dCas9-KRAB in cells transfected with CXCR4 sgRNA and activated with Raji cells.

Example 18: Ligand-Dependent Down-Regulation of PD-1 and Cell Killing Assay with CAR-T Cells T cells were isolated and transduced with LAT-TEV lentivirus and anti-CD19-CAR-dCas9-KRAB fusion protein lentivirus. Cells expressing both lentiviral payloads were then transduced with #2, #3, and #4 PD-1 sg RNA lentiviruses. Cells expressing both lentiviral payloads can be optionally enriched, for example by cell sorting. The transduced T cells were then co-cultured with Raji cells (lymphoma cells expressing CD19) in order to activate the anti-CD19-CAR, leading to ligand dependent cleavage of dCas9-KRAB from the CAR fusion protein. Cells were analyzed for PD-1 expression levels and tumor killing efficiency.

For the cell killing assay, the CD19-CAR T cells with PD-1 sgRNAs, CD19 CAR T cells with control sg RNAs, or control T cells were incubated with Raji cells expressing PD-L1 for 1 day, 2 days, or 3 days. The ratio of T cells versus Raji-PD-L1 cells was 1:1 or 2:1 as indicated in Table 11. The cells were stained with anti-CD19 antibody and analyzed by flow cytometry to detect remaining Raji-PD-L1 cells. Cells were analyzed by flow cytometry after 1 day, 2 days, and 3 days. APC-A750 was used to detect CD19 on the surface of Raji-PD-L1 cells. The experiment was done in duplicate.

TABLE 11

|  | Ratio | Ratio |
|---|---|---|
| Control T cells:Raji-PD-L-1 cells | 1:1 | 2:1 |
| CD19-CAR-T cells with control sgRNAs:Raji-PD-L-1 cells | 1:1 | 2:1 |
| CD19-CAR-T cells with PD-1 sgRNAs:Raji-PD-L-1 cells | 1:1 | 2:1 |

T cells versus Raji-PD-L1 cells at a 1:1 ratio analyzed after 1 day incubation are depicted in FIGS. 44A and 44B (Control T cells vs Raji-PD-L1 cells), FIGS. 44C and 44D (CD19-CAR-T cells with control sgRNAs vs Raji-PD-L1 cells), and FIGS. 44E and 44F (CD19-CAR-T cells with PD-1 sgRNAs vs Raji-PD-L1 cells). Percentages indicate percentage of remaining Raji-PD-L1 cells.

T cells versus Raji-PD-L1 cells at a 2:1 ratio analyzed after 1 day incubation are depicted in FIGS. 44G and 44H (Control T cells vs Raji-PD-L1 cells), FIGS. 44I and 44J (CD19-CAR-T cells with control sgRNA vs Raji-PD-L1 cells), and FIGS. 44K and 44L (CD19-CAR-T cells with PD-1 sgRNAs vs Raji-PD-L1 cells). Percentages indicate percentage of remaining Raji-PD-L1 cells.

FIGS. 45A-45D show expression of PD-1 in CD19-CAR-T cells with control sgRNA (FIGS. 45A and 45B) and in CD19-CAR-T cells with PD-1 sgRNAs (FIGS. 45C and 45D) after 1 day incubation with Raji-PD-L1 cells (at a 1:1 ratio).

FIGS. 45E-45H show expression of PD-1 in CD19-CAR-T cells with control sgRNA (FIGS. 45E and 45F) and in CD19-CAR-T cells with PD-1 sgRNAs (FIGS. 45G and 4511) after 1 day incubation with Raji-PD-L1 cells (at a 2:1 ratio).

Figure 46E:
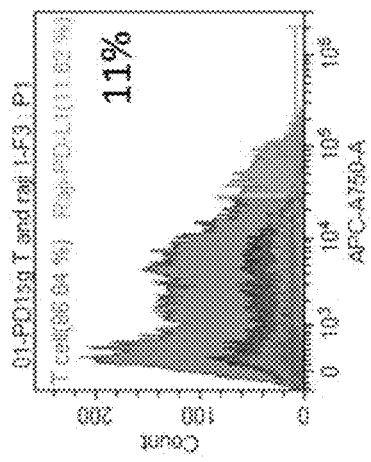
FIGS. 46A, 46B, 46C, 46D, 46E, 46F, 46G, 46H, 46I, 46J, 46K, and 46L depict flow cytometry data using APC-A750 to detect CD19 expression.
Figure 46C:
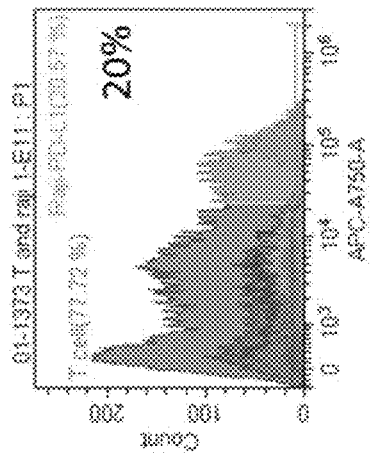
Figure 46A:
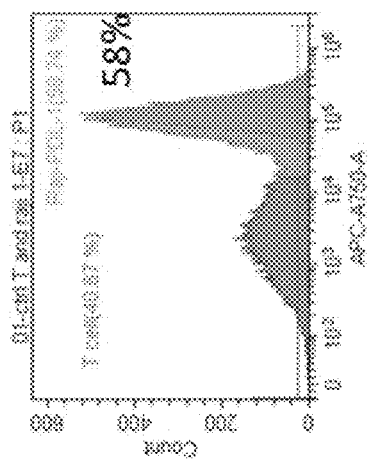
Figure 46F:
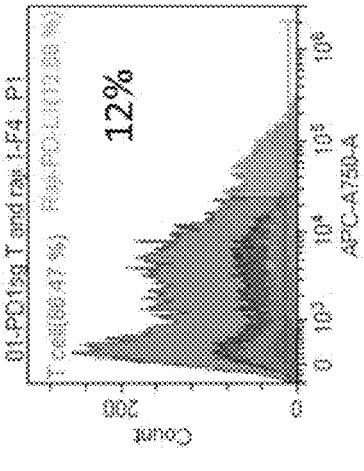
Figure 46D:
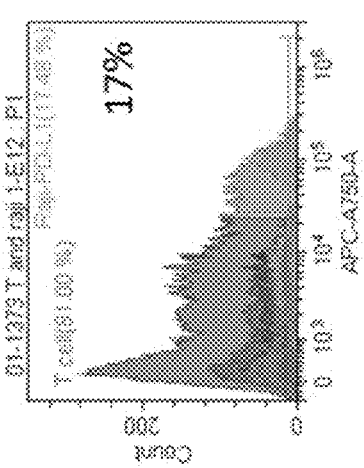
Figure 46B:
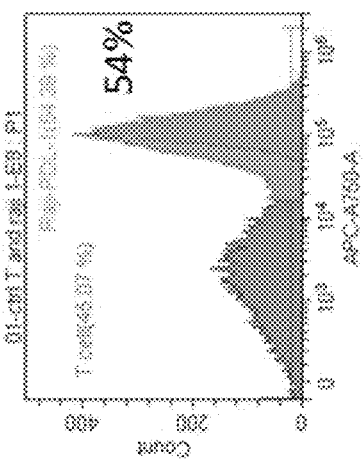

T cells versus Raji-PD-L1 cells at a 1:1 ratio analyzed after 2 days incubation are depicted in FIGS. 46A and 46B (Control T cells vs Raji-PD-L1 cells), FIGS. 46C and 46D (CD19-CAR-T cells with control sgRNA vs Raji-PD-L1 cells), and FIGS. 46E and 46F (CD19-CAR-T cells with PD-1 sgRNAs vs Raji-PD-L1 cells). Percentages indicate percentage of remaining Raji-PD-L1 cells.

Figure 46G:
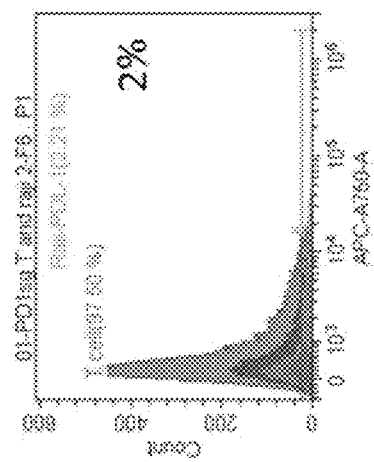
Figure 46I:
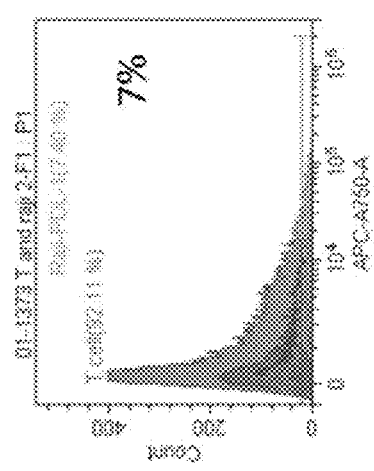
Figure 46K:
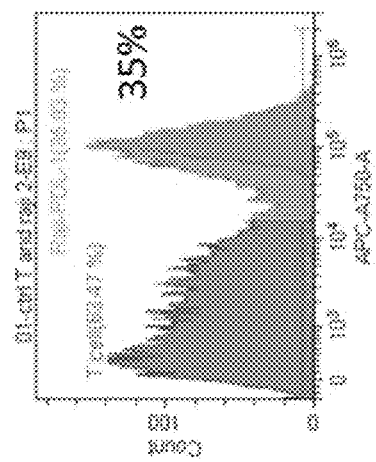
Figure 46H:
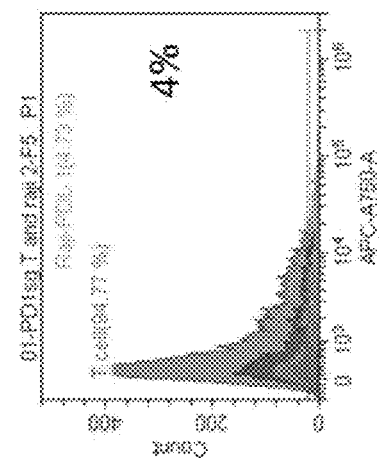
Figure 46J:
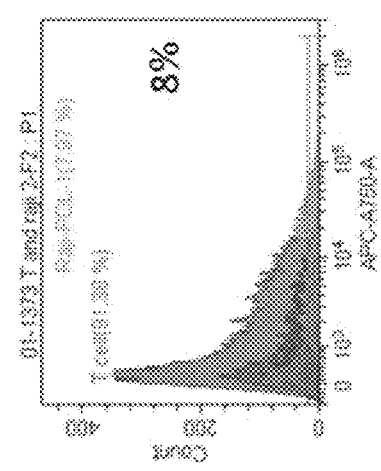
Figure 46L:
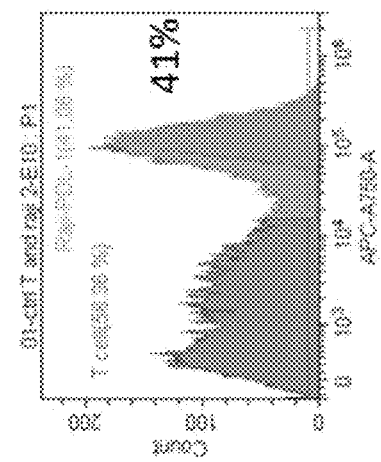
Figure 47A:
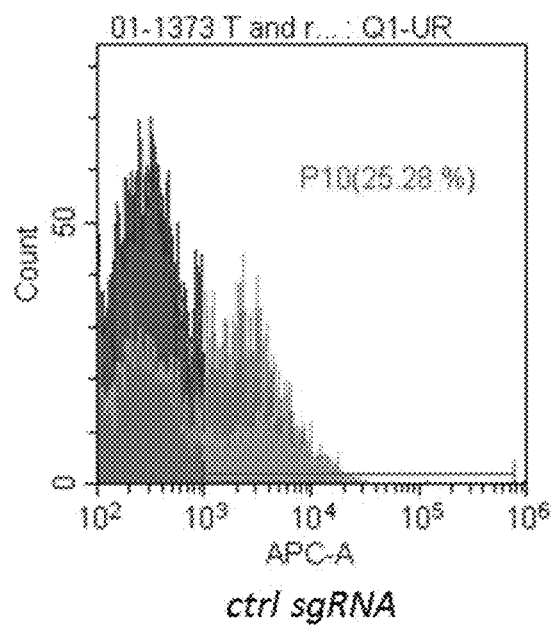
FIGS. 47A, 47B, 47C, 47D, 47E, 47F, 47G, and 47H depict flow cytometry data using APC-A750 to detect PD-1.
Figure 47C:
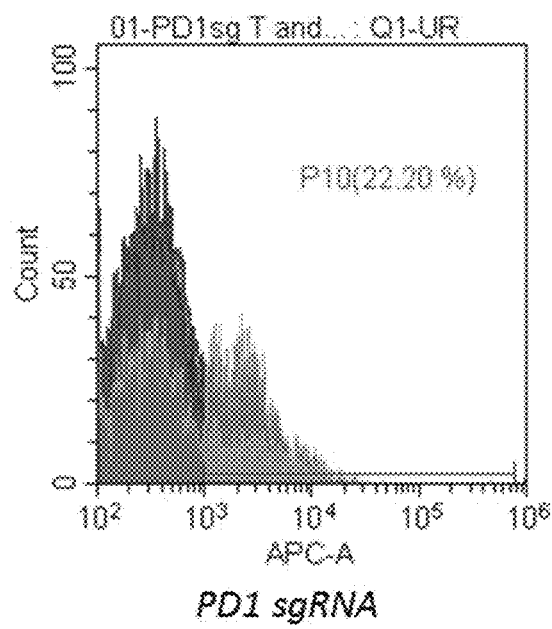
Figure 47B:
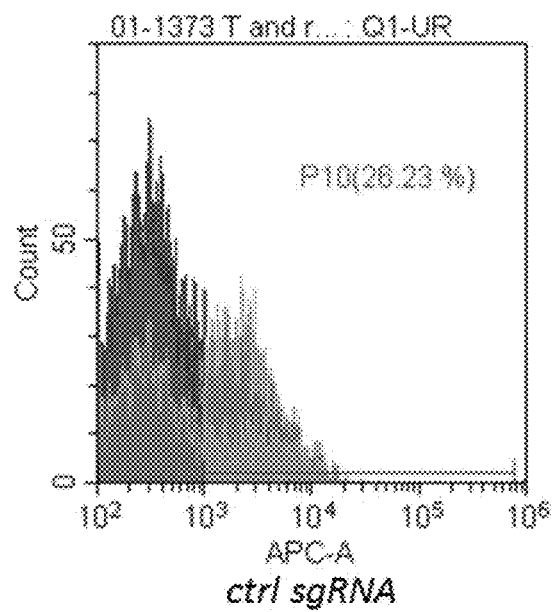
Figure 47D:
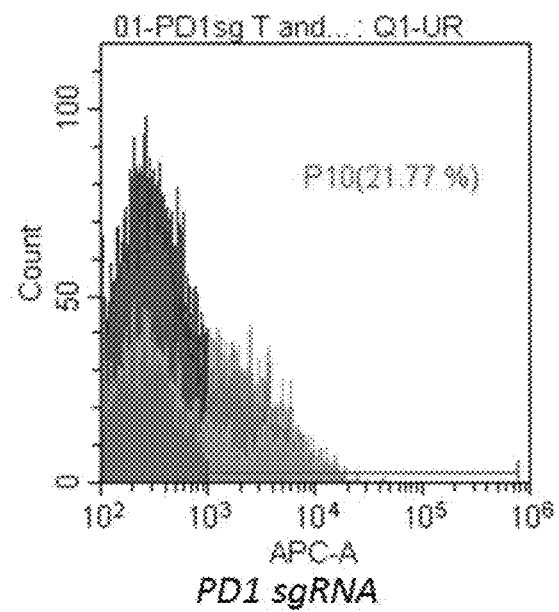
Figure 47E:
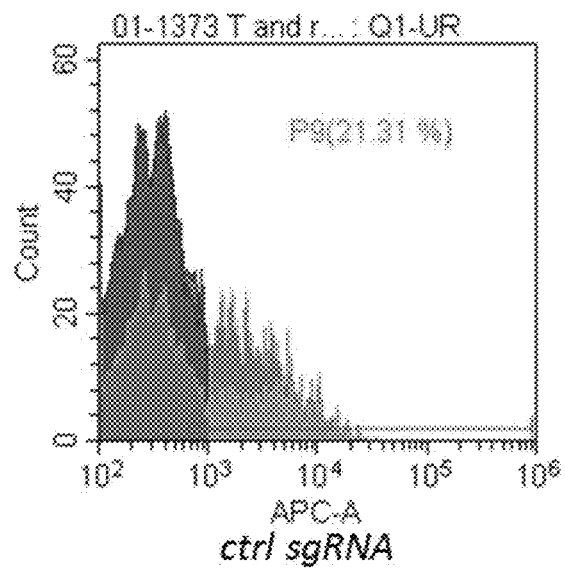
Figure 47G:
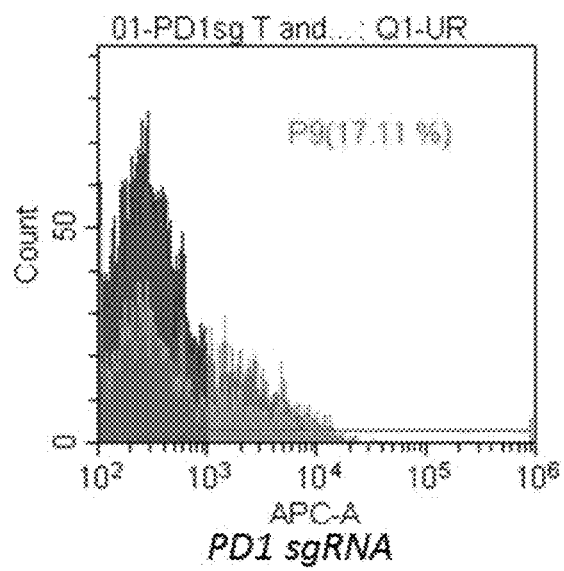
Figure 47F:
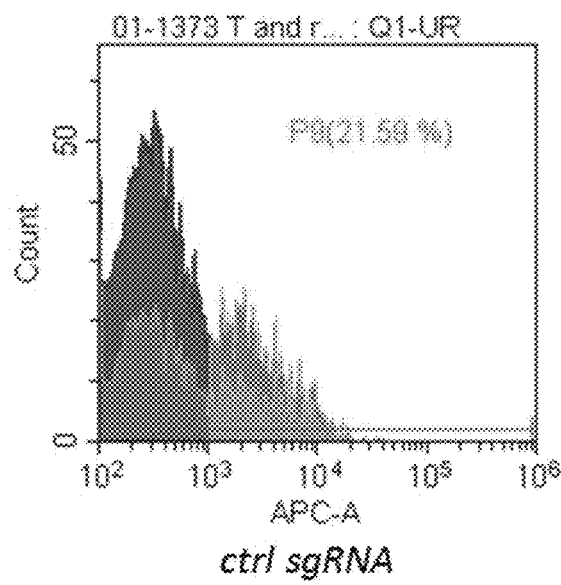
Figure 47H:
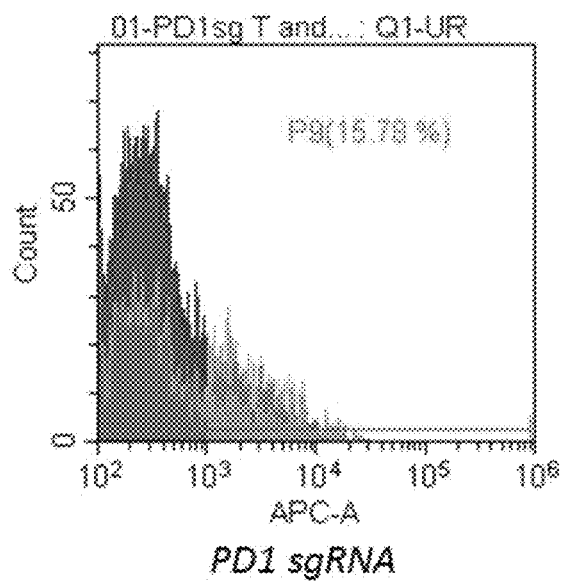

T cells versus Raji-PD-L1 cells at a 2:1 ratio analyzed after 2 days incubation are depicted in FIGS. 46G and 46H (Control T cells vs Raji-PD-L1 cells), FIGS. 46I and 46J (CD19-CAR-T cells with control sgRNA vs Raji-PD-L1 cells), and FIGS. 46K and 46L (CD19-CAR-T cells with PD-1 sgRNAs vs Raji-PD-L1 cells). Percentages indicate percentage of remaining Raji-PD-L1 cells.

FIGS. 47A-D show expression of PD-1 in CD19-CAR-T cells with control sgRNA (FIGS. 47A and 47B) and in CD19-CAR-T cells with PD-1 sgRNAs (FIGS. 47C and 47D) after 2 days incubation with Raji-PD-L1 cells (at a 1:1 ratio).

FIGS. 47E-H show expression of PD-1 in CD19-CAR-T cells with control sgRNA (FIGS. 47E and 47F) and in CD19-CAR-T cells with PD-1 sgRNAs (FIGS. 47G and 47H) after 2 days incubation with Raji-PD-L1 cells (at a 2:1 ratio).

T cells versus Raji-PD-L1 cells at a 1:1 ratio analyzed after 3 days incubation are depicted in FIGS. 48A and 48B (Control T cells vs Raji-PD-L1 cells), FIGS. 48C and 48D (CD19-CAR-T cells with control sgRNA vs Raji-PD-L1 cells), and FIGS. 48E and 48F (CD19-CAR-T cells with PD-1 sgRNAs vs Raji-PD-L1 cells). Percentages indicate percentage of remaining Raji-PD-L1 cells.

Figure 48G:
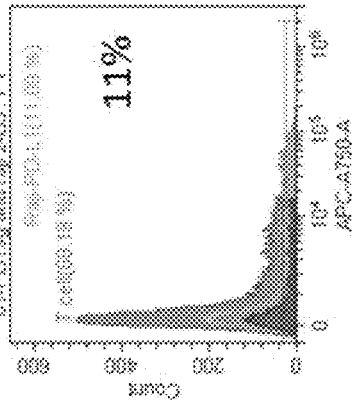
Figure 48I:
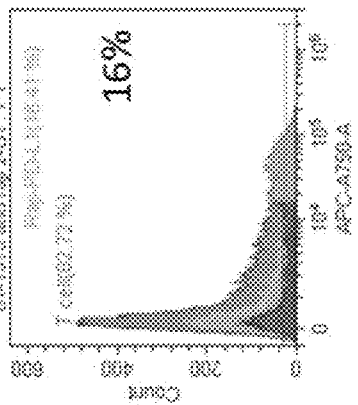
Figure 48K:
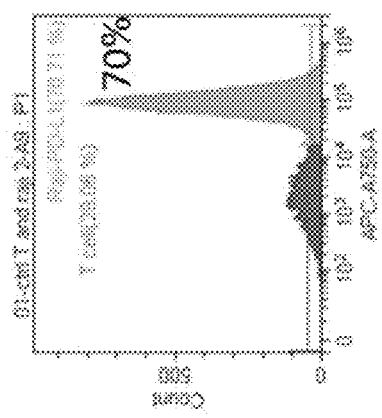
Figure 48H:
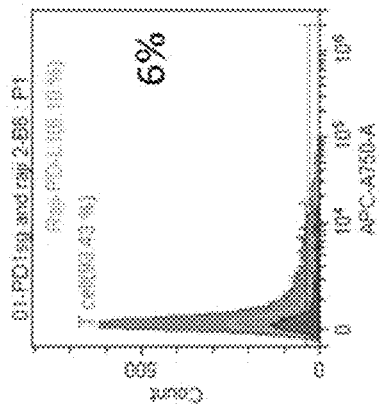
Figure 48J:
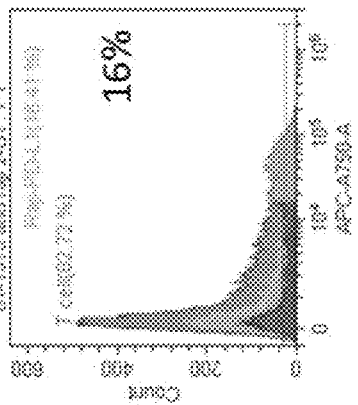
Figure 48L:
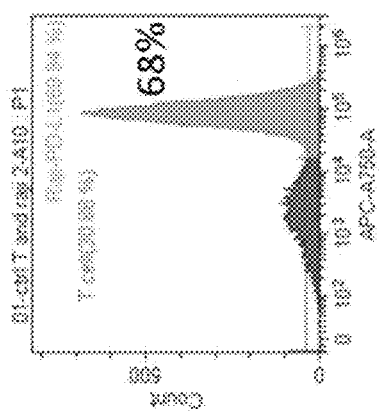

T cells versus Raji-PD-L1 cells at a 2:1 ratio analyzed after 3 days incubation are depicted in FIGS. 48G and 48H (Control T cells vs Raji-PD-L1 cells), FIGS. 48I and 48J (CD19-CAR-T cells with control sgRNA vs Raji-PD-L1 cells), and FIGS. 48K and 48L (CD19-CAR-T cells with PD-1 sgRNAs vs Raji-PD-L1 cells). Percentages indicate percentage of remaining Raji-PD-L1 cells.

Figure 49A:
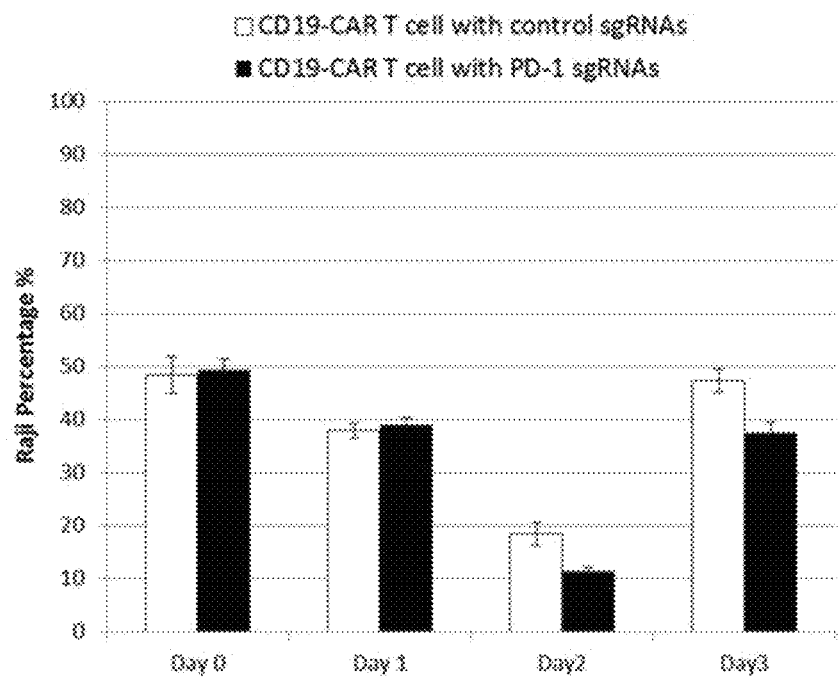
FIGS. 49A and 49B quantify the ratio of T cell to Raji cell after 1 day, 2 days, or 3 days in co-culture.
Figure 49B:
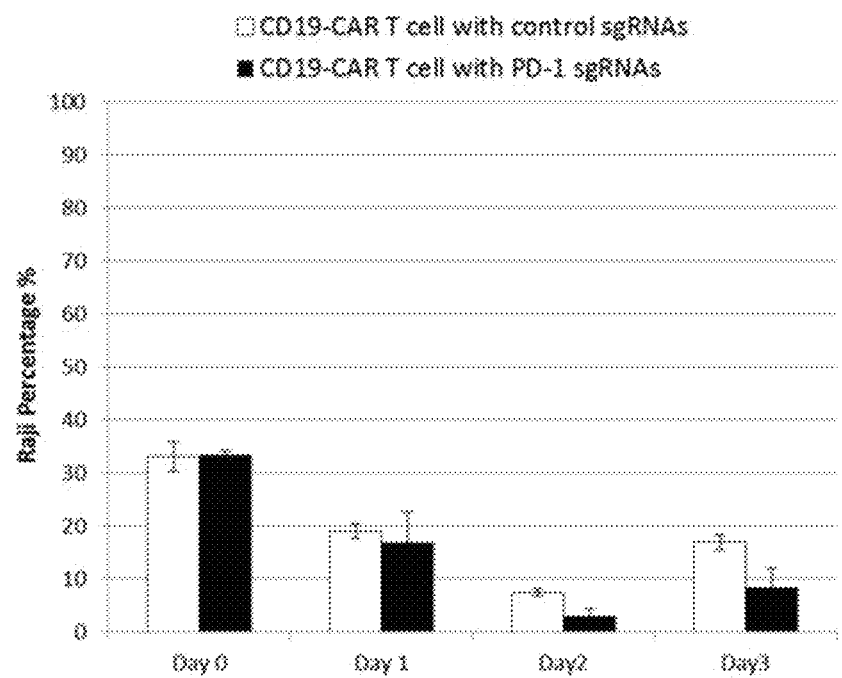

The percentage of Raji cells after co-culture with T cells for 1 day, 2 days, and 3 days at a starting ratio of 1:1 is shown FIG. 49A. The percentage of Raji cells after co-culture with T cells for 1 day, 2 days, and 3 days at a starting ratio of 2:1 is shown FIG. 49B. These data demonstrated that the CD19-CAR-T cells with PD-1 sgRNAs (with PD-1 downregulation) are more effective than CD19-CAR-T cells with control sgRNA (without PD-1 downregulation) in killing Raji lymphoma cells expressing PD-L1 after 2 days co-culture.

Example 19: Ligand-Dependent Cleavage of dCas9-KRAB in Primary Human T Cells

Lentiviruses encoding one of eight adaptors fused to TEV are cotransduced into primary human T cells along with an rtTA lentivirus and a third lentivirus encoding CD19 CAR-dCas9-KRAB fusion protein. The transduced cells are then activated with Raji cells and subjected to CytoFlex analysis to detect CD19-CAR-dCas9-KRAB and Adaptor-TEV expression. Co-expressing cells are the analyzed by western blot to detect dCas9-KRAB cleavage.

Example 20: Adaptor-Dependent Cleavage Contributes to Ligand-Dependent Cleavage in Jurkat Cells, an Immortalized Line of Human T Cells Jurkat cells were co-transduced with 1) a lentivirus encoding TEV with no adaptor, GADS-TEV, or LET-TEV, and 2) a lentivirus encoding CD19-CAR-dCas9-KRAB fusion protein. Co-transduced cells were activated with CD19+ Raji cells, cultured for 24 hours, and then analyzed by western blot to detect dCas9-KRAB cleavage. CD19-CAR-dCas9-KRAB expression was driven by the EF1a promoter, and adaptor-TEV expression was driven by Tet3g promoter.

Figure 50A:
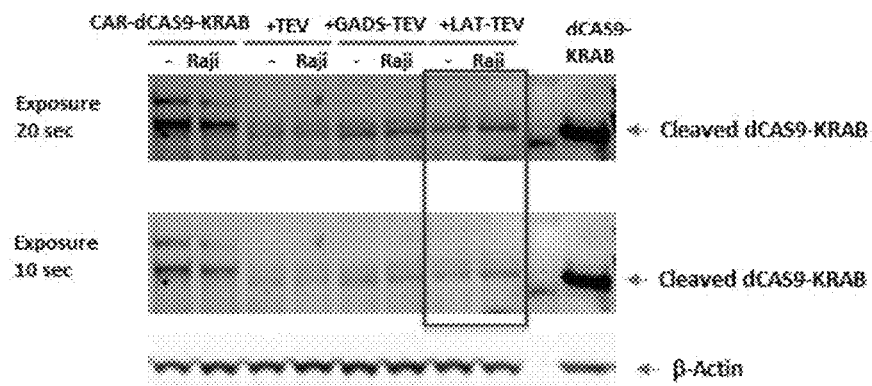
FIGS. 50A, 50B, and 50C depict a western blot (FIG. 50A) detecting cleaved dCas9-KRAB in the indicated samples and beta-actin as a loading control, and densitometry quantification of the cleaved dCas9-KRAB western blot signal (FIGS. 50B and 50C).
Figure 50B:
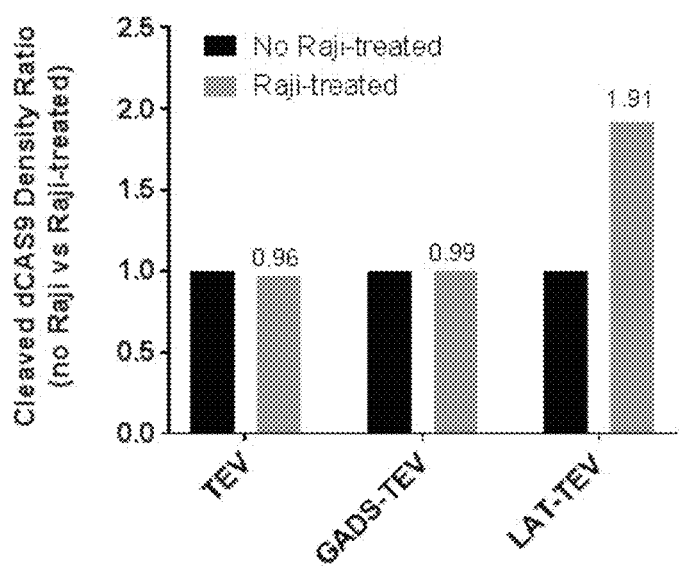
Figure 50C:
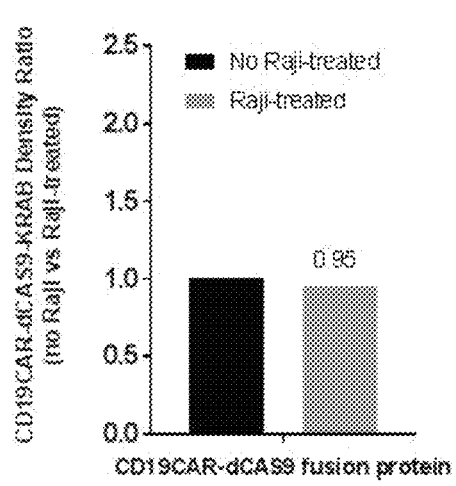

FIG. 50A depicts a western blot of the aforementioned cells after incubation with or without the Raji cells. Beta-actin was used as a loading control. The results are quantified based on the density ratio of the western blots, which is depicted in FIGS. 50B and 50C. These data demonstrate adaptor-dependent cleavage of dCas9-KRAB with LAT-TEV in transduced Jurkat cells activated by CD19+ Raji cells.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein can be employed in practicing the invention. It is intended that the following claims define the scope of the invention and that methods and structures within the scope of these claims and their equivalents be covered thereby.

What is claimed is:

1. A system capable of inducing death of a target cell, comprising:
   (a) a chimeric transmembrane receptor polypeptide (receptor) comprising a ligand binding domain, an immune cell signaling domain, and a gene modulating polypeptide (GMP), the GMP comprising an actuator moiety linked to a cleavage recognition site, wherein the actuator moiety modulates expression and/or activity of an immune regulatory protein of the lymphocyte, and wherein the immune regulatory protein enhances lymphocyte cytotoxicity and/or reduces a side effect of lymphocyte activation; and
   (b) a chimeric adaptor polypeptide (adaptor) comprising a receptor binding moiety linked to a cleavage moiety, wherein the cleavage moiety is capable of cleaving the cleavage recognition site on the receptor when the receptor binding moiety of the adaptor binds the immune cell signaling domain of the receptor in response to binding of the ligand binding domain of the receptor to a ligand present on the target cell, and wherein the adaptor does not bind a ligand present on the target cell,
   wherein the receptor is activatable upon binding to the ligand present on the target cell to recruit the adaptor to the receptor, and wherein the recruited adaptor releases the actuator moiety from the GMP of the receptor by action of the cleavage moiety at the cleavage recognition site to induce death of the target cell.

2. The system of claim 1, wherein the ligand binding domain comprises a single-chain variable fragment (scFv).

3. The system of claim 1, wherein the ligand binding domain binds CD19 or a fragment thereof.

4. The system of claim 1, wherein the immune cell signaling domain comprises an immunoreceptor tyrosine-based activation motif (ITAM).

5. The system of claim 1, wherein the actuator moiety comprises a CRISPR-associated polypeptide (Cas), a zinc finger nuclease (ZFN), a transcription activator-like effector nuclease (TALEN), a meganuclease, a recombinase, a flippase, a transposase, or an Argonaute protein.

6. The system of claim 1, wherein the actuator moiety comprises a Cas protein that forms a complex with a guide RNA (gRNA).

7. The system of claim 6, wherein the Cas protein is Cas9, Cpf1, or C2c2.

8. The system of claim 6, wherein the Cas protein substantially lacks DNA cleavage activity.

9. The system of claim 6, wherein the Cas protein is linked to a transcriptional repressor or a transcriptional activator.

10. The system of claim 1, wherein the cleavage recognition site comprises a polypeptide sequence and the cleavage moiety comprises a protease.

11. The system of claim 1, wherein the cleavage moiety is a TEV protease, and wherein the cleavage recognition site is a TEV protease cleavage site.

12. A lymphocyte expressing the system of claim 1.

13. A population of lymphocyte cells, individual lymphocyte cells expressing the system of claim 1, wherein said population of lymphocyte cells is characterized in that: upon exposing said population of lymphocyte cells to a target cell population in an in vitro cell death assay, the population of lymphocyte cells induces death of at least 45% of the target cells within about 2 days when the ratio of the number of lymphocyte cells in said population of lymphocyte cells to the number of target cells in the target cell population is about 1:2 or less.

* * * * *

SEQUENCE LISTING

<160> NUMBER OF SEQ ID NOS: 21

<210> SEQ ID NO 1

<400> SEQUENCE: 1

000

<210> SEQ ID NO 2
<211> LENGTH: 7
<212> TYPE: PRT
<213> ORGANISM: Artificial Sequence

```
<220> FEATURE:
<223> OTHER INFORMATION: Synthetic Construct

<400> SEQUENCE: 2

Pro Lys Lys Lys Arg Lys Val
1               5

<210> SEQ ID NO 3
<211> LENGTH: 16
<212> TYPE: PRT
<213> ORGANISM: Artificial Sequence
<220> FEATURE:
<223> OTHER INFORMATION: Synthetic Construct

<400> SEQUENCE: 3

Lys Arg Pro Ala Ala Thr Lys Lys Ala Gly Gln Ala Lys Lys Lys Lys
1               5                   10                  15

<210> SEQ ID NO 4
<211> LENGTH: 9
<212> TYPE: PRT
<213> ORGANISM: Artificial Sequence
<220> FEATURE:
<223> OTHER INFORMATION: Synthetic Construct

<400> SEQUENCE: 4

Pro Ala Ala Lys Arg Val Lys Leu Asp
1               5

<210> SEQ ID NO 5
<211> LENGTH: 11
<212> TYPE: PRT
<213> ORGANISM: Artificial Sequence
<220> FEATURE:
<223> OTHER INFORMATION: Synthetic Construct

<400> SEQUENCE: 5

Arg Gln Arg Arg Asn Glu Leu Lys Arg Ser Pro
1               5                   10

<210> SEQ ID NO 6
<211> LENGTH: 38
<212> TYPE: PRT
<213> ORGANISM: Artificial Sequence
<220> FEATURE:
<223> OTHER INFORMATION: Synthetic Construct

<400> SEQUENCE: 6

Asn Gln Ser Ser Asn Phe Gly Pro Met Lys Gly Gly Asn Phe Gly Gly
1               5                   10                  15

Arg Ser Ser Gly Pro Tyr Gly Gly Gly Gly Gln Tyr Phe Ala Lys Pro
            20                  25                  30

Arg Asn Gln Gly Gly Tyr
        35

<210> SEQ ID NO 7
<211> LENGTH: 42
<212> TYPE: PRT
<213> ORGANISM: Artificial Sequence
<220> FEATURE:
<223> OTHER INFORMATION: Synthetic Construct
```

```
<400> SEQUENCE: 7

Arg Met Arg Ile Glx Phe Lys Asn Lys Gly Lys Asp Thr Ala Glu Leu
1               5                   10                  15

Arg Arg Arg Arg Val Glu Val Ser Val Glu Leu Arg Lys Ala Lys Lys
            20                  25                  30

Asp Glu Gln Ile Leu Lys Arg Arg Asn Val
        35                  40

<210> SEQ ID NO 8
<211> LENGTH: 8
<212> TYPE: PRT
<213> ORGANISM: Artificial Sequence
<220> FEATURE:
<223> OTHER INFORMATION: Synthetic Construct

<400> SEQUENCE: 8

Val Ser Arg Lys Arg Pro Arg Pro
1               5

<210> SEQ ID NO 9
<211> LENGTH: 8
<212> TYPE: PRT
<213> ORGANISM: Artificial Sequence
<220> FEATURE:
<223> OTHER INFORMATION: Synthetic Construct

<400> SEQUENCE: 9

Pro Pro Lys Lys Ala Arg Glu Asp
1               5

<210> SEQ ID NO 10
<211> LENGTH: 8
<212> TYPE: PRT
<213> ORGANISM: Artificial Sequence
<220> FEATURE:
<223> OTHER INFORMATION: Synthetic Construct

<400> SEQUENCE: 10

Pro Gln Pro Lys Lys Lys Pro Leu
1               5

<210> SEQ ID NO 11
<211> LENGTH: 12
<212> TYPE: PRT
<213> ORGANISM: Artificial Sequence
<220> FEATURE:
<223> OTHER INFORMATION: Synthetic Construct

<400> SEQUENCE: 11

Ser Ala Leu Ile Lys Lys Lys Lys Lys Met Ala Pro
1               5                   10

<210> SEQ ID NO 12
<211> LENGTH: 5
<212> TYPE: PRT
<213> ORGANISM: Artificial Sequence
<220> FEATURE:
<223> OTHER INFORMATION: Synthetic Construct

<400> SEQUENCE: 12

Asp Arg Leu Arg Arg
1               5
```

```
<210> SEQ ID NO 13
<211> LENGTH: 7
<212> TYPE: PRT
<213> ORGANISM: Artificial Sequence
<220> FEATURE:
<223> OTHER INFORMATION: Synthetic Construct

<400> SEQUENCE: 13

Pro Lys Gln Lys Lys Arg Lys
1               5

<210> SEQ ID NO 14
<211> LENGTH: 10
<212> TYPE: PRT
<213> ORGANISM: Artificial Sequence
<220> FEATURE:
<223> OTHER INFORMATION: Synthetic Construct

<400> SEQUENCE: 14

Arg Lys Leu Lys Lys Lys Ile Lys Lys Leu
1               5                   10

<210> SEQ ID NO 15
<211> LENGTH: 10
<212> TYPE: PRT
<213> ORGANISM: Artificial Sequence
<220> FEATURE:
<223> OTHER INFORMATION: Synthetic Construct

<400> SEQUENCE: 15

Arg Glu Lys Lys Lys Phe Leu Lys Arg Arg
1               5                   10

<210> SEQ ID NO 16
<211> LENGTH: 20
<212> TYPE: PRT
<213> ORGANISM: Artificial Sequence
<220> FEATURE:
<223> OTHER INFORMATION: Synthetic Construct

<400> SEQUENCE: 16

Lys Arg Lys Gly Asp Glu Val Asp Gly Val Asp Glu Val Ala Lys Lys
1               5                   10                  15

Lys Ser Lys Lys
            20

<210> SEQ ID NO 17
<211> LENGTH: 17
<212> TYPE: PRT
<213> ORGANISM: Artificial Sequence
<220> FEATURE:
<223> OTHER INFORMATION: Synthetic Construct

<400> SEQUENCE: 17

Arg Lys Cys Leu Gln Ala Gly Met Asn Leu Glu Ala Arg Lys Thr Lys
1               5                   10                  15

Lys

<210> SEQ ID NO 18
<211> LENGTH: 5
<212> TYPE: PRT
<213> ORGANISM: Artificial Sequence
<220> FEATURE:
<223> OTHER INFORMATION: Synthetic Construct
```

```
<220> FEATURE:
<221> NAME/KEY: VARIANT
<222> LOCATION: (4)..(4)
<223> OTHER INFORMATION: Xaa = any amino acid

<400> SEQUENCE: 18

Met Gly Cys Xaa Cys
1               5

<210> SEQ ID NO 19
<211> LENGTH: 20
<212> TYPE: PRT
<213> ORGANISM: Artificial Sequence
<220> FEATURE:
<223> OTHER INFORMATION: Synthetic Construct

<400> SEQUENCE: 19

Glu Thr Gln Arg Cys Thr Trp His Met Gly Glu Leu Val Trp Cys Glu
1               5                   10                  15

Arg Glu His Asn
            20

<210> SEQ ID NO 20
<211> LENGTH: 20
<212> TYPE: PRT
<213> ORGANISM: Artificial Sequence
<220> FEATURE:
<223> OTHER INFORMATION: Synthetic Construct

<400> SEQUENCE: 20

Lys Glu Ala Ser Cys Ser Tyr Trp Leu Gly Glu Leu Val Trp Cys Val
1               5                   10                  15

Ala Gly Val Glu
            20

<210> SEQ ID NO 21
<211> LENGTH: 13
<212> TYPE: PRT
<213> ORGANISM: Artificial Sequence
<220> FEATURE:
<223> OTHER INFORMATION: Synthetic Construct

<400> SEQUENCE: 21

Asp Cys Ala Trp His Leu Gly Glu Leu Val Trp Cys Thr
1               5                   10
```